United States Patent
Mali et al.

(10) Patent No.: US 11,332,727 B2
(45) Date of Patent: May 17, 2022

(54) METHOD FOR REDUCING AN IMMUNE RESPONSE BY ADMINISTERING AN IMMUNE EVADING ADENO-ASSOCIATED AAV8 OR AAVDJ VIRAL VECTOR

(71) Applicant: The Regents of the University of California, Oakland, CA (US)

(72) Inventors: Prashant Mali, La Jolla, CA (US); Ana Moreno Collado, La Jolla, CA (US); Nathan Palmer, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 164 days.

(21) Appl. No.: 16/494,269

(22) PCT Filed: Mar. 13, 2018

(86) PCT No.: PCT/US2018/022258
§ 371 (c)(1),
(2) Date: Sep. 13, 2019

(87) PCT Pub. No.: WO2018/170015
PCT Pub. Date: Sep. 20, 2018

(65) Prior Publication Data
US 2020/0299657 A1    Sep. 24, 2020

Related U.S. Application Data

(60) Provisional application No. 62/471,267, filed on Mar. 14, 2017, provisional application No. 62/614,875, filed on Jan. 8, 2018.

(51) Int. Cl.
| | | |
|---|---|---|
| A61K 48/00 | (2006.01) | |
| C12N 15/86 | (2006.01) | |
| A61K 49/00 | (2006.01) | |
| G01N 33/50 | (2006.01) | |
| C12N 9/22 | (2006.01) | |
| C12N 15/11 | (2006.01) | |

(52) U.S. Cl.
CPC ............ *C12N 9/22* (2013.01); *A61K 48/005* (2013.01); *A61K 49/0008* (2013.01); *C12N 15/111* (2013.01); *C12N 15/86* (2013.01); *G01N 33/50* (2013.01); *C12N 2310/20* (2017.05); *C12N 2750/14143* (2013.01)

(58) Field of Classification Search
CPC .. A61K 49/0008; A61K 48/005; G01N 33/50; C12N 15/86
See application file for complete search history.

(56) References Cited

U.S. PATENT DOCUMENTS

| | | | |
|---|---|---|---|
| 6,730,507 B1 | 5/2004 | Graham et al. | |
| 7,615,217 B2 | 11/2009 | Gillies et al. | |
| 2004/0185038 A1 | 9/2004 | Carr et al. | |
| 2016/0017295 A1 | 1/2016 | Schaffer et al. | |

FOREIGN PATENT DOCUMENTS

| | | |
|---|---|---|
| WO | 2015/153789 A1 | 10/2015 |
| WO | 2016/033246 A1 | 3/2016 |

OTHER PUBLICATIONS

Kathleen Pratt. (Mar. 2016) Cell Immunol. 301: 12-17. (published online Nov. 2, 1015 at doi:10.1016/j.cellimm.2015.10.008).*
Griesinger, Irina, Supplementary Partial European Search Report, European Patent Office, Application No. 18768009.5, dated May 10, 2021.
Mack et al., "Circumvention of Anti-Adenovirus Neutralizing Immunity by Administration of an Adenoviral Vector of an Alternate Serotype", Human Gene Therapy, 8:99-109, Jan. 1, 1997.
Roy et al., "Circumvention of Immunity to the Adenovirus Major Coat Protein Hexon", Journal of Virology, Aug. 1998, vol. 2, No. 8, pp. 6875-6879.
Degroot et al., "Prediction of immunogenicity for therapeutic proteins: State of the art," Current Opin. in Drug. Disc & Develop., vol. 10, No. 3, pp. 1-9, 2007.
Moise et al., "Effect of HLA DR epitope de-immunization of Factor VIII in vitro and in vivo," Clinical Immunol., vol. 142, No. 3, pp. 320-331, 2012.
Moreno et al., "Exploring protein orthogonality in immune space: a case study with AAV and Cas9," bioRxiv, pp. 1-24, Jan. 10, 2018.
Sant'angelo et al., "Recognition of core and flanking amino acids of MHC class II-bound peptides by the T cell receptor," Eur. J. of Immunol., vol. 32, No. 9, pp. 2510-2520, 2002.
Chew, Wei Leong et al., "A multifunctional AAV-CRISPR-Cas9 and its host response", Nature Methods, vol. 13, No. 10, Oct. 1, 2016, pp. 868-874.
Daugherty, Kimberly K., "Review of Insulin Therapy," Journal of Pharmacy Practice, vol. 17, No. 1, Feb. 1, 2004, pp. 10-19.
Griesinger, Irina, Supplementary Partial European Search Report, European Patent Office, Application No. 18768009.5, dated Jan. 12, 2021.
Copenheaver, Blaine R., International Search Report and Written Opinion, PCT/US2018/022258, United States Patent and Trademark Office, dated Jun. 25, 2018.
Mineko, Mohri, International Preliminary Report on Patentability and Written Opinion, PCT/US2018/022258, The International Bureau of WIPO, dated Sep. 26, 2019.

(Continued)

*Primary Examiner* — Robert S Landsman
(74) *Attorney, Agent, or Firm* — Gavrilovich, Dodd & Lindsey LLP

(57) ABSTRACT

Described herein are methods of avoiding an immune response in a subject being administered a regimen requiring Cas9 in order to optimize and broaden the application of CRIPSR based therapeutics comprising administering immune orthogonal Cas9. Also described herein are methods to modify a Cas9 protein by swapping highly immunogenic peptides or amino acids with less immunogenic counterparts. These methods are particularly useful to enable the application of Cas9 arsenal for repeat treatments. Further provided are Cas9 proteins modified to reduce immunogenicity.

9 Claims, 17 Drawing Sheets
Specification includes a Sequence Listing.

(56) References Cited

OTHER PUBLICATIONS

Mingozzi, F. et al. Pharmacological Modulation of Humoral Immunity in a Nonhuman Primate Model of AAV Gene Transfer for Hemophilia B. Mol. Ther. 20, 1410-1416 (2017).
Mingozzi, F. et al. Prevalence and pharmacological modulation of humoral immunity to AAV vectors in gene transfer to synovial tissue. Gene Ther 20, 417-424 (2013).
Ran, F. A. et al. In vivo genome editing using *Staphylococcus aureus* Cas9. Nature 520, 186-190 (2015).
Riechmann, L., Clark, M., Waldmann, H. & Winter, G. Reshaping human antibodies for therapy. Nature 332, 323-7 (1988).
Ruppert, J. et al. Prominent role of secondary anchor residues in peptide binding to HLA-A2.1 molecules. Cell 74, 929-937 (2017).
Salvat, R. S., Choi, Y., Bishop, A., Bailey-Kellogg, C. & Griswold, K. E. Protein deimmunization via structure-based design enables efficient epitope deletion at high mutational loads. Biotechnol. Bioeng. 112, 1306-1318 (2015).
Sathish, J. G. et al. Challenges and approaches for the development of safer immunomodulatory biologics. Nat Rev Drug Discov 12, 306-324 (2013).
Shmakov et al., Diversity and evolution of class 2 CRISPR-Cas systems, Nat. Rev. Microbiol., 16(3):169-182, Mar. 2017.
Sollner, J. et al. Analysis and prediction of protective continuous B-cell epitopes on pathogen proteins. Immunome Res. 4, 1 (2008).
Song, S. et al. Sustained secretion of human alpha-1-antitrypsin from murine muscle transduced with adeno-associated virus vectors. Proc. Natl. Acad. Sci. U.S.A. 95, 14384-8 (1998).
Sun, P. et al. Bioinformatics resources and tools for conformational B-cell epitope prediction. Computational and Mathematical Methods in Medicine 2013, (2013).
Tangri, S. et al. Rationally Engineered Therapeutic Proteins with Reduced Immunogenicity. J. Immunol. 174, 3187 LP-3196 (2005).
Tong, S Y C et al. (2015) *Staphylococcus aureus* Infections: Epidemiology, Pathophysiology, Clinical Manifestations, and Management. Clinical Microbiology Reviews. 28: 603661.
Unzu, C. et al. Transient and intensive pharmacological immunosuppression fails to improve AAV-based liver gene transfer in non-human primates. J. Transl. Med. 10, 122 (2012).
Veronese, F. M. & Mero, A. The impact of PEGylation on biological therapies. BioDrugs 22, 315-329 (2008).
Vita, R. et al. The immune epitope database (IEDB) 3.0. Nucleic Acids Res. 43, D405-12 (2015).
Wagner, J. a et al. Safety and biological efficacy of an adenoassociated virus vector-cystic fibrosis transmembrane regulator (AAV-CFTR) in the cystic fibrosis maxillary sinus. Laryngoscope 109, 266-74 (1999).
Wang et al., Adenovirus-Mediated Somatic Genome diting of Pten by CRISPR/Cas9 in Mouse Liver in Spite of Cas9-Specific Immune Responses, Human Gene Therapy, 26(7):432-442, 2015.
Zabel, F. et al. Distinct T helper cell dependence of memory B-cell proliferation versus plasma cell differentiation. Immunology 150, 329-342 (2017).
Zhang, H. G. et al. Genetic analysis of the antibody response to AAV2 and factor IX. Mol. Ther. 11, 866-874 (2005).
Zhu, J., Huang, X. & Yang, Y. The TLR9-MyD88 pathway is critical for adaptive immune responses to adeno-associated virus gene therapy vectors in mice. J. Clin. Invest. 119, 2388-2398 (2009).
Zinn, E. et al. In Silico Reconstruction of the Viral Evolutionary Lineage Yields a Potent Gene Therapy Vector. Cell Rep. 12, 1056-1068 (2017).
Andreatta, M. & Nielsen, M. Gapped sequence alignment using artificial neural networks: application to the MHC class I system. Bioinformatics 32, 511-517 (2015).
Armstrong, J. K. et al. Antibody against poly(ethylene glycol) adversely affects PEG-asparaginase therapy in acute lymphoblastic leukemia patients. Cancer 110, 103-111 (2007).
Baker, M. P., Reynolds, H. M., Lumicisi, B. & Bryson, C. J. Immunogenicity of protein therapeutics: The key causes, consequences and challenges. Self Nonself 1, 314-322 (2010).

Basner-Tschakarjan, E., Bijjiga, E. & Martino, A. T. Pre-clinical assessment of immune responses to adeno-associated virus (AAV) vectors. Front. Immunol. 5, (2014).
Boutini et al., Prevalence of Serum IgG and Neutralizing Factors Against Adeno-Associated Virus (AAV) Types 1, 2, 5, 6, 8, and 9 in the Healthy Population: Implications for Gene Therapy Using AAV Vectors. Hum. Gene Ther. 21, 704-712 (2010).
Calcedo, R. & Wilson, J. M. AAV Natural Infection Induces Broad Cross-Neutralizing Antibody Responses to Multiple AAV Serotypes in Chimpanzees. Hum. Gene Ther. Clin. Dev. 27, 79-82 (2016).
Chew et al., A multi-functional AAV-CRISPR-Cas9 and its host response, Nat. Methods, 13(10:868-874, Oct. 2016.
Chirmule, N. et al. Humoral Immunity to Adeno-Associated Virus Type 2 Vectors following Administration to Murine and Nonhuman Primate Muscle. J. Virol. 74, 2420-2425 (2000).
Choi Y and Chan A P (2015) PROVEAN web server: a tool to predict the functional effect of amino acid substitutions and indels. Bioinformatics 31(16): 27452747.
Chylinski, K., Makarova, K. S., Charpentier, E. & Koonin, E. V. Classification and evolution of type II CRISPR-Cas systems. Nucleic Acids Research 42, 6091-6105 (2014).
Cong et al., Multiplex Genome Engineering Using CRISPR/Cas Systems, Science, 339(6121):819-823, 2013.
Courtenay-Luck, N. S., Epenetos, A. A. & Moore, R. Development of primary and secondary immune responses to mouse monoclonal antibodies used in the diagnosis and therapy of malignant neoplasms. Cancer Res. 46, 6489-6493 (1986).
Dalkas, G. A. & Rooman, M. SEPla, a knowledge-driven algorithm for predicting conformational B-cell epitopes from the amino acid sequence. BMC Bioinformatics 18, 95 (2017).
De Groot, a S., Knopp, P. M. & Martin, W. De-immunization of therapeutic proteins by T-cell epitope modification. Dev. Biol. (Basel). 122, 171-194 (2005).
Ding, Q. et al. Permanent Alteration of PCSK9 With In Vivo CRISPR-Cas9 Genome Editing. Circ. Res. 115, 488-492 (2014).
El-Manzalawy, Y., Dobbs, D. & Honavar, V. Predicting linear B-cell epitopes using string kernels. J. Mol. Recognit. 21, 243-255 (2008).
Ertl, H. C. J. & High, K. A. Impact of AAV Capsid-Specific T-Cell Responses on Design and Outcome of Clinical Gene Transfer Trials with Recombinant Adeno-Associated Viral Vectors: An Evolving Controversy. Hum. Gene Ther. 28, 328-337 (2017).
Fields, P. a et al. Risk and prevention of anti-factor IX formation in AAV-mediated gene transfer in the context of a large deletion of F9. Mol. Ther. 4, 201-210 (2001).
Fonfara, I. et al. Phylogeny of Cas9 determines functional exchangeability of dual-RNA and Cas9 among orthologous type II CRISPR-Cas systems. Nucleic Acids Res. 42, 2577-2590 (2014).
Ganson, N. J., Kelly, S. J., Scarlett, E., Sundy, J. S. & Hershfield, M. S. Control of hyperuricemia in subjects with refractory gout, and induction of antibody against poly(ethylene glycol) (PEG), in a phase I trial of subcutaneous PEGylated urate oxidase. Arthritis Res. Ther. 8, R12-R12 (2006).
Gao, G.-P. et al. Novel adeno-associated viruses from rhesus monkeys as vectors for human gene therapy. Proc. Natl. Acad. Sci. 99, 11854-11859 (2002).
Gasiunas, G., Barrangou, R., Horvath, P. & Siksnys, V. Cas9-crRNA ribonucleoprotein complex mediates specific DNA cleavage for adaptive immunity in bacteria. Proc. Natl. Acad. Sci. 109, E2579-E2586 (2012).
Gemoux, G. et al. Early Interaction of Adeno-Associated Virus Serotype 8 Vector with the Host Immune System Following Intramuscular Delivery Results in Weak but Detectable Lymphocyte and Dendritic Cell Transduction. Hum. Gene Ther. 26, 1-13 (2015).
Gemoux, G., Wilson, J. M. & Mueller, C. Regulatory and Exhausted T Cell Responses to AAV Capsid. Hum. Gene Ther. 28, 338-349 (2017).
Güiell, M., Yang, L. & Church, G. M. Genome editing assessment using CRISPR Genome Analyzer (CRISPR-GA). Bioinformatics 30, 2968-2970 (2014).
Harbison, C. E. et al. Examining the cross-reactivity and neutralization mechanisms of a panel of mabs against adeno-associated virus serotypes 1 and 5. J. Gen. Virol. 93, (2012).

(56) References Cited

OTHER PUBLICATIONS

Harding, F. A., Stickler, M. M., Razo, J. & DuBridge, R. B. The immunogenicity of humanized and fully human antibodies: Residual immunogenicity resides in the CDR regions. MAbs 2, 256-265 (2010).

Herzog, R. W. et al. Influence of vector dose on factor IX-specific T and B cell responses in muscle-directed gene therapy. Hum. Gene Ther. 13, 1281-91 (2002).

Hsu, P. D., Lander, E. S. & Zhang, F. Development and applications of CRISPR-Cas9 for genome engineering. Cell 157, 1262-1278 (2014).

Jacobs, F., Gordts, S. C., Muthuramu, I. & De Geest, B. The liver as a target organ for gene therapy: state of the art, challenges, and future perspectives. Pharmaceuticals (Basel). 5, 1372-92 (2012).

Jevsevar, S., Kunstelj, M. & Porekar, V. G. PEGylation of therapeutic proteins. Biotechnol. J. 5, 113-128 (2010).

Jinek, M. et al. A Programmable Dual-RNA—Guided DNA Endonuclease in Adaptice Bacterial Immunity. Science 337, 816-822 (2012).

Jinek, M. et al. RNA-programmed genome editing in human cells. Elife 2013, (2013).

Jooss, K., Yang, Y., Fisher, K. J. & Wilson, J. M. Transduction of Dendritic Cells by DNA Viral Vectors Directs the Immune Response to Transgene Products in Muscle Fibers. J. Virol. 72, 4212-4223 (1998).

Kok, C. Y. et al. Adeno-associated Virus-mediated Rescue of Neonatal Lethality in Argininosuccinate Synthetase-deficient Mice. Mol. Ther. 21, 1823-1831 (2013).

Kotterman, M. A., Chalberg, T. W. & Schaffer, D. V. Viral Vectors for Gene Therapy: Translational and Clinical Outlook. Annu. Rev. Biomed. Eng. 17, 63-89 (2015).

Kurosaki, T., Kometani, K. & Ise, W. Memory B cells. Nat. Rev. Immunol. 15, 149-159 (2015).

Larsen, J. E. P., Lund, O. & Nielsen, M. Improved method for predicting linear B-cell epitopes. Immunome Res. 2, 2 (2006).

Liepe, J. et al. A large fraction of HLA class I ligands are proteasome-generated spliced peptides. Science (80-.). 354, (2016).

Lozier, J. N., Tayebi, N. & Zhang, P. Mapping of genes that control the antibody response to human factor IX in mice. Blood 105, 1029-1035 (2005).

Lundegaard C, et al. (2010) "Major Histocompatibility Complex Class I Binding Predictions as a Tool in Epitope Discovery." Immunology 130.3 (2010): 309-318. PMC. Web. Nov. 7, 2016.

Majowicz, A. et al. Successful Repeated Hepatic Gene Delivery in Mice and Non-human Primates Achieved by Sequential Administration of AAV5ch and AAV1. Mol. Ther. 25, 1831-1842 (2017).

Mali, P., Esvelt, K. M. & Church, G. M. Cas9 as a versatile tool for engineering biology. Nat. Methods 10, 957-963 (2013).

Mali et al., RNA-Guided Human Genome Engineering via Cas9, Science, 339(6121):823-826, 2013.

Manno, C. S. et al. Successful transduction of liver in hemophilia by AAV-Factor IX and limitations imposed by the host immune response. Nat. Med. 12, 342-347 (2006).

Makarova, K. S. et al. An updated evolutionary classification of CRISPR-Cas systems. Nat. Rev. Microbiol. 13, 722-736 (2015).

Mays, L. E. & Wilson, J. M. The Complex and Evolving Story of T cell Activation to AAV Vector-encoded Transgene Products. Mol. Ther. 19, 16-27 (2011).

McIntosh, J. H. et al. Successful attenuation of humoral immunity to viral capsid and transgenic protein following AAV-mediated gene transfer with a non-depleting CD4 antibody and cyclosporine. Gene Ther 19, 78-85 (2012).

Mingozzi, F. & High, K. A. Immune responses to AAV vectors: overcoming barriers to successful gene therapy. Blood 122, 23-36 (2013).

Mingozzi, F. & High, K. A. Therapeutic in vivo gene transfer for genetic disease using AAV: progress and challenges. Nat. Rev. Genet. 12, 341-355 (2011).

\* cited by examiner

A

B

METHOD FOR REDUCING AN IMMUNE RESPONSE BY ADMINISTERING AN IMMUNE EVADING ADENO-ASSOCIATED AAV8 OR AAVDJ VIRAL VECTOR

CROSS-REFERENCE TO RELATED APPLICATIONS

This application is a U.S. National Stage Application filed under 35 U.S.C. § 371 and claims priority to International Application No. PCT/US2018/022258, filed Mar. 13, 2018, which claims priority under 35 U.S.C. 119(e) to U.S. Ser. No. 62/471,267, filed Mar. 14, 2017, and U.S. Ser. No. 62/614,875, filed Jan. 8, 2018, the entirety of each of which are incorporated by reference herein.

INCORPORATION BY REFERENCE OF SEQUENCE LISTING

Accompanying this filing is a Sequence Listing entitled, "Sequence-Listing_ST25.txt, created on Mar. 23, 2020 and having 1,406,286 bytes of data, machine formatted on IBM-PC, MS-Windows operating system. The sequence listing is hereby incorporated herein by reference in its entirety for all purposes.

BACKGROUND

Immune responses against in vivo CRISPR/Cas9 for genome engineering purposes remain poorly characterized. Cas9 is a foreign protein, with prokaryotic origins, and could potentially elicit a strong immune response, which could ultimately result in the elimination of gene-edited cells or of the Cas9 protein by cytotoxic T cell mediated immune responses.

Cas9 specific cytotoxic cellular responses may be elicited due to the need of recurrent treatments for two reasons: 1) the current overall efficacy of in vivo CRISPRCas9 mediated genome editing is low which can require repetitive treatments, and 2) if genome regulation by dCas9 is a referred gene therapy method, repeat treatments will be necessary for continued repression/activation. Additionally, under certain delivery systems, such as AAV mediated delivery, Cas9 may have long term expression, further increasing the potential of Cas9 specific cytotoxic cellular responses, hampering long-term therapeutic efficacy. New methods of administering Cas9 that reduce immunogenicity to evade immune detection are needed. This disclosure addresses this need and provides related advantages as well.

SUMMARY

Novel methods to circumvent the problem of immune response to Cas9 include utilizing orthologous Cas9 proteins for each treatment and/or engineering a Cas9 that does not elicit an immune response. Thus, provided herein are methods of avoiding an immune response in a subject being administered a regimen requiring Cas9 in order to optimize and broaden the application of CRIPSR based therapeutics comprising administering immune orthogonal Cas9. Also provided herein are methods to modify a Cas9 protein by swapping highly immunogenic peptides or amino acids with less immunogenic counterparts. These methods are particularly useful to enable the application of Cas9 arsenal for repeat treatments. Further provided are Cas9 proteins modified to reduce immunogenicity.

Aspects of the disclosure relate to a method of generating a protein comprising: identifying one or more regions of a protein with affinity for a major histocompatibility complex (MHC), and modifying the one or more regions of the protein with affinity for the MHC through one or more amino acid substitutions, such that the modified region has no affinity for the MHC, wherein the resulting modified protein is immunosilent upon administration of the modified protein or a polynucleotide encoding the modified protein to a subject. In some embodiments, the affinity for the MHC is high affinity. In some embodiments, at least one substituted amino acid is an amino acid which does not serve as an MHC protein core residue. In some embodiments, the protein is selected from the group of a cytidine deaminase, an adenosine deaminase, a zinc finger nuclease, a transcriptional activator-like effector nuclease, a Cas9, or an AAV capsid protein. In some embodiments, the protein is Cas9, optionally SpCas9.

Further aspects relate to a modified Cas9 protein produced according to the method disclosed above. Still further aspects relate to a modified Cas9 protein comprising one or more, two or more, three or more, four or more, five or more, six or more, seven or more, eight or more, nine or more, ten or more, fifteen or more, or twenty or more of the amino acid modifications provided in Table 1. Some embodiments relate to an isolated polynucleotide encoding the modified Cas9. Further embodiments, relate to a vector comprising the isolated polynucleotide, optionally an AAV vector, and still further optionally an AAV5 vector. Additional embodiments relate to an AAV capsid comprising the vector. In some embodiments, one or more of the AAV capsid proteins has been modified to be immunosilent.

Aspects of the disclosure relate to a method of identifying immune orthogonal orthologs comprising: determining a set of affinities of a protein or regions thereof to a plurality of major histocompatibility complexes (MHCs), comparing the set of affinities of the protein or regions thereof to sets of affinities of orthologs of the protein to the plurality of MHCs, and determining a set of immune orthogonal orthologs based on non-overlapping sets of affinites. In some embodiments, the affinity for the MHC is high affinity. In some embodiments, the protein is selected from the group of a cytidine deaminase, an adenosine deaminase, a zinc finger nuclease, a transcriptional activator-like effector nuclease, a Cas9, or an AAV capsid protein. In some embodiments, the protein is Cas9, optionally SpCas9 or SaCas9. In some embodiments, the Cas9 proteins the orthologs are selected from *S. pyogenes* Cas9 (spCas9), *S. aureus* Cas9 (saCas9), *B. longum* Cas9, *A. muiciniphilia* Cas9, or *O. laneus* Cas9.

Some aspects relate to a method of avoiding immune response in a subject being administered a regimen requiring a protein, the method comprising: administering to the subject, in sequence, two or more proteins that are immune orthogonal. In some embodiments, the proteins that are immune orthogonal do not share an amino acid sequence of greater than 5 consecutive amino acids. In some embodiments, the proteins that are immune orthogonal do not share affinity for a major histocompatibility complex (MHC). In some embodiments, three or more, four or more, five or more, six or more, seven or more, eight or more, nine or more, or ten or more proteins that are immune orthogonal are administered in sequence.

Non-limiting exemplary aspects relate to a method of avoiding immune response in a subject being administered a regimen requiring Cas9 and/or gene editing or gene regulation in a subject and/or treating a subject in need of gene editing or gene regulation, the method comprising:

administering to the subject, in sequence, two or more Cas9 proteins that are immune orthogonal. In some embodiments, the Cas9 proteins that are immune orthogonal do not share an amino acid sequence of greater than 5 consecutive amino acids. In some embodiments, the Cas9 proteins that are immune orthogonal do not share affinity for a major histocompatibility complex (MHC). In some embodiments, three or more, four or more, five or more, six or more, seven or more, eight or more, nine or more, or ten or more Cas9 proteins that are immune orthogonal are administered in sequence. In some embodiments, each Cas9 protein that is immune orthogonal is a Cas9 derived from a distinct species of bacteria. In some embodiments, the Cas9 proteins that are immune orthogonal are selected from *S. pyogenes* Cas9 (spCas9), *S. aureus* Cas9 (saCas9), *B. longum* Cas9, *A. muiciniphilia* Cas9, or *O. laneus* Cas9. In some embodiments, the Cas9 proteins that are immune orthogonal comprise spCas9 and saCas9. In some embodiments, at least one of the two or more Cas9 proteins is modified to reduce immunogenicity upon administration to the subject. In some embodiments, at least one of the two or more Cas9 proteins is modified according the method disclosed above. In some embodiments, at least one of the two or more Cas9 proteins or polynucleotides encoding said Cas9 proteins is comprised in an AAV vector. In some embodiments, the AAV vector is an AAV5 vector. In some embodiments, the AAV vector is comprised in an AAV capsid. In some embodiments, two or more Cas9 proteins or polynucleotides encoding said Cas9 proteins are comprised in AAV vectors. In some embodiments, each AAV vector is comprised in an AAV capsid, optionally wherein the AAV capsids are immune orthogonal to one another. In some embodiments, the method further comprises administering one or more guide RNAs to the subject. In some embodiments, the guide RNA is selected to treat a disease, disorder, or condition selected from the group of achromatopsia, adenosine deaminase (ADA) deficiency, alpha-1-antitrypsin deficiency, Alzheimer's disease, amyotrophic lateral sclerosis, aromatic amino acid decarboxylase deficiency, Batten disease, choroideremia, Crigler Najjar syndrome, cystic fibrosis, fragile X syndrome, hemophilia, hepatitis B, hepatitis C, homozygous familial hypercholesteremia, Huntington's Disease, Leber congenital amaurosis, macular degeneration, maple syrup urine disease (MSUD), mucopolysarccharidosis (I-IX), multiple sclerosis, muscular dystrophy, myotonic dystrophy, neurofibramotosis type 1, ornithine transcarbamylase deficiency, pachyonychia congenita, Parkinson's disease, phenylketonuria, polycystic kidney disease, Pompe disease, retinal degeneration, Rett's syndrome, rickets, spinal muscular atrophy, severe combined immunodeficiency, sickle cell disease, Smith-Lemli-Opitz syndrome, Y-linked nonobstructive spermatogenic failure, thalassemia, Tay-Sachs disease, Wilson's disease, cardiovascular disease, metabolic syndrome, pain management, and X-linked retinoschisis.

BRIEF DESCRIPTION OF DRAWINGS

(FIG. 5A) Proteins have substantial therapeutic potential, but a major drawback is the immune response to both the therapeutic protein and its delivery vehicle. (FIG. 5B) As a case study, we explored the CRISPR-Cas9 systems and corresponding delivery vehicles based on AAVs. (FIG. 5C) Mice were injected retro-orbitally with $10^{12}$ vg/mouse of AAV8-SaCas9 targeting the PCSK9 gene or a non-targeting control (empty vector). A decrease in PCSK9 serum levels, due to successful gene targeting, can be seen in mice receiving AAV-SaCas9-PCSK9 virus (n=6 mice for each group). (FIG. 5D) Immune response to the payload was detected in ELISAs for the SaCas9 protein. (n=12) (FIG. 5E) Immune response to the delivery vehicle was detected in ELISAs for the AAV8 virus capsid (n=12 mice). (FIG. 5F) In silico workflow used to find immune orthogonal protein homolog cliques. (FIG. 5G) Immunologically uninformed sequence comparison was carried out by checking all k-mers in a protein for their presence in another protein sequence with either zero or one mismatch. The x-axis corresponds to k, while MHC I and MHC II show overlap only of peptides predicted to bind to MHC class I and class II molecules. 48% of Cas9 pairs show no 6-mer overlap, and 83% of pairs show no overlapping MHC-binding peptides. (FIG. 5H) Same as (g) but for AAV VP1 capsid proteins. All AAV pairs contain overlapping MHC-binding peptides.

(FIG. 6A) Mice were exposed to antigens via retro-orbital injections at $10^{12}$ vg/mouse. Serum was harvested prior to injection on day 0, and at multiple points over the course of 4-6 weeks. (FIG. 6B) anti-SpCas9 antibodies generated in mice injected with SpCas9 (n=6) and SaCas9 (n=12), and anti-SaCas9 antibodies generated in mice injected with SpCas9 (n=6) and SaCas9 (n=12). (FIG. 6C) anti-SpCas9 and anti-SaCas9 antibodies generated by mice injected with AAV8 SpCas9 (n=12; left panel), or AAVDJ SpCas9 (n=12; right panel). (FIG. 6D) anti-AAV8/DJ/2/5 antibodies generated against mice injected with AAV8 or AAVDJ (n=4 for all panels). (FIG. 6E) anti-AAV8/DJ/2/5 antibodies generated against mice injected with AAV2 or AAV5 (n=5 for all panels).

(FIG. 8A) Cas9 MHC class I peptide overlap vs. phylogenetic distance. (FIG. 8B) AAV MHC class I peptide overlap vs. phylogenetic distance. (FIG. 8C) Cas9 MHC class II peptide overlap vs. phylogenetic distance. (FIG. 8D) AAV MHC class II peptide overlap vs. phylogenetic distance.

(FIG. 9A) AAV immune orthogonal cliques over 81 HLA alleles. AAV5 is the most immune-divergent in comparison to the other serotypes. No orthogonal cliques exist. (FIG. 9B) AAV phylogeny showing major serotype groupings as well as the position of the reconstructed sequence Anc80L65.

DETAILED DESCRIPTION

Figure 1:
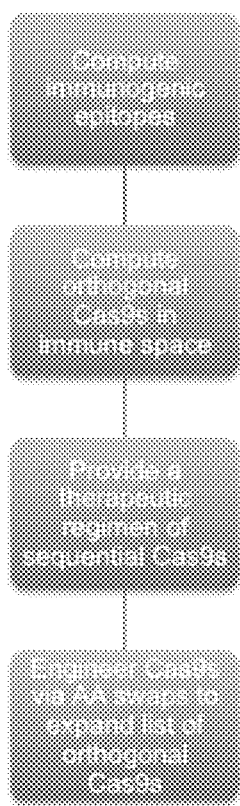
FIG. 1: is a flow diagram depicting the process described in Example 1.
Figure 2:
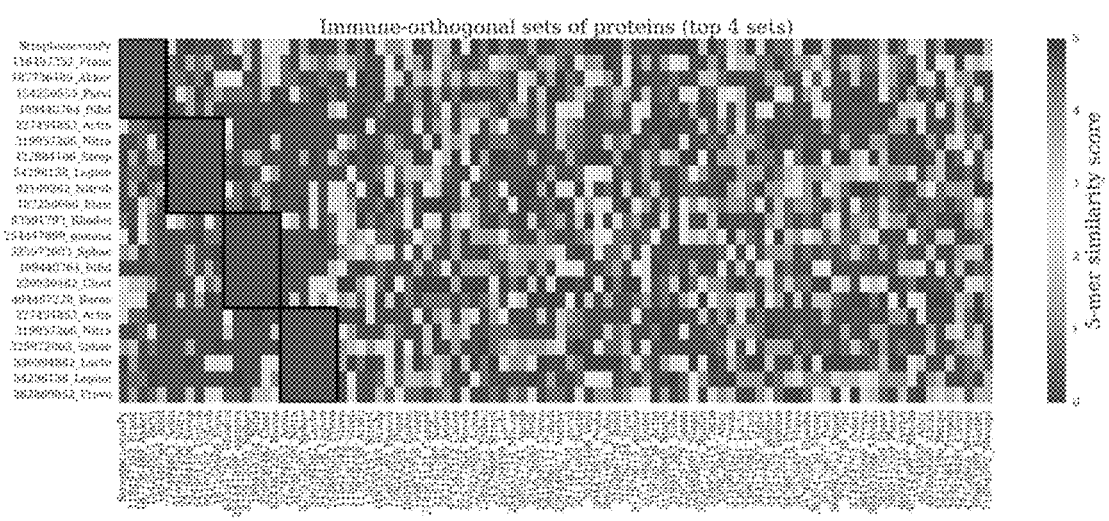
FIG. 2: shows (A) sets of immune-orthogonal proteins, located with a recursive clique-finding algorithm (Bold outlines indicate top 4 sets of orthogonal proteins. Color indicates number of 5-mer overlaps between protein pairs. This method is guaranteed to find all maximal sets of orthogonal proteins. *Streptococcus pyogenes* belongs to a set of 5 mutually orthogonal proteins.) (B) the number of maximal cliques containing each protein, broken down by size (Cliques of size 4 are the most frequent).
Figure 2:
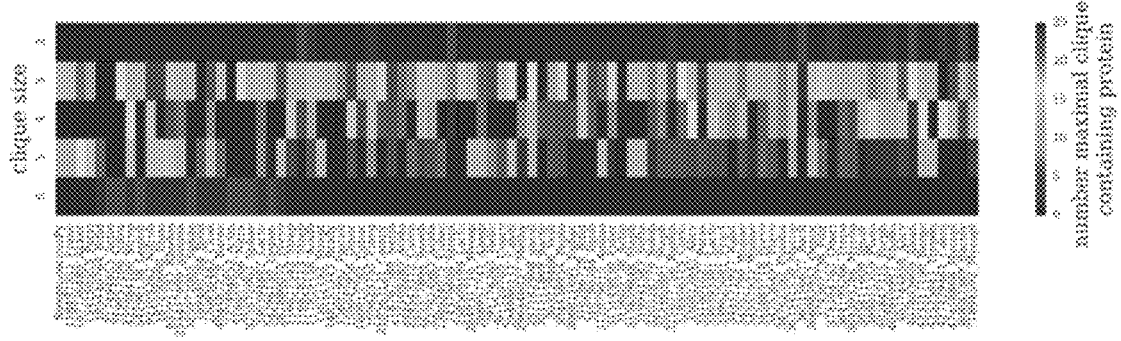
Figure 3:
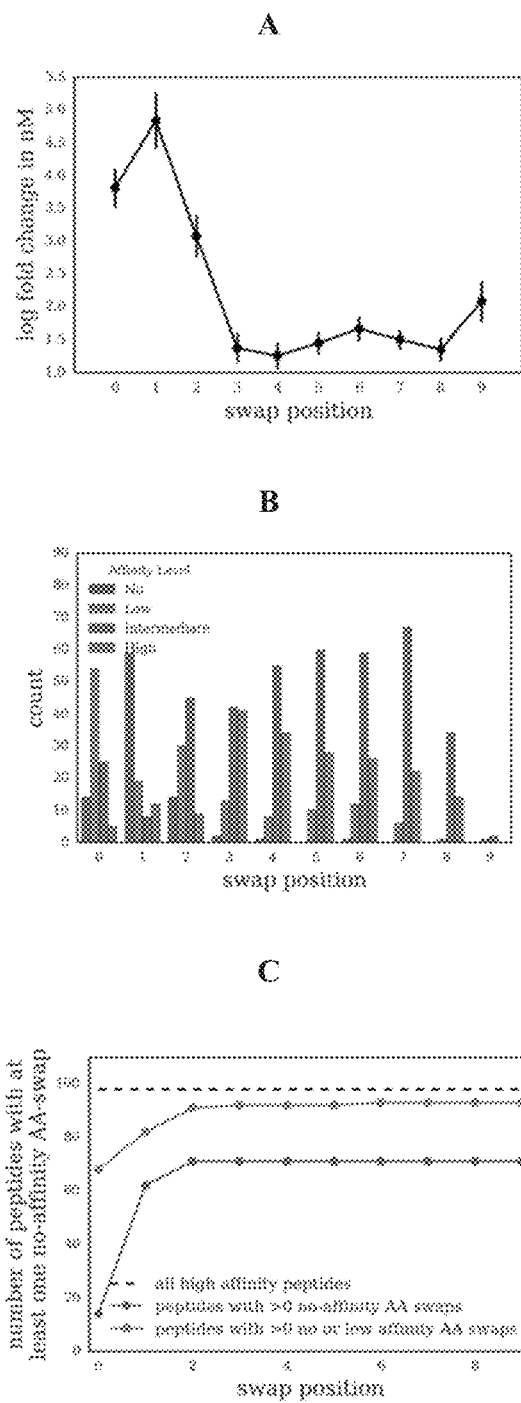
FIG. 3: shows (A) change in affinity resulting from swaps in each peptide position (Data are shown averaged over 98 high-affinity peptides found in *Streptococcus pyogenes*) (B) after swapping, distribution of peptides in each affinity category, by swap position (Swapping out amino acids at the beginning of the high affinity peptide have the biggest effect) (C) cumulative sum showing number of peptides with at least one no-affinity swap option (blue), or at least one no-affinity or low-affinity swap option (green) (There are 98 high affinity peptides in this protein (black dotted line)).

Embodiments according to the present disclosure will be described more fully hereinafter. Aspects of the disclosure may, however, be embodied in different forms and should not be construed as limited to the embodiments set forth herein. Rather, these embodiments are provided so that this disclosure will be thorough and complete, and will fully convey the scope of the invention to those skilled in the art. The terminology used in the description herein is for the purpose of describing particular embodiments only and is not intended to be limiting.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. While not explicitly defined below, such terms should be interpreted according to their common meaning.

The terminology used in the description herein is for the purpose of describing particular embodiments only and is not intended to be limiting of the invention. All publications, patent applications, patents and other references mentioned herein are incorporated by reference in their entirety.

The practice of the present technology will employ, unless otherwise indicated, conventional techniques of tissue culture, immunology, molecular biology, microbiology, cell biology, and recombinant DNA, which are within the skill of the art.

Unless the context indicates otherwise, it is specifically intended that the various features of the invention described herein can be used in any combination. Moreover, the disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless explicitly indicated otherwise, all specified embodiments, features, and terms intend to include both the recited embodiment, feature, or term and biological equivalents thereof.

All numerical designations, e.g., pH, temperature, time, concentration, and molecular weight, including ranges, are approximations which are varied (+) or (−) by increments of 1.0 or 0.1, as appropriate, or alternatively by a variation of +/−15%, or alternatively 10%, or alternatively 5%, or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

Definitions

As used in the description of the invention and the appended claims, the singular forms "a," "an" and "the" are intended to include the plural forms as well, unless the context clearly indicates otherwise.

The term "about," as used herein when referring to a measurable value such as an amount or concentration and the like, is meant to encompass variations of 20%, 10%, 5%, 1%, 0.5%, or even 0.1% of the specified amount.

The terms or "acceptable," "effective," or "sufficient" when used to describe the selection of any components, ranges, dose forms, etc. disclosed herein intend that said component, range, dose form, etc. is suitable for the disclosed purpose.

The term "adeno-associated virus" or "AAV" as used herein refers to a member of the class of viruses associated with this name and belonging to the genus dependoparvovirus, family Parvoviridae. Multiple serotypes of this virus are known to be suitable for gene delivery; all known serotypes can infect cells from various tissue types. At least 11 or 12, sequentially numbered, are disclosed in the prior art. Non-limiting exemplary serotypes useful in the methods disclosed herein include any of the 11 or 12 serotypes, e.g., AAV2, AAV5, and AAV8, or variant serotypes, e.g. AAV-DJ. The AAV structural particle is composed of 60 protein molecules made up of VP1, VP2 and VP3. Each particle contains approximately 5 VP1 proteins, 5 VP2 proteins and 50 VP3 proteins ordered into an icosahedral structure. Non-limiting exemplary VP1 sequences useful in the methods disclosed herein are provided below.

AAT46339.1 AAV-11

(SEQ ID NO: 1)

MAADGYLPDWLEDNLSEGIREWWDLKPGAPKPKANQQKQDDGRGLVLPGYKYLG

PFNGLDKGEPVNAADAAALEHDKAYDQQLKAGDNPYLRYNHADAEFQERLQEDTS

FGGNLGRAVFQAKKRVLEPLGLVEEGAKTAPGKKRPLESPQEPDSSSGIGKKGKQPA

RKRLNFEEDTGAGDGPPEGSDTSAMSSDIEMRAAPGGNAVDAGQGSDGVGNASGD

-continued

WHCDSTWSEGKVTTTSTRTWVLPTYNNHLYLRLGTTSSSNTYNGFSTPWGYFDFNR

FHCHFSPRDWQRLINNNWGLRPKAMRVKIFNIQVKEVTTSNGETTVANNLTSTVQIF

ADSSYELPYVMDAGQEGSLPPFPNDVFMVPQYGYCGIVTGENQNQTDRNAFYCLEY

FPSQMLRTGNNFEMAYNFEKVPFHSMYAHSQSLDRLMNPLLDQYLWHLQSTTSGET

LNQGNAATTFGKIRSGDFAFYRKNWLPGPCVKQQRFSKTASQNYKIPASGGNALLK

YDTHYTLNNRWSNIAPGPPMATAGPSDGDFSNAQLIFPGPSVTGNTTTSANNLLFTSE

EEIAATNPRDTDMFGQIADNNQNATTAPITGNVTAMGVLPGMVWQNRDIYYQGPIW

AKIPHADGHFHPSPLIGGFGLKHPPPQIFIKNTPVPANPATTFTAARVDSFITQYSTGQ

VAVQIEWEIEKERSKRWNPEVQFTSNYGNQSSMLWAPDTTGKYTEPRVIGSRYLTN

HL pdb|4IOV|AAAV-rh32
(SEQ ID NO: 2)
MAADGYLPDWLEDNLSEGIREWWDLKPGAPKPKANQQKQDDGRGLVLPGYKYLG

PFNGLDKGEPVNAADAAALEHDKAYDQQLKAGDNPYLRYNHADAEFQERLQEDTS

FGGNLGRAVFQAKKRVLEPLGLVEEGAKTAPGKKRPLESPQEPDSSSGIGKKGKQPA

KKRLNFEEDTGAGDGPPEGSDTSAMSSDIEMRAAPGGNAVDAGQGSDGVGNASGD

WHCDSTWSEGKVTTTSTRTWVLPTYNNHLYLRLGTTSNSNTYNGFSTPWGYFDFNR

FHCHFSPRDWQRLINNNWGLRPKAMRVKIFNIQVKEVTTSNGETTVANNLTSTVQIF

ADSSYELPYVMDAGQEGSLPPFPNDVFMVPQYGYCGIVTGENQNQTDRNAFYCLEY

FPSQMLRTGNNFEMAYNFEKVPFHSMYAHSQSLDRLMNPLLDQYLWHLQSTTSGET

LNQGNAATTFGKIRSGDFAFYRKNWLPGPCVKQQRFSKTASQNYKIPASGGNALLK

YDTHYTLNNRWSNIAPGPPMATAGPSDGDFSNAQLIFPGPSVTGNTTTSANNLLFTSE

EEIAATNPRDTDMFGQIADNNQNATTAPITGNVTAMGVLPGMVWQNRDIYYQGPIW

AKIPHADGHFHPSPLIGGFGLKHPPPQIFIKNTPVPANPATTFTAARVDSFITQYSTGQ

VAVQIEWEIEKERSKRWNPEVQFTSNYGNQSSMLWAPDTTGKYTEPRVIGSRYLTN

HL

ABI16639.1 AAV-12
(SEQ ID NO: 3)
MAADGYLPDWLEDNLSEGIREWWALKPGAPQPKANQQHQDNGRGLVLPGYKYLG

PFNGLDKGEPVNEADAAALEHDKAYDKQLEQGDNPYLKYNHADAEFQQRLATDTS

FGGNLGRAVFQAKKRILEPLGLVEEGVKTAPGKKRPLEKTPNRPTNPDSGKAPAKKK

QKDGEPADSARRTLDFEDSGAGDGPPEGSSSGEMSHDAEMRAAPGGNAVEAGQGA

DGVGNASGDWHCDSTWSEGRVTTTSTRTWVLPTYNNHLYLRIGTTANSNTYNGFST

PWGYFDFNRFHCHFSPRDWQRLINNNWGLRPKSMRVKIFNIQVKEVTTSNGETTVA

NNLTSTVQIFADSTYELPYVMDAGQEGSFPPFPNDVFMVPQYGYCGVVTGKNQNQT

DRNAFYCLEYFPSQMLRTGNNFEVSYQFEKVPFHSMYAHSQSLDRMMNPLLDQYL

WHLQSTTTGNSLNQGTATTTYGKITTGDFAYYRKNWLPGACIKQQKFSKNANQNY

KIPASGGDALLKYDTHTTLNGRWSNMAPGPPMATAGAGDSDFSNSQLIFAGPNPSG

NTTTSSNNLLFTSEEEIATTNPRDTDMFGQIADNNQNATTAPHIANLDAMGIVPGMV

WQNRDIYYQGPIWAKVPHTDGHFHPSPLMGGFGLKHPPPQIFIKNTPVPANPNTTFSA

ARINSFLTQYSTGQVAVQIDWEIQKEHSKRWNPEVQFTSNYGTQNSMLWAPDNAGN

YHELRAIGSRFLTHHL

-continued

NP_044927.1 AAV-4
(SEQ ID NO: 4)
MTDGYLPDWLEDNLSEGVREWWALQPGAPKPKANQQHQDNARGLVLPGYKYLGP

GNGLDKGEPVNAADAAALEHDKAYDQQLKAGDNPYLKYNHADAEFQQRLQGDTS

FGGNLGRAVFQAKKRVLEPLGLVEQAGETAPGKKRPLIESPQQPDSSTGIGKKGKQP

AKKKLVFEDETGAGDGPPEGSTSGAMSDDSEMRAAAGGAAVEGGQGADGVGNAS

GDWHCDSTWSEGHVTTTSTRTWVLPTYNNHLYKRLGESLQSNTYNGFSTPWGYFD

FNRFHCHFSPRDWQRLINNNWGMRPKAMRVKIFNIQVKEVTTSNGETTVANNLTST

VQIFADSSYELPYVMDAGQEGSLPPFPNDVFMVPQYGYCGLVTGNTSQQQTDRNAF

YCLEYFPSQMLRTGNNFEITYSFEKVPFHSMYAHSQSLDRLMNPLIDQYLWGLQSTT

TGTTLNAGTATTNFTKLRPTNFSNFKKNWLPGPSIKQQGFSKTANQNYKIPATGSDSL

IKYETHSTLDGRWSALTPGPPMATAGPADSKFSNSQLIFAGPKQNGNTATVPGTLIFT

SEEELAATNATDTDMWGNLPGGDQSNSNLPTVDRLTALGAVPGMVWQNRDIYYQG

PIWAKIPHTDGHFHPSPLIGGFGLKHPPPQIFIKNTPVPANPATTFSSTPVNSFITQYSTG

QVSVQIDWEIQKERSKRWNPEVQFTSNYGQQNSLLWAPDAAGKYTEPRAIGTRYLT

HHL

YP_077178.1 AAV-7
(SEQ ID NO: 5)
MAADGYLPDWLEDNLSEGIREWWDLKPGAPKPKANQQKQDNGRGLVLPGYKYLG

PFNGLDKGEPVNAADAAALEHDKAYDQQLKAGDNPYLRYNHADAEFQERLQEDTS

FGGNLGRAVFQAKKRVLEPLGLVEEGAKTAPAKKRPVEPSPQRSPDSSTGIGKKGQQ

PARKRLNFGQTGDSESVPDPQPLGEPPAAPSSVGSGTVAAGGGAPMADNNEGADGV

GNASGNWHCDSTWLGDRVITTSTRTWALPTYNNHLYKQISSETAGSTNDNTYFGYS

TPWGYFDFNRFHCHFSPRDWQRLINNNWGFRPKKLRFKLFNIQVKEVTTNDGVTTIA

NNLTSTIQVFSDSEYQLPYVLGSAHQGCLPPFPADVFMIPQYGYLTLNNGSQSVGRSS

FYCLEYFPSQMLRTGNNFEFSYSFEDVPFHSSYAHSQSLDRLMNPLIDQYLYYLART

QSNPGGTAGNRELQFYQGGPSTMAEQAKNWLPGPCFRQQRVSKTLDQNNNSNFAW

TGATKYHLNGRNSLVNPGVAMATHKDDEDRFFPSSGVLIFGKTGATNKTTLENVLM

TNEEEIRPTNPVATEEYGIVSSNLQAANTAAQTQVVNNQGALPGMVWQNRDVYLQ

GPIWAKIPHTDGNFHPSPLMGGFGLKHPPPQILIKNTPVPANPPEVFTPAKFASFITQYS

TGQVSVEIEWELQKENSKRWNPEIQYTSNFEKQTGVDFAVDSQGVYSEPRPIGTRYL

TRNL

YP_077180.1 AAV-8
(SEQ ID NO: 6)
MAADGYLPDWLEDNLSEGIREWWALKPGAPKPKANQQKQDDGRGLVLPGYKYLG

PFNGLDKGEPVNAADAAALEHDKAYDQQLQAGDNPYLRYNHADAEFQERLQEDTS

FGGNLGRAVFQAKKRVLEPLGLVEEGAKTAPGKKRPVEPSPQRSPDSSTGIGKKGQQ

PARKRLNFGQTGDSESVPDPQPLGEPPAAPSGVGPNTMAAGGGAPMADNNEGADG

VGSSSGNWHCDSTWLGDRVITTSTRTWALPTYNNHLYKQISNGTSGGATNDNTYFG

YSTPWGYFDFNRFHCHFSPRDWQRLINNNWGFRPKRLSFKLFNIQVKEVTQNEGTKT

IANNLTSTIQVFTDSEYQLPYVLGSAHQGCLPPFPADVFMIPQYGYLTLNNGSQAVGR

SSFYCLEYFPSQMLRTGNNFQFTYTFEDVPFHSSYAHSQSLDRLMNPLIDQYLYYLSR

TQTTGGTANTQTLGFSQGGPNTMANQAKNWLPGPCYRQQRVSTTTGQNNNSNFAW

-continued

TAGTKYHLNGRNSLANPGIAMATHKDDEERFFPSNGILIFGKQNAARDNADYSDVM

LTSEEEIKTTNPVATEEYGIVADNLQQQNTAPQIGTVNSQGALPGMVWQNRDVYLQ

GPIWAKIPHTDGNFHPSPLMGGFGLKHPPPQILIKNTPVPADPPTTFNQSKLNSFITQY

STGQVSVEIEWELQKENSKRWNPEIQYTSNYYKSTSVDFAVNTEGVYSEPRPIGTRYL

TRNL

AAT46337.1 AAV-10
(SEQ ID NO: 7)
MAADGYLPDWLEDNLSEGIREWWDLKPGAPKPKANQQKQDDGRGLVLPGYKYLG

PFNGLDKGEPVNAADAAALEHDKAYDQQLKAGDNPYLRYNHADAEFQERLQEDTS

FGGNLGRAVFQAKKRVLEPLGLVEEAAKTAPGKKRPVEPSPQRSPDSSTGIGKKGQQ

PAKKRLNFGQTGESESVPDPQPIGEPPAGPSGLGSGTMAAGGGAPMADNNEGADGV

GSSSGNWHCDSTWLGDRVITTSTRTWALPTYNNHLYKQISNGTSGGSTNDNTYFGY

STPWGYFDFNRFHCHFSPRDWQRLINNNWGFRPKRLSFKLFNIQVKEVTQNEGTKTI

ANNLTSTIQVFTDSEYQLPYVLGSAHQGCLPPFPADVFMIPQYGYLTLNNGSQAVGR

SSFYCLEYFPSQMLRTGNNFEFSYTFEDVPFHSSYAHSQSLDRLMNPLIDQYLYYLSR

TQSTGGTQGTQQLLFSQAGPANMSAQAKNWLPGPCYRQQRVSTTLSQNNNSNFAW

TGATKYHLNGRDSLVNPGVAMATHKDDEERFFPSSGVLMFGKQGAGRDNVDYSSV

MLTSEEEIKTTNPVATEQYGVVADNLQQANTGPIVGNVNSQGALPGMVWQNRDVY

LQGPIWAKIPHTDGNFHPSPLMGGFGLKHPPPQILIKNTPVPADPPTTFSQAKLASFIT

QYSTGQVSVEIEWELQKENSKRWNPEIQYTSNYYKSTNVDFAVNTEGTYSEPRPIGT

RYLTRNL

AAS99264.1 AAV-9
(SEQ ID NO: 8)
MAADGYLPDWLEDNLSEGIREWWALKPGAPQPKANQQHQDNARGLVLPGYKYLG

PGNGLDKGEPVNAADAAALEHDKAYDQQLKAGDNPYLKYNHADAEFQERLKEDTS

FGGNLGRAVFQAKKRLLEPLGLVEEAAKTAPGKKRPVEQSPQEPDSSAGIGKSGAQP

AKKRLNFGQTGDTESVPDPQPIGEPPAAPSGVGSLTMASGGGAPVADNNEGADGVG

SSSGNWHCDSQWLGDRVITTSTRTWALPTYNNHLYKQISNSTSGGSSNDNAYFGYS

TPWGYFDFNRFHCHFSPRDWQRLINNNWGFRPKRLNFKLFNIQVKEVTDNNGVKTI

ANNLTSTVQVFTDSDYQLPYVLGSAHEGCLPPFPADVFMIPQYGYLTLNDGSQAVG

RSSFYCLEYFPSQMLRTGNNFQFSYEFENVPFHSSYAHSQSLDRLMNPLIDQYLYYLS

KTINGSGQNQQTLKFSVAGPSNMAVQGRNYIPGPSYRQQRVSTTVTQNNNSEFAWP

GASSWALNGRNSLMNPGPAMASHKEGEDRFFPLSGSLIFGKQGTGRDNVDADKVMI

TNEEEIKTTNPVATESYGQVATNHQSAQAQAQTGWVQNQGILPGMVWQDRDVYLQ

GPIWAKIPHTDGNFHPSPLMGGFGMKHPPPQILIKNTPVPADPPTAFNKDKLNSFITQ

YSTGQVSVEIEWELQKENSKRWNPEIQYTSNYYKSNNVEFAVNTEGVYSEPRPIGTR

YLTRNL

NP_049542.1 AAV-1
(SEQ ID NO: 9)
MAADGYLPDWLEDNLSEGIREWWDLKPGAPKPKANQQKQDDGRGLVLPGYKYLG

PFNGLDKGEPVNAADAAALEHDKAYDQQLKAGDNPYLRYNHADAEFQERLQEDTS

FGGNLGRAVFQAKKRVLEPLGLVEEGAKTAPGKKRPVEQSPQEPDSSSGIGKTGQQP

AKKRLNFGQTGDSESVPDPQPLGEPPATPAAVGPTTMASGGGAPMADNNEGADGV

GNASGNWHCDSTWLGDRVITTSTRTWALPTYNNHLYKQISSASTGASNDNHYFGYS

-continued

TPWGYFDFNRFHCHFSPRDWQRLINNNWGFRPKRLNFKLFNIQVKEVTTNDGVTTIA

NNLTSTVQVFSDSEYQLPYVLGSAHQGCLPPFPADVFMIPQYGYLTLNNGSQAVGRS

SFYCLEYFPSQMLRTGNNFTFSYTFEEVPFHSSYAHSQSLDRLMNPLIDQYLYYLNRT

QNQSGSAQNKDLLFSRGSPAGMSVQPKNWLPGPCYRQQRVSKTKTDNNNSNFTWT

GASKYNLNGRESIINPGTAMASHKDDEDKFFPMSGVMIFGKESAGASNTALDNVMIT

DEEEIKATNPVATERFGTVAVNFQSSSTDPATGDVHAMGALPGMVWQDRDVYLQG

PIWAKIPHTDGHFHPSPLMGGFGLKNPPPQILIKNTPVPANPPAEFSATKFASFITQYST

GQVSVEIEWELQKENSKRWNPEVQYTSNYAKSANVDFTVDNNGLYTEPRPIGTRYL

TRPL

AAB95450.1 AAV-6
(SEQ ID NO: 10)
MAADGYLPDWLEDNLSEGIREWWDLKPGAPKPKANQQKQDDGRGLVLPGYKYLG

PFNGLDKGEPVNAADAAALEHDKAYDQQLKAGDNPYLRYNHADAEFQERLQEDTS

FGGNLGRAVFQAKKRVLEPFGLVEEGAKTAPGKKRPVEQSPQEPDSSSGIGKTGQQP

AKKRLNFGQTGDSESVPDPQPLGEPPATPAAVGPTTMASGGGAPMADNNEGADGV

GNASGNWHCDSTWLGDRVITTSTRTWALPTYNNHLYKQISSASTGASNDNHYFGYS

TPWGYFDFNRFHCHFSPRDWQRLINNNWGFRPKRLNFKLFNIQVKEVTTNDGVTTIA

NNLTSTVQVFSDSEYQLPYVLGSAHQGCLPPFPADVFMIPQYGYLTLNNGSQAVGRS

SFYCLEYFPSQMLRTGNNFTFSYTFEDVPFHSSYAHSQSLDRLMNPLIDQYLYYLNRT

QNQSGSAQNKDLLFSRGSPAGMSVQPKNWLPGPCYRQQRVSKTKTDNNNSNFTWT

GASKYNLNGRESIINPGTAMASHKDDKDKFFPMSGVMIFGKESAGASNTALDNVMI

TDEEEIKATNPVATERFGTVAVNLQSSSTDPATGDVHVMGALPGMVWQDRDVYLQ

GPIWAKIPHTDGHFHPSPLMGGFGLKHPPPQILIKNTPVPANPPAEFSATKFASFITQYS

TGQVSVEIEWELQKENSKRWNPEVQYTSNYAKSANVDFTVDNNGLYTEPRPIGTRY

LTRPL

NP_043941.1 AAV-3
(SEQ ID NO: 11)
MAADGYLPDWLEDNLSEGIREWWALKPGVPQPKANQQHQDNRRGLVLPGYKYLG

PGNGLDKGEPVNEADAAALEHDKAYDQQLKAGDNPYLKYNHADAEFQERLQEDTS

FGGNLGRAVFQAKKRILEPLGLVEEAAKTAPGKKGAVDQSPQEPDSSSGVGKSGKQ

PARKRLNFGQTGDSESVPDPQPLGEPPAAPTSLGSNTMASGGGAPMADNNEGADGV

GNSSGNWHCDSQWLGDRVITTSTRTWALPTYNNHLYKQISSQSGASNDNHYFGYST

PWGYFDFNRFHCHFSPRDWQRLINNNWGFRPKKLSFKLFNIQVRGVTQNDGTTTIAN

NLTSTVQVFTDSEYQLPYVLGSAHQGCLPPFPADVFMVPQYGYLTLNNGSQAVGRS

SFYCLEYFPSQMLRTGNNFQFSYTFEDVPFHSSYAHSQSLDRLMNPLIDQYLYYLNR

TQGTTSGTTNQSRLLFSQAGPQSMSLQARNWLPGPCYRQQRLSKTANDNNNSNFPW

TAASKYHLNGRDSLVNPGPAMASHKDDEEKFFPMHGNLIFGKEGTTASNAELDNV

MITDEEEIRTTNPVATEQYGTVANNLQSSNTAPTTGTVNHQGALPGMVWQDRDVYL

QGPIWAKIPHTDGHFHPSPLMGGFGLKHPPPQIMIKNTPVPANPPTTFSPAKFASFITQ

YSTGQVSVEIEWELQKENSKRWNPEIQYTSNYNKSVNVDFTVDTNGVYSEPRPIGTR

YLTRNL

-continued

ABZ10812.1 AAV-13

(SEQ ID NO: 12)

MTDGYLPDWLEDNLSEGVREWWALQPGAPKPKANQQHQDNARGLVLPGYKYLGP

GNGLDKGEPVNAADAAALEHDKAYDQQLKAGDNPYLKYNHADAEFQERLQEDTSF

GGNLGRAVFQAKKRILEPLGLVEEAAKTAPGKKRPVEQSPAEPDSSSGIGKSGQQPA

RKRLNFGQTGDTESVPDPQPLGQPPAAPSGVGSTTMASGGGAPMADNNEGADGVG

NSSGNWHCDSQWLGDRVITTSTRTWALPTYNNHLYKQISSQSGATNDNHYFGYSTP

WGYFDFNRFHCHFSPRDWQRLINNNWGFRPKRLNFKLFNIQVKEVTQNDGTTTIAN

NLTSTVQVFTDSEYQLPYVLGSAHQGCLPPFPADVFMVPQYGYLTLNNGSQAVGRS

SFYCLEYFPSQMLRTGNNFQFSYTFEDVPFHSSYAHSQSLDRLMNPLIDQYLYYLNR

TQTASGTQQSRLLFSQAGPTSMSLQAKNWLPGPCYRQQRLSKQANDNNNSNFPWTG

ATKYHLNGRDSLVNPGPAMASHKDDKEKFFPMHGTLIFGKEGTNANNADLENVMIT

DEEEIRTTNPVATEQYGTVSNNLQNSNAGPTTGTVNHQGALPGMVWQDRDVYLQG

PIWAKIPHTDGHFHPSPLMGGFGLKHPPPQIMIKNTPVPANPPTNFSAAKFASFITQYS

TGQVSVEIEWELQKENSKRWNPEIQYTSNYNKSVNVDFTVDTNGVYSEPRPIGTRYL

TRNL

YP_680426.1 AAV-2

(SEQ ID NO: 13)

MAADGYLPDWLEDTLSEGIRQWWKLKPGPPPPKPAERHKDDSRGLVLPGYKYLGPF

NGLDKGEPVNEADAAALEHDKAYDRQLDSGDNPYLKYNHADAEFQERLKEDTSFG

GNLGRAVFQAKKRVLEPLGLVEEPVKTAPGKKRPVEHSPVEPDSSSGTGKAGQQPA

RKRLNFGQTGDADSVPDPQPLGQPPAAPSGLGTNTMATGSGAPMADNNEGADGVG

NSSGNWHCDSTWMGDRVITTSTRTWALPTYNNHLYKQISSQSGASNDNHYFGYSTP

WGYFDFNRFHCHFSPRDWQRLINNNWGFRPKRLNFKLFNIQVKEVTQNDGTTTIAN

NLTSTVQVFTDSEYQLPYVLGSAHQGCLPPFPADVFMVPQYGYLTLNNGSQAVGRS

SFYCLEYFPSQMLRTGNNFTFSYTFEDVPFHSSYAHSQSLDRLMNPLIDQYLYYLSRT

NTPSGTTTQSRLQFSQAGASDIRDQSRNWLPGPCYRQQRVSKTSADNNNSEYSWTG

ATKYHLNGRDSLVNPGPAMASHKDDEEKFFPQSGVLIFGKQGSEKTNVDIEKVMITD

EEEIRTTNPVATEQYGSVSTNLQRGNRQAATADVNTQGVLPGMVWQDRDVYLQGPI

WAKIPHTDGHFHPSPLMGGFGLKHPPPQILIKNTPVPANPSTTFSAAKFASFITQYSTG

QVSVEIEWELQKENSKRWNPEIQYTSNYNKSVNVDFTVDTNGVYSEPRPIGTRYLTR

NL

YP_068409.1 AAV-5

(SEQ ID NO: 14)

MSFVDHPPDWLEEVGEGLREFLGLEAGPPKPKPNQQHQDQARGLVLPGYNYLGPGN

GLDRGEPVNRADEVAREHDISYNEQLEAGDNPYLKYNHADAEFQEKLADDTSFGGN

LGKAVFQAKKRVLEPFGLVEEGAKTAPTGKRIDDHFPKRKKARTEEDSKPSTSSDAE

AGPSGSQQLQIPAQPASSLGADTMSAGGGGPLGDNNQGADGVGNASGDWHCDSTW

MGDRVVTKSTRTWVLPSYNNHQYREIKSGSVDGSNANAYFGYSTPWGYFDFNRFH

SHWSPRDWQRLINNYWGFRPRSLRVKIFNIQVKEVTQNDSTTTIANNLTSTVQVFTD

DDYQLPYVVGNGTEGCLPAFPPQVFTLPQYGYATLNRDNTENPTERSSFFCLEYFPS

KMLRTGNNFEFTYNFEEVPFHSSFAPSQNLFKLANPLVDQYLYRFVSTNNTGGVQFN

KNLAGRYANTYKNWFPGPMGRTQGWNLGSGVNRASVSAFATTNRMELEGASYQV

-continued

PPQPNGMTNNLQGSNTYALENTMIFNSQPANPGTTATYLEGNMLITSESETQPVNRV

AYNVGGQMATNNQSSTTAPATGTYNLQEIVPGSVWMERDVYLQGPIWAKIPETGAH

FHPSPAMGGFGLKHPPPMMLIKNTPVPGNITSFSDVPVSSFITQYSTGQVTVEMEWEL

KKENSKRWNPEIQYTNNYNDPQFVDFAPDSTGEYRTTRPIGTRYLTRPL

3J1Q_A AAV-DJ
(SEQ ID NO: 15)
MAADGYLPDWLEDTLSEGIRQWWKLKPGPPPPKPAERHKDDSRGLVLPGYKYLGPF

NGLDKGEPVNEADAAALEHDKAYDRQLDSGDNPYLKYNHADAEFQERLKEDTSFG

GNLGRAVFQAKKRLLEPLGLVEEAAKTAPGKKRPVEHSPVEPDSSSGTGKAGQQPA

RKRLNFGQTGDADSVPDPQPIGEPPAAPSGVGSLTMAAGGGAPMADNNEGADGVG

NSSGNWHCDSTWMGDRVITTSTRTWALPTYNNHLYKQISNSTSGGSSNDNAYFGYS

TPWGYFDFNRFHCHFSPRDWQRLINNNWGFRPKRLSFKLFNIQVKEVTQNEGTKTIA

NNLTSTIQVFTDSEYQLPYVLGSAHQGCLPPFPADVFMIPQYGYLTLNNGSQAVGRS

SFYCLEYFPSQMLRTGNNFQFTYTFEDVPFHSSYAHSQSLDRLMNPLIDQYLYYLSRT

QTTGGTTNTQTLGFSQGGPNTMANQAKNWLPGPCYRQQRVSKTSADNNNSEYSWT

GATKYHLNGRDSLVNPGPAMASHKDDEEKFFPQSGVLIFGKQGSEKTNVDIEKVMIT

DEEEIRTTNPVATEQYGSVSTNLQRGNRQAATADVNTQGVLPGMVWQDRDVYLQG

PIWAKIPHTDGHFHPSPLMGGFGLKHPPPQILIKNTPVPADPPTTFNQSKLNSFITQYST

GQVSVEIEWELQKENSKRWNPEIQYTSNYYKSTSVDFAVNTEGVYSEPRPIGTRYLT

RNL

AKU89595.1 Anc80
(SEQ ID NO: 16)
MAADGYLPDWLEDNLSEGIREWWDLKPGAPKPKANQQKQDDGRGLVLPGYKYLG

PFNGLDKGEPVNAADAAALEHDKAYDQQLKAGDNPYLRYNHADAEFQERLQEDTS

FGGNLGRAVFQAKKRVLEPLGLVEEGAKTAPGKKRPVEQSPQEPDSSSGIGKKGQQP

ARKRLNFGQTGDSESVPDPQPLGEPPAAPSGVGSNTMAAGGGAPMADNNEGADGV

GNASGNWHCDSTWLGDRVITTSTRTWALPTYNNHLYKQISSQSGGSTNDNTYFGYS

TPWGYFDFNRFHCHFSPRDWQRLINNNWGFRPKKLNFKLFNIQVKEVTTNDGTTTIA

NNLTSTVQVFTDSEYQLPYVLGSAHQGCLPPFPADVFMIPQYGYLTLNNGSQAVGRS

SFYCLEYFPSQMLRTGNNFQFSYTFEDVPFHSSYAHSQSLDRLMNPLIDQYLYYLSRT

QTTSGTAGNRTLQFSQAGPSSMANQAKNWLPGPCYRQQRVSKTTNQNNNSNFAWT

GATKYHLNGRDSLVNPGPAMATHKDDEDKFFPMSGVLIFGKQGAGNSNVDLDNVM

ITNEEEIKTTNPVATEEYGTVATNLQSANTAPATGTVNSQGALPGMVWQDRDVYLQ

GPIWAKIPHTDGHFHPSPLMGGFGLKHPPPQILIKNTPVPANPPTTFSPAKFASFITQYS

TGQVSVEIEWELQKENSKRWNPEIQYTSNYNKSTNVDFAVDTNGVYSEPRPIGTRYL

TRNL

Also as used herein, "and/or" refers to and encompasses any and all possible combinations of one or more of the associated listed items, as well as the lack of combinations when interpreted in the alternative ("or").

The term "aptamer" as used herein refers to single stranded DNA or RNA molecules that can bind to one or more selected targets with high affinity and specificity. Non-limiting exemplary targets include by are not limited to proteins or peptides.

The term "Cas9" refers to a CRISPR-associated, RNA-guided endonuclease such as *Streptococcus pyogenes* Cas9 (spCas9) and orthologs and biological equivalents thereof. Biological equivalents of Cas9 include but are not limited to C2c1 from *Alicyclobacillus acideterrestris* and Cpf1 (which performs cutting functions analogous to Cas9) from various bacterial species including *Acidaminococcus* spp. and *Francisella novicida* U112. Cas9 may refer to an endonuclease that causes double stranded breaks in DNA, a nickase variant such as a RuvC or HNH mutant that causes a single stranded break in DNA, as well as other variations such as deadCas-9 or dCas9, which lack endonuclease activity. Cas9 may also refer to "split-Cas9" in which CAs9 is split into two halves—C-Cas9 and N-Cas9—and fused with a two intein moieties. See, e.g., U.S. Pat. No. 9,074,199 B1; Zetsche et al. (2015) Nat Biotechnol. 33(2):139-42; Wright et al. (2015) PNAS 112(10) 2984-89. Non-limiting examples of commercially available sources of SpCas9 comprising plasmids can be found under the following AddGene reference numbers:

42230: PX330; SpCas9 and single guide RNA
48138: PX458; SpCas9-2A-EGFP and single guide RNA
62988: PX459; SpCas9-2A-Puro and single guide RNA
48873: PX460; SpCas9n (D10A nickase) and single guide RNA
48140: PX461; SpCas9n-2A-EGFP (D10A nickase) and single guide RNA
62987: PX462; SpCas9n-2A-Puro (D10A nickase) and single guide RNA
48137: PX165; SpCas9

Further examples of Cas9 are provided in the table below:

| Name | Protein Sequence |
|---|---|
| S. pyogenes Cas9 (SEQ ID NO: 17) | MDKKYSIGLDIGTNSVGWAVITDEYKVPSKKFKVLGNTDRHSIKKNLIGALLFD SGETAEATRLKRTARRRYTRRKNRICYLQEIFSNEMAKVDDSFFHRLEESFLVE EDKKHERHPIFGNIVDEVAYHEKYPTIYHLRKKLVDSTDKADLRLIYLALAHMI KFRGHFLIEGDLNPDNSDVDKLFIQLVQTYNQLFEENPINASGVDAKAILSARLS KSRRLENLIAQLPGEKKNGLFGNLIALSLGLTPNFKSNFDLAEDAKLQLSKDTY DDDLDNLLAQIGDQYADLFLAAKNLSDAILLSDILRVNTEITKAPLSASMIKRYD EHHQDLTLLKALVRQQLPEKYKEIFFDQSKNGYAGYIDGGASQEEFYKFIKPILE KMDGTEELLVKLNREDLLRKQRTFDNGSIPHQIHLGELHAILRRQEDFYPFLKD NREKIEKILTFRIPYYVGPLARGNSRFAWMTRKSEETITPWNFEEVVDKGASAQ SFIERMTNFDKNLPNEKVLPKHSLLYEYFTVYNELTKVKYVTEGMRKPAFLSGE QKKAIVDLLFKTNRKVTVKQLKEDYFKKIECFDSVEISGVEDRFNASLGTYHDL LKIIKDKDFLDNEENEDILEDIVLTLTLFEDREMIEERLKTYAHLFDDKVMKQLK RRRYTGWGRLSRKLINGIRDKQSGKTILDFLKSDGFANRNFMQLIHDDSLTFKE DIQKAQVSGQGDSLHEHIANLAGSPAIKKGILQTVKVVDELVKVMGRHKPENIV IEMARENQTTQKGQKNSRERMKRIEEGIKELGSQILKEHPVENTQLQNEKLYLY YLQNGRDMYVDQELDINRLSDYDVDHIVPQSFLKDDSIDNKVLTRSDKNRGKS DNVPSEEVVKKMKNYWRQLLNAKLITQRKFDNLTKAERGGLSELDKAGFIKR QLVETRQITKHVAQILDSRMNTKYDENDKLIREVKVITLKSKLVSDFRKDFQFY KVREINNYHHAHDAYLNAVVGTALIKKYPKLESEFVYGDYKVYDVRKMIAKS EQEIGKATAKYFFYSNIMNFFKTEITLANGEIRKRPLIETNGETGEIVWDKGRDF ATVRKVLSMPQVNIVKKTEVQTGGFSKESILPKRNSDKLIARKKDWDPKKYGG FDSPTVAYSVLVVAKVEKGKSKKLKSVKELLGITIMERSSFEKNPIDFLEAKGY KEVKKDLIIKLPKYSLFELENGRKRMLASAGELQKGNELALPSKYVNFLYLASH YEKLKGSPEDNEQKQLFVEQHKYLDEIIEQISEFSKRVILADANLDKVLSAYN KHRDKPIREQAENIIHLFTLTNLGAPAAFKYFDTTIDRKRYTSTKEVLDATLIHQS ITGLYETRIDLSQLGGD* |
| Staphylococcus aureus Cas9 (SEQ ID NO: 18) | MKRNYILGLDIGITSVGYGIIDYETRDVIDAGVRLFKEANVENNEGRRSKRGAR RLKRRRRHRIQRVKKLLFDYNLLTDHSELSGINPYEARVKGLSQKLSEEEFSAA LLHLAKRRGVHNVNEVEEDTGNELSTKEQISRNSKALEEKYVAELQLERLKKD GEVRGSINRFKTSDYVKEAKQLLKVQKAYHQLDQSFIDTYIDLLETRRTYYEGP GEGSPFGWKDIKEWYEMLMGHCTYFPEELRSVKYAYNADLYNALNDLNNLVI TRDENEKLEYYEKFQIIENVFKQKKKPTLKQIAKEILVNEEDIKGYRVTSTGKPE FTNLKVYHDIKDITARKEIIENAELLDQIAKILTIYQSSEDIQEELTNLNSELTQEEI EQISNLKGYTGTHNLSLKAINLILDELWHTNDNQIAIFNRLKLVPKKVDLSQQKE IPTTLVDDFILSPVVKRSFIQSIKVINAIIKKYGLPNDIIIELAREKNSKDAQKMINE MQKRNRQTNERIEEIIRTTGKENAKYLIEKIKLHDMQEGKCLYSLEAIPLEDLLN NPFNYEVDHIIPRSVSFDNSFNNKVLVKQEENSKKGNRTPFQYLSSSDSKISYET FKKHILNLAKGKGRISKTKKEYLLEERDINRFSVQKDFINRNLVDTRYATRGLM NLLRSYFRVNNLDVKVKSINGGFTSFLRRKWKFKKERNKGYKHHAEDALIIAN ADFIFKEWKKLDKAKKVMENQMFEEKQAESMPEIETEQEYKEIFITPHQIKHIK DFKDYKYSHRVDKKPNRELINDTLYSTRKDDKGNTLIVNNLNGLYDKDNDKL KKLINKSPEKLLMYHHDPQTYQKLKLIMEQYGDEKNPLYKYYEETGNYLTKYS KKDNGPVIKKIKYYGNKLNAHLDITDDYPNSRNKVVKLSLKPYRFDVYLDNGV YKFVTVKNLDVIKKENYYEVNSKCYEEAKKLKKISNQAEFIASFYNNDLIKING ELYRVIGVNNDLLNRIEVNMIDITYREYLENMNDKRPPRIIKTIASKTQSIKKYST DILGNLYEVKSKKHPQIIKKG* |
| S. thermophilus CRISPR 1 Cas9 (SEQ ID NO: 19) | MSDLVLGLDIGIGSVGVGILNKVTGEIIHKNSRIFPAAQAENNLVRRTNRQGRRL ARRKKHRRVRLNRLFEESGLITDFTKISINLNPYQLRVKGLTDELSNEELFIALKN MVKHRGISYLDDASDDGNSSVGDYAQIVKENSKQLETKTPGQIQLERYQTYGQ LRGDFTVEKDGKKHRLINVFPTSAYRSEALRILQTQQEFNPQITDEFINRYLEILT GKRKYYHGPGNEKSRTDYGRYRTSGETLDNIFGILIGKCTFYPDEFRAAKASYT AQEFNLLNDLNNLTVPTETKKLSKEQKNQIINYVKNEKAMGPAKLFKYIAKLLS CDVADIKGYRIDKSGKAEIHTFEAYRKMKTLETLDIEQMDRETLDKLAYVLTLN TEREGIQEALEHEFADGSFSQKQVDELVQFRKANSSIFGKGWHNFSVKLMMELI PELYETSEEQMTILTRLGKQKTTSSSNKTKYIDEKLLTEEIYNPVVAKSVRQAIKI VNAAIKEYGDFDNIVIEMARETNEDDEKKAIQKIQKANKDEKDAAMLK AANQYNGKAELPHSVFHGHKQLATKIRLWHQQGERCLYTGKTISIHDLINNSN QFEVDHILPLSITFDDSLANKVLVYATANQEKGQRTPYQALDSMDDAWSFREL KAFVRESKTLSNKKKEYLLTEEDISKFDVRKKFIERNLVDTRYASRVVLNALQE HFRAHKIDTKVSVVRGQFTSQLRRHWGIEKTRDTYHHHAVDALIIAASSQLNL WKKQKNTLVSYSEDQLLDIETGELISDDEYKESVFKAPYQHFVDTLKSKEFEDSI LFSYQVDSKFNRKISDATIYATRQAKVGKDKADETYVLGKIKDIYTQDGYDAF MKIYKKDKSKFLMYRHDPQTFEKVIEPILENYPNKQINDKGKEVPCNPFLKYKE EHGYIRKYSKKGNGPEIKSLKYYDSKLGNHIDITPKDSNNKVVLQSVSPWRADV YFNKTTGKYEILGLKYADLPFDKGTGTYKISQEKYNDIKKKEGVDSDSEFKFTL |

-continued

| Name | Protein Sequence |
|---|---|
| | YKNDLLLVKDTETKEQQLFRFLSRTMPKQKHYVELKPYDKQKFEGGEALIKVL<br>GNVANSGQCKKGLGKSNISIYKVRTDVLGNQHIIKNEGDKPKLDF* |
| N. meningitidis Cas 9<br>(SEQ ID NO: 20) | MAAFKPNPINYILGLDIGIASVGWAMVEIDEDENPICLIDLGVRVFERAEVPKTG<br>DSLAMARRLARSVRRLTRRRAHRLLRARRLLKREGVLQAADFDENGLIKSLPN<br>TPWQLRAAALDRKLTPLEWSAVLLHLIKHRGYLSQRKNEGETADKELGALLKG<br>VADNAHALQTGDFRTPAELALNKFEKESGHIRNQRGDYSHTFSRKDLQAELILL<br>FEKQKEFGNPHVSGGLKEGIETLLMTQRPALSGDAVQKMLGHCTEPAEPKAA<br>KNTYTAERFIWLTKLNNLRILEQGSERPLTDTERATLMDEPYRKSKLTYAQARK<br>LLGLEDTAFFKGLRYGKDNAEASTLMEMKAYHAISRALEKEGLKDKKSPLNLS<br>PELQDEIGTAFSLFKTDEDITGRLKDRIQPEILEALLKHISFDKFVQISLKALRRIV<br>PLMEQGKRYDEACAEIYGDHYGKKNTEEKIYLPPIPADEIRNPVVLRALSQARK<br>VINGVVRRYGSPARIHIETAREVGKSFKDRKEIEKRQEENRKDREKAAAKFREY<br>FPNFVGEPKSKDILKLRLYEQQHGKCLYSGKEINLGRLNEKGYVEIDHALPFSRT<br>WDDSFNNKVLVLGSENQNKGNQTPYEYFNGKDNSREWQEFKARVETSRFPRS<br>KKQRILLQKFDEDGFKERNLNDTRYVNRFLCQFVADRMRLTGKGKKRVFASN<br>GQITNLLRGFWGLRKVRAENDRHHALDAVVVACSTVAMQQKITRFVRYKEMN<br>AFDGKTIDKETGEVLHQKTHFPQPWEFFAQEVMIRVFGKPDGKPEFEEADTPEK<br>LRTLLAEKLSSRPEAVHEYVTPLFVSRAPNRKMSGQGHMETVKSAKRLDEGVS<br>VLRVPLTQLKLKDLEKMVNREREPKLYEALKARLEAHKDDPAKAFAEPFYKY<br>DKAGNRTQQVKAVRVEQVQKTGVWVRNHNGIADNATMVRVDVFEKGDKYY<br>LVPIYSWQVAKGILPDRAVVQGKDEEDWQLIDDSFNFKFSLHPNDLVEVITKKA<br>RMFGYFASCHRGTGNINIRIHDLDHKIGKNGILEGIGVKTALSFQKYQIDELGKEI<br>RPCRLKKRPPVR* |
| Parvibaculum<br>lavamentivorans<br>Cas9<br>(SEQ ID NO: 21) | MERIFGFDIGTTSIGFSVIDYSSTQSAGNIQRLGVRIFPEARDPDGTPLNQQRRQK<br>RMMRRQLRRRRIRRKALNETLHEAGFLPAYGSADWPVVMADEPYELRRRGLE<br>EGLSAYEFGRAIYHLAQHRHFKGRELEESDTPDPDVDDEKEAANERAATLKAL<br>KNEQTTLGAWLARRPPSDRKRGIHAHRNVVAEEFERLWEVQSKFHPALKSEEM<br>RARISDTIFAQRPVFWRKNTLGECRFMPGEPLCPKGSWLSQQRRMLEKLNNLAI<br>AGGNARPLDAEERDAILSKLQQQASMSWPGVRSALKALYKQRGEPGAEKSLK<br>FNLELGGESKLLGNALEAKLADMFGPDWPAHPRKQEIRHAVHERLWAADYGE<br>TPDKKRVIILSEKDRKAHREAAANSFVADFGITGEQAAQLQALKLPTGWEPYSI<br>PALNLFLAELEKGERFGALVNGPDWEGWRRTNFPHRNQPTGEILDKLPSPASKE<br>ERERISQLRNPTVVRTQNELRKVVNNLIGLYGKPDRIRIEVGRDVGKSKREREEI<br>QSGIRRNEKQRKKATEDLIKNGIANPSRDDVEKWILWKEGQERCPYTGDQIGFN<br>ALFREGRYEVEHIWPRSRSFDNSPRNKTLCRKDVNIEKGNRMPFEAFGHDEDR<br>WSAIQORLQGMVSAKGGTGMSPGKVKRFLAKTMPEDFAARQLNDTRYAAKQI<br>LAQLKRLWPDMGPEAPVKVEAVTGQVTAQLRKLWTLNNILADDGEKTRADH<br>RHHAIDALTVACTHPGMTNKLSRYWQLRDDPRAEKPALTPPWDTIRADAEKA<br>VSEIVVSHRVRKKVSGPLHKETTYGDTGTDIKTKSGTYRQFVTRKKIESLSKGEL<br>DEIRDPRIKEIVAAHVAGRGGDPKKAFPPYPCVSPGGPEIRKVRLTSKQQLNLM<br>AQTGNGYADLGSNHHIAIYRLPDGKADFEIVSLFDASRRLAQRNPIVQRTRADG<br>ASFVMSLAAGEAIMIPEGSKKGIWIVQGVWASGQVVLERDTDADHSTTTRPMP<br>NPILKDDAKKVSIDPIGRVRPSND* |
| Corynebacter<br>diphtheria Cas9<br>(SEQ ID NO: 22) | MKYHVGIDVGTFSVGLAAIEVDDAGMPIKTLSLVSHIHDSGLDPDEIKSAVTRL<br>ASSGIARRTRRLYRRKRRRLQQLDKFIQRQGWPVIELEDYSDPLYPWKVRAELA<br>ASYIADEKERGEKLSVALRHIARHRGWRNPYAKVSSLYLPDGLPAKFAIREEI<br>KRASGQPVPETATVGQMVTLCELGTLKLRGEGGVLSARLQQSDYAREIQEICR<br>MQEIGQELYRKIIDVVFAAESPKGSASSRVGKDPLQPGKNRALKASDAFQRYRI<br>AALIGNLRVRVDGEKRILSVEEKNLVFDHLVNLTPKKEPEWVTIAEILGIDRGQL<br>IGTATMTDDGERAGARPPTHDTNRSIVNSRIAPLVDWWKTASALEQHAMVKAL<br>SNAEVDDFDSPEGAKVQAFFADLDDDVHAKLDSLHLPVGRAAYSEDTLVRLTR<br>RMLSDGVDLYTARLQEFGIEPSWTPPTPRIGEPVGNPAVDRVLKTVSRWLESAT<br>KTWGAPERVIIEHVREGFVTEKRAREMDGDMRRRAARNAKLFQEMQEKLNVQ<br>GKPSRADLWRYQSVQRQNCQCAYCGSPITFSNSEMDHIVPRAGQGSTNTRENL<br>VAVCHRCNQSKGNTPFAIWAKNTSIEGVSVKEAVERTRHWVTDTGMRSTDFK<br>KFTKAVVERFQRATMDEEIDARSMESVAWMANELRSRVAQHFASHGTTVRVY<br>RGSLTAEARRASGISGKLKFFDGVGKSRLDRRHHAIDAAVIAFTSDYVAETLAV<br>RSNLKQSQAHRQEAPQWREFTGKDAEHRAAWRVWCQKMEKLSALLTEDLRD<br>DRVVVMSNVRLRLGNGSAHKETIGKLSKVKLSSQLSVSDIDKASSEALWCALT<br>REPGFDPKEGLPANPERHIRVNGTHVYAGDNIGLFPVSAGSIALRGGYAELGSSF<br>HHARVYKITSGKKPAFAMLRVYTIDLLPYRNQDLFSVELKPQTMSMRQAEKKL<br>RDALATGNAEYLGWLVVDDELVVDTSKIATDQVKAVEAELGTIRRWRVDGFF<br>SPSKLRLRPLQMSKEGIKKESAPELSKIIDRPGWLPAVNKLFSDGNVTVVRRDSL<br>GRVRLESTAHLPVTWKVQ* |
| Streptococcus<br>pasteurianus Cas9<br>(SEQ ID NO: 23) | MTNGKILGLDIGIASVGVGIIEAKTGKVVHANSRLFSAANAENNAERRGFRGSR<br>RLNRRKKHRVKRVRDLFEKYGIVTDFRNLNLNPYELRVKGLTEQLKNEELFAA<br>LRTISKRRGISYLDDAEDDSTGSTDYAKSIDENRRLLKNKTPGQIQLERLEKYGQ<br>LRGNFTVYDENGEAHRLINVFSTSDYEKEARKILETQADYNKKITAEFIDDYVEI<br>LTQKRKYYHGPGNEKSRTDYGRFRTDGTTLENIFGILIGKCNFYPDEYRASKAS<br>YTAQEYNFLNDLNNLKVSTETGKLSTEQKESLVEFAKNTATLGPAKLLKEIAKI<br>LDCKVDEIKGYREDDKGKPDLHTFEPYRKLKFNLESINIDDLSREVIDKLADILT<br>LNTEREGIEDAIKRNLPNQFTEEQISEIIKVRSQSTAFNKGWHSFSAKLMNELIP<br>ELYATSDEQMTILTRLEKFKVNKKSSKNIKTIDEKEVTDEIYNPVVAKSVRQTIK |

| Name | Protein Sequence |
|---|---|
| | IINAAVKKYGDFDKIVIEMPRDKNADDEKKFIDKRNKENKKEKDDALKRAAYL<br>YNSSDKLPDEVFHGNKQLETKIRLWYQQGERCLYSGKPISIQELVHNSNNFEID<br>HILPLSLSFDDSLANKVLVYAWTNQEKGQKTPYQVIDSMDAAWSFREMKDYV<br>LKQKGLGKKKRDYLLTTENIDKIEVKKKFIERNLVDTRYASRVVLNSLQSALRE<br>LGKDTKVSVVRGQFTSQLRRKWKIDKSRETYHHHAVDALIIAASSQLKLWEKQ<br>DNPMFVDYGKNQVVDKQTGEILSVSDDEYKELVFQPPYQGFVNTISSKGFEDEI<br>LFSYQVDSKYNRKVSDATIYSTRKAKIGKDKKEETYVLGKIKDIYSQNGFDTFIK<br>KYNKDKTQFLMYQKDSLTWENVIEVILRDYPTTKKSEDGKNDVKCNPFEEYRR<br>ENGLICKYSKKGKGTPIKSLKYYDKKLGNCIDITPEESRNKVILQSINPWRADVY<br>FNPETLKYELMGLKYSDLSEEKGTGNYHISQEKYDAIKEKEGIGKKSEFKFTLY<br>RNDLILIKDIASGEQEIYRFLSRTMPNVNHYVELKPYDKEKFDNVQELVEALGE<br>ADKVGRCIKGLNKPNISIYKVRTDVLGNKYFVKKKGDKPKLDFKNNKK* |
| Neisseria cinerea Cas9 (SEQ ID NO: 24) | MAAFKPNPMNYILGLDIGIASVGWAIVEIDEEENPIRLIDLGVRVFERAEVPKTG<br>DSLAAAARRLARSVRRLTRRRAHRLLRARRLLKREGVLQAADFDENGLIKSLPN<br>TPWQLRAAALDRKLTPLEWSAVLLHLIKHRGYLSQRKNEGETADKELGALLKG<br>VADNTHALQTGDFRTPAELALNKFEKESGHIRNQRGDYSHTFNRKDLQAELNL<br>LFEKQKEFGNPHVSDGLKEGIETLLMTQRPALSGDAVQKMLGHCTFEPTEPKA<br>AKNTYTAERFVWLTKLNNLRILEQGSERPLTDTERATLMDEPYRKSKLTYAQA<br>RKLLDLDDTAFFKGLRYGKDNAEASTLMEMKAYHAISRALEKEGLKDKKSPL<br>NLSPELQDEIGTAFSLFKTDEDITGRLKDRVQPEILEALLKHISFDKFVQISLKAL<br>RRIVPLMEQGNRYDEACTEIYGDHYGKKNTEEKIYLPPIPADEIRNPVVLRALSQ<br>ARKVINGVVRRYGSPARIHIETAREVGKSFKDRKEIEKRQEENRKDREKSAAKF<br>REYFPNFVGEPKSKDILKLRLYEQQHGKCLYSGKEINLGRLNEKGYVEIDHALP<br>FSRTWDDSFNNKVLALGSENQNKGNQTPYEYFNGKDNSREWQEFKARVETSR<br>FPPRSKKQRILLQKFDEDGFKERNLNDTRYINRFLCQFVADHMLLTGKGKRRVF<br>ASNGQITNLLRGFWGLRKVRAENDRHHALDAVVVACSTIAMQQKITRFVRYKE<br>MNAFDGKTIDKETGEVLHQKAHFPQPWEFFAQEVMIRVFGKPDGKPEFEEADT<br>PEKLRTLLAEKLSSRPEAVHKYVTPLFISRAPNRKMSGQGHMETVKSAKRLDE<br>GISVLRVPLTQLKLKDLEKMVNEREREPKLYEALKARLEAHKDDPAKAFAEPPFY<br>KYDKAGNRTQQVKAVRVEQVQKTGVWVHNHNGIADNATIVRVDVFEKGGKY<br>YLVPIYSWQVAKGILPDRAVVQGKDEEDWTVMDDSFEFKFVLYANDLIKLTAK<br>KNEFLGYFVSLNRATGAIDIRTHDTDSTKGKNGIFQSVGVKTALSFQKYQIDEL<br>GKEIRPCRLKKRPPVR* |
| Campylobacter lari Cas9 (SEQ ID NO: 25) | MRILGFDIGINSIGWAFVENDELKDCGVRIFTKAENPKNKESLALPRRNARSSRR<br>RLKRRKARLIAIKRILAKELKLNYKDYVAADGELPKAYEGSLASVYELRYKALT<br>QNLETKDLARVILHIAKHRGYMNKNEKKSNDAKKGILSALKNNALKLENYQS<br>VGEYFYKEFFQKYKKNTKNFIKIRNTKDNYNNCVLSSDLEKELKLILEKQKEFG<br>YNYSEDFINEILKVAFFQRPLKDFSHLVGACTFFEEEKRACKNSYSAWEFVALT<br>KIINEIKSLEKISGEIVPTQTINEVLNLILDKGSITYKKFRSCINLHESISFKSLKYDK<br>ENAENAKLIDFRKLVEFKKALGVHSLSRQELDQISTHITLIKDNVKLKTVLEKYN<br>LSNEQINNLLEIEFNDYINLSFKALGMILPLMREGKRYDEACEIANLKPKTVDEK<br>KDFLPAFCDSIFAHELSNPVVNRAISEYRKVLNALLKKYGKVHKIHLELARDVG<br>LSKKAREKIEKEQKENQAVNAWALKECENIGLKASAKNILKLKLWKEQKEICIY<br>SGNKISIEHLKDEKALEVDHIYPYSRSFDDSFINKVLVFTKENQEKLNKTPFEAF<br>GKNIEKWSKIQTLAQNLPYKKKNKILDENFKDKQQEDFISRNLNDTRYIATLIAK<br>YTKEYLNFLLLSENENANLKSGEKGSKIHVQTISGMLTSVLRHTWGFDKKDRN<br>NHLHHALDAIIVAYSTNSIIKAFSDFRKNQELLKARFYAKELTSDNYKHQVKFFE<br>PFKSFREKILSKIDEIFVSKPPRKRARRALHKDTFHSENKIIDKCSYNSKEGLQIAL<br>SCGRVRKIGTKYVENDTIVRVDIFKKQNKFYAIPIYAMDFALGILPNKIVITGKD<br>KNNNPKQWQTIDESYEFCFSLYKNDLILLQKKNMQEPEFAYYNDFSISTSSICVE<br>KHDNKFENLTSNQKLLFSNAKEGSVKVESLGIQNLKVFEKYIITPLGDKIKADFQ<br>PRENISLKTSKKYGLR* |
| T. denticola Cas9 (SEQ ID NO: 26) | MKKEIKDYFLGLDVGTGSVGWAVTDTDYKLLKANRKDLWGMRCFETAETAE<br>VRRLHRGARRRIERRKRIKLLQELFSQEIAKTDEGFFQRMKESPFYAEDKTILQ<br>ENTLFNDKDFADKTYHKAYPTINHLIKAWIENKVKPDPRLLYLACHNIIKKRGH<br>FLFEGDFDSENQFDTSIQALFEYLREDMEVDIDADSQKVKEILKDSSLKNSEKQS<br>RLNKILGLKPSDKQKKAITNLISGNKINFADLYDNPDLKDAEKNSISFSKDDFDA<br>LSDDLASILGDSFELLLLKAKAVYNCSVLSKVIGDEQYLSFAKVKIYEKHKTDLT<br>KLKNVIKKHFPKDYKKVFGYNKNEKNNNNYSGYVGVCKTKSKKLIINNSVNQ<br>EDFYKFLKTILSAKSEIKEVNDILTEIETGTFLPKQISKSNAEIPYQLRKMELEKIL<br>SNAEKHFSFLKQKDEKGLSHSEKIIMLLTFKIPYYIGPINDNHKKFFPDRCWVVK<br>KEKSPSGKTTPWNFFDHIDKEKTAEAFITSRTNFCTYLVGESVLPKSSLLYSEYT<br>VLNEINNLQIIIDGKNICDIKLKQKIYEDLFKKYKKITQKQISTFIKHEGICNKTDE<br>VIILGIDKECTSSLKSYIELKNIFGKQVDEISTKNMLEEIIRWATIYDEGEGKTILK<br>TKIKAEYGKYCSDEQIKKILNLKFSGWGRLSRKFLETVTSEMPGFSEPVNIITAM<br>RETQNNLMELLSSEFTFTENIKKINSGFEDAEKQFSYDGLVKPLFLSPSVKKML<br>WQTLKLVKEISHITQAPPKKIFIEMAKGAELEPARTKTRLKILQDLYNNCKNDA<br>DAFSSEIKDLSGKIENEDNLRLRSDKLYLYYTQLGKMCYCGKPIEIGHVFDTSNY<br>DIDHIYPQSKIKDDSISNRVLVCSSCNKNKEDKYPLKSEIQSKQRGFWNFLQRNN<br>FISLEKLNRLTRATPISDDETAKFIARQLVETRQATKVAAKVLEKMFPETKIVYS<br>KAETVSMFRNKFDIVKCREINDPHHAHDAYLNIVVGNVYNTKFTNNPWNFIKE<br>KRDNPKIADTYNYYKVFDYDVKRNNITAWEKGKTIITVKDMLKRNTPIYTRQA<br>ACKKGELFNQTMKKGLGQHPLKKEGPFSNISKYGGYNKVSAAYYTLIEYEEK<br>GNKIRSLETIPLYLVKDIQKDQDVLKSYLTDLLGKKEFKILVPKIKINSLLKINGF |

| Name | Protein Sequence |
|---|---|
| | PCHITGKTNDSFLLRPAVQFCCSNNEVLYFKKIIRFSEIRSQREKIGKTISPYEDLS<br>FRSYIKENLWKKTKNDEIGEKEFYDLLQKKNLEIYDMLLTKHKDTIYKKRPNSA<br>TIDILVKGKEKFKSLIIENQFEVILEILKLFSATRNVSDLQHIGGSKYSGVAKIGNK<br>ISSLDNCILIYQSITGIFEKRIDLLKV* |
| S. mutans Cas9<br>(SEQ ID NO: 27) | MKKPYSIGLDIGTNSVGWAVVTDDYKVPAKKMKVLGNTDKSHIEKNLLGALL<br>FDSGNTAEDRRLKRTARRRYTRRRNRILYLQEIFSEEMGKVDDSFFHRLEDSFL<br>VTEDKRGERHPIFGNLEEEVKYHENFPTIYHLRQYLADNPEKVDLRLVYLALAH<br>IIKFRGHFLIEGKFDTRNNDVQRLFQEFLAVYDNTFENSSLQEQNVQVEEILTDKI<br>SKSAKKDRVLKLFPNEKSNGRFAEFLKLIVGNQADFKKHFELEEKAPLQFSKDT<br>YEEELEVLLAQIGDNYAELFLSAKKLYDSILLSGILTVTDVGTKAPLSASMIQRY<br>NEHQMDLAQLKQFIRQKLSDKYNEVFSDVSKDGYAGYIDGKTNQEAFYKYLK<br>GLLNKIEGSGYFLDKIEREDFLRKQRTFDNGSIPHQIHLQEMRAIIRRQAEFYPFL<br>ADNQDRIEKLLTFRIPYYVGPLARGKSDFAWLSRKSADKITPWNFDEIVDKESS<br>AEAFINRMTNYDLYLPNQKVLPKHSLLYEKFTVYNELTKVKYKTEQGKTAFFD<br>ANMKQEIFDGVFKVYRKVTKDKLMDFLEKEFDEFRIVDLTGLDKENKVFNASY<br>GTYHDLCKILDKDFLDNSKNEKILEDIVLTLTLFEDREMIRKRLENYSDLLTKEQ<br>VKKLERRHYTGWGRLSAELIHGIRNKESRKTILDYLIDDGNSRNFMQLINDDA<br>LSFKEEIAKAQVIGETDNLNQVVSDIAGSPAIKKGILQSLKIVDELVKIMGHQPE<br>NIVVEMARENQFTNQGRRNSQQRLKGLTDSIKEFGSQILKEHPVENSQLQNDRL<br>FLYYLQNGRDMYTGEELDIDYLSQYDIDHIIPQAFIKDNSIDNRVLTSSKENRGK<br>SDDVPSKDVVRKMKSYWSKLLSAKLITQRKFDNLTKAERGGLTDDDKAGFIKR<br>QLVETRQITKHVARILDERFNTETEDENNKKIRQVKIVTLKSNLVSNFRKEFELYK<br>VREINDYHHAHDAYLNAVIGKALLGVYPQLEPEFVYGDYPHFHGHKENKATA<br>KKFFYSNIMNFFKKDDVRTDKNGEIIWKKDEHISNIKKVLSYPQVNIVKKVEEQ<br>TGGFSKESILPKGNSDKLIPRKTKKFYWDTKKYGGFDSPIVAYSILVIADIEKGKS<br>KKLKTVKALVGVTIMEKMTFERDPVAFLERKGYRNVQEENIIKLPKYSLFKLEN<br>GRKRLLASARELQKGNEIVLPNHLGTLLYHAKNIHKVDEPKHLDYVDKHKDEF<br>KELLDVVSNFSKKYTLAEGNLEKIKELYAQNNGEDLKELASSFINLLTFTAIGAP<br>ATFKFFDKNIDRKRYTSTTEILNATLIHQSITGLYETRIDLNKLGGD |
| S. thermophilus<br>CRISPR 3 Cas9<br>(SEQ ID NO: 28) | MTKPYSIGLDIGTNSVGWAVTTDNYKVPSKKMKVLGNTSKKYIKKNLLGVLLF<br>DSGITAEGRRLKRTARRRYTRRRNRILYLQEIFSTEMATLDDAFFQRLDDSFLVP<br>DDKRDSKYPIFGNLVEEKAYHDEPTIYHLRKYLADSTKKADLRLVYLALAHM<br>IKYRGHFLIEGEFNSKNNDIQKNFQDFLDTYNAIFESDLSLENSKQLEEIVKDKIS<br>KLEKKDRILKLFPGEKNSGIFSEFLKLIVGNQADFRKCFNLDEKASLHFSKESYD<br>EDLETLLGYIGDDYSDVFLKAKKLYDAILLSGFLTVTDNETEAPLSSAMIKRYN<br>EHKEDLALLKEYIRNISLKTYNEVFKDDTKNGYAGYIDGKTNQEDFYVYLKKL<br>LAEFEGADYFLEKIDREDFLRKQRTFDNGSIPYQIHLQEMRAILDKQAKFYPFLA<br>KNKERIEKILTFRIPYYVGPLARGNSDFAWSIRKRNEKITPWNFEDVIDKESSAE<br>AFINRMTSFDLYLPEEKVLPKHSLLYETFNVYNELTKVRFIAESMRDYQFLDSK<br>QKKDIVRLYFKDKRKVTDKDIIEYLHAIYGYDGIELKGIEKQFNSSLSTYHDLLN<br>IINDKEFLDDSSNEAIIEEIIHTLTIFEDREMIKQRLSKFENIFDKSVLKKLSRRHYT<br>GWGKLSAKLINGIRDEKSGNTILDYLIDDGISNRNFMLIHDDALSFKKKIQKAQ<br>IIGDEDKGNIKEVVKSLPGSPAIKKGILQSIKIVDELVKVMGGRKPESIVVEMARE<br>NQYTNQGKSNSQQRLKRLEKSLKELGSKILKENIPAKLSKIDNNALQNDRLYLY<br>YLQNGKDMYTGDDLDIDRLSNYDIDHIIPQAFLKDNSIDNKVLVSSASNRGKSD<br>DVPSLEVVKKRKTFWYQLLKSKLISQRKFDNLTKAERGGLSPEDKAGFIQRQLV<br>ETRQITKHVARLLDEKFNNKKDENNRAVRTVKIITLKSTLVSQFRKDFELYKVR<br>EINDFHHAHDAYLNAVVASALLKKYPKLEPEFVYGDYPKYNSFRERKSATEKV<br>YFYSNIMNIFKKSISLADGRVIERPLIEVNEETGESVWNKESDLATVRRVLSYPQ<br>VNVVKKVEEQNHGLDRGKPKGLFNANLSSKPKPNSENENLVGAKEYLDPKKYG<br>GYAGISNSFTVLVKGTIEKGAKKKITNVLEFQGISILDRINYRKDKLNFLLEKGY<br>KDIELIIELPKYSLFELSDGSRRMLASILSTNNKRGEIHKGNQIFLSQKFVKLLYH<br>AKRISNTINENHRKYVENHKKEFEELFYYILEFNENYVGAKKNGKLLNSAFQSW<br>QNHSIDELCSSFIGPTGSERKGLFELTSRGSAADFEFLGVKIPRYRDYTPSSLLKD<br>ATLIHQSVTGLYETRIDLAKLGEG |
| C. jejuni Cas9 (SEQ<br>ID NO: 29) | MARILAFDIGISSIGWAFSENDELKDCGVRIFTKVENPKTGESLALPRRLARSAR<br>KRLARRKARLNHLKHLIANEFKLNYEDYQSFDESLAKAYKGSLISPYELRFRAL<br>NELLSKQDFARVILHIAKRRGYDDIKNSDDKEKGAILKAIKQNEEKLANYQSVG<br>EYLYKEYFQKFKENSKEFTNVRNKKESYERCIAQSFLKDELKLIFKKQREFGFSF<br>SKKFEEEVLSVAFYKRALKDFSHLVGNCSFFTDEKRAPKNSPLAFMFVALTRII<br>NLLNNLKNTEGILYTKDDLNALLNEVLKNGTLTYKQTKKLLGLSDDYEFKGEKG<br>TYFIEFKKYKEFIKALGEHNLSQDDLNEIAKDITLIKDEIKLKKALAKYDLNQNQ<br>IDSLSKLEFKDHLNISFPKALKLVTPLMLEGKKKYDEACNELNLKVAINEDKKDFL<br>PAFNETYYKDEVTNPVVLRAIKEYRKVLNALLKKYGKVHKINIELAREVGKNH<br>SQRAKIEKEQNENYKAKKDAELECEKLGLKINSKNILKLRLFKEQKEFCAYSGE<br>KIKISDLQDEKMLEIDHIYPYSRSFDDSYMNKVLVFTKQNQEKLNQTPPEAFGN<br>DSAKWQKIEVLAKNLPTKKQKRILDKNYKDKEQKNFKDRNLNDTRYIARLVL<br>NYTKDYLDFLPLSDDENTKLNDTQKGSKVHVEAKSGMLTSALRHTWGFSAKD<br>RNNHLHHAIDAVIIAYANNSIVKAFSDFKKEQESNSAELYAKKISELDYKNKRK<br>FFEEPFSGFRQKVLDKIDEIFVSKPERKKPSGALHEETFRKEEEFYQSYGGKEGVL<br>KALELGKIRKVNGKIVKNGDMFRVDIFKHKKTNKFYAVPIYTMDFALKVLPNK<br>AVARSKKGEIKDWILMDENYEFCFSLYKDSLILIQTKDMQEPEFVYYNAFTSST<br>VSLIVSKHDNKFETLSKNQKILFKNANEKEVIAKSIGIQNLKVFEKYIVSALGEVT<br>KAEFRQREDFKK |

-continued

| Name | Protein Sequence |
|---|---|
| P. multocida Cas9 (SEQ ID NO: 30) | MQTTNLSYILGLDLGIASVGWAVVEINENEDPIGLIDVGVRIFERAEVPKTGESL<br>ALSRRLARSTRRLIRRRAHRLLLAKRFLKREGILSTIDLEKGLPNQAWELRVAGL<br>ERRLSAIEWGAVLLHLIKHRGYLSKRKNESQTNNKELGALLSGVAQNHQLLQS<br>DDYRTPAELALKKFAKEEGHIRNQRGAYTHTFNRLDLLAELNLLFAQQHQFGN<br>PHCKEHIQQYMTELLMWQKPALSGEAILKMLGKCTHEKNEFKAAKHTYSAER<br>FVWLTKLNNLRILEDGAERALNEEERQLLINHPYEKSKLTYAQVRKLLGLSEQA<br>IFKHLRYSKENAESATFMELKAWHAIRKALENQGLKDTWQDLAKKPDLLDEIG<br>TAFSLYKTDEDIQQYLTNKVPNSVINALLVSLNFDKFIELSLKSLRKILPLMEQG<br>KRYDQACREIYGHHYGEANQKTSQLLPAIPAQEIRNPVVLRTLSQARKVINAIIR<br>QYGSPARVHIETGRELGKSFKERREIQKQQEDNRTKRESAVQKFKELFSDFSSEP<br>KSKDILKFRLYEQQHGKCLYSGKEINIHRLNEKGYVEIDHALPFSRTWDDSFNN<br>KVLVLASENQNKGNQTPYEWLQGKINSERWKNFVALVLGSQCSAAKKQRLLT<br>QVIDDNKFIDRNLNDTRYIARFLSNYIQENLLLVGKNKKNVFTPNGQITALLRSR<br>WGLIKARENNNRHHALDAIVVACATPSMQQKITRFIRFKEVHPYKIENRYEMV<br>DQESGEIISPHFPEPWAYFRQEVNIRVFDNHPDTVLKEMLPDRPQANHQFVQPL<br>FVSRAPTRKMSGQGHMETIKSAKRLAEGISVLRIPLTQLKPNLLENMVNKEREP<br>ALYAGLKARLAEFNQDPAKAFATPFYKQGGQQVKAIRVEQVQKSGVLVRENN<br>GVADNASIVRTDVFIKNNKFFLVPIYTWQVAKGILPNKAIVAHKNEDEWEEMD<br>EGAKFKFSLFPNDLVELKTKKEYFFGYYIGLDRATGNISLKEHDGEISKGKDGV<br>YRVGVKLALSEEKYQVDELGKNRQICRPQQRQPVR |
| F. novicida Cas9 (SEQ ID NO: 31) | MNFKILPIAIDLGVKNTGVFSAFYQKGTSLERLDNKNGKVYELSKDSYTLLMNN<br>RTARRHQRRGIDRKQLVKRLFKLIWTEQLNLEWDKDTQQAISFLFNRRGFSFIT<br>DGYSPEYLNIVPEQVKAILMDIFDDYNGEDDLDSYLKLATEQESKISEIYNKLM<br>QKILEFKLMKLCTDIKDDKVSTKTLKEITSYEFELLADYLANYSESLKTQKFSYT<br>DKQGNLKELSYYHHDKYNIQEFLKRHATINDRILDTLLTDDLDIWNFNFEKFDF<br>DKNEEKLQNQEDKDHIQAHLHHFVFAVNKIKSEMASGGRHRSQYFQEITNVLD<br>ENNHQEGYLKNFCENLHNKKYSNLSVKNLVNLIGNLSNLELKPLRKYFNDKIH<br>AKADHWDEQKFTETYCHWILGEWRVGVKDQDKKDGAKYSYKDLCNELKQK<br>VTKAGLVDFLLELDPCRTIPPYLDNNNRKPPKCQSLILNPKFLDNQYPNWQQYL<br>QELKKLQSIQNYLDSEETDLKVLKSSKDQPYFVEYKSSNQQIASGQRDYKDLDA<br>RILQFIFDRVKASDELLLNEIYFQAKKLKQKASSELEKLESSKKLDEVIANSQLSQ<br>ILKSQHTNGIFEQGTFLHLVCKYYKQRQRARDSRLYIMPEYRYDKKLHKYNNT<br>GRFDDDNQLLTYCNHKPRQKRYQLLNDLAGVLQVSPNFLKDKIGSDDDLFISK<br>WLVEHIRGFKKACEDSLKIQKDNRGLLNHKINIARNTKGKCEKEIFNLICKIEGS<br>EDKKGNYKHGLAYELGVLLFGEPNEASKPEFDRKIKKFNSIYSFAQIQQIAFAER<br>KGNANTCAVCSADNAHRMQQIKITEPVEDNKDKIILSAKAQRLPAIPTRIVDGA<br>VKKMATILAKNIVDDNWQNIKQVLSAKHQLHIPIITESNAFETEPALADVKGKS<br>LKDRRKKALERISPENIFKDKNNRIKEFAKGISAYSGANLTDGDFDGAKEELDHI<br>IPRSHKKYGTLNDEANLICVTRGDNKNKGNRIFCLRDLADNYKLKQFETTDDLE<br>IEKKIADTIWDANKKDFKFGNYRSFINLTPQEQKAFRHALFLADENPIKQAVIRA<br>INNRNRTFVNGTQRYFAEVLANNIYLRAKKENLNTDKISFDYFGIPTIGNGRGIA<br>EIRQLYEKVDSDIQAYAKGDKPQASYSHLIDAMLAFCIAADEHRNDGSIGLEID<br>KNYSLYPLDKNTGEVFTKDIFSQIKITDNEFSDKKLVRKKAIEGFNTHRQMTRD<br>GIYAENYLPILIHKELNEVRKGYTWKNSEEIKIFKGKKYDIQQLNNLVYCLKFV<br>DKPISIDIQISTLEELRNILTTNNIAATAEYYYINLKTQKLHEYYIENYNTALGYK<br>KYSKEMEFLRSLAYRSERVKIKSIDDVKQVLDKDSNFIIGKITLPFKKEWQRLYR<br>EWQNTTIKDDYEFLKSFFNVKSITKLHKKVRKDFSLPISTNEGKFLVKRKTWDN<br>NFIYQILNDSDSRADGTKPFIPAFDISKNEIVEAIIDSFTSKNIFWLPKNIELQKVD<br>NKNIFAIDTSKWFEVETPSDLRDIGIATIQYKIDNNSRPKVRVKLDYVIDDDSKIN<br>YFMNHSLLKSRYPDKVLEILKQSTIIEFESSGFNKTIKEMLGMKLAGIYNETSNN |
| Lactobacillus buchneri Cas9 (SEQ ID NO: 32) | MKVNNYHIGLDIGTSSIGWVAIGKDGKPLRVKGKTAIGARLFQEGNPAADRRM<br>FRTTRRRLSRRKWRLKLLEEIFDPYITPVDSTFFARLKQSNLSPKDSRKEFKGSM<br>LFPDLTDMQYHKNYPTIYHLRHALMTQDKKFDIRMVYLAIHHIVKYRGNFLNS<br>TPVDSFKASKVDFVDQFKKLNELYAAINPEESFKINLANSEDIGHQPFLDPSIRKF<br>DKKKQIPKIVPVMMNDKVTDRLNGKIASEIIHAILGYKAKLDVVLQCTPVDSKP<br>WALKFDDEDIDAKLEKILPEMDENQQSIVAILQNLYSQVTLNQIVPNGMSLSES<br>MIEKYNDHHDHLKLYKKLIDQLADPKKKAVLKKAYSQYVGDDGKVIEQAEFW<br>SSVKKNLDDSELSKQIMDLIDAEKFMPKQRTSQNGVIPHQLYQRELDEIIEHQSK<br>YYPWLVEINPNKHDLHLAKYKIEQLVAFRVPYYVGPMITPKDQAESAETVFSW<br>MERKGTETGQITPWNFDEKVDRKASANRFIKRMTTKDTYLIGEDVLPDESLLYE<br>KFKVLNELNMVRVNGKLLKVADKQAIFQDLFENYKHVSVKKLQNYIKAKTGL<br>PSDPEISGLSDPEHFNNSLGTYNDFKKLFGSKVDEPDLQDDFEKIVEWSTVFEDK<br>KILREKLNEITWLSDQQKDVLESSRYQGWGRLSKKLLTGIVNDQGERIIDKLWN<br>TNKNFMQIQSDDDFAKRIHEANADQMQAVDVEDVLADAYTSPQNKKAIRQVV<br>KVVDDIQKAMGGVAPKYISIEFTRSEDRNPRRTISRQRQLENTLKDTAKSLAKSI<br>NPELLSELDNAAKSKKGLTDRLYLYFTQLGKDIYTGEPINIDELNKYDIDHILPQ<br>AFIKDNSLDNRVLVLTAVNNGKSDNVPLRMFGAKMGHFWKQLAEAGLISKRK<br>LKNLQTDPDTISKYAMHGFIRRQLVETSQVIKLVANILGDKYRNDDTKIIEITAR<br>MNHQMRDEFGFIKNREINDYHHAFDAYLTAFLGRYLYHRYIKLRPYFVYGDFK<br>KFREDKVTMRNFNFPHDLTDDTQEKIADAETGEVIWDRENSIQQLKDVYHYKF<br>MLISHEVYTLRGAMFNQTVYPASDAGKRKLIPVKADRPVNVYGGYSGSADAY<br>MAIVRIHNKKGDKYRVVGVPMRALDRLDAAKNVSDADFDRALKDVLAPQLT<br>KTKKSRKTGEITQVIEDEEIVLGKVMYRQLMIDGDKKFMLGSSTYQYNAKQLV<br>LSDQSVKTLASKGRLDPLQESMDYNNVYTEILDKVNQYFSLYDMNKFRHKLN |

-continued

| Name | Protein Sequence |
|---|---|
| | LGFSKFISFPNHNVLDGNTKVSSGKREILQEILNGLHANPTFGNLKDVGITTPFG<br>QLQQPNGILLSDETKIRYQSPTGLFERTVSLKDL |
| *Listeria innocua*<br>Cas9<br>(SEQ ID NO: 33) | MKKPYTIGLDIGTNSVGWAVLTDQYDLVKRKMKIAGDSEKKQIKKNFWGVRL<br>FDEGQTAADRRMARTARRRIERRRNRISYLQGIFAEEMSKTDANFFCRLSDSFY<br>VDNEKRNSRHPFFATIEEEVEYHKNYPTIYHLREELVNSSEKADLRLVYLALAHI<br>IKYRGNFLIEGALDTQNTSVDGIYKQFIQTYNQVFASGIEDGSLKKLEDNKDVA<br>KILVEKVTRKEKLERILKLYPGEKSAGMFAQFISLIVGSKGNFQKPFDLIEKSDIE<br>CAKDSYEEDLESLLALIGDEYAELFVAAKNAYSAVVLSSIITVAETETNAKLSAS<br>MIERFDTHEEDLGELKAFIKLHLPKHYEEIFSNTEKHGYAGYIDGKTKQADFYK<br>YMKMTLENIEGADYFIAKIEKENFLRKQRTFDNGAIPHQLHLEELEAILHQQAK<br>YYPFLKENYDKIKSLVTFRIPYFVGPLANGQSEFAWLTRKADGEIRPWNIEEKV<br>DFGKSAVDFIEKMTNKDTYLPKENVLPKHSLCYQKYLVYNELTKVRYINDQGK<br>TSYFSGQEKEQIFNDLFKQKRKVKKKDLELFLRNMSHVESPTIEGLEDSFNSSYS<br>TYHDLLKVGIKQEILDNPVNTEMLENIVKILTVFEDKRMIKEQLQQFSDVLDGV<br>VLKKLERRHYTGWGRLSAKLLMGIRDKQSHLTILDYLMNDDGLNRNLMQLIN<br>DSNLSFKSIIEKEQVTTADKDIQSIVADLAGSPAIKKGILQSLKIVDELVSVMGYP<br>PQTIVVEMARENQTTGKGKNNSRPRYKSLEKAIKEFGSQILKEHPTDNQELRNN<br>RLYLYYLQNGKDMYTGQDLDIHNLSNYDIDHIVPQSFITDNSIDNLVLTSSAGN<br>REKGDDVPPLEIVRKRKVFWEKLYQGNLMSKRKFDYLTKAERGGLTEADKAR<br>FIHRQLVETRQITKNVANILHQRFNYEKDDHGNTMKQVRIVTLKSALVSQFRKQ<br>FQLYKVRDVNDYHHAHDAYLNGVVANTLLKVYPQLEPEFVYGDYHQFDWFK<br>ANKATAKKQFYTNIMLFFAQKDRIIDENGEILWDKKYLDTVKKVMSYRQMNIV<br>KKTEIQKGEFSKATIKPKGNSSKLIPRKTNWDPMKYGGLDSPNMAYAVVIEYA<br>KGKNKLVFEKKIIRVTIMERKAFEKDEKAFLEEQGYRQPKVLAKLPKYTLYECE<br>EGRRRMLASANEAQKGNQQVLPNHLVTLLHHAANCEVSDGKSLDYIESNREM<br>FAELLAHVSEFAKRYTLAEANLNKINQLFEQNKEGDIKAIAQSFVDLMAFNAM<br>GAPASFKFFETTIERKRYNNLKELLNSTIIYQSITGLYESRKRLDD |
| *L. pneumophilia*<br>Cas9<br>(SEQ ID NO: 34) | MESSQILSPIGIDLGGKFTGVCLSHLEAFAELPNHANTKYSVILIDHNNFQLSQA<br>QRRATRHRVRNKKRNQFVKRVALQLFQHILSRDLNAKEETALCHYLNNRGYT<br>YVDTDLDEYIKDETTINLLKELLPSESEHNFIDWFLQKMQSSEFRKILVSKVEEK<br>KDDKELKNAVKNIKNFITGFEKNSVEGHRHRKVYFENIKSDITKDNQLDSIKKKI<br>PSVCLSNLLGHLSNLQWKNLHRYLAKNPKQFDEQTFGNEFLRMLKNFRHLKGS<br>QESLAVRNLIQQLEQSQDYISILEKTPPEITIPPYEARTNTGMEKDQSLLLNPEKL<br>NNLYPNWRNLIPGIIDAHPFLEKDLEHTKLRDRKRIISPSKQDEKRDSYILQRYLD<br>LNKKIDKFKIKKQLSFLGQGKQLPANLIETQKEMETHFNSSLVSVLIQIASAYNK<br>EREDAAQGIWFDNAFSLCELSNINPPRKQKILPLLVGAILSEDFINNKDKWAKFK<br>IFWNTHKIGRTSLKSKCKEIEEARKNSGNAFKIDYEEALNHPEHSNNKALIKIIQT<br>IPDIIQAIQSHLGHNDSQALIYHNPFSLSQLYTILETKRDGFHKNCVAVTCENYW<br>RSQKTEIDPEISYASRLPADSVRPFDGVLARMMQRLAYEIAMAKWEQIKHIPDN<br>SSLLIPIYLEQNRFEFEESFKKIKGSSSDKTLEQAIEKQNIQWEEKFQRIINASMNI<br>CPYKGASIGGQGEIDHIYPRSLSKKHFGVIFNSEVNLIYCSSQGNREKKEEHYLL<br>EHLSPLYLKHQFGTDNVSDIKNFISQNVANIKKYISFHLLTPEQQKAARHALFLD<br>YDDEAFKTITKFLMSQQKARVNGTQKFLGKQIMEFLSTLADSKQLQLEFSIKQIT<br>AEEVHDHRELLSKQEPKLVKSRQQSFPSHAIDATLTMSIGLKEFPQFSQELDNS<br>WFINHLMPDEVHLNPVRSKEKYNKPNISSTPLFKDSLYAERFIPVWVKGETFAIG<br>FSEKDLEEIKPSNKEKLFTLLKTYSTKNPGESLQELQAKSKAKWLYFPINKTLAL<br>EFLHHYFHKEIVTPDDTTVCHFINSLRYYTKKESITVKILKEPMPVLSVKFESSKK<br>NVLGSFKHTIALPATKDWERLFNHPNFLALKANPAPNPKEFNEFIRKYFLSDNN<br>PNSDIPNNGHNIKPQKHKAVRKVFSLPVIPGNAGTMMRIRRKDNKGQPLYQLQ<br>TIDDTPSMGIQINEDRLVKQEVLMDAYKTRNLSTIDGINNSEGQAYATFDNWLT<br>LPVSTFKPEIIKLEMKPHSKTRRYIRITQSLADFIKTIDEALMIKPSDSIDDPLNMP<br>NEIVCKNKLFGNELKPRDGKMKIVSTGKIVTYEFESDSTPQWIQTLYVTQLKKQ<br>P |
| *N. lactamica* Cas9<br>(SEQ ID NO: 35) | MAAFKPNPMNYILGLDIGIASVGWAMVEVDEEENPIRLIDLGVRVFERAEVPKT<br>GDSLAMARRLARSVRRLTRRRAHRLLRARRLLKREGVLQDADFDENGLVKSL<br>PNTPWQLRAAALDRKLTCLEWSAVLLHLVKHRGYLSQRKNEGETADKELGAL<br>LKGVADNAHALQTGDFRTPAELALNKFEKESGHIRNQRGDYSHTFSRKDLQAE<br>LNLLFEKQKEFGNPHVSDGLKEDIETLLMAQRPALSGDAVQKMLGHCTFEPAE<br>PKAAKNTYTAERFIWLTKLNNLRILEQGSERPLTDTERATLMDEPYRKSKLTYA<br>QARKLLGLEDTAFFKGLRYGKDNAEASTLMEMKAYHAISRALEKEGLKDKKS<br>PLNLSTELQDEIGTAFSLFKTDKDITGRLKDRVQPEILEALLKHISFDKFVQISLK<br>ALRRIVPLMEQGKRYDEACAEIYGDHYCKKNAEEKIYLPPIPADEIRNPVVLRA<br>LSQARKVINCVVRRYGSPARIHIETAREVGKSFKDRKEIEKRQEENRKDREKAA<br>AKFREYFPNFVGEPKSKDILKLRLYEQQHGKCLYSGKEINLVRLNEKGYVEIDH<br>ALPFSRTWDDSFNNKVLVLGSENQNKGNQTPYEYFNGKDNSREWQEFKARVE<br>TSRFPRSKKQRILLQKFDEEGFKERNLNDTRYVNRFLCQFVADHILLTGKGKRR<br>VFASNGQITNLLRGFWGLRKVRTENDRHHALDAVVVACSTVAMQQKITRFVR<br>YKEMNAFDGKTIDKETGEVLHQKAHFPQPWEFFAQEVMIRVFGKPDGKPEFEE<br>ADTPEKLRTLLAEKLSSRPEAVHEYVTPLFVSRAPNRKMSGQGHMETVKSAKR<br>LDEGISVLRVPLTQLKLKGLEKMVNREREPKLYDALKAQLETHKDDPAKAFAE<br>PFYKYDKAGSRTQQVKAVRIEQVQKTGVWVRNHNGIADNATMVRVDVFEKG<br>GKYYLVPIYSWQVAKGILPDRAVVAFKDEEDWTVMDDSFEFRFVLYANDLIKL<br>TAKKNEFLGYFVSLNRATGAIDRTHDTDSTKGKNGIFQSVGVKTALSFQKNQI<br>DELGKEIRPCRLKKRPPVR |

-continued

| Name | Protein Sequence |
|---|---|
| *N. meningitides* Cas9 (SEQ ID NO: 36) | MAAFKPNPINYILGLDIGIASVGWAMVEIDEDENPICLIDLGVRVFERAEVPKTG
DSLAMARRLARSVRRLTRRRAHRLLRARRLLKREGVLQAADFDENGLIKSLPN
TPWQLRAAALDRKLTPLEWSAVLLHLIKHRGYLSQRKNEGETADKELGALLKG
VADNAHALQTGDFRTPAELALNKFEKESGHIRNQRGDYSHTFSRKDLQAELILL
FEKQKEFGNPHVSGGLKEGIETLLMTQRPALSGDAVQKMLGHCTFEPAEPKAA
KNTYTAERFIWLTKLNNLRILEQGSERPLTDTERATLMDEPYRKSKLTYAQARK
LLGLEDTAFFKGLRYGKDNAEASTLMEMKAYHAISRALEKEGLKDKKSPLNLS
PELQDEIGTAFSLFKTDEDITGRLKDRIQPEILEALLKHISFDKFVQISLKALRRIV
PLMEQGKRYDEACAEIYGDHYGKKNTEEKIYLPPIPADEIRNPVVLRALSQARK
VINGVVRRYGSPARIHIETAREVGKSFKDRKEIEKRQEENRKDREKAAAKFREY
FPNFVGEPKSKDILKLRLYEQQHGKCLYSGKEINLGRLNEKGYVEIDHALPFSRT
WDDSFNNKVLVLGSENQNKGNQTPYEYFNGKDNSREWQEFKARVETSRFPRS
KKQRILLQKFDEDGFKERNLNDTRYVNRFLCQFVADRMRLTGKGKKRVFASN
GQITNLLRGFWGLRKVRAENDRHHALDAVVVACSTVAMQQKITRFVRYKEMN
AFDGKTIDKETGEVLHQKTHFPQPWEFFAQEVMIRVFGKPDGKPEFEEADTPEK
LRTLLAEKLSSRPEAVHEYVTPLFVSRAPNRKMSGQGHMETVKSAKRLDEGVS
VLRVPLTQLKLKDLEKMVNREREPKLYEALKARLEAHKDDPAKAFAEPFYKY
DKAGNRTQQVKAVRVEQVQKTGVWVRNHNGIADNATMVRVDVFEKGDKYY
LVPIYSWQVAKGILPDRAVVQGKDEEDWQLIDDSFNFKFSLHPNDLVEVITKKA
RMFGYFASCHRGTGNINIRIHDLDHKIGKNGILEGIGVKTALSFQKYQIDELGKEI
RPCRLKKRPPVR |
| *B. longum* Cas9 (SEQ ID NO: 37) | MLSRQLLGASHLARPVSYSYNVQDNDVHCSYGERCFMRGKRYRIGIDVGLNSV
GLAAVEVSDENSPVRLLNAQSVIHDGGVDPQKNKEAITRKNMSGVARRTRRM
RRRKRERLHKLDMLLGKFGYPVIEPESLDKPFEEWHVRAELATRYIEDDELRRE
SISIALRHMARHRGWRNPYRQVDSLISDNPYSKQYGELKEKAKAYNDDATAAE
EESTPAQLVVAMLDAGYAEAPRLRWRTGSKKPDAEGYLPVRLMQEDNANELK
QIFRVQRVPADEWKPLFRSVFYAVSPKGSAEQRVGQDPLAPEQARALKASLAF
QEYRIANVITNLRIKDASAELRKLTVDEKQSIYDQLVSPSSEDITWSDLCDFLGF
KRSQLKGVGSLTEDGEERISSRPPRLTSVQRIYESDNKIRKPLVAWWKSASDNE
HEAMIRLLSNTVDIDKVREDVAYASAIEFIDGLDDDALTKLDSVDLPSGRAAYS
VETLQKLTRQMLTTDDDLHEARKTLFNVTDSWRPPADPIGEPLGNPSVDRVLK
NVNRYLMNCQQRWGNPVSVNIEHVRSSFSSVAFARKDKREYEKNNEKRSIFRS
SLSEQLRADEQMEKVRESDLRRLEAIQRQNGQCLYCGRTITFRTCEMDHIVPRK
GVGSTNTRTNFAAVCAECNRMKSNTPFAIWARSEDAQTRGVSLAEAKKRVTM
FTFNPKSYAPREVKAFKQAVIARLQQTEDDAAIDNRSIESVAWMADELHRRID
WYFNAKQYVNSASIDDAEAETMKTTVSVFQGRVTASARRAAGIEGKIHFIGQQ
SKTRLDRRHHAVDASVIAMMNTAAAQTLMERESLRESQRLIGLMPGERSWKE
YPYEGTSRYESFHLWLDNMDVLLELLNDALDNDRIAVMQSQRYVLGNSIAHD
ATIHPLEKVPLGSAMSADLIRRASTPALWCALTRLPDYDEKEGLPEDSHREIRV
HDTRYSADDEMGFFASQAAQIAVQEGSADIGSAIHHARVYRCWKTNAKGVRK
YFYGMIRVFQTDLLRACHDDLFTVPLPPQSISMRYGEPRVVQALQSGNAQYLG
SLVVGDEIEMDFSSLDVDGQIGEYLQFFSQFSGGNLAWKHWVVDGFFNQTQLR
IRPRYLAAEGLAKAFSDDVVPDGVQKIVTKQGWLPPVNTASKTAVRIVRRNAF
GEPRLSSAHHMPCSWQWRHE |
| *A. muciniphila* Cas9 (SEQ ID NO: 38) | MSRSLTFSFDIGYASIGWAVIASASHDDADPSVCGCGTVLFPKDDCQAFKRREY
RRLRRNIRSRRVRIERIGRLLVQAQIITPEMKETSGHPAPFYLASEALKGHRTLAP
IELWHVLRWYAHNRGYDNNASWSNSLSEDGGNGEDTERVKHAQDLMDKHGT
ATMAETICRELKLEEGKADAPMEVSTPAYKNLNTAFPRLIVEKEVRRILELSAPL
IPGLTAEIIELIAQHHPLTTEQRGVLLQHGIKLARRYRGSLLFGQLIPRFDNRIISR
CPVTWAQVYEAELKKGNSEQSARERAEKLSKVPTANCPEFYEYRMARILCNIR
ADGEPLSAEIRRELMNQARQEGKLTKASLEKAISSRLGKETETNVSNYFTLHPD
SEEALYLNPAVEVLQRSGIGQILSPSVYRIAANRLRRGKSVTPNYLLNLLKSRGE
SGEALEKKIEKESKKKEADYADTPLKPKYATGRAPYARTVLKKVVEEILDGEDP
TRPARGEAHPDGELKAHDGCLYCLLDTDSSVNQHQKERRLDTMTNNHLVRHR
MLILDRLLKDLIQDFADGQKDRISRVCVEVGKELTTFSAMDSKKIQRELTLRQK
SHTDAVNRLKRKLPGKALSANLIRKCRIAMDMNWTCPFTGATYGDHELENLEL
EHIVPHSFRQSNALSSLVLTWPGVNRMKGQRTGYDFVEQEQENPVPDKPNLHI
CSLNNYRELVEKLDDKKGHEDDRRRKKKRKALLMVRGLSHKHQSQNHEAMK
EIGMTEGMMTQSSHLMKLACKSIKTSLPDAHIDMIPGAVTAEVRKAWDVFGVF
KELCPEAADPDSGKILKENLRSLTHLHHALDACVLGLIPYIIPAHHNGLLRRVLA
MRRIPEKLIPQVRPVANQRHYVLNDDGRMMLRDLSASLKENIREQLMEQRVIQ
HVPADMGGALLKETMQRVLSVDGSGEDAMVSLSKKKDGKKEKNQVKASKLV
GVFPEGPSKLKALKAAIEIDGNYGVALDPKPVVIRHIKVFKRIMALKEQNGGKP
VRILKKGMLIHLTSSKDPKHAGVWRIESIQDSKGGVKLDLQRAHCAVPKNKTH
ECNWREVDLISLLKKYQMKRYPTSYTGTPR |
| *O. laneus* Cas9 (SEQ ID NO: 39) | METTLGIDLGTNSIGLALVDQEEHQILYSGVRIFPEGINKDTIGLGEKEESRNATR
RAKRQMRRQYFRKKLRKAKLLELLIAYDMCPLKPEDVRRWKNWDKQQKSTV
RQFPDTPAFREWLKQNPYELRKQAVTEDVTRPELGRILYQMIQRRGFLSSRKGK
EEGKIFTGKDRMVGIDETRKNLQKQTLGAYLYDIAPKNGEKYRFRTERVRARY
TLRDMYIREFEIIWRQAGHLGLAHEQATRKKNIFLEGSATNVRNSKLITHLQA
KYGRGHVLIEDTRITVTFQLPLKEVLGGKIEIEEEQLKFKSNESVLFWQRPLRSQ
KSLLSKCVFEGRNFYDPVHQKWIIAGPTPAPLSHPEFEEFRAYQFINNIIYGKNEH
LTAIQREAVFELMCTESKDFNFEKIPKHLKLFEKFNFDDTTKVPACTTISQLRKL |

| Name | Protein Sequence |
|---|---|
| | FPHPVWEEKREEIWHCFYFYDDNTLLFEKLQKDYALQTNDLEKIKKIRLSESYG
NVSLKAIRRINPYLKKGYAYSTAVLLGGIRNSFGKRFEYFKEYEPEIEKAVCRIL
KEKNAEGEVIRKIKDYLVHNRFGFAKNDRAFQKLYHHSQAITTQAQKERLPET
GNLRNPIVQQGLNELRRTVNKLLATCREKYGPSFKFDHIHVEMGRELRSSKTER
EKQSRQIRENEKKNEAAKVKLAEYGLKAYRDNIQKYLLYKEIEEKGGTVCCPY
TGKTLNISHTLGSDNSVQIEHIIPYSISLDDSLANKTLCDATFNREKGELTPYDFY
QKDPSPEKWGASSWEEIEDRAFRLLPYAKAQRFIRRKPQESNEFISRQLNDTRYI
SKKAVEYLSAICSDVKAFPGQLTAELRHLWGLNNILQSAPDITFPLPVSATENHR
EYYVITNEQNEVIRLFPKQGETPRTEKGELLLTGEVERKVFRCKGMQEFQTDVS
DGKYWRRIKLSSSVTWSPLFAPKPISADGQIVLKGRIEKGVFVCNQLKQKLKTG
LPDGSYWISLPVISQTFKEGESVNNSKLTSQQVQLFGRVREGIFRCHNYQCPASG
ADGNFWCTLDTDTAQPAFTPIKNAPPGVGGGQIILTGDVDDKGIFHADDDLHYE
LPASLPKGKYYGIFTVESCDPTLIPIELSAPKTSKGENLIEGNIWVDEHTGEVRFD
PKKNRE -continued

QVLDKDSNFIIGKITLPFKKEWQRLYREWQNTTIKDDYEFLKSFFNVKSITKLHKKVR

KDFSLPISTNEGKFLVKRKTWDNNFIYQILNDSDSRADGTKPFIPAFDISKNEIVEAIID

SFTSKNIFWLPKNIELQKVDNKNIFAIDTSKWFEVETPSDLRDIGIATIQYKIDNNSRPK

VRVKLDYVIDDDSKINYFMNHSLLKSRYPDKVLEILKQSTIIEFESSGFNKTIKEMLG

MKLAGIYNETSNN

ZP_05061364.1 CRISPR-associated large protein (provisional), putative
[gamma proteobacterium HTCC5015]
(SEQ ID NO: 41)

MTKNYISPIAIDLGAKFTGVALYQYLEGADCTQEVAKGLLVDDRGNVTWSQEGRRG

KRHQVRGYKRRKMAKRLLWLILDSEYGIKREEVTEPLLKFINGLLNRRGYTYISEEV

DEESMNVSPLPFSEMMPDYFNSSAPLLEQLAKLLSDKNKLVRFRAEGKIPSNKNEFK

KLLDTALDGKYKDEKKELSEAWGNILIASENVLKSTVDGHKSRSEYLANIKEDIKSN

EELEKQISSKEIDGFYNLVGHLSNFQLRLLRKYFNDPNMSGVSYWDEKRLEKYFYQ

WVQGWHTKGGTDEAEKKNIILKTKGAPLLKTLKSLSADLTIPPYEDQNNRRPPKCQS

VLLSDEKLTMHYPKWKEWVGQLVKQNDNAYLNENVTLANALHRIVERSRSIDPYQ

LRLLISITDAEKRNDLAGYKRLKLSLGSEVDEFLLLVKNIVDETKEAREGLWFETENK

LFFKCGKTPPRKEKLKSTLLSAVLGKNLSDDEQSSFIEEFWKSGTPKIERRNVRGWCR

LASQVQKTYGVYLKEYGLQQLHKLEAGKKLDDKPLALLYKNSGLIASKIGEALNIEP

DEVSRFASPHSLAQIFNIIEGDVAGFNKTCRACTYENIWRMQEEKVESLLTNQLLSEIH

GERKVPLKSAMCTRLSADSTRPFDGQMASIIEHIARKIAQHKIAQINDVPKEFSIDIPIII

ESNQFSFTAELEEIKRGRGSAKAKKAKELGEKSKAGWVSKTERIKTSSEGICPYTGAP

LGGSGEIDHIIPRSLTGRTKKTVFNSEANLIYCSSKGNHDKGNRVYVIEQLNDKYLKK

QFSTSDVNLIKKKIKTTIQRFTEGGEKLRSFSELSREDQKAFRHALFVPELKSEVTSLL

AVKNITRVNGTQAWLAKKIASLLAEHLDKQGRDYTLSAHQIDPWSVSKQRKMLASA

EPIWAKKDPQPAASHVVDAVCTFLEALEQPHTASRLKTISSTSFEKTGWRSALIPDLIK

VDALDRRPKYRRYNIGSTSLFKDGIYAERFLPILIDENGLMAGYDIDNSLKAKGADV

VFESLSPFLLFKGEEVGAQSLSDWQERIDGRYLYMSIDKVKAFDYLQEKVGEKDIAA

ELLNSIHFTQRKTELRAKFSDDSGKKMKTLDAIRKSLKLTVTVNEIGKRKEKCGFSGT

IGIPAKSAWENLLDEPLLETYWGTKMPPQEIWEKVYRKHFPRNIPNQAHRKVRKDFS

LPVVDSVSGGFRVKRKTPNGYNYQLLAIDGYSAVGFKKEGDNVDFKSPALVPQIAES

KSVTPISSELVHLDKNEIVYFDEWRKIDISDSDLKQFVSSLELAPGSQNRFYIRFTVDE

DQFERHFKSALRVNGIQDLDTVNKTFDWNREIPSLLIPPRSNLFLLETGQKITFEYIAN

GANAEVKKAYSLRRA

ZP_08324662.1 CRISPR-associated protein, Csx12 family [*Parasutterella excrementihominis* YIT 11859]
(SEQ ID NO: 42)

MGKTHIIGVGLDLGGTYTGTFITSHPSDEAEHRDHSSAFTVVNSEKLSFSSKSRTAVR

HRVRSYKGFDLRRRLLLLVAEYQLLQKKQTLAPEERENLRIALSGYLKRRGYARTEA

ETDTSVLESLDPSVFSSAPSFTNFFNDSEPLNIQWEAIANSPETTKALNKELSGQKEAD

FKKYIKTSFPEYSAKEILANYVEGRRAILDASKYIANLQSLGHKHRSKYLSDILQDMK

RDSRITRLSEAFGSTDNLWRIIGNISNLQERAVRWYFNDAKFEQGQEQLDAVKLKNV

LVRALKYLRSDDKEWSASQKQIIQSLEQSGDVLDVLAGLDPDRTIPPYEDQNNRRPP

EDQTLYLNPKALSSEYGEKWKSWANKFAGAYPLLTEDLTEILKNTDRKSRIKIRSDV

LPDSDYRLAYILQRAFDRSIALDECSIRRTAEDFENGVVIKNEKLEDVLSGHQLEEFLE

-continued

FANRYYQETAKAKNGLWFPENALLERADLHPPMKNKILNVIVGQALGVSPAEGTDFI

EEIWNSKVKGRSTVRSICNAIENERKTYGPYFSEDYKFVKTALKEGKTEKELSKKFA

AVIKVLKMVSEVVPFIGKELRLSDEAQSKFDNLYSLAQLYNLIETERNGFSKVSLAAH

LENAWRMTMTDGSAQCCRLPADCVRPFDGFIRKAIDRNSWEVAKRIAEEVKKSVDF

TNGTVKIPVAIEANSFNFTASLTDLKYIQLKEQKLKKKLEDIQRNEENQEKRWLSKEE

RIRADSHGICAYTGRPLDDVGEIDHIIPRSLTLKKSESIYNSEVNLIFVSAQGNQEKKN

NIYLLSNLAKNYLAAVFGTSDLSQITNEIESTVLQLKAAGRLGYFDLLSEKERACARH

ALFLNSDSEARRAVIDVLGSRRKASVNGTQAWFVRSIFSKVRQALAAWTQETGNELI

FDAISVPAADSSEMRKRFAEYRPEFRKPKVQPVASHSIDAMCIYLAACSDPFKTKRM

GSQLAIYEPINFDNLFTGSCQVIQNTPRNFSDKTNIANSPIFKETIYAERFLDIIVSRGEIF

IGYPSNMPFEEKPNRISIGGKDPFSILSVLGAYLDKAPSSEKEKLTIYRVVKNKAFELFS

KVAGSKFTAEEDKAAKILEALHFVTVKQDVAATVSDLIKSKKELSKDSIENLAKQKG

CLKKVEYSSKEFKFKGSLIIPAAVEWGKVLWNVFKENTAEELKDENALRKALEAAW

PSSFGTRNLHSKAKRVFSLPVVATQSGAVRIRRKTAFGDFVYQSQDTNNLYSSFPVK

NGKLDWSSPIIHPALQNRNLTAYGYRFVDHDRSISMSEFREVYNKDDLMRIELAQGT

SSRRYLRVEMPGEKFLAWFGENSISLGSSFKFSVSEVFDNKIYTENAEFTKFLPKPRED

NKHNGTIFFELVGPRVIFNYIVGGAASSLKEIFSEAGKERS

YP_122507.1 hypothetical protein lpp0160 [*Legionella pneumophila* str. *Paris*] (SEQ ID NO: 43)

MESSQILSPIGIDLGGKFTGVCLSHLEAFAELPNHANTKYSVILIDHNNFQLSQAQRRA

TRHRVRNKKRNQFVKRVALQLFQHILSRDLNAKEETALCHYLNNRGYTYVDTDLDE

YIKDETTINLLKELLPSESEHNFIDWFLQKMQSSEFRKILVSKVEEKKDDKELKNAVK

NIKNFITGFEKNSVEGHRHRKVYFENIKSDITKDNQLDSIKKKIPSVCLSNLLGHLSNL

QWKNLHRYLAKNPKQFDEQTFGNEFLRMLKNFRHLKGSQESLAVRNLIQQLEQSQD

YISILEKTPPEITIPPYEARTNTGMEKDQSLLLNPEKLNNLYPNWRNLIPGIIDAHPFLE

KDLEHTKLRDRKRIISPSKQDEKRDSYILQRYLDLNKKIDKFKIKKQLSFLGQGKQLP

ANLIETQKEMETHFNSSLVSVLIQIASAYNKEREDAAQGIWFDNAFSLCELSNINPPRK

QKILPLLVGAILSEDFINNKDKWAKFKIFWNTHKIGRTSLKSKCKEIEEARKNSGNAF

KIDYEEALNHPEHSNNKALIKIIQTIPDIIQAIQSHLGHNDSQALIYHNPFSLSQLYTILE

TKRDGFHKNCVAVTCENYWRSQKTEIDPEISYASRLPADSVRPFDGVLARMMQRLA

YEIAMAKWEQIKHIPDNSSLLIPIYLEQNRFEFEESFKKIKGSSSDKTLEQAIEKQNIQW

EEKFQRIINASMNICPYKGASIGGQGEIDHIYPRSLSKKHFGVIFNSEVNLIYCSSQGNR

EKKEEHYLLEHLSPLYLKHQFGTDNVSDIKNFISQNVANIKKYISFHLLTPEQQKAAR

HALFLDYDDEAFKTITKFLMSQQKARVNGTQKFLGKQIMEFLSTLADSKQLQLEFSI

KQITAEEVHDHRELLSKQEPKLVKSRQQSFPSHAIDATLTMSIGLKEFPQFSQELDNS

WFINHLMPDEVHLNPVRSKEKYNKPNISSTPLFKDSLYAERFIPVWVKGETFAIGFSE

KDLFEIKPSNKEKLFTLLKTYSTKNPGESLQELQAKSKAKWLYFPINKTLALEFLHHY

FHKEIVTPDDTTVCHFINSLRYYTKKESITVKILKEPMPVLSVKFESSKKNVLGSFKHT

IALPATKDWERLFNHPNFLALKANPAPNPKEFNEFIRKYFLSDNNPNSDIPNNGHNIK

PQKHKAVRKVFSLPVIPGNAGTMMRIRRKDNKGQPLYQLQTIDDTPSMGIQINEDRL

VKQEVLMDAYKTRNLSTIDGINNSEGQAYATFDNWLTLPVSTFKPEIIKLEMKPHSK

-continued

TRRYIRITQSLADFIKTIDEALMIKPSDSIDDPLNMPNEIVCKNKLFGNELKPRDGKMK

IVSTGKIVTYEFESDSTPQWIQTLYVTQLKKQP

NP_907747.1 hypothetical protein WS1613 [Wolinella succinogenes DSM 1740]
(SEQ ID NO: 44)

MLVSPISVDLGGKNTGFFSFTDSLDNSQSGTVIYDESFVLSQVGRRSKRHSKRNNLRN

KLVKRLFLLILQEHHGLSIDVLPDEIRGLFNKRGYTYAGFELDEKKKDALESDTLKEF

LSEKLQSIDRDSDVEDFLNQIASNAESFKDYKKGFEAVFASATHSPNKKLELKDELKS

EYGENAKELLAGLRVTKEILDEFDKQENQGNLPRAKYFEELGEYIATNEKVKSFFDS

NSLKLTDMTKLIGNISNYQLKELRRYFNDKEMEKGDIWIPNKLHKITERFVRSWHPK

NDADRQRRAELMKDLKSKEIMELLTTTEPVMTIPPYDDMNNRGAVKCQTLRLNEEY

LDKHLPNWRDIAKRLNHGKFNDDLADSTVKGYSEDSTLLHRLLDTSKEIDIYELRGK

KPNELLVKTLGQSDANRLYGFAQNYYELIRQKVRAGIWVPVKNKDDSLNLEDNSN

MLKRCNHNPPHKKNQIHNLVAGILGVKLDEAKFAEFEKELWSAKVGNKKLSAYCK

NIEELRKTHGNTFKIDIEELRKKDPAELSKEEKAKLRLTDDVILNEWSQKIANFFDIDD

KHRQRFNNLFSMAQLHTVIDTPRSGFSSTCKRCTAENRFRSETAFYNDETGEFHKKA

TATCQRLPADTQRPFSGKIERYIDKLGYELAKIKAKELEGMEAKEIKVPIILEQNAFEY

EESLRKSKTGSNDRVINSKKDRDGKKLAKAKENAEDRLKDKDKRIKAFSSGICPYCG

DTIGDDGEIDHILPRSHTLKIYGTVFNPEGNLIYVHQKCNQAKADSIYKLSDIKAGVSA

QWIEEQVANIKGYKTFSVLSAEQQKAFRYALFLQNDNEAYKKVVDWLRTDQSARV

NGTQKYLAKKIQEKLTKMLPNKHLSFEFILADATEVSELRRQYARQNPLLAKAEKQA

PSSHAIDAVMAFVARYQKVFKDGTPPNADEVAKLAMLDSWNPASNEPLTKGLSTNQ

KIEKMIKSGDYGQKNMREVFGKSIFGENAIGERYKPIVVQEGGYYIGYPATVKKGYE

LKNCKVVTSKNDIAKLEKIIKNQDLISLKENQYIKIFSINKQTISELSNRYFNMNYKNL

VERDKEIVGLLEFIVENCRYYTKKVDVKFAPKYIHETKYPFYDDWRRFDEAWRYLQ

ENQNKTSSKDRFVIDKSSLNEYYQPDKNEYKLDVDTQPIWDDFCRWYFLDRYKTAN

DKKSIRIKARKTFSLLAESGVQGKVFRAKRKIPTGYAYQALPMDNNVIAGDYANILL

EANSKTLSLVPKSGISIEKQLDKKLDVIKKTDVRGLAIDNNSFFNADFDTHGIRLIVEN

TSVKVGNFPISAIDKSAKRMIFRALFEKEKGKRKKKTTISFKESGPVQDYLKVFLKKI

VKIQLRTDGSISNIVVRKNAADFTLSFRSEHIQKLLK

ADX75954.1 CRISPR-associated protein, Csn1 family [Staphylococcus
pseudintermedius ED99]
(SEQ ID NO: 45)

MGRKPYILSLDIGTGSVGYACMDKGFNVLKYHDKDALGVYLFDGALTAQERRQFRT

SRRRKNRRIKRLGLLQELLAPLVQNPNFYQFQRQFAWKNDNMDFKNKSLSEVLSFL

GYESKKYPTIYHLQEALLLKDEKFDPELIYMALYHLVKYRGHFLFDHLKIENLTNND

NMHDFVELIETYENLNNIKLNLDYEKTKVIYEILKDNEMTKNDRAKRVKNMEKKLE

QFSIMLLGLKFNEGKLFNHADNAEELKGANQSHTFADNYEENLTPFLTVEQSEFIERA

NKIYLSLTLQDILKGKKSMAMSKVAAYDKFRNELKQVKDIVYKADSTRTQFKKIFVS

SKKSLKQYDATPNDQTFSSLCLFDQYLIRPKKQYSLLIKELKKIIPQDSELYFEAENDT

LLKVLNTTDNASIPMQINLYEAETILRNQQKYHAEITDEMIEKVLSLIQFRIPYYVGPL

VNDHTASKFGWMERKSNESIKPWNFDEVVDRSKSATQFIRRMTNKCSYLINEDVLP

KNSLLYQEMEVLNELNATQIRLQTDPKNRKYRMMPQIKLFAVEHIFKKYKTVSHSKF

LEIMLNSNHRENFMNHGEKLSIFGTQDDKKFASKLSSYQDMTKIFGDIEGKRAQIEEII

-continued

QWITIFEDKKILVQKLKECYPELTSKQINQLKKLNYSGWGRLSEKLLTHAYQGHSIIE

LLRHSDENFMEILTNDVYGFQNFIKEENQVQSNKIQHQDIANLTTSPALKKGIWSTIK

LVRELTSIFGEPEKIIMEFATEDQQKGKKQKSRKQLWDDNIKKNKLKSVDEYKYIIDV

ANKLNNEQLQQEKLWLYLSQNGKCMYSGQSIDLDALLSPNATKHYEVDHIFPRSFIK

DDSIDNKVLVIKKMNQTKGDQVPLQFIQQPYERIAYWKSLNKAGLISDSKLHKLMKP

EFTAMDKEGFIQRQLVETRQISVHVRDFLKEEYPNTKVIPMKAKMVSEFRKKFDIPKI

RQMNDAHHAIDAYLNGVVYHGAQLAYPNVDLFDFNFKWEKVREKWKALGEFNTK

QKSRELFFFKKLEKMEVSQGERLISKIKLDMNHFKINYSRKLANIPQQFYNQTAVSPK

TAELKYESNKSNEVVYKGLTPYQTYVVAIKSVNKKGKEKMEYQMIDHYVFDFYKF

QNGNEKELALYLAQRENKDEVLDAQIVYSLNKGDLLYINNHPCYFVSRKEVINAKQ

FELTVEQQLSLYNVMNNKETNVEKLLIEYDFIAEKVINEYHHYLNSKLKEKRVRTFFS

ESNQTHEDFIKALDELFKVVTASATRSDKIGSRKNSMTHRAFLGKGKDVKIAYTSISG

LKTTKPKSLFKLAESRNEL

ZP_10206685.1 CRISPR-associated protein, Csn1 family [*Planococcus antarcticus* DSM 14505]

(SEQ ID NO: 46)

MKNYTIGLDIGVASVGWVCIDENYKILNYNNRHAFGVHEFESAESAAGRRLKRGMR

RRYNRRKKRLQLLQSLFDSYITDSGFFSKTDSQHFWKNNNEFENRSLTEVLSSLRISS

RKYPTIYHLRSDLIESNKKMDLRLVYLALHNLVKYRGHFLQEGNWSEAASAEGMDD

QLLELVTRYAELENLSPLDLSESQWKAAETLLLNRNLTKTDQSKELTAMFGKEYEPF

CKLVAGLGVSLHQLFPSSEQALAYKETKTKVQLSNENVEEVMELLLEEESALLEAVQ

PFYQQVVLYELLKGETYVAKAKVSAFKQYQKDMASLKNLLDKTFGEKVYRSYFISD

KNSQREYQKSHKVEVLCKLDQFNKEAKFAETPYKDLKKLLEDKSKTSIGTTEKDEM

LRIIKAIDSNQFLQKQKGIQNAAIPHQNSLYEAEKILRNQQAHYPFITTEWIEKVKQIL

AFRIPYYIGPLVKDTTQSPFSWVERKGDAPITPWNFDEQIDKAASAEAFISRMRKTCT

YLKGQEVLPKSSLTYERFEVLNELNGIQLRTTGAESDFRHRLSYEMKCWIIDNVFKQ

YKTVSTKRLLQELKKSPYADELYDEHTGEIKEVFGTQKENAFATSLSGYISMKSILGA

VVDDNPAMTEELIYWIAVFEDREILHLKIQEKYPSITDVQRQKLALVKLPGWGRFSRL

LIDGLPLDEQGQSVLDHMEQYSSVFMEVLKNKGFGLEKKIQKMNQHQVDGTKKIRY

EDIEELAGSPALKRGIWRSVKIVEELVSIFGEPANIVLEVAREDGEKKRTKSRKDQWE

ELTKTTLKNDPDLKSFIGEIKSQGDQRFNEQRFWLYVTQQGKCLYTGKALDIQNLSM

YEVDHILPQNFVKDDSLDNLALVMPEANQRKNQVGQNKMPLEIIEANQQYAMRTL

WERLHELKLISSGKLGRLKKPSFDEVDKDKFIARQLVETRQIIKHVRDLLDERFSKSDI

HLVKAGIVSKFRRFSEIPKIRDYNNKHHAMDALFAAALIQSILGKYGKNFLAFDLSKK

DRQKQWRSVKGSNKEFFLFKNFGNLRLQSPVTGEEVSGVEYMKHVYFELPWQTTK

MTQTGDGMFYKESIFSPKVKQAKYVSPKTEKFVHDEVKNHSICLVEFTFMKKEKEV

QETKFIDLKVIEHHQFLKEPESQLAKFLAEKETNSPIIHARIIRTIPKYQKIWIEHFPYYFI

STRELHNARQFEISYELMEKVKQLSERSSVEELKIVFGLLIDQMNDNYPIYTKSSIQD

RVQKFVDTQLYDFKSFEIGFEELKKAVAANAQRSDTFGSRISKKPKPEEVAIGYESIT

GLKYRKPRSVVGTKR

ZP_16930555.1 csn1 family CRISPR-associated protein [*Streptococcus sanguinis* SK49]
(SEQ ID NO: 47)

MTKFNKNYSIGLDIGVSSVGYAVVTEDYRVPAFKFKVLGNTEKEKIKKNLIGSTTFVS

AQPAKGTRVFRVNRRRIDRRNHRITYLRDIFQKEIEKVDKNFYRRLDESFRVLGDKSE

DLQIKQPFFGDKELETAYHKKYPTIYHLRKHLADADKNSPVADIREVYMAISHILKY

RGHFLTLDKINPNNINMQNSWIDFIESCQEVFDLEISDESKNIADIFKSSENRQEKVKKI

LPYFQQELLKKDKSIFKQLLQLLFGLKTKFKDCFELEEEPDLNFSKENYDENLENFLG

SLEEDFSDVFAKLKVLRDTILLSGMLTYTGATHARFSATMVERYEEHRKDLQRFKFF

IKQNLSEQDYLDIFGRKTQNGFDVDKETKGYVGYITNKMVLTNPQKQKTIQQNFYD

YISGKITGIEGAEYFLNKISDGTFLRKLRTSDNGAIPNQIHAYELEKIIERQGKDYPFLL

ENKDKLLSILTFKIPYYVGPLAKGSNSRFAWIKRATSSDILDDNDEDTRNGKIRPWNY

QKLINMDETRDAFITNLIGNDIILLNEKVLPKRSLIYEEVMLQNELTRVKYKDKYGKA

HFFDSELRQNIINGLFKNNSKRVNAKSLIKYLSDNHKDLNAIEIVSGVEKGKSFNSTLK

TYNDLKTIFSEELLDSEIYQKELEEIIKVITVFDDKKSIKNYLTKFFGHLEILDEEKINQL

SKLRYSGWGRYSAKLLLLDIRDEDTGFNLLQFLRNDEENRNLTKLISDNTLSFEPKIKDI

QSKSTIEDDIFDEIKKLAGSPAIKRGILNSIKIVDELVQIIGYPPHNIVIEMARENMTTEE

GQKKAKTRKTKLESALKNIENSLLENGKVPHSDEQLQSEKLYLYYLQNGKDMYTLD

KTGSPAPLYLDQLDQYEVDHIIPYSFLPIDSIDNKVLTHRENNQQKLNNIPDKETVAN

MKPFWEKLYNAKLISQTKYQRLTTSERTPDGVLTESMKAGFIERQLVETRQIIKHVA

RILDNRFSDTKIITLKSQLITNFRNTFHIAKIRELNDYHHAHDAYLAVVVGQTLLKVYP

KLAPELIYGHHAHFNRHEENKATLRKHLYSNIMRFFNNPDSKVSKDIWDCNRDLPIIK

DVIYNSQINFVKRTMIKKGAFYNQNPVGKFNKQLAANNRYPLKTKALCLDTSIYGG

YGPMNSALSIIIIAERFNEKKGKIETVKEFHDIFIIDYEKFNNNPFQFLNDTSENGFLKK

NNINRVLGFYRIPKYSLMQKIDGTRMLFESKSNLHKATQFKLTKTQNELFFHMKRLL

TKSNLMDLKSKSAIKESQNFILKHKEEFDNISNQLSAFSQKMLGNTTSLKNLIKGYNE

RKIKEIDIRDETIKYFYDNFIKMFSFVKSGAPKDINDFFDNKCTVARMRPKPDKKLLN

ATLIHQSITGLYETRIDLSKLGED

AAK33936.1 conserved hypothetical protein [*Streptococcus pyogenes* M1 GAS]
(SEQ ID NO: 48)

MDKKYSIGLDIGTNSVGWAVITDEYKVPSKKFKVLGNTDRHSIKKNLIGALLFDSGE

TAEATRLKRTARRRYTRRKNRICYLQEIFSNEMAKVDDSFFHRLEESFLVEEDKKHE

RHPIFGNIVDEVAYHEKYPTIYHLRKKLVDSTDKADLRLIYLALAHMIKFRGHFLIEG

DLNPDNSDVDKLFIQLVQTYNQLFEENPINASGVDAKAILSARLSKSRRLENLIAQLP

GEKKNGLFGNLIALSLGLTPNFKSNFDLAEDAKLQLSKDTYDDDLDNLLAQIGDQYA

DLFLAAKNLSDAILLSDILRVNTEITKAPLSASMIKRYDEHHQDLTLLKALVRQQLPE

KYKEIFFDQSKNGYAGYIDGGASQEEFYKFIKPILEKMDGTEELLVKLNREDLLRKQR

TFDNGSIPHQIHLGELHAILRRQEDFYPFLKDNREKIEKILTFRIPYYVGPLARGNSRFA

WMTRKSEETITPWNFEEVVDKGASAQSFIERMTNFDKNLPNEKVLPKHSLLYEYFTV

YNELTKVKYVTEGMRKPAFLSGEQKKAIVDLLFKTNRKVTVKQLKEDYFKKIECFD

SVEISGVEDRFNASLGTYHDLLKIIKDKDFLDNEENEDILEDIVLTLTLFEDREMIEERL

KTYAHLFDDKVMKQLKRRRYTGWGRLSRKLINGIRDKQSGKTILDFLKSDGFANRN

FMQLIHDDSLTFKEDIQKAQVSGQGDSLHEHIANLAGSPAIKKGILQTVKVVDELVK

-continued

VMGRHKPENIVIEMARENQTTQKGQKNSRERMKRIEEGIKELGSQILKEHPVENTQL

QNEKLYLYYLQNGRDMYVDQELDINRLSDYDVDHIVPQSFLKDDSIDNKVLTRSDK

NRGKSDNVPSEEVVKKMKNYWRQLLNAKLITQRKFDNLTKAERGGLSELDKAGFIK

RQLVETRQITKHVAQILDSRMNTKYDENDKLIREVKVITLKSKLVSDFRKDFQFYKV

REINNYHHAHDAYLNAVVGTALIKKYPKLESEFVYGDYKVYDVRKMIAKSEQEIGK

ATAKYFFYSNIMNFFKTEITLANGEIRKRPLIETNGETGEIVWDKGRDFATVRKVLSM

PQVNIVKKTEVQTGGFSKESILPKRNSDKLIARKKDWDPKKYGGFDSPTVAYSVLVV

AKVEKGKSKKLKSVKELLGITIMERSSFEKNPIDFLEAKGYKEVKKDLIIKLPKYSLFE

LENGRKRMLASAGELQKGNELALPSKYVNFLYLASHYEKLKGSPEDNEQKQLFVEQ

HKHYLDEIIEQISEFSKRVILADANLDKVLSAYNKHRDKPIREQAENIIHLFTLTNLGA

PAAFKYFDTTIDRKRYTSTKEVLDATLIHQSITGLYETRIDLSQLGGD

YP_820832.1 CRISPR-system-like protein [*Streptococcus thermophilus* LMD-9]

(SEQ ID NO: 49)

MTKPYSIGLDIGTNSVGWAVTTDNYKVPSKKMKVLGNTSKKYIKKNLLGVLLFDSGI

TAEGRRLKRTARRRYTRRRNRILYLQEIFSTEMATLDDAFFQRLDDSFLVPDDKRDS

KYPIFGNLVEEKAYHDEFPTIYHLRKYLADSTKKADLRLVYLALAHMIKYRGHFLIE

GEFNSKNNDIQKNFQDFLDTYNAIFESDLSLENSKQLEEIVKDKISKLEKKDRILKLFP

GEKNSGIFSEFLKLIVGNQADFRKCFNLDEKASLHFSKESYDEDLETLLGYIGDDYSD

VFLKAKKLYDAILLSGFLTVTDNETEAPLSSAMIKRYNEHKEDLALLKEYIRNISLKT

YNEVFKDDTKNGYAGYIDGKTNQEDFYVYLKKLLAEFEGADYFLEKIDREDFLRKQ

RTFDNGSIPYQIHLQEMRAILDKQAKFYPFLAKNKERIEKILTFRIPYYVGPLARGNSD

FAWSIRKRNEKITPWNFEDVIDKESSAEAFINRMTSFDLYLPEEKVLPKHSLLYETFN

VYNELTKVRFIAESMRDYQFLDSKQKKDIVRLYFKDKRKVTDKDIIEYLHAIYGYDG

IELKGIEKQFNSSLSTYHDLLNIINDKEFLDDSSNEAIIEEIIHTLTIFEDREMIKQRLSKF

ENIFDKSVLKKLSRRHYTGWGKLSAKLINGIRDEKSGNTILDYLIDDGISNRNFMQLI

HDDALSFKKKIQKAQIIGDEDKGNIKEVVKSLPGSPAIKKGILQSIKIVDELVKVMGG

RKPESIVVEMARENQYTNQGKSNSQQRLKRLEKSLKELGSKILKENIPAKLSKIDNNA

LQNDRLYLYYLQNGKDMYTGDDLDIDRLSNYDIDHIIPQAFLKDNSIDNKVLVSSAS

NRGKSDDVPSLEVVKKRKTFWYQLLKSKLISQRKFDNLTKAERGGLSPEDKAGFIQR

QLVETRQITKHVARLLDEKFNNKKDENNRAVRTVKIITLKSTLVSQFRKDFELYKVR

EINDFHHAHDAYLNAVVASALLKKYPKLEPEFVYGDYPKYNSFRERKSATEKVYFY

SNIMNIFKKSISLADGRVIERPLIEVNEETGESVWNKESDLATVRRVLSYPQVNVVKK

VEEQNHGLDRGKPKGLFNANLSSKPKPNSNENLVGAKEYLDPKKYGGYAGISNSFT

VLVKGTIEKGAKKKITNVLEFQGISILDRINYRKDKLNFLLEKGYKDIELIIELPKYSLF

ELSDGSRRMLASILSTNNKRGEIHKGNQIFLSQKFVKLLYHAKRISNTINENHRKYVE

NHKKEFEELFYYILEFNENYVGAKKNGKLLNSAFQSWQNHSIDELCSSFIGPTGSERK

GLFELTSRGSAADFEFLGVKIPRYRDYTPSSLLKDATLIHQSVTGLYETRIDLAKLGEG

NP_721764.1 hypothetical protein SMU_1405c [*Streptococcus mutans* UA159]

(SEQ ID NO: 50)

MKKPYSIGLDIGTNSVGWAVVTDDYKVPAKKMKVLGNTDKSHIEKNLLGALLFDSG

NTAEDRRLKRTARRRYTRRRNRILYLQEIFSEEMGKVDDSFFHRLEDSFLVTEDKRG

ERHPIFGNLEEEVKYHENFPTIYHLRQYLADNPEKVDLRLVYLALAHIIKFRGHFLIEG

-continued

KFDTRNNDVQRLFQEFLAVYDNTFENSSLQEQNVQVEEILTDKISKSAKKDRVLKLF

PNEKSNGRFAEFLKLIVGNQADFKKHFELEEKAPLQFSKDTYEEELEVLLAQIGDNY

AELFLSAKKLYDSILLSGILTVTDVGTKAPLSASMIQRYNEHQMDLAQLKQFIRQKLS

DKYNEVFSDVSKDGYAGYIDGKTNQEAFYKYLKGLLNKIEGSGYFLDKIEREDFLRK

QRTFDNGSIPHQIHLQEMRAIIRRQAEFYPFLADNQDRIEKLLTFRIPYYVGPLARGKS

DFAWLSRKSADKITPWNFDEIVDKESSAEAFINRMTNYDLYLPNQKVLPKHSLLYEK

FTVYNELTKVKYKTEQGKTAFFDANMKQEIFDGVFKVYRKVTKDKLMDFLEKEFDE

FRIVDLTGLDKENKVFNASYGTYHDLCKILDKDFLDNSKNEKILEDIVLTLTLFEDRE

MIRKRLENYSDLLTKEQVKKLERRHYTGWGRLSAELIHGIRNKESRKTILDYLIDDG

NSNRNFMQLINDDALSFKEEIAKAQVIGETDNLNQVVSDIAGSPAIKKGILQSLKIVDE

LVKIMGHQPENIVVEMARENQFTNQGRRNSQQRLKGLTDSIKEFGSQILKEHPVENS

QLQNDRLFLYYLQNGRDMYTGEELDIDYLSQYDIDHIIPQAFIKDNSIDNRVLTSSKE

NRGKSDDVPSKDVVRKMKSYWSKLLSAKLITQRKFDNLTKAERGGLTDDDKAGFIK

RQLVETRQITKHVARILDERFNTETDENNKKIRQVKIVTLKSNLVSNFRKEFELYKVR

EINDYHHAHDAYLNAVIGKALLGVYPQLEPEFVYGDYPHFGHKENKATAKKFFYS

NIMNFFKKDDVRTDKNGEIIWKKDEHISNIKKVLSYPQVNIVKKVEEQTGGFSKESIL

PKGNSDKLIPRKTKKFYWDTKKYGGFDSPIVAYSILVIADIEKGKSKKLKTVKALVG

VTIMEKMTFERDPVAFLERKGYRNVQEENIIKLPKYSLFKLENGRKRLLASARELQK

GNEIVLPNHLGTLLYHAKNIHKVDEPKHLDYVDKHKDEFKELLDVVSNFSKKYTLA

EGNLEKIKELYAQNNGEDLKELASSFINLLTFTAIGAPATFKFFDKNIDRKRYTSTTEI

LNATLIHQSITGLYETRIDLNKLGGD

YP_004373648.1 CRISPR-associated protein, Csn1 family [*Coriobacterium glomerans* PW2]

(SEQ ID NO: 51)

MKLRGIEDDYSIGLDMGTSSVGWAVTDERGTLAHFKRKPTWGSRLFREAQTAAVAR

MPRGQRRRYVRRRWRLDLLQKLFEQQMEQADPDFFIRLRQSRLLRDDRAEEHADY

RWPLFNDCKFTERDYYQRFPTIYHVRSWLMETDEQADIRLIYLALHNIVKHRGNFLR

EGQSLSAKSARPDEALNHLRETLRVWSSERGFECSIADNGSILAMLTHPDLSPSDRRK

KIAPLFDVKSDDAAADKKLGIALAGAVIGLKTEFKNIFGDFPCEDSSIYLSNDEAVDA

VRSACPDDCAELFDRLCEVYSAYVLQGLLSYAPGQTISANMVEKYRRYGEDLALLK

KLVKIYAPDQYRMFFSGATYPGTGIYDAAQARGYTKYNLGPKKSEYKPSESMQYDD

FRKAVEKLFAKTDARADERYRMMMDRFDKQQFLRRLKTSDNGSIYHQLHLEELKAI

VENQGRFYPFLKRDADKLVSLVSFRIPYYVGPLSTRNARTDQHGENRFAWSERKPG

MQDEPIFPWNWESIIDRSKSAEKFILRMTGMCTYLQQEPVLPKSSLLYEEFCVLNELN

GAHWSIDGDDEHRFDAADREGIIEELFRRKRTVSYGDVAGWMERERNQIGAHVCGG

QGEKGFESKLGSYIFFCKDVFKVERLEQSDYPMIERIILWNTLFEDRKILSQRLKEEYG

SRLSAEQIKTICKKRFTGWGRLSEKFLTGITVQVDEDSVSIMDVLREGCPVSGKRGRA

MVMMEILRDEELGFQKKVDDFNRAFFAENAQALGVNELPGSPAVRRSLNQSIRIVDE

IASIAGKAPANIFIEVTRDEDPKKKGRRTKRRYNDLKDALEAFKKEDPELWRELCETA

PNDMDERLSLYFMQRGKCLYSGRAIDIHQLSNAGIYEVDHIIPRTYVKDDSLENKAL

VYREENQRKTDMLLIDPEIRRRMSGYWRMLHEAKLIGDKKFRNLLRSRIDDKALKG

FIARQLVETGQMVKLVRSLLEARYPETNIISVKASISHDLRTAAELVKCREANDFHHA

HDAFLACRVGLFIQKRHPCVYENPIGLSQVVRNYVRQQADIFKRCRTIPGSSGFIVNS

FMTSGFDKETGEIFKDDWDAEAEVEGIRRSLNFRQCFISRMPFEDHGVFWDATIYSPR

AKKTAALPLKQGLNPSRYGSFSREQFAYFFIYKARNPRKEQTLFEFAQVPVRLSAQIR

QDENALERYARELAKDQGLEFIRIERSKILKNQLIEIDGDRLCITGKEEVRNACELAFA

QDEMRVIRMLVSEKPVSRECVISLFNRILLHGDQASRRLSKQLKLALLSEAFSEASDN

VQRNVVLGLIAIFNGSTNMVNLSDIGGSKFAGNVRIKYKKELASPKVNVHLIDQ SVT

GMFERRTKIGL

ZP_08576281.1 possible CRISPR associated protein [*Lactobacillus farciminis* KCTC 3681]

(SEQ ID NO: 52)

MTKKEQPYNIGLDIGTSSVGWAVTNDNYDLLNIKKKNLWGVRLFEEAQTAKETRLN

RSTRRRYRRRKNRINWLNEIFSEELAKTDPSFLIRLQNSWVSKKDPDRKRDKYNLFID

GPYTDKEYYREFPTIFHLRKELILNKDKADIRLIYLALHNILKYRGNFTYEHQKFNISN

LNNNLSKELIELNQQLIKYDISFPDDCDWNHISDILIGRGNATQKSSNILKDFTLDKET

KKLLKEVINLILGNVAHLNTIFKTSLTKDEEKLNFSGKDIESKLDDLDSILDDDQFTVL

DAANRIYSTITLNEILNGESYFSMAKVNQYENHAIDLCKLRDMWHTTKNEEAVEQSR

QAYDDYINKPKYGTKELYTSLKKFLKVALPTNLAKEAEEKISKGTYLVKPRNSENGV

VPYQLNKIEMEKIIDNQSQYYPFLKENKEKLLSILSFRIPYYVGPLQSAEKNPFAWME

RKSNGHARPWNFDEIVDREKSSNKFIRRMTVTDSYLVGEPVLPKNSLIYQRYEVLNE

LNNIRITENLKTNPIGSRLTVETKQRIYNELFKKYKKVTVKKLTKWLIAQGYYKNPILI

GLSQKDEFNSTLTTYLDMKKIFGSSFMEDNKNYDQIEELIEWLTIFEDKQILNEKLHSS

KYSYTPDQIKKISNMRYKGWGRLSKKILMDITTETNTPQLLQLSNYSILDLMWATNN

NFISIMSNDKYDFKNYIENHNLNKNEDQNISDLVNDIHVSPALKRGITQSIKIVQEIVK

FMGHAPKHIFIEVTRETKKSEITTSREKRIKRLQSKLLNKANDFKPQLREYLVPNKKIQ

EELKKHKNDLSSERIMLYFLQNGKSLYSEESLNINKLSDYQVDHILPRTYIPDDSLEN

KALVLAKENQRKADDLLLNSNVIDRNLERWTYMLNNNMIGLKKFKNLTRRVITDK

DKLGFIHRQLVQTSQMVKGVANILDNMYKNQGTTCIQARANLSTAFRKALSGQDDT

YHFKHPELVKNRNVNDFHHAQDAYLASFLGTYRLRRFPTNEMLLMNGEYNKFYGQ

VKELYSKKKKLPDSRKNGFIISPLVNGTTQYDRNTGEIIWNVGFRDKILKIFNYHQCN

VTRKTEIKTGQFYDQTIYSPKNPKYKKLIAQKKDMDPNIYGGFSGDNKSSITIVKIDN

NKIKPVAIPIRLINDLKDKKTLQNWLEENVKHKKSIQIIKNNVPIGQIIYSKKVGLLSLN

SDREVANRQQLILPPEHSALLRLLQIPDEDLDQILAFYDKNILVEILQELITKMKKFYPF

YKGEREFLIANIENFNQATTSEKVNSLEELITLLHANSTSAHLIFNNIEKKAFGRKTHG

LTLNNTDFIYQSVTGLYETRIHIE

ZP_03683851.1 hypothetical protein CATMIT_02512, partial [*Catenibacterium mitsuokai* DSM 15897]

(SEQ ID NO: 53)

IVDYCIGLDLGTGSVGWAVVDMNHRLMKRNGKHLWGSRLFSNAETAANRRASRSI

RRRYNKRRERIRLLRAILQDMVLEKDPTFFIRLEHTSFLDEEDKAKYLGTDYKDNYN

LFIDEDFNDYTYYHKYPTIYHLRKALCESTEKADPRLIYALHHIVKYRGNFLYEGQK

FNMDASNIEDKLSDIFTQFTSFNNIPYEDDEKKNLEILEILKKPLSKKAKVDEVMTLIA

PEKDYKSAFKELVTGIAGNKMNVTKMILCEPIKQGDSEIKLKFSDSNYDDQFSEVEK

DLGEYVEFVDALHNVYSWVELQTIMGATHTDNASISEAMVSRYNKHHDDLKLLKD

-continued

CIKNNVPNKYFDMFRNDSEKSKGYYNYINRPSKAPVDEFYKYVKKCIEKVDTPEAK

QILNDIELENFLLKQNSRTNGSVPYQMQLDEMIKIIDNQAEYYPILKEKREQLLSILTF

RIPYYFGPLNETSEHAWIKRLEGKENQRILPWNYQDIVDVDATAEGFIKRMRSYCTY

FPDEEVLPKNSLIVSKYEVYNELNKIRVDDKLLEVDVKNDIYNELFMKNKTVTEKKL

KNWLVNNQCCSKDAEIKGFQKENQFSTSLTPWIDFTNIFGKIDQSNFDLIENIIYDLTV

FEDKKIMKRRLKKKYALPDDKVKQILKLKYKDWSRLSKKLLDGIVADNRFGSSVTV

LDVLEMSRLNLMEIINDKDLGYAQMIEEATSCPEDGKFTYEEVERLAGSPALKRGIW

QSLQIVEEITKVMKCRPKYIYIEFERSEEAKERTESKIKKLENVYKDLDEQTKKEYKS

VLEELKGFDNTKKISSDSLFLYFTQLGKCMYSGKKLDIDSLDKYQIDHIVPQSLVKDD

SFDNRVLVVPSENQRKLDDLVVPFDIRDKMYRFWKLLFDHELISPKKFYSLIKTEYTE

RDEERFINRQLVETRQITKNVTQIIEDHYSTTKVAAIRANLSHEFRVKNHIYKNRDIND

YHHAHDAYIVALIGGFMRDRYPNMHDSKAVYSEYMKMFRKNKNDQKRWKDGFVI

NSMNYPYEVDGKLIWNPDLINEIKKCFYYKDCYCTTKLDQKSGQLFNLTVLSNDAH

ADKGVTKAVVPVNKNRSDVHKYGGFSGLQYTIVAIEGQKKKGKKTELVKKISGVPL

HLKAASINEKINYIEEKEGLSDVRIIKDNIPVNQMIEMDGGEYLLTSPTEYVNARQLVL

NEKQCALIADIYNAIYKQDYDNLDDILMIQLYIELTNKMKVLYPAYRGIAEKFESMN

ENYVVISKEEKANIIKQMLIVMHRGPQNGNIVYDDFKISDRIGRLKTKNHNLNNIVFIS

QSPTGIYTKKYKL

YP_003171950.1 CRISPR-associated protein Csn1 [*Lactobacillus rhamnosus*
GG]

(SEQ ID NO: 54)

MTKLNQPYGIGLDIGSNSIGFAVVDANSHLLRLKGETAIGARLFREGQSAADRRGSRT

TRRRLSRTRWRLSFLRDFFAPHITKIDPDFFLRQKYSEISPKDKDRFKYEKRLFNDRTD

AEFYEDYPSMYHLRLHLMTHTHKADPREIFLAIHHILKSRGHFLTPGAAKDFNTDKV

DLEDIFPALTEAYAQVYPDLELTFDLAKADDFKAKLLDEQATPSDTQKALVNLLLSS

DGEKEIVKKRKQVLTEFAKAITGLKTKFNLALGTEVDEADASNWQFSMGQLDDKW

SNIETSMTDQGTEIFEQIQELYRARLLNGIVPAGMSLSQAKVADYGQHKEDLELFKTY

LKKLNDHELAKTIRGLYDRYINGDDAKPFLREDFVKALTKEVTAHPNEVSEQLLNR

MGQANFMLKQRTKANGAIPIQLQQRELDQIIANQSKYYDWLAAPNPVEAHRWKMP

YQLDELLNFHIPYYVGPLITPKQQAESGENVFAWMVRKDPSGNITPYNFDEKVDREA

SANTFIQRMKTTDTYLIGEDVLPKQSLLYQKYEVLNELNNVRINNECLGTDQKQRLI

REVFERHSSVTIKQVADNLVAHGDFARRPEIRGLADEKRFLSSLSTYHQLKEILHEAI

DDPTKLLDIENIITWSTVFEDHTIFETKLAEIEWLDPKKINELSGIRYRGWGQFSRKLL

DGLKLGNGHTVIQELMLSNHNLMQILADETLKETMTELNQDKLKTDDIEDVINDAY

TSPSNKKALRQVLRVVEDIKHAANGQDPSWLFIETADGTGTAGKRTQSRQKQIQTVY

ANAAQELIDSAVRGELEDKIADKASFTDRLVLYFMQGGRDIYTGAPLNIDQLSHYDI

DHILPQSLIKDDSLDNRVLVNATINREKNNVFASTLFAGKMKATWRKWHEAGLISGR

KLRNLMLRPDEIDKFAKGFVARQLVETRQIIKLTEQIAAAQYPNTKIIAVKAGLSHQL

REELDFPKNRDVNHYHHAFDAFLAARIGTYLLKRYPKLAPFFTYGEFAKVDVKKFR

EFNFIGALTHAKKNIIAKDTGEIVWDKERDIRELDRIYNFKRMLITHEVYFETADLFK

QTIYAAKDSKERGGSKQLIPKKQGYPTQVYGGYTQESGSYNALVRVAEADTTAYQV

IKISAQNASKIASANLKSREKGKQLLNEIVVKQLAKRRKNWKPSANSFKIVIPRFGMG

-continued

TLFQNAKYGLFMVNSDTYYRNYQELWLSRENQKLLKKLFSIKYEKTQMNHDALQV

YKAIIDQVEKFFKLYDINQFRAKLSDAIERFEKLPINTDGNKIGKTETLRQILIGLQANG

TRSNVKNLGIKTDLGLLQVGSGIKLDKDTQIVYQSPSGLFKRRIPLADL

YP_003937986.1 CRISPR associated protein [*Bifidobacterium bifidum* S17]
(SEQ ID NO: 55)

MSRKNYVDDYAISLDIGNASVGWSAFTPNYRLVRAKGHELIGVRLFDPADTAESRR

MARTTRRRYSRRRWRLRLLLDALFDQALSEIDPSFLARRKYSWVHPDDENNADCWY

GSVLFDSNEQDKRFYEKYPTIYHLRKALMEDDSQHDIREIYLAIHHMVKYRGNFLVE

GTLESSNAFKEDELLKLLGRITRYEMSEGEQNSDIEQDDENKLVAPANGQLADALCA

TRGSRSMRVDNALEALSAVNDLSREQRAIVKAIFAGLEGNKLDLAKIFVSKEFSSEN

KKILGIYFNKSDYEEKCVQIVDSGLLDDEEREFLDRMQGQYNAIALKQLLGRSTSVS

DSKCASYDAHRANWNLIKLQLRTKENEKDINENYGILVGWKIDSGQRKSVRGESAY

ENMRKKANVFFKKMIETSDLSETDKNRLIHDIEEDKLFPIQRDSDNGVIPHQLHQNEL

KQIIKKQGKYYPFLLDAFEKDGKQINKIEGLLTFRVPYFVGPLVVPEDLQKSDNSENH

WMVRKKKGEITPWNFDEMVDKDASGRKFIERLVGTDSYLLGEPTLPKNSLLYQEYE

VLNELNNVRLSVRTGNHWNDKRRMRLGREEKTLLCQRLFMKGQTVTKRTAENLLR

KEYGRTYELSGLSDESKFTSSLSTYGKMCRIFGEKYVNEHRDLMEKIVELQTVFEDK

ETLLHQLRQLEGISEADCALLVNTHYTGWGRLSRKLLTTKAGECKISDDFAPRKHSII

EIMRAEDRNLMEIITDKQLGFSDWIEQENLGAENGSSLMEVVDDLRVSPKVKRGIIQS

IRLIDDISKAVGKRPSRIFLELADDIQPSGRTISRKSRLQDLYRNANLGKEFKGIADELN

ACSDKDLQDDRLFLYYTQLGKDMYTGEELDLDRLSSAYDIDHIIPQAVTQNDSIDNR

VLVARAENARKTDSFTYMPQIADRMRNFWQILLDNGLISRVKFERLTRQNEFSEREK

ERFVQRSLVETRQIMKNVATLMRQRYGNSAAVIGLNAELTKEMHRYLGFSHKNRDI

NDYHHAQDALCVGIAGQFAANRGFFADGEVSDGAQNSYNQYLRDYLRGYREKLSA

EDRKQGRAFGFIVGSMRSQDEQKRVNPRTGEVVWSEEDKDYLRKVMNYRKMLVT

QKVGDDFGALYDETRYAATDPKGIKGIPFDGAKQDTSLYGGFSSAKPAYAVLIESKG

KTRLVNVTMQEYSLLGDRPSDDELRKVLAKKKSEYAKANILLRHVPKMQLIRYGGG

LMVIKSAGELNNAQQLWLPYEEYCYFDDLSQGKGSLEKDDLKKLLDSILGSVQCLY

PWHRFTEEELADLHVAFDKLPEDEKKNVITGIVSALHADAKTANLSIVGMTGSWRR

MNNKSGYTFSDEDEFIFQSPSGLFEKRVTVGELKRKAKKEVNSKYRTNEKRLPTLSG

ASQP

EHN59352.1 CRISPR-associated protein [*Oenococcus kitaharae* DSM 17330]
(SEQ ID NO: 56)

MARDYSVGLDIGTSSVGWAAIDNKYHLIRAKSKNLIGVRLFDSAVTAEKRRGYRTTR

RRLSRRHWRLRLLNDIFAGPLTDFGDENFLARLKYSWVHPQDQSNQAHFAAGLLFD

SKEQDKDFYRKYPTIYHLRLALMNDDQKHDLREVYLAIHHLVKYRGHFLIEGDVKA

DSAFDVHTFADAIQRYAESNNSDENLLGKIDEKKLSAALTDKHGSKSQRAETAETAF

DILDLQSKKQIQAILKSVVGNQANLMAIFGLDSSAISKDEQKNYKFSFDDADIDEKIA

DSEALLSDTEFEFLCDLKAAFDGLTLKMLLGDDKTVSAAMVRRFNEHQKDWEYIKS

HIRNAKNAGNGLYEKSKKFDGINAAYLALQSDNEDDRKKAKKIFQDEISSADIPDDV

KADFLKKIDDDQFLPIQRTKNNGTIPHQLHRNELEQIIEKQGIYYPFLKDTYQENSHEL

NKITALINFRVPYYVGPLVEEEQKIADDGKNIPDPTNHWMVRKSNDTITPWNLSQVV

DLDKSGRRFIERLTGTDTYLIGEPTLPKNSLLYQKFDVLQELNNIRVSGRRLDIRAKQ

```
DAFEHLFKVQKTVSATNLKDFLVQAGYISEDTQIEGLADVNGKNFNNALTTYNYLV

SVLGREFVENPSNEELLEEITELQTVFEDKKVLRRQLDQLDGLSDHNREKLSRKHYT

GWGRISKKLLTTKIVQNADKIDNQTFDVPRMNQSIIDTLYNTKMNLMEIINNAEDDF

GVRAWIDKQNTTDGDEQDVYSLIDELAGPKEIKRGIVQSFRILDDITKAVGYAPKRV

YLEFARKTQESHLTNSRKNQLSTLLKNAGLSELVTQVSQYDAAALQNDRLYLYFLQ

QGKDMYSGEKLNLDNLSNYDIDHIIPQAYTKDNSLDNRVLVSNITNRRKSDSSNYLP

ALIDKMRPFWSVLSKQGLLSKHKFANLTRTRDFDDMEKERFIARSLVETRQIIKNVAS

LIDSHFGGETKAVAIRSSLTADMRRYVDIPKNRDINDYHHAFDALLFSTVGQYTENS

GLMKKGQLSDSAGNQYNRYIKEWIHAARLNAQSQRVNPFGFVVGSMRNAAPGKLN

PETGEITPEENADWSIADLDYLHKVMNFRKITVTRRLKDQKGQLYDESRYPSVLHDA

KSKASINFDKHKPVDLYGGFSSAKPAYAALIKFKNKFRLVNVLRQWTYSDKNSEDYI

LEQIRGKYPKAEMVLSHIPYGQLVKKDGALVTISSATELHNFEQLWLPLADYKLINTL

LKTKEDNLVDILHNRLDLPEMTIESAFYKAFDSILSFAFNRYALHQNALVKLQAHRD

DFNALNYEDKQQTLERILDALHASPASSDLKKINLSSGFGRLFSPSHFTLADTDEFIFQ

SVTGLFSTQKTVAQLYQETK

ZP_08660870.1 possible CRISPR associated protein [Fructobacillus fructosus
KCTC 3544]
                                                                (SEQ ID NO: 57)
MVYDVGLDIGTGSVGWVALDENGKLARAKGKNLVGVRLFDTAQTAADRRGFRTT

RRRLSRRKWRLRLLDELFSAEINEIDSSFFQRLKYSYVHPKDEENKAHYYGGYLFPTE

EETKKFHRSYPTIYHLRQELMAQPNKRFDIREIYLAIHHLVKYRGHFLSSQEKITIGST

YNPEDLANAIEVYADEKGLSWELNNPEQLTEIISGEAGYGLNKSMKADEALKLFEFD

NNQDKVAIKTLLAGLTGNQIDFAKLFGKDISDKDEAKLWKLKLDDEALEEKSQTILS

QLTDEEIELFHAVVQAYDGFVLIGLLNGADSVSAAMVQLYDQHREDRKLLKSLAQK

AGLKHKRFSEIYEQLALATDEATIKNGISTARELVEESNLSKEVKEDTLRRLDENEFLP

KQRTKANSVIPHQLHLAELQKILQNQGQYYPFLLDTFEKEDGQDNKIEELLRFRIPYY

VGPLVTKKDVEHAGGDADNHWVERNEGFEKSRVTPWNFDKVFNRDKAARDFIERL

TGNDTYLIGEKTLPQNSLRYQLFTVLNELNNVRVNGKKFDSKTKADLINDLFKARKT

VSLSALKDYLKAQGKGDVTITGLADESKFNSSLSSYNDLKKTFDAEYLENEDNQETL

EKIIEIQTVFEDSKIASRELSKLPLDDDQVKKLSQTHYTGWGRLSEKLLDSKIIDERGQ

KVSILDKLKSTSQNFMSIINNDKYGVQAWITEQNTGSSKLTFDEKVNELTTSPANKRG

IKQSFAVLNDIKKAMKEEPRRVYLEFAREDQTSVRSVPRYNQLKEKYQSKSLSEEAK

VLKKTLDGNKNKMSDDRYFLYFQQQGKDMYTGRPINFERLSQDYDIDHIIPQAFTKD

DSLDNRVLVSRPENARKSDSFAYTDEVQKQDGSLWTSLLKSGFINRKKYERLTKAG

KYLDGQKTGFIARQLVETRQIIKNVASLIEGEYENSKAVAIRSEITADMRLLVGIKKH

REINSFHHAFDALLITAAGQYMQNRYPDRDSTNVYNEFDRYTNDYLKNLRQLSSRD

EVRRLKSFGFVVGTMRKGNEDWSEENTSYLRKVMMFKNILTTKKTEKDRGPLNKET

IFSPKSGKKLIPLNSKRSDTALYGGYSNVYSAYMTLVRANGKNLLIKIPISIANQIEVG

NLKINDYIVNNPAIKKFEKILISKLPLGQLVNEDGNLIYLASNEYRHNAKQLWLSTTD

ADKIASISENSSDEELLEAYDILTSENVKNRFPFFKKDIDKLSQVRDEFLDSDKRIAVIQ

TILRGLQIDAAYQAPVKIISKKVSDWHKLQQSGGIKLSDNSEMIYQSATGIFETRVKIS

DLL
```

YP_001691366.1 hypothetical protein FMG_0058 [*Finegoldia magna* ATCC 29328]

(SEQ ID NO: 58)

MKSEKKYYIGLDVGTNSVGWAVTDEFYNILRAKGKDLWGVRLFEKADTAANTRIFR

SGRRRNDRKGMRLQILREIFEDEIKKVDKDFYDRLDESKFWAEDKKVSGKYSLFND

KNFSDKQYFEKFPTIFHLRKYLMEEHGKVDIRYYFLAINQMMKRRGHFLIDGQISHV

TDDKPLKEQLILLINDLLKIELEEELMDSIFEILADVNEKRTDKKNNLKELIKGQDFNK

QEGNILNSIFESIVTGKAKIKNIISDEDILEKIKEDNKEDFVLTGDSYEENLQYFEEVLQ

ENITLFNTLKSTYDFLILQSILKGKSTLSDAQVERYDEHKKDLEILKKVIKKYDEDGKL

FKQVFKEDNGNGYVSYIGYYLNKNKKITAKKKISNIEFTKYVKGILEKQCDCEDEDV

KYLLGKIEQENFLLKQISSINSVIPHQIHLFELDKILENLAKNYPSFNNKKEEFTKIEKIR

KTFTFRIPYYVGPLNDYHKNNGGNAWIFRNKGEKIRPWNFEKIVDLHKSEEEFIKRM

LNQCTYLPEETVLPKSSILYSEYMVLNELNNLRINGKPLDTDVKLKLTEELFKKKTKV

TLKSIRDYMVRNNFADKEDFDNSEKNLEIASNMKSYIDFNNILEDKFDVEMVEDLIE

KITIHTGNKKLLKKYIEETYPDLSSSQIQKIINLKYKDWGRLSRKLLDGIKGTKKETEK

TDTVINFLRNSSDNLMQIIGSQNYSFNEYIDKLRKKYIPQEISYEVVENLYVSPSVKKM

IWQVIRVTEEITKVMGYDPDKIFIEMAKSEEEKKTTISRKNKLLDLYKAIKKDERDSQ

YEKLLTGLNKLDDSDLRSRKLYLYYTQMGRDMYTGEKIDLDKLFDSTHYDKDHIIP

QSMKKDDSIINNLVLVNKNANQTTKGNIYPVPSSIRNNPKIYNYWKYLMEKEFISKE

KYNRLIRNTPLTNEELGGFINRQLVETRQSTKAIKELFEKFYQKSKIIPVKASLASDLR

KDMNTLKSREVNDLHHAHDAFLNIVAGDVWNREFTSNPINYVKENREGDKVKYSLS

KDFTRPRKSKGKVIWTPEKGRKLIVDTLNKPSVLISNESHVKKGELFNATIAGKKDY

KKGKIYLPLKKDDRLQDVSKYGGYKAINGAFFFLVEHTKSKKRIRSIELFPLHLLSKF

YEDKNTVLDYAINVLQLQDPKIIIDKINYRTEIIIDNFSYLISTKSNDGSITVKPNEQMY

WRVDEISNLKKIENKYKKDAILTEEDRKIMESYIDKIYQQFKAGKYKNRRTTDTIIEK

YEIIDLDTLDNKQLYQLLVAFISL SYKTSNNAVDFTVIGLGTECGKPRITNLPDNTYLV

YKSITGIYEKRIRIK

ZP_07316256.1 CRISPR-associated protein, Csn1 family [*Veillonella atypica* ACS-134-V-Col7a]

(SEQ ID NO: 59)

METQTSNQLITSHLKDYPKQDYFVGLDIGTNSVGWAVTNTSYELLKFHSHKMWGSR

LFEEGESAVTRRGFRSMRRRLERRKLRLKLLEELFADAMAQVDSTFFIRLHESKYHY

EDKTTGHSSKHILFIDEDYTDQDYFTEYPTIYHLRKDLMENGTDDIRKLFLAVHHILK

YRGNFLYEGATFNSNAFTFEDVLKQALVNITFNCFDTNSAISSISNILMESGKTKSDK

AKAIERLVDTYTVFDEVNTPDKPQKEQVKEDKKTLKAFANLVLGLSANLIDLFGSVE

DIDDDLKKLQIVGDTYDEKRDELAKVWGDEIHIIDDCKSVYDAIILMSIKEPGLTISQS

KVKAFDKHKEDLVILKSLLKLDRNVYNEMFKSDKKGLHNYVHYIKQGRTEETSCSR

EDFYKYTKKIVEGLADSKDKEYILNEIELQTLLPLQRIKDNGVIPYQLHLEELKVILDK

CGPKFPFLHTVSDGFSVTEKLIKMLEFRIPYYVGPLNTHHNIDNGGFSWAVRKQAGR

VTPWNFEEKIDREKSAAAFIKNLTNKCTYLFGEDVLPKSSLLYSEFMLLNELNNVRID

GKALAQGVKQHLIDSIFKQDHKKMTKNRIELFLKDNNYITKKHKPEITGLDGEIKND

LTSYRDMVRILGNNFDVSMAEDIITDITIFGESKKMLRQTLRNKFGSQLNDETIKKLS

KLRYRDWGRLSKKLLKGIDGCDKAGNGAPKTIIELMRNDSYNLMEILGDKFSFMECI

-continued

EEENAKLAQGQVVNPHDIIDELALSPAVKRAVWQALRIVDEVAHIKKALPSRIFVEV

ARTNKSEKKKKDSRQKRLSDLYSAIKKDDVLQSGLQDKEFGALKSGLANYDDAALR

SKKLYLYYTQMGRCAYTGNIIDLNQLNTDNYDIDHIYPRSLTKDDSFDNLVLCERTA

NAKKSDIYPIDNRIQTKQKPFWAFLKHQGLISERKYERLTRIAPLTADDLSGFIARQLV

ETNQSVKATTTLLRRLYPDIDVVFVKAENVSDFRHNNNFIKVRSLNHHHHAKDAYL

NIVVGNVYHEKFTRNFRLFFKKNGANRTYNLAKMFNYDVICTNAQDGKAWDVKTS

MNTVKKMMASNDVRVTRRLLEQSGALADATIYKASVAAKAKDGAYIGMKTKYSV

FADVTKYGGMTKIKNAYSIIVQYTGKKGEEIKEIVPLPIYLINRNATDIELIDYVKSVIP

KAKDISIKYRKLCINQLVKVNGFYYYLGGKTNDKIYIDNAIELVVPHDIATYIKLLDK

YDLLRKENKTLKASSITTSIYNINTSTVVSLSNKVGIDVFDYFMSKLRTPLYMKMKGN

KVDELSSTGRSKFIKMTLEEQSIYLLEVLNLLTNSKTTFDVKPLGITGSRSTIGVKIHNL

DEFKIINESITGLYSNEVTIV

ZP_08029929.1 CRISPR-associated protein, Csn1 family [*Solobacterium moorei* F0204]

(SEQ ID NO: 60)

MEGQMKNNGNNLQQGNYYLGLDVGTSSVGWAVTDTDYNVLKFRGKSMWGARLF

DEASTAEEERRTHRGNRRRLARRKYRLLLLEQLFEKEIRKIDDNFFVRLHESNLWADD

KSKPSKFLLFNDTNFTDKDYLKKYPTIYHLRSDLIHNSTEHDIRLVFLALHHLIKYRG

HFIYDNSANGDVKTLDEAVSDFEEYLNENDIEFNIENKKEFINVLSDKHLTKKEKKIS

LKKLYGDITDSENINISVLIEMLSGSSISLSNLFKDIEFDGKQNLSLDSDIEETLNDVVDI

LGDNIDLLIHAKEVYDIAVLTSSLGKHKYLCDAKVELFEKNKKDLMILKKYIKKNHP

EDYKKIFSSPTEKKNYAAYSQTNSKNVCSQEEFCLFIKPYIRDMVKSENEDEVRIAKE

VEDKSFLTKLKGTNNSVVPYQIHERELNQILKNIVAYLPFMNDEQEDISVVDKIKLIFK

FKIPYYVGPLNTKSTRSWVYRSDEKIYPWNFSNVIDLDKTAHEFMNRLIGRCTYTND

PVLPMDSLLYSKYNVLNEINPIKVNGKAIPVEVKQAIYTDLFENSKKKVTRKSIYIYLL

KNGYIEKEDIVSGIDIEIKSKLKSHHDFTQIVQENKCTPEEIERIIKGILVYSDDKSMLRR

WLKNNIKGLSENDVKYLAKLNYKEWGRLSKTLLTDIYTINPEDGEACSILDIMWNTN

ATLMEILSNEKYQFKQNIENYKAENYDEKQNLHEELDDMYISPAARRSIWQALRIVD

EIVDIKKSAPKKIFIEMAREKKSAMKKKRTESRKDTLLELYKSCKSQADGFYDEELFE

KLSNESNSRLRRDQLYLYYTQMGRSMYTGKRIDFDKLINDKNTYDIDHIYPRSKIKD

DSITNRVLVEKDINGEKTDIYPISEDIRQKMQPFWKILKEKGLINEEKYKRLTRNYELT

DEELSSFVARQLVETQQSTKALATLLKKEYPSAKIVYSKAGNVSEFRNRKDKELPKF

REINDLHHAKDAYLNIVVGNVYDTKFTEKFFNNIRNENYSLKRVFDFSVPGAWDAK

GSTFNTIKKYMAKNNPIIAFAPYEVKGELFDQQIVPKGKGQFPIKQGKDIEKYGGYNK

LSSAFLAVEYKGKKARERSLETVYIKDVELYLQDPIKYCESVLGLKEPQIIKPKILMG

SLFSINNKKLVVTGRSGKQYVCHHIYQLSINDEDSQYLKNIAKYLQEEPDGNIERQNI

LNITSVNNIKLFDVLCTKFNSNTYEIILNSLKNDVNEGREKFSELDILEQCNILLQLLKA

FKCNRESSNLEKLNNKKQAGVIVIPHLFTKCSVFKVIHQSITGLFEKEMDLLK

ZP_03989815.1 crispr-associated protein [*Acidaminococcus* sp. D21]

(SEQ ID NO: 61)

MGKMYYLGLDIGTNSVGYAVTDPSYHLLKFKGEPMWGAHVFAAGNQSAERRSFRT

SRRRLDRRQQRVKLVQEIFAPVISPIDPRFFIRLHESALWRDDVAETDKHIFFNDPTYT

DKEYYSDYPTIHHLIVDLMESSEKHDPRLVYLAVAWLVAHRGHFLNEVDKDNIGDV

-continued

LSFDAFYPEFLAFLSDNGVSPWVCESKALQATLLSRNSVNDKYKALKSLIFGSQKPE

DNFDANISEDGLIQLLAGKKVKVNKLFPQESNDASFTLNDKEDAIEEILGTLTPDECE

WIAHIRRLFDWAIMKHALKDGRTISESKVKLYEQHFIHDLTQLKYFVKTYLAKEYDD

IFRNVDSETTKNYVAYSYHVKEVKGTLPKNKATQEEFCKYVLGKVKNIECSEADKV

DFDEMIQRLTDNSFMPKQVSGENRVIPYQLYYYELKTILNKAASYLPFLTQCGKDAIS

NQDKLLSIMTFRIPYFVGPLRKDNSEHAWLERKAGKIYPWNFNDKVDLDKSEEAFIR

RMTNTCTYYPGEDVLPLDSLIYEKFMILNEINNIRIDGYPISVDVKQQVFGLFEKKRR

VTVKDIQNLLLSLGALDKHGKLTGIDTTIHSNYNTYHHFKSLMERGVLTRDDVERIV

ERMTYSDDTKRVRLWLNNNYGTLTADDVKHISRLRKHDFGRLSKMFLTGLKGVHK

ETGERASILDFMWNTNDNLMQLLSECYTFSDEITKLQEAYYAKAQLSLNDFLDSMYI

SNAVKRPIYRTLAVVNDIRKACGTAPKRIFIEMARDGESKKKRSVTRREQIKNLYRSI

RKDFQQEVDFLEKILENKSDGQLQSDALYLYFAQLGRDMYTGDPIKLEHIKDQSFYN

IDHIYPQSMVKDDSLDNKVLVQSEINGEKSSRYPLDAAIRNKMKPLWDAYYNHGLI

SLKKYQRLTRSTPFTDDEKWDFINRQLVETRQSTKALAILLKRKFPDTEIVYSKAGLS

SDFRHEFGLVKSRNINDLHHAKDAFLAIVTGNVYHERFNRRWFMVNQPYSVKTKTL

FTHSIKNGNFVAWNGEEDLGRIVKMLKQNKNTIHFTRFSFDRKEGLFDIQPLKASTGL

VPRKAGLDVVKYGGYDKSTAAYYLLVRFTLEDKKTQHKLMMIPVEGLYKARIDHD

KEFLTDYAQTTISEILQKDKQKVINIMFPMGTRHIKLNSMISIDGFYLSIGGKSSKGKS

VLCHAMVPLIVPHKIECYIKAMESFARKFKENNKLRIVEKFDKITVEDNLNLYELFLQ

KLQHNPYNKFFSTQFDVLTNGRSTFTKLSPEEQVQTLLNILSIFKTCRSSGCDLKSING

SAQAARIMISADLTGLSKKYSDIRLVEQSASGLFVSKSQNLLEYL

ZP_07455288.1 csn1 family CRISPR-associated protein [*Eubacterium yurii*
subsp. *margaretiae* ATCC 43715]

(SEQ ID NO: 62)

MENKQYYIGLDVGTNSVGWAVTDTSYNLLRAKGKDMWGARLFEKANTAAERRTK

RTSRRRSEREKARKAMLKELFADEINRVDPSFFIRLEESKFFLDDRSENNRQRYTLFN

DATFTDKDYYEKYKTIFHLRSALINSDEKFDVRLVFLAILNLFSHRGHFLNASLKGDG

DIQGMDVFYNDLVESCEYFEIELPRITNIDNFEKILSQKGKSRTKILEELSEELSISKKD

KSKYNLIKLISGLEASVVELYNIEDIQDENKKIKIGFRESDYEESSLKVKEIIGDEYFDL

VERAKSVHDMGLLSNIIGNSKYLCEARVEAYENHHKDLLKIKELLKKYDKKAYNDM

FRKMTDKNYSAYVGSVNSNIAKERRSVDKRKIEDLYKYIEDTALKNIPDDNKDKIEIL

EKIKLGEFLKKQLTASNGVIPNQLQSRELRAILKKAENYLPFLKEKGEKNLTVSEMIIQ

LFEFQIPYYVGPLDKNPKKDNKANSWAKIKQGGRILPWNFEDKVDVKGSRKEFIEK

MVRKCTYISDEHTLPKQSLLYEKFMVLNEINNIKIDGEKISVEAKQKIYNDLFVKGKK

VSQKDIKKELISLNIMDKDSVLSGTDTVCNAYLSSIGKFTGVFKEEINKQSIVDMIEDII

FLKTVYGDEKRFVKEEIVEKYGDEIDKDKIKRILGFKFSNWGNLSKSFLELEGADVGT

GEVRSIIQSLWETNFNLMELLSSRFTYMDELEKRVKKLEKPLSEWTIEDLDDMYLSSP

VKRMIWQSMKIVDEIQTVIGYAPKRIFVEMTRSEGEKVRTKSRKDRLKELYNGIKED

SKQWVKELDSKDESYFRSKKMYLYYLQKGRCMYSGEVIELDKLMDDNLYDIDHIYP

RSFVKDDSLDNLVLVKKEINNRKQNDPITPQIQASCQGFWKILHDQGFMSNEKYSRL

TRKTQEFSDEEKLSFINRQIVETGQATKCMAQILQKSMGEDVDVVFSKARLVSEFRH

KFELFKSRLINDFHHANDAYLNIVVGNSYFVKFTRNPANFIKDARKNPDNPVYKYH

-continued

MDRFFERDVKSKSEVAWIGQSEGNSGTIVIVKKTMAKNSPLITKKVEEGHGSITKETI

VGVKEIKFGRNKVEKADKTPKKPNLQAYRPIKTSDERLCNILRYGGRTSISISGYCLV

EYVKKRKTIRSLEAIPVYLGRKDSLSEEKLLNYFRYNLNDGGKDSVSDIRLCLPFISTN

SLVKIDGYLYYLGGKNDDRIQLYNAYQLKMKKEEVEYIRKIEKAVSMSKFDEIDREK

NPVLTEEKNIELYNKIQDKFENTVFSKRMSLVKYNKKDLSFGDFLKNKKSKFEEIDLE

KQCKVLYNIIFNLSNLKEVDLSDIGGSKSTGKCRCKKNITNYKEFKLIQQSITGLYSCE

KDLMTI

CBK78998.1 CRISPR-associated endonuclease, Csn1 family [*Coprococcus catus* GD/7]

(SEQ ID NO: 63)

MKQEYFLGLDMGTGSLGWAVTDSTYQVMRKHGKALWGTRLFESASTAEERRMFR

TARRRLDRRNWRIQVLQEIFSEEISKVDPGFFLRMKESKYYPEDKRDAEGNCPELPY

ALFVDDNYTDKNYHKDYPTIYHLRKMLMETTEIPDIRLVYLVLHHMMKHRGHFLLS

GDISQIKEFKSTFEQLIQNIQDEELEWHISLDDAAIQFVEHVLKDRNLTRSTKKSRLIK

QLNAKSACEKAILNLLSGGTVKLSDIFNNKELDESERPKVSFADSGYDDYIGIVEAEL

AEQYYTIASAKAVYDWSVLVEILGNSVSISEAKIKVYQKHQADLKTLKKIVRQYMTK

EDYKRVFVDTEEKLNNYSAYIGMTKKNGKKVDLKSKQCTQADFYDFLKKNVIKVID

HKEITQEIESEIEKENFLPKQVTKDNGVIPYQVHDYELKKILDNLGTRMPFIKENAEKI

QQLFEFRIPYYVGPLNRVDDGKDGKFTWSVRKSDARTYPWNFTEVIDVEASAEKFIR

RMTNKCTYLVGEDVLPKDSLVYSKFMVLNELNNLRLNGEKISVELKQRIYEELFCKY

RKVTRKKLERYLVIEGIAKKGVEITGIDGDFKASLTAYHDFKERLTDVQLSQRAKEAI

VLNVVLFGDDKKLLKQRLSKMYPNLTTGQLKGICSLSYQGWGRLSKTFLEEITVPAP

GTGEVWNIMTALWQTNDNLMQLLSRNYGFTNEVEEFNTLKKETDLSYKTVDELYV

SPAVKRQIWQTLKVVKEIQKVMGNAPKRVFVEMAREKQEGKRSDSRKKQLVELYR

ACKNEERDWITELNAQSDQQLRSDKLFLYYIQKGRCMYSGETIQLDELWDNTKYDI

DHIYPQSKTMDDSLNNRVLVKKNYNAIKSDTYPLSLDIQKKMMSFWKMLQQQGFIT

KEKYVRLVRSDELSADELAGFIERQIVETRQSTKAVATILKEALPDTEIVYVKAGNVS

NFRQTYELLKVREMNDLHHAKDAYLNIVVGNAYFVKFTKNAAWFIRNNPGRSYNL

KRMFEFDIERSGEIAWKAGNKGSIVTVKKVMQKNNILVTRKAYEVKGGLFDQQIMK

KGKGQVPIKGNDERLADIEKYGGYNKAAGTYFMLVKSLDKKGKEIRTIEFVPLYLKN

QIEINHESAIQYLAQERGLNSPEILLSKIKIDTLFKVDGFKMWLSGRTGNQLIFKGANQ

LILSHQEAAILKGVVKYVNRKNENKDAKLSERDGMTEEKLLQINDTFLDKLSNTVY

SIRLSAQIKTLTEKRAKFIGLSNEDQCIVLNEILHMFQCQSGSANLKLIGGPGSAGILV

MNNNITACKQISVINQSPTGIYEKEIDLIKL

ZP_00143587.1 hypothetical protein [*Fusobacterium nucleatum* subsp. *vincentii* ATCC 49256]

(SEQ ID NO: 64)

MKKQKFSDYYLGFDIGTNSVGWCVTDLDYNVLRFNKKDMWGSRLFDEAKTAAER

RVQRNSRRRLKRRKWRLNLLEEIFSDEIMKIDSNFFRRLKESSLWLEDKNSKEKFTLF

NDDNYKDYDFYKQYPTIFHLRDELIKNPEKKDIRLIYLALHSIFKSRGHFLFEGQNLK

EIKNFETLYNNLISFLEDNGINKSIDKDNIEKLEKIICDSGKGLKDKEKEFKGIFNSDKQ

LVAIFKLSVGSSVSLNDLFDTDEYKKEEVEKEKISFREQIYEDDKPIYYSILGEKIELLD

IAKSFYDFMVLNNILSDSNYISEAKVKLYEEHKKDLKNLKYIIRKYNKENYDKLFKD

KNENNYPAYIGLNKEKDKKEVVEKSRLKIDDLIKVIKGYLPKPERIEEKDKTIFNEILN

-continued

KIELKTILPKQRISDNGTLPYQIHEVELEKILENQSKYYDFLNYEENGVSTKDKLLKTF

KFRIPYYVGPLNSYHKDKGGNSWIVRKEEGKILPWNFEQKVDIEKSAEEFIKRMTNK

CTYLNGEDVIPKDSFLYSEYIILNELNKVQVNDEFLNEENKRKIIDELFKENKKVSEKK

FKEYLLVNQIANRTVELKGIKDSFNSNYVSYIKFKDIFGEKLNLDIYKEISEKSILWKC

LYGDDKKIFEKKIKNEYGDILNKDEIKKINSFKFNTWGRLSEKLLTGIEFINLETGECY

SSVMEALRRTNYNLMELLSSKFTLQESIDNENKEMNEVSYRDLIEESYVSPSLKRAIL

QTLKIYEEIKKITGRVPKKVFIEMARGGDESMKNKKIPARQEQLKKLYDSCGNDIANF

SIDIKEMKNSLSSYDNNSLRQKKLYLYYLQFGKCMYTGREIDLDRLLQNNDTYDIDH

IYPRSKVIKDDSFDNLVLVLKNENAEKSNEYPVKKEIQEKMKSFWRFLKEKNFISDEK

YKRLTGKDDFELRGFMARQLVNVRQTTKEVGKILQQIEPEIKIVYSKAEIASSFREMF

DFIKVRELNDTHHAKDAYLNIVAGNVYNTKFTEKPYRYLQEIKENYDVKKIYNYDIK

NAWDKENSLEIVKKNMEKNTVNITRFIKEEKGELFNLNPIKKGETSNEIISIKPKLYDG

KDNKLNEKYGYYTSLKAAYFIYVEHEKKNKKVKTFERITRIDSTLIKNEKNLIKYLVS

QKKLLNPKIIKKIYKEQTLIIDSYPYTFTGVDSNKKVELKNKKQLYLEKKYEQILKNA

LKFVEDNQGETEENYKFIYLKKRNNNEKNETIDAVKERYNIEFNEMYDKFLEKLSSK

DYKNYINNKLYTNFLNSKEKFKKLKLWEKSLILREFLKIFNKNTYGKYEIKDSQTKE

KLFSFPEDTGRIRLGQSSLGNNKELLEESVTGLFVKKIKL

YP_005054169.1 CRISPR-associated protein, Csn1 family [*Filifactor alocis* ATCC 35896]

(SEQ ID NO: 65)

MTKEYYLGLDVGTNSVGWAVTDSQYNLCKFKKKDMWGIRLFESANTAKDRRLQR

GNRRRLERKKQRIDLLQEIFSPEICKIDPTFFIRLNESRLHLEDKSNDFKYPLFIEKDYS

DIEYYKEFPTIFHLRKHLIESEEKQDIRLIYLALHNIIKTRGHFLIDGDLQSAKQLRPILD

TFLLSLQEEQNLSVSLSENQKDEYEEILKNRSIAKSEKVKKLKNLFEISDELEKEEKKA

QSAVIENFCKFIVGNKGDVCKFLRVSKEELEIDSFSFSEGKYEDDIVKNLEEKVPEKV

YLFEQMKAMYDWNILVDILETEEYISFAKVKQYEKHKTNLRLLRDIILKYCTKDEYN

RMFNDEKEAGSYTAYVGKLKKNNKKYWIEKKRNPEEFYKSLGKLLDKIEPLKEDLE

VLTMMIEECKNHTLLPIQKNKDNGVIPHQVHEVELKKILENAKKYYSFLTETDKDGY

SVVQKIESIFRFRIPYYVGPLSTRHQEKGSNVWMVRKPGREDRIYPWNMEEIIDFEKS

NENFITRMTNKCTYLIGEDVLPKHSLLYSKYMVLNELNNVKVRGKKLPTSLKQKVFE

DLFENKSKVTGKNLLEYLQIQDKDIQIDDLSGFDKDFKTSLKSYLDFKKQIFGEEIEKE

SIQNMIEDIIKWITIYGNDKEMLKRVIRANYSNQLTEEQMKKITGFQYSWGNFSKMF

LKGISGSDVSTGETFDIITAMWETDNNLMQILSKKFTFMDNVEDFNSGKVGKIDKITY

DSTVKEMFLSPENKRAVWQTIQVAEEIKKVMGCEPKKIFIEMARGGEKVKKRTKSR

KAQLLELYAACEEDCRELIKEIEDRDERDFNSMKLFLYYTQFGKCMYSGDDIDINELI

RGNSKWDRDHIYPQSKIKDDSIDNLVLVNKTYNAKKSNELLSEDIQKKMHSFWLSLL

NKKLITKSKYDRLTRKGDFTDEELSGFIARQLVETRQSTKAIADIFKQIYSSEVVYVKS

SLVSDFRKKPLNYLKSRRVNDYHHAKDAYLNIVVGNVYNKKFTSNPIQWMKKNRD

TNYSLNKVFEHDVVINGEVIWEKCTYHEDTNTYDGGTLDRIRKIVERDNILYTEYAY

CEKGELFNATIQNKNGNSTVSLKKGLDVKKYGGYFSANTSYFSLIEFEDKKGDRARH

IIGVPIYIANMLEHSPSAFLEYCEQKGYQNVRILVEKIKKNSLLIINGYPLRIRGENEVD

TSFKRAIQLKLDQKNYELVRNIEKFLEKYVEKKGNYPIDENRDHITHEKMNQLYEVL

LSKMKKFNKKGMADPSDRIEKSKPKFIKLEDLIDKINVINKMLNLLRCDNDTKADLS

LIELPKNAGSFVVKKNTIGKSKIILVNQSVTGLYENRREL

ZP_07398877.1 csn1 family CRISPR-associated protein [*Peptoniphilus duerdenii* ATCC BAA-1640]

(SEQ ID NO: 66)

MKNLKEYYIGLDIGTASVGWAVTDESYNIPKFNGKKMWGVRLFDDAKTAEERRTQ

RGSRRRLNRRKERINLLQDLFATEISKVDPNFFLRLDNSDLYREDKDEKLKSKYTLFN

DKDFKDRDYHKKYPTIHHLIMDLIEDEGKKDIRLLYLACHYLLKNRGHFIFEGQKFD

TKNSFDKSINDLKIHLRDEYNIDLEFNNEDLIDITDTTLNKTNKKKELKNIVGDTKFL

KAISAIMIGSSQKLVDLFEDGEFEETTVKSVDFSTTAFDDKYSEYEEALGDTISLLNIL

KSIYDSSILENLLKDADKSKDGNKYISKAFVKKFNKHGKDLKTLKRIIKKYLPSEYAN

IFRNKSINDNYVAYTKSNITSNKRTKASKFTKQEDFYKFIKKHLDTIKETKLNSSENED

LKLIDEMLTDIEFKTFIPKLKSSDNGVIPYQLKLMELKKILDNQSKYYDFLNESDEYGT

VKDKVESIMEFRIPYYVGPLNPDSKYAWIKRENTKITPWNFKDIVDLDSSREEFIDRLI

GRCTYLKEEKVLPKASLIYNEFMVLNELNNLKLNEFLITEEMKKAIFEELFKTKKKVT

LKAVSNLLKKEFNLTGDILLSGTDGDFKQGLNSYIDFKNIIGDKVDRDDYRIKIEEIIK

LIVLYEDDKTYLKKKIKSAYKNDFTDDEIKKIAALNYKDWGRLSKRFLTGIEGVDKT

TGEKGSIIYFMREYNLNLMELMSGHYTFTEEVEKLNPVENRELCYEMVDELYLSPSV

KRMLWQSLRVVDEIKRIIGKDPKKIFIEMARAKEAKNSRKESRKNKLLEFYKFGKKA

FINEIGEERYNYLLNEINSEEESKFRWDNLYLYYTQLGRCMYSLEPIDLADLKSNNIY

DQDHIYPKSKIYDDSLENRVLVKKNLNHEKGNQYPIPEKVLNKNAYGFWKILFDKGL

IGQKKYTRLTRRTPFEERELAEFIERQIVETRQATKETANLLKNICQDSEIVYSKAENA

SRFRQEFDIIKCRTVNDLHHMHDAYLNIVVGNVYNTKFTKNPLNFIKDKDNVRSYNL

ENMFKYDVVRGSYTAWIADDSEGNVKAATIKKVKRELEGKNYRFTRMSYIGTGGL

YDQNLMRKGKGQIPQKENTNKSNIEKYGGYNKASSAYFALIESDGKAGRERTLETIPI

MVYNQEKYGNTEAVDKYLKDNLELQDPKILKDKIKINSLIKLDGFLYNIKGKTGDSL

STAGSVQLIVNKEEQKLIKKMDKFLVKKKDNKDIKVTSFDNIKEEELIKLYKTLSDKL

NNGIYSNKRNNQAKNISEALDKFKEISIEEKIDVLNQIILLFQSYNNGCNLKSIGLSAKT

GVVFIPKKLNYKECKLINQSITGLFENEVDLLNL

NP_970941.1 CRISPR-associated Cas5e [*Treponema denticola* ATCC 35405]

(SEQ ID NO: 67)

MKKEIKDYFLGLDVGTGSVGWAVTDTDYKLLKANRKDLWGMRCFETAETAEVRR

LHRGARRRIERRKKRIKLLQELFSQEIAKTDEGFFQRMKESPFYAEDKTILQENTLFN

DKDFADKTYHKAYPTINHLIKAWIENKVKPDPRLLYLACHNIIKKRGHFLFEGDFDSE

NQFDTSIQALFEYLREDMEVDIDADSQKVKEILKDSSLKNSEKQSRLNKILGLKPSDK

QKKAITNLISGNKINFADLYDNPDLKDAEKNSISFSKDDFDALSDDLASILGDSFELLL

KAKAVYNCSVLSKVIGDEQYLSFAKVKIYEKHKTDLTKLKNVIKKHFPKDYKKVFG

YNKNEKNNNNYSGYVGVCKTKSKKLIINNSVNQEDFYKFLKTILSAKSEIKEVNDILT

EIETGTFLPKQISKSNAEIPYQLRKMELEKILSNAEKHFSFLKQKDEKGLSHSEKIIMLL

TFKIPYYIGPINDNHKKFFPDRCWVVKKEKSPSGKTTPWNFFDHIDKEKTAEAFITSR

TNFCTYLVGESVLPKSSLLYSEYTVLNEINNLQIIIDGKNICDIKLKQKIYEDLFKKYK

KITQKQISTFIKHEGICNKTDEVIILGIDKECTSSLKSYIELKNIFGKQVDEISTKNMLEEI

IRWATIYDEGEGKTILKTKIKAEYGKYCSDEQIKKILNLKFSGWGRLSRKFLETVTSE

MPGFSEPVNIITAMRETQNNLMELLSSEFTFTENIKKINSGFEDAEKQFSYDGLVKPLF

LSPSVKKMLWQTLKLVKEISHITQAPPKKIFIEMAKGAELEPARTKTRLKILQDLYNN

CKNDADAFSSEIKDLSGKIENEDNLRLRSDKLYLYYTQLGKCMYCGKPIEIGHVFDTS

NYDIDHIYPQSKIKDDSISNRVLVCSSCNKNKEDKYPLKSEIQSKQRGFWNFLQRNNF

ISLEKLNRLTRATPISDDETAKFIARQLVETRQATKVAAKVLEKMFPETKIVYSKAET

VSMFRNKFDIVKCREINDFHHAHDAYLNIVVGNVYNTKFTNNPWNFIKEKRDNPKIA

DTYNYYKVFDYDVKRNNITAWEKGKTIITVKDMLKRNTPIYTRQAACKKGELFNQT

IMKKGLGQHPLKKEGPFSNISKYGGYNKVSAAYYTLIEYEEKGNKIRSLETIPLYLVK

DIQKDQDVLKSYLTDLLGKKEFKILVPKIKINSLLKINGFPCHITGKTNDSFLLRPAVQ

FCCSNNEVLYFKKIIRFSEIRSQREKIGKTISPYEDLSFRSYIKENLWKKTKNDEIGEKE

FYDLLQKKNLEIYDMLLTKHKDTIYKKRPNSATIDILVKGKEKFKSLIIENQFEVILEIL

KLFSATRNVSDLQHIGGSKYSGVAKIGNKISSLDNCILIYQSITGIFEKRIDLLKV

ZP_07912707.1 conserved hypothetical protein [*Staphylococcus lugdunensis* M23590]
(SEQ ID NO: 68)

MNQKFILGLDIGITSVGYGLIDYETKNIIDAGVRLFPEANVENNEGRRSKRGSRRLKR

RRIHRLERVKKLLEDYNLLDQSQIPQSTNPYAIRVKGLSEALSKDELVIALLHIAKRRG

IHKIDVIDSNDDVGNELSTKEQLNKNSKLLKDKFVCQIQLERMNEGQVRGEKNRFKT

ADIIKEIIQLLNVQKNFHQLDENFINKYIELVEMRREYFEGPGKGSPYGWEGDPKAW

YETLMGHCTYFPDELRSVKYAYSADLFNALNDLNNLVIQRDGLSKLEYHEKYHIIEN

VFKQKKKPTLKQIANEINVNPEDIKGYRITKSGKPQFTEFKLYHDLKSVLFDQSILENE

DVLDQIAEILTIYQDKDSIKSKLTELDILLNEEDKENIAQLTGYTGTHRLSLKCIRLVLE

EQWYSSRNQMEIFTHLNIKPKKINLTAANKIPKAMIDEFILSPVVKRTFGQAINLINKII

EKYGVPEDIIIELARENNSKDKQKFINEMQKKNENTRKRINEIIGKYGNQNAKRLVEK

IRLHDEQEGKCLYSLESIPLEDLLNNPNHYEVDHIIPRSVSFDNSYHNKVLVKQSENSK

KSNLTPYQYFNSGKSKLSYNQFKQHILNLSKSQDRISKKKKEYLLEERDINKFEVQKE

FINRNLVDTRYATRELTNYLKAYFSANNMNVKVKTINGSFTDYLRKVWKFKKERNH

GYKHHAEDALIIANADFLFKENKKLKAVNSVLEKPEIESKQLDIQVDSEDNYSEMFIIP

KQVQDIKDFRNFKYSHRVDKKPNRQLINDTLYSTRKKDNSTYIVQTIKDIYAKDNTT

LKKQFDKSPEKFLMYQHDPRTFEKLEVIMKQYANEKNPLAKYHEETGEYLTKYSKK

NNGPIVKSLKYIGNKLGSHLDVTHQFKSSTKKLVKLSIKPYRFDVYLTDKGYKFITIS

YLDVLKKDNYYYIPEQKYDKLKLGKAIDKNAKFIASFYKNDLIKLDGEIYKIIGVNSD

TRNMIELDLPDIRYKEYCELNNIKGEPRIKKTIGKKVNSIEKLTTDVLGNVFTNTQYT

KPQLLFKRGN

ZP_02077990.1 hypothetical protein EUBDOL_01797 [*Eubacterium dolichum* DSM 3991]
(SEQ ID NO: 69)

MMEVFMGRLVLGLDIGITSVGFGIIDLDESEIVDYGVRLFKEGTAAENETRRTKRGGR

RLKRRRVTRREDMLHLLKQAGIISTSFHPLNNPYDVRVKGLNERLNGEELATALLHL

CKHRGSSVETIEDDEAKAKEAGETKKVLSMNDQLLKSGKYVCEIQKERLRTNGHIRG

HENNFKTRAYVDEAFQILSHDLSNELKSAIITIISRKRMYYDGPGGPLSPTPYGRYTY

FGQKEPIDLIEKMRGKCSLFPNEPRAPKLAYSAELFNLLNDLNNLSIEGEKLTSEQKA

MILKIVHEKGKITPKQLAKEVGVSLEQIRGFRIDTKGSPLLSELTGYKMIREVLEKSND

-continued

EHLEDHVFYDEIAEILTKTKDIEGRKKQISELSSDLNEESVHQLAGLTKFTAYHSLSFK

ALRLINEEMLKTELNQMQSITLFGLKQNNELSVKGMKNIQADDTAILSPVAKRAQRE

TFKVVNRLREIYGEFDSIVVEMAREKNSEEQRKAIRERQKFFEMRNKQVADIIGDDR

KINAKLREKLVLYQEQDGKTAYSLEPIDLKLLIDDPNAYEVDHIIPISISLDDSITNKVL

VTHRENQEKGNLTPISAFVKGRFTKGSLAQYKAYCLKLKEKNIKTNKGYRKKVEQY

LLNENDIYKYDIQKEFINRNLVDTSYASRVVLNTLTTYFKQNEIPTKVFTVKGSLTNA

FRRKINLKKDRDEDYGHHAIDALIIASMPKMRLLSTIFSRYKIEDIYDESTGEVFSSGD

DSMYYDDRYFAFIASLKAIKVRKFSHKIDTKPNRSVADETIYSTRVIDGKEKVVKKY

KDIYDPKFTALAEDILNNAYQEKYLMALHDPQTFDQIVKVVNYYFEEMSKSEKYFT

KDKKGRIKISGMNPLSLYRDEHGMLKKYSKKGDGPAITQMKYFDGVLGNHIDISAH

YQVRDKKVVLQQISPYRTDFYYSKENGYKFVTIRYKDVRWSEKKKKYVIDQQDYA

MKKAEKKIDDTYEFQFSMHRDELIGITKAEGEALIYPDETWHNFNFFFHAGETPEILK

FTATNNDKSNKIEVKPIHCYCKMRLMPTISKKIVRIDKYATDVVGNLYKVKKNTLKF

EFD

YP_820161.1 CRISPR-system-like protein [*Streptococcus thermophilus* LMD-9]

(SEQ ID NO: 70)

MSDLVLGLDIGIGSVGVGILNKVTGEIIHKNSRIFPAAQAENNLVRRTNRQGRRLARR

KKHRRVRLNRLFEESGLITDFTKISINLNPYQLRVKGLTDELSNEELFIALKNMVKHR

GISYLDDASDDGNSSVGDYAQIVKENSKQLETKTPGQIQLERYQTYGQLRGDFTVEK

DGKKHRLINVFPTSAYRSEALRILQTQQEFNPQITDEFINRYLEILTGKRKYYHGPGNE

KSRTDYGRYRTSGETLDNIFGILIGKCTFYPDEFRAAKASYTAQEFNLLNDLNNLTVP

TETKKLSKEQKNQIINYVKNEKAMGPAKLFKYIAKLLSCDVADIKGYRIDKSGKAEI

HTFEAYRKMKTLETLDIEQMDRETLDKLAYVLTLNTEREGIQEALEHEFADGSFSQK

QVDELVQFRKANSSIFGKGWHNFSVKLMMELIPELYETSEEQMTILTRLGKQKTTSSS

NKTKYIDEKLLTEEIYNPVVAKSVRQAIKIVNAAIKEYGDFDNIVIEMARETNEDDEK

KAIQKIQKANKDEKDAAMLKAANQYNGKAELPHSVFHGHKQLATKIRLWHQQGER

CLYTGKTISIHDLINNSNQFEVDHILPLSITFDDSLANKVLVYATANQEKGQRTPYQA

LDSMDDAWSFRELKAFVRESKTLSNKKKEYLLTEEDISKFDVRKKFIERNLVDTRYA

SRVVLNALQEHFRAHKIDTKVSVVRGQFTSQLRRHWGIEKTRDTYHHHAVDALIIAA

SSQLNLWKKQKNTLVSYSEDQLLDIETGELISDDEYKESVFKAPYQHFVDTLKSKEFE

DSILFSYQVDSKFNRKISDATIYATRQAKVGKDKADETYVLGKIKDIYTQDGYDAFM

KIYKKDKSKFLMYRHDPQTFEKVIEPILENYPNKQINEKGKEVPCNPFLKYKEEHGYI

RKYSKKGNGPEIKSLKYYDSKLGNHIDITPKDSNNKVVLQSVSPWRADVYFNKTTG

KYEILGLKYADLQFEKGTGTYKISQEKYNDIKKKEGVDSDSEFKFTLYKNDLLLVKD

TETKEQQLFRFLSRTMPKQKHYVELKPYDKQKFEGGEALIKVLGNVANSGQCKKGL

GKSNISIYKVRTDVLGNQHIIKNEGDKPKLDF

EFT93846.1 CRISPR-associated protein, Csn1 family [*Enterococcus faecalis* TX0012]

(SEQ ID NO: 71)

MYSIGLDLGISSVGWSVIDERTGNVIDLGVRLFSAKNSEKNLERRTNRGGRRLIRRKT

NRLKDAKKILAAVGFYEDKSLKNSCPYQLRVKGLTEPLSRGEIYKVTLHILKKRGISY

LDEVDTEAAKESQDYKEQVRKNAQLLTKYTPGQIQLQRLKENNRVKTGINAQGNYQ

LNVFKVSAYANELATILKTQQAFYPNELTDDWIALFVQPGIAEEEAGLIYRKRPYYHG

-continued

PGNEANNSPYGRWSDFQKTGEPATNIFDKLIGKDFQGELRASGLSLSAQQYNLLNDL

TNLKIDGEVPLSSEQKEYILTELMTKEFTRFGVNDVVKLLGVKKERLSGWRLDKKGK

PEIHTLKGYRNWRKIFAEAGIDLATLPTETIDCLAKVLTLNTEREGIENTLAFELPELSE

SVKLLVLDRYKELSQSISTQSWHRFSLKTLHLLIPELMNATSEQNTLLEQFQLKSDVR

KRYSEYKKLPTKDVLAEIYNPTVNKTVSQAFKVIDALLVKYGKEQIRYITIEMPRDDN

EEDEKKRIKELHAKNSQRKNDSQSYFMQKSGWSQEKFQTTIQKNRRFLAKLLYYYE

QDGICAYTGLPISPELLVSDSTEIDHIIPISISLDDSINNKVLVLSKANQVKGQQTPYDA

WMDGSFKKINGKFSNWDDYQKWVESRHFSHKKENNLLETRNIFDSEQVEKFLARNL

NDTRYASRLVLNTLQSFFTNQETKVRVVNGSFTHTLRKKWGADLDKTRETHHHHA

VDATLCAVTSFVKVSRYHYAVKEETGEKVMREIDFETGEIVNEMSYWEFKKSKKYE

RKTYQVKWPNFREQLKPVNLHPRIKFSHQVDRKANRKLSDATIYSVREKTEVKTLKS

GKQKITTDEYTIGKIKDIYTLDGWEAFKKKQDKLLMKDLDEKTYERLLSIAETTPDFQ

EVEEKNGKVKRVKRSPFAVYCEENDIPAIQKYAKKNNGPLIRSLKYYDGKLNKHINI

TKDSQGRPVEKTKNGRKVTLQSLKPYRYDIYQDLETKAYYTVQLYYSDLRFVEGKY

GITEKEYMKKVAEQTKGQVVRFCFSLQKNDGLEIEWKDSQRYDVRFYNFQSANSIN

FKGLEQEMMPAENQFKQKPYNNGAINLNIAKYGKEGKKLRKFNTDILGKKHYLFYE

KEPKNIIK

YP_002937591.1 CRISPR-system related protein [*Eubacterium rectale* ATCC 33656]

(SEQ ID NO: 72)

MNYTEKEKLFMKYILALDIGIASVGWAILDKESETVIEAGSNIFPEASAADNQLRRDM

RGAKRNNRRLKTRINDFIKLWENNNLSIPQFKSTEIVGLKVRAITEEITLDELYLILYSY

LKHRGISYLEDALDDTVSGSSAYANGLKLNAKELETHYPCEIQQERLNTIGKYRGQS

QIINENGEVLDLSNVFTIGAYRKEIQRVFEIQKKYHPELTDEFCDGYMLIFNRKRKYY

EGPGNEKSRTDYGRFTTKLDANGNYITEDNIFEKLIGKCSVYPDELRAAAASYTAQE

YNVLNDLNNLTINGRKLEENEKHEIVERIKSSNTINMRKIISDCMGENIDDFAGARIDK

SGKEIFHKFEVYNKMRKALLEIGIDISNYSREELDEIGYIMTINTDKEAMMEAFQKSW

IDLSDDVKQCLINMRKTNGALFNKWQSFSLKIMNELIPEMYAQPKEQMTLLTEMGV

TKGTQEEFAGLKYIPVDVVSEDIFNPVVRRSVRISFKILNAVLKKYKALDTIVIEMPRD

RNSEEQKKRINDSQKLNEKEMEYIEKKLAVTYGIKLSPSDFSSQKQLSLKLKLWNEQ

DGICLYSGKTIDPNDIINNPQLFEIDHIIPRSISFDDARSNKVLVYRSENQKKGNQTPYY

YLTHSHSEWSFEQYKATVMNLSKKKEYAISRKKIQNLLYSEDITKMDVLKGFINRNI

NDTSYASRLVLNTIQNFFMANEADTKVKVIKGSYTHQMRCNLKLDKNRDESYSHHA

VDAMLIGYSELGYEAYHKLQGEFIDFETGEILRKDMWDENMSDEVYADYLYGKKW

ANIRNEVVKAEKNVKYWHYVMRKSNRGLCNQTIRGTREYDGKQYKINKLDIRTKE

GIKVFAKLAFSKKDSDRERLLVYLNDRRTFDDLCKIYEDYSDAANPFVQYEKETGDII

RKYSKKHNGPRIDKLKYKDGEVGACIDISHKYGFEKGSKKVILESLVPYRMDVYYKE

ENHSYYLVGVKQSDIKFEKGRNVIDEEAYARILVNEKMIQPGQSRADLENLGFKFKL

SFYKNDIIEYEKDGKIYTERLVSRTMPKQRNYIETKPIDKAKFEKQNLVGLGKTKFIK

KYRYDILGNKYSCSEEKFTSFC

YP_015730.1 hypothetical protein MMOB0330 [*Mycoplasma mobile* 163K]
(SEQ ID NO: 73)

MYFYKNKENKLNKKVVLGLDLGIASVGWCLTDISQKEDNKFPIILHGVRLFETVDDS

DDKLLNETRRKKRGQRRRNRRLFTRKRDFIKYLIDNNIIELEFDKNPKILVRNFIEKYI

NPFSKNLELKYKSVTNLPIGFHNLRKAAINEKYKLDKSELIVLLYFYLSLRGAFFDNP

EDTKSKEMNKNEIEIFDKNESIKNAEFPIDKIIEFYKISGKIRSTINLKFGHQDYLKEIKQ

VFEKQNIDFMNYEKFAMEEKSFFSRIRNYSEGPGNEKSFSKYGLYANENGNPELIINE

KGQKIYTKIFKTLWESKIGKCSYDKKLYRAPKNSFSAKVFDITNKLTDWKHKNEYIS

ERLKRKILLSRFLNKDSKSAVEKILKEENIKFENLSEIAYNKDDNKINLPIINAYHSLTT

IFKKHLINFENYLISNENDLSKLMSFYKQQSEKLFVPNEKGSYEINQNNNVLHIFDAIS

NILNKFSTIQDRIRILEGYFEFSNLKKDVKSSEIYSEIAKLREFSGTSSLSFGAYYKFIPN

LISEGSKNYSTISYEEKALQNQKNNFSHSNLFEKTWVEDLIASPTVKRSLRQTMNLLK

EIFKYSEKNNLEIEKIVVEVTRSSNNKHERKKIEGINKYRKEKYEELKKVYDLPNENT

TLLKKLWLLRQQQGYDAYSLRKIEANDVINKPWNYDIDHIVPRSISFDDSFSNLVIVN

KLDNAKKSNDLSAKQFIEKIYGIEKLKEAKENWGNWYLRNANGKAFNDKGKFIKLY

TIDNLDEFDNSDFINRNLSDTSYITNALVNHLTFSNSKYKYSVVSVNGKQTSNLRNQI

AFVGIKNNKETEREWKRPEGFKSINSNDFLIREEGKNDVKDDVLIKDRSFNGHHAED

AYFITIISQYFRSFKRIERLNVNYRKETRELDDLEKNNIKFKEKASFDNFLLINALDELN

EKLNQMRFSRMVITKKNTQLFNETLYSGKYDKGKNTIKKVEKLNLLDNRTDKIKKIE

EFFDEDKLKENELTKLHIFNHDKNLYETLKIIWNEVKIEIKNKNLNEKNYFKYFVNKK

LQEGKISFNEWVPILDNDFKIIRKIRYIKFSSEEKETDEIIFSQSNFLKIDQRQNFSFHNT

LYWVQIWVYKNQKDQYCFISIDARNSKFEKDEIKINYEKLKTQKEKLQIINEEPILKIN

KGDLFENEEKELFYIVGRDEKPQKLEIKYILGKKIKDQKQIQKPVKKYFPNWKKVNL

TYMGEIFKK

ZP_09312133.1 hypothetical protein MoviS_00710 [*Mycoplasma ovipneumoniae* SC01]
(SEQ ID NO: 74)

MHNKKNITIGFDLGIASIGWAIIDSTTSKILDWGTRTFEERKTANERRAFRSTRRNIRR

KAYRNQRFINLILKYKDLFELKNISDIQRANKKDTENYEKIISFFTEIYKKCAAKHSNIL

EVKVKALDSKIEKLDLIWILHDYLENRGFFYDLEEENVADKYEGIEHPSILLYDFFKK

NGFFKSNSSIPKDLGGYSFSNLQWVNEIKKLFEVQEINPEFSEKFLNLFTSVRDYAKGP

GSEHSASEYGIFQKDEKGKVFKKYDNIWDKTIGKCSFFVEENRSPVNYPSYEIFNLLN

QLINLSTDLKTTNKKIWQLSSNDRNELLDELLKVKEKAKIISISLKKNEIKKIILKDFGF

EKSDIDDQDTIEGRKIIKEEPTTKLEVTKHLLATIYSHSSDSNWININNILEFLPYLDAIC

IILDREKSRGQDEVLKKLTEKNIFEVLKIDREKQLDFVKSIFSNTKFNFKKIGNFSLKAI

REFLPKMFEQNKNSEYLKWKDEEIRRKWEEQKSKLGKTDKKTKYLNPRIFQDEIISP

GTKNTFEQAVLVLNQIIKKYSKENIIDAIIIESPREKNDKKTIEEIKKRNKKGKGKTLEK

LFQILNLENKGYKLSDLETKPAKLLDRLRFYHQQDGIDLYTLDKINIDQLINGSQKYEI

EHIIPYSMSYDNSQANKILTEKAENLKKGKLIASEYIKRNGDEFYNKYYEKAKELFIN

KYKKNKKLDSYVDLDEDSAKNRFRFLTLQDYDEFQVEFLARNLNDTRYSTKLFYHA

LVEHFENNEFFTYIDENSSKHKVKISTIKGHVTKYFRAKPVQKNNGPNENLNNNKPE

KIEKNRENNEHHAVDAAIVAIIGNKNPQIANLLTLADNKTDKKFLLHDENYKENIETG

ELVKIPKFEVDKLAKVEDLKKIIQEKYEEAKKHTAIKFSRKTRTILNGGLSDETLYGF

-continued

KYDEKEDKYFKIIKKKLVTSKNEELKKYFENPFGKKADGKSEYTVLMAQSHLSEFNK

LKEIFEKYNGFSNKTGNAFVEYMNDLALKEPTLKAEIESAKSVEKLLYYNFKPSDQF

TYHDNINNKSFKRFYKNIRIIEYKSIPIKFKILSKHDGGKSFKDTLFSLYSLVYKVYEN

GKESYKSIPVTSQMRNFGIDEFDFLDENLYNKEKLDIYKSDFAKPIPVNCKPVFVLKK

GSILKKKSLDIDDFKETKETEEGNYYFISTISKRFNRDTAYGLKPLKLSVVKPVAEPST

NPIFKEYIPIHLDELGNEYPVKIKEHTDDEKLMCTIK

ADC31648.1 Csn1 family CRISPR-associated protein [*Mycoplasma galliscepticum* str. F]

(SEQ ID NO: 75)

MNNSIKSKPEVTIGLDLGVGSVGWAIVDNETNIIHHLGSRLFSQAKTAEDRRSFRGVR

RLIRRRKYKLKRFVNLIWKYNSYFGFKNKEDILNNYQEQQKLHNTVLNLKSEALNA

KIDPKALSWILHDYLKNRGHFYEDNRDFNVYPTKELAKYFDKYGYYKGIIDSKEDN

DNKLEEELTKYKFSNKHWLEEVKKVLSNQTGLPEKFKEEYESLFSYVRNYSEGPGSI

NSVSPYGIYHLDEKEGKVVQKYNNIWDKTIGKCNIFPDEYRAPKNSPIAMIFNEINELS

TIRSYSIYLTGWFINQEFKKAYLNKLLDLLIKTNGEKPIDARQFKKLREETIAESIGKET

LKDVENEEKLEKEDHKWKLKGLKLNTNGKIQYNDLSSLAKFVHKLKQHLKLDFLLE

DQYATLDKINFLQSLFVYLGKHLRYSNRVDSANLKEFSDSNKLFERILQKQKDGLFK

LFEQTDKDDEKILAQTHSLSTKAMLLAITRMTNLDNDEDNQKNNDKGWNFEAIKNF

DQKFIDITKKNNNLSLKQNKRYLDDRFINDAILSPGVKRILREATKVFNAILKQFSEEY

DVTKVVIELARELSEEKELENTKNYKKLIKKNGDKISEGLKALGISEDEIKDILKSPTK

SYKFLLWLQQDHIDPYSLKEIAFDDIFTKTEKFEIDHIIPYSISFDDSSSNKLLVLAESNQ

AKSNQTPYEFISSGNAGIKWEDYEAYCRKFKDGDSSLLDSTQRSKKFAKMMKTDTS

SKYDIGFLARNLNDTRYATIVFRDALEDYANNHLVEDKPMFKVVCINGSVTSFLRKN

FDDSSYAKKDRDKNIHHAVDASIISIFSNETKTLFNQLTQFADYKLFKNTDGSWKKID

PKTGVVTEVTDENWKQIRVRNQVSEIAKVIEKYIQDSNIERKARYSRKIENKTNISLFN

DTVYSAKKVGYEDQIKRKNLKTLDIHESAKENKNSKVKRQFVYRKLVNVSLLNNDK

LADLFAEKEDILMYRANPWVINLAEQIFNEYTENKKIKSQNVFEKYMLDLTKEFPEK

FSEFLVKSMLRNKTAIIYDDKKNIVHRIKRLKMLSSELKENKLSNVIIRSKNQSGTKLS

YQDTINSLALMIMRSIDPTAKKQYIRVPLNTLNLHLGDHDFDLHNMDAYLKKPKFVK

YLKANEIGDEYKPWRVLTSGTLLIHKKDKKLMYISSFQNLNDVIEIKNLIETEYKEND

DSDSKKKKKANRFLMTLSTILNDYILLDAKDNFDILGLSKNRIDEILNSKLGLDKIVK

YP_278700.1 hypothetical protein MS53_0582 [*Mycoplasma synoviae* 53]

(SEQ ID NO: 76)

MLRLYCANNLVLNNVQNLWKYLLLLIFDKKIIFLFKIKVILIRRYMENNNKEKIVIGF

DLGVASVGWSIVNAETKEVIDLGVRLFSEPEKADYRRAKRTTRRLLRRKKFKREKFH

KLILKNAEIFGLQSRNEILNVYKDQSSKYRNILKLKINALKEEIKPSELVWILRDYLQN

RGYFYKNEKLTDEFVSNSFPSKKLHEHYEKYGFFRGSVKLDNKLDNKKDKAKEKDE

EEESDAKKESEELIFSNKQWINEIVKVFENQSYLTESFKEEYLKLFNYVRPFNKGPGS

KNSRTAYGVFSTDIDPETNKFKDYSNIWDKTIGKCSLFEEEIRAPKNLPSALIFNLQNEI

CTIKNEFTEFKNWWLNAEQKSEILKFVFTELFNWKDKKYSDKKFNKNLQDKIKKYL

LNFALENFNLNEEILKNRDLENDTVLGLKGVKYYEKSNATADAALEFSSLKPLYVFI

KFLKEKKLDLNYLLGLENTEILYFLDSIYLAISYSSDLKERNEWFKKLLKELYPKIKN

NNLEIIENVEDIFEITDQEKFESFSKTHSLSREAFNHIIPLLLSNNEGKNYESLKHSNEEL

-continued

KKRTEKAELKAQQNQKYLKDNFLKEALVPLSVKTSVLQAIKIFNQIIKNFGKKYEISQ

VVIEMARELTKPNLEKLLNNATNSNIKILKEKLDQTEKFDDFTKKKFIDKIENSVVFR

NKLFLWFEQDRKDPYTQLDIKINEIEDETEIDHVIPYSKSADDSWFNKLLVKKSTNQL

KKNKTVWEYYQNESDPEAKWNKFVAWAKRIYLVQKSDKESKDNSEKNSIFKNKKP

NLKFKNITKKLFDPYKDLGFLARNLNDTRYATKVFRDQLNNYSKHHSKDDENKLFK

VVCMNGSITSFLRKSMWRKNEEQVYRFNFWKKDRDQFFHHAVDASIIAIFSLLTKTL

YNKLRVYESYDVQRREDGVYLINKETGEVKKADKDYWKDQHNFLKIRENAIEIKNV

LNNVDFQNQVRYSRKANTKLNTQLFNETLYGVKEFENNFYKLEKVNLFSRKDLRKF

ILEDLNEESEKNKKNENGSRKRILTEKYIVDEILQILENEEFKDSKSDINALNKYMDSL

PSKFSEFFSQDFINKCKKENSLILTFDAIKHNDPKKVIKIKNLKFFREDATLKNKQAVH

KDSKNQIKSFYESYKCVGFIWLKNKNDLEESIFVPINSRVIHFGDKDKDIFDFDSYNKE

KLLNEINLKRPENKKFNSINEIEFVKFVKPGALLLNFENQQIYYISTLESSSLRAKIKLL

NKMDKGKAVSMKKITNPDEYKIIEHVNPLGINLNWTKKLENNN

E1E39736.1 Csn1 family CRISPR-associated protein [*Mycoplasma canis* PG
14]
(SEQ ID NO: 77)

MEKKRKVTLGFDLGIASVGWAIVDSETNQVYKLGSRLFDAPDTNLERRTQRGTRRL

LRRRKYRNQKFYNLVKRTEVFGLSSREAIENRFRELSIKYPNIIELKTKALSQEVCPDE

IAWILHDYLKNRGYFYDEKETKEDFDQQTVESMPSYKLNEFYKKYGYFKGALSQPT

ESEMKDNKDLKEAFFFDFSNKEWLKEINYFFNVQKNILSETFIEEFKKIFSFTRDISKG

PGSDNMPSPYGIFGEFGDNGQGGRYEHIWDKNIGKCSIFTNEQRAPKYLPSALIFNFL

NELANIRLYSTDKKNIQPLWKLSSVDKLNILLNLFNLPISEKKKKLTSTNINDIVKKESI

KSIMISVEDIDMIKDEWAGKEPNVYGVGLSGLNIEESAKENKFKFQDLKILNVLINLL

DNVGIKFEFKDRNDIIKNLELLDNLYLFLIYQKESNNKDSSIDLFIAKNESLNIENLKLK

LKEFLLGAGNEFENHNSKTHSLSKKAIDEILPKLLDNNEGWNLEAIKNYDEEIKSQIE

DNSSLMAKQDKKYLNDNFLKDAILPPNVKVTFQQAILIFNKIIQKFSKDFEIDKVVIEL

AREMTQDQENDALKGIAKAQKSKKSLVEERLEANNIDKSVFNDKYEKLIYKIFLWIS

QDFKDPYTGAQISVNEIVNNKVEIDHIIPYSLCFDDSSANKVLVHKQSNQEKSNSLPY

EYIKQGHSGWNWDEFTKYVKRVFVNNVDSILSKKERLKKSENLLTASYDGYDKLGF

LARNLNDTRYATILFRDQLNNYAEHHLIDNKKMFKVIAMNGAVTSFIRKNMSYDNK

LRLKDRSDFSHHAYDAAIIALFSNKTKTLYNLIDPSLNGIISKRSEGYWVIEDRYTGEI

KELKKEDWTSIKNNVQARKIAKEIEEYLIDLDDEVFFSRKTKRKTNRQLYNETIYGIA

TKTDEDGITNYYKKEKFSILDDKDIYLRLLEREREKFVINQSNPEVIDQIIEIIESYGKEN

NIPSRDEAINIKYTKNKINYNLYLKQYMRSLTKSLDQFSEEFINQMIANKTFVLYNPT

KNTTRKIKFLRLVNDVKINDIRKNQVINKFNGKNNEPKAFYENINSLGAIVFKNSANN

FKTLSINTQIAIFGDKNWDIEDFKTYNMEKIEKYKEIYGIDKTYNFHSFIFPGTILLDKQ

NKEFYYISSIQTVRDIIEIKFLNKIEFKDENKNQDTSKTPKRLMFGIKSIMNNYEQVDIS

PFGINKKIFE

NP_907605.1 hypothetical protein WS1445 [*Wolinella succinogenes* DSM 1740]
(SEQ ID NO: 78)

MIERILGVDLGISSLGWAIVEYDKDDEAANRIIDCGVRLFTAAETPKKKESPNKARRE

ARGIRRVLNRRRVRMNMIKKLFLRAGLIQDVDLDGEGGMFYSKANRADVWELRHD

GLYRLLKGDELARVLIHIAKHRGYKFIGDDEADEESGKVKKAGVVLRQNFEAAGCR

TVGEWLWRERGANGKKRNKHGDYEISIHRDLLVEEVEAIFVAQQEMRSTIATDALK

AAYREIAFFVRPMQRIEKMVGHCTYFPEERRAPKSAPTAEKFIAISKFFSTVIIDNEGW

EQKIIERKTLEELLDFAVSREKVEFRHLRKFLDLSDNEIFKGLHYKGKPKTAKKREAT

LFDPNEPTELEFDKVEAEKKAWISLRGAAKLREALGNEFYGRFVALGKHADEATKIL

TYYKDEGQKRRELTKLPLEAEMVERLVKIGFSDFLKLSLKAIRDILPAMESGARYDE

AVLMLGVPHKEKSAILPPLNKTDIDILNPTVIRAFAQFRKVANALVRKYGAFDRVHF

ELAREINTKGEIEDIKESQRKNEKERKEAADWIAETSFQVPLTRKNILKKRLYIQQDG

RCAYTGDVIELERLFDEGYCEIDHILPRSRSADDSFANKVLCLARANQQKTDRTPYE

WFGHDAARWNAFETRTSAPSNRVRTGKGKIDRLLKKNFDENSEMAFKDRNLNDTR

YMARAIKTYCEQYWVFKNSHTKAPVQVRSGKLTSVLRYQWGLESKDRESHTHHAV

DAIIIAFSTQGMVQKLSEYYRFKETHREKERPKLAVPLANFRDAVEEATRIENTETVK

EGVEVKRLLISRPPRARVTGQAHEQTAKPYPRIKQVKNKKKWRLAPIDEEKFESFKA

DRVASANQKNFYETSTIPRVDVYHKKGKFHLVPIYLHEMVLNELPNLSLGTNPEAM

DENFFKFSIFKDDLISIQTQGTPKKPAKIIMGYFKNMHGANMVLSSINNSPCEGFTCTP

VSMDKKHKDKCKLCPEENRIAGRCLQGFLDYWSQEGLRPPRKEFECDQGVKFALDV

KKYQIDPLGYYYEVKQEKRLGTIPQMRSAKKLVKK

YP_002344900.1 CRISPR-associated protein [*Campylobacter jejuni* subsp. *jejuni* NCTC 11168 = ATCC 700819]
(SEQ ID NO: 79)

MARILAFDIGISSIGWAFSENDELKDCGVRIFTKVENPKTGESLALPRRLARSARKRL

ARRKARLNHLKHLIANEFKLNYEDYQSFDESLAKAYKGSLISPYELRFRALNELLSK

QDFARVILHIAKRRGYDDIKNSDDKEKGAILKAIKQNEEKLANYQSVGEYLYKEYFQ

KFKENSKEFTNVRNKKESYERCIAQSFLKDELKLIFKKQREFGFSFSKKFEEEVLSVAF

YKRALKDFSHLVGNCSFFTDEKRAPKNSPLAFMFVALTRIINLLNNLKNTEGILYTKD

DLNALLNEVLKNGTLTYKQTKKLLGLSDDYEFKGEKGTYFIEFKKYKEFIKALGEHN

LSQDDLNEIAKDITLIKDEIKLKKALAKYDLNQNQIDSLSKLEFKDHLNISFKALKLVT

PLMLEGKKYDEACNELNLKVAINEDKKDFLPAFNETYYKDEVTNPVVLRAIKEYRK

VLNALLKKYGKVHKINIELAREVGKNHSQRAKIEKEQNENYKAKKDAELECEKLGL

KINSKNILKLRLFKEQKEFCAYSGEKIKISDLQDEKMLEIDHIYPYSRSFDDSYMNKVL

VFTKQNQEKLNQTPFEAFGNDSAKWQKIEVLAKNLPTKKQKRILDKNYKDKEQK

NFKDRNLNDTRYIARLVLNYTKDYLDFLPLSDDENTKLNDTQKGSKVHVEAKSGML

TSALRHTWGFSAKDRNNHLHHAIDAVIIAYANNSIVKAFSDFKKEQESNSAELYAKK

ISELDYKNKRKFFEPFSGFRQKVLDKIDEIFVSKPERKKPSGALHEETFRKEEEFYQSY

GGKEGVLKALELGKIRKVNGKIVKNGDMFRVDIFKHKKTNKFYAVPIYTMDFALKV

LPNKAVARSKKGEIKDWILMDENYEFCFSLYKDSLILIQTKDMQEPEFVYYNAFTSST

VSLIVSKHDNKFETLSKNQKILFKNANEKEVIAKSIGIQNLKVFEKVIVSALGEVTKAE

FRQREDFKK

YP_003516037.1 CRISPR associated protein [*Helicobacter mustelae* 12198]
(SEQ ID NO: 80)

MIRTLGIDIGIASIGWAVIEGEYTDKGLENKEIVASGVRVFTKAENPKNKESLALPRTL

ARSARRRNARKKGRIQQVKHYLSKALGLDLECFVQGEKLATLFQTSKDFLSPWELR

ERALYRVLDKEELARVILHIAKRRGYDDITYGVEDNDSGKIKKAIAENSKRIKEEQCK

TIGEMMYKLYFQKSLNVRNKKESYNRCVGRSELREELKTIFQIQQELKSPWVNEELI

YKLLGNPDAQSKQEREGLIFYQRPLKGFGDKIGKCSHIKKGENSPYRACKHAPSAEE

FVALTKSINFLKNLTNRHGLCFSQEDMCVYLGKILQEAQKNEKGLTYSKLKLLLDLP

SDFEFLGLDYSGKNPEKAVFLSLPSTFKLNKITQDRKTQDKIANILGANKDWEAILKE

LESLQLSKEQIQTIKDAKLNFSKHINLSLEALYHLLPLMREGKRYDEGVEILQERGIFS

KPQPKNRQLLPPLSELAKEESYFDIPNPVLRRALSEFRKVVNALLEKYGGFHYFHIEL

TRDVCKAKSARMQLEKINKKNKSENDAASQLLEVLGLPNTYNNRLKCKLWKQQEE

YCLYSGEKITIDHLKDQRALQIDHAFPLSRSLDDSQSNKVLCLTSSNQEKSNKTPYEW

LGSDEKKWDMYVGRVYSSNFSPSKKRKLTQKNFKERNEEDFLARNLVDTGYIGRVT

KEYIKHSLSFLPLPDGKKEHIRIISGSMTSTMRSFWGVQEKNRDHHLHHAQDAIIIACI

EPSMIQKYTTYLKDKETHRLKSHQKAQILREGDHKLSLRWPMSNFKDKIQESIQNIIP

SHHVSHKVTGELHQETVRTKEFYYQAFGGEEGVKKALKFGKIREINQGIVDNGAMV

RVDIFKSKDKGKFYAVPIYTYDFAIGKLPNKAIVQGKKNGIIKDWLEMDENYEFCFSL

FKNDCIKIQTKEMQEAVLAIYKSTNSAKATIELEHLSKYALKNEDEEKMFTDTDKEK

NKTMTRESCGIQGLKVFQKVKLSVLGEVLEHKPRNRQNIALKTTPKHV

ZP_06887976.1 CRISPR-associated protein, Csn1 family [*Methylosinus trichosporium* OB3b]

(SEQ ID NO: 81)

MRVLGLDAGIASLGWALIEIEESNRGELSQGTIIGAGTWMFDAPEEKTQAGAKLKSE

QRRTFRGQRRVVRRRRQRMNEVRRILHSHGLLPSSDRDALKQPGLDPWRIRAEALD

RLLGPVELAVALGHIARHRGFKSNSKGAKTNDPADDTSKMKRAVNETREKLARFGS

AAKMLVEDESFVLRQTPTKNGASEIVRRFRNREGDYSRSLLRDDLAAEMRALFTAQ

ARFQSAIATADLQTAFTKAAFFQRPLQDSEKLVGPCPFEVDEKRAPKRGYSFELFRFL

SRLNHVTLRDGKQERTLTRDELALAAADFGAAAKVSFTALRKKLKLPETTVFVGVK

ADEESKLDVVARSGKAAEGTARLRSVIVDALGELAWGALLCSPEKLDKIAEVISFRS

DIGRISEGLAQAGCNAPLVDALTAAASDGRFDPFTGAGHISSKAARNILSGLRQGMT

YDKACCAADYDHTASRERGAFDVGGHGREALKRILQEERISRELVGSPTARKALIESI

KQVKAIVERYGVPDRIHVELARDVGKSIEEREEITRGIEKRNRQKDKLRGLFEKEVGR

PPQDGARGKEELLRFELWSEQMGRCLYTDDYISPSQLVATDDAVQVDHILPWSRFA

DDSYANKTLCMAKANQDKKGRTPYEWFKAEKTDTEWDAFIVRVEALADMKGFKK

RNYKLRNAEEAAAKFRNRNLNDTRWACRLLAEALKQLYPKGEKDKDGKERRRVFS

RPGALTDRLRRAWGLQWMKKSTKGDRIPDDRHHALDAIVIAATTESLLQRATREVQ

EIEDKGLHYDLVKNVTPPWPGFREQAVEAVEKVFVARAERRRARGKAHDATIRHIA

VREGEQRVYERRKVAELKLADLDRVKDAERNARLIEKLRNWIEAGSPKDDPPLSPK

GDPIFKVRLVTKSKVNIALDTGNPKRPGTVDRGEMARVDVFRKASKKGKYEYYLVP

IYPHDIATMKTPPIRAVQAYKPEDEWPEMDSSYEFCWSLVPMTYLQVISSKGEIFEGY

YRGMNRSVGAIQLSAHSNS SDVVQGIGARTLTEFKKFNVDRFGRKHEVERELRTWR

GETWRGKAYI

YP_003968716.1 CRISPR-associated protein, Csn1 family (plasmid) [*Ilyobacter polytropus* DSM 2926]

(SEQ ID NO: 82)

MKYSIGLDIGIASVGWSVINKDKERIEDMGVRIFQKAENPKDGSSLASSRREKRGSRR

RNRRKKHRLDRIKNILCESGLVKKNEIEKIYKNAYLKSPWELRAKSLEAKISNKEIAQI

LLHIAKRRGFKSFRKTDRNADDTGKLLSGIQENKKIMEEKGYLTIGDMVAKDPKFNT

-continued

HVRNKAGSYLFSFSRKLLEDEVRKIQAKQKELGNTHFTDDVLEKYIEVFNSQRNFDE

GPSKPSYYSEIGQIAKMIGNCTFESSEKRTAKNTWSGERFVFLQKLNNFRIVGLSGK

RPLTEEERDIVEKEVYLKKEVRYEKLRKILYLKEEERFGDLNYSKDEKQDKKTEKTK

FISLIGNYTIKKLNLSEKLKSEIEEDKSKLDKIIEILTFNKSDKTIESNLKKLELSREDIEIL

LSEEFSGTLNLSLKAIKKILPYLEKGLSYNEACEKADYDYKNNGIKFKRGELLPVVDK

DLIANPVVLRAISQTRKVVNAIIRKYGTPHTIHVEVARDLAKSYDDRQTIIKENKKRE

LENEKTKKFISEEFGIKNVKGKLLLKYRLYQEQEGRCAYSRKELSLSEVILDESMTDI

DHIIPYSRSMDDSYSNKVLVLSGENRKKSNLLPKEYFDRQGRDWDTFVLNVKAMKI

HPRKKSNLLKEKFTREDNKDWKSRALNDTRYISRFVANYLENALEYRDDSPKKRVF

MIPGQLTAQLRARWRLNKVRENGDLHHALDAAVVAVTDQKAINNISNISRYKELKN

CKDVIPSIEYHADEETGEVYFEEVKDTRFPMPWSGFDLELQKRLESENPREEFYNLLS

DKRYLGWFNYEEGFIEKLRPVFVSRMPNRGVKGQAHQETIRSSKKISNQIAVSKKPL

NSIKLKDLEKMQGRDTDRKLYEALKNRLEEYDDKPEKAFAEPFYKPTNSGKRGPLV

RGIKVEEKQNVGVYVNGGQASNGSMVRIDVFRKNGKFYTVPIYVHQTLLKELPNRA

INGKPYKDWDLIDGSFEFLYSFYPNDLIEIEFGKSKSIKNDNKLTKTEIPEVNLSEVLG

YYRGMDTSTGAATIDTQDGKIQMRIGIKTVKNIKKYQVDVLGNVYKVKREKRQTF

ZP_09352959.1 CRISPR-associated protein cas9/csn1, subtype II/nmemi
[*Bacillus smithii* 7_3_47FAA]

(SEQ ID NO: 83)

MNYKMGLDIGIASVGWAVINLDLKRIEDLGVRIFDKAEHPQNGESLALPRRIARSAR

RRLRRRKHRLERIRRLLVSENVLTKEEMNLLFKQKKQIDVWQLRVDALERKLNNDE

LARVLLHLAKRRGFKSNRKSERNSKESSEFLKNIEENQSILAQYRSVGEMIVKDSKFA

YHKRNKLDSYSNMIARDDLEREIKLIFEKQREFNNPVCTERLEEKYLNIWSSQRPFAS

KEDIEKKVGFCTFEPKEKRAPKATYTFQSFIVWEHINKLRLVSPDETRALTEIERNLLY

KQAFSKNKMTYYDIRKLLNLSDDIHFKGLLYDPKSSLKQIENIRFLELDSYHKIRKCIE

NVYGKDGIRMFNETDIDTFGYALTIFKDDEDIVAYLQNEYITKNGKRVSNLANKVYD

KSLIDELLNLSFSKFAHLSMKAIRNILPYMEQGEIYSKACELAGYNFTGPKKKEKALL

LPVIPNIANPVVMRALTQSRKVVNAIIKKYGSPVSIHIELARDLSHSFDERKKIQKDQT

ENRKKNETAIKQLIEYELTKNPTGLDIVKFKLWSEQQGRCMYSLKPIELERLLEPGYV

EVDHILPYSRSLDDSYANKVLVLTKENREKGNHTPVEYLGLGSERWKKFEKFVLAN

KQFSKKKKQNLLRLRYEETEEKEFKERNLNDTRYISKFFANFIKEHLKFADGDGGQK

VYTINGKITAHLRSRWDFNKNREESDLHHAVDAVIVACATQGMIKKITEFYKAREQN

KESAKKKEPIFPQPWPHFADELKARLSKFPQESIEAFALGNYDRKKLESLRPVFVSRM

PKRSVTGAAHQETLRRCVGIDEQSGKIQTAVKTKLSDIKLDKDGHFPMYQKESDPRT

YEAIRQRLLEHNNDPKKAFQEPLYKPKKNGEPGPVIRTVKIIDTKNKVVHLDGSKTV

AYNSNIVRTDVFEKDGKYYCVPVYTMDIMKGTLPNKAIEANKPYSEWKEMTEEYTF

QFSLFPNDLVRIVLPREKTIKTSTNEEIIIKDIFAYYKTIDSATGGLELISHDRNFSLRGV

GSKTLKRFEKYQVDVLGNIHKVKGEKRVGLAAPTNQKKGKTVDSLQSVSD

YP_002507391.1 CRISPR-associated protein, Csn1 family [*Clostridium cellulolyticum* H10]

(SEQ ID NO: 84)

MKYTLGLDVGIASVGWAVIDKDNNKIIDLGVRCFDKAEESKTGESLATARRIARGM

RRRISRRSQRLRLVKKLFVQYEIIKDSSEFNRIFDTSRDGWKDPWELRYNALSRILKPY

ELVQVLTHITKRRGFKSNRKEDLSTTKEGVVITSIKNNSEMLRTKNYRTIGEMIFMET

```
PENSNKRNKVDEYIHTIAREDLLNEIKYIFSIQRKLGSPFVTEKLEHDFLNIWEFQRPFA

SGDSILSKVGKCTLLKEELRAPTSCYTSEYFGLLQSINNLVLVEDNNTLTLNNDQRAK

IIEYAHFKNEIKYSEIRKLLDIEPEILFKAHNLTHKNPSGNNESKKFYEMKSYHKLKST

LPTDIWGKLHSNKESLDNLFYCLTVYKNDNEIKDYLQANNLDYLIEYIAKLPTFNKF

KHLSLVAMKRIIPFMEKGYKYSDACNMAELDFTGSSKLEKCNKLTVEPIIENVTNPV

VIRALTQARKVINAIIQKYGLPYMVNIELAREAGMTRQDRDNLKKEHENNRKAREKI

SDLIRQNGRVASGLDILKWRLWEDQGGRCAYSGKPIPVCDLLNDSLTQIDHIYPYSRS

MDDSYMNKVLVLTDENQNKRSYTPYEVWGSTEKWEDFEARIYSMHLPQSKEKRLL

NRNFITKDLDSFISRNLNDTRYISRFLKNYIESYLQFSNDSPKSCVVCVNGQCTAQLRS

RWGLNKNREESDLHHALDAAVIACADRKIIKEITNYYNERENHNYKVKYPLPWHSF

RQDLMETLAGVFISRAPRRKITGPAHDETIRSPKHFNKGLTSVKIPLTTVTLEKLETMV

KNTKGGISDKAVYNVLKNRLIEHNNKPLKAFAEKIYKPLKNGTNGAIIRSIRVETP SY

TGVFRNEGKGISDNSLMVRVDVFKKKDKYYLVPIYVAHMIKKELPSKAIVPLKPESQ

WELIDSTHEFLFSLYQNDYLVIKTKKGITEGYYRSCHRGTGSLSLMPHFANNKNVKID

IGVRTAISIEKYNVDILGNKSIVKGEPRRGMEKYNSFKSN
```

YP_002551549.1 crispr-associated protein, csn1 family [Acidoyorax ebreus TPSY]

(SEQ ID NO: 85)

```
MAQHVFGLDIGIASVGWAILGEQRIIDLGVRCFDKAETAKEGDPLNLTRRQARLLRR

RLYRRAWRLTQLRLLKRKGLIADAKLFAKAPSYGDSAWELRRQGLDRLLTPLEWAR

VIYHQCKHRGFHWTSKAEEEAKADSDAEGGRVKQGLAHTKALMQAKNYRSAAEMV

LAEFPDAQRNKRGQYDKALSRVLLGEELALLFATQRRLGNPHASDFFEKLILGDGDR

KSGLFWQQKPALSGADLLKMLGKCTFEKGEYRAPKASFSVERHVWLTRLNNLRIVV

DGRSRPLNEAERQAALLLPYQTETSKYKTLKNAFIKAGLWGDGVRFGGLAYPSQAQI

DAEKTKDPEDQFLVKLPAWHELRKAFKAAGHEALWQQISTPALDGDPTLLDQIATV

LSVYKDGAEVVQQLRQLALPEPAASIAVLEKISFDKFSSLSLKALRRIVPLMQSGLRY

DEAVAQIPEYGHHSQRIEPGAAKHLYLPPFYEAQRKYAGKGDHIGSMQFRDDADIPR

NPVVLRALNQARKVVNALIREYGSPIAVNIEMARDLSRPLDERNKVKRAQEEFRDRN

DRARSEFERDFGYKPKAAAFEKWMLYREQLGQCAYSQQPLDIQRVLDDHNYAQVD

HALPYSRSYDDSKNNKVLVLTHENQNKGNRTAFEYLTSFPDGEDGERWRTFVAWV

QGNKAYRMAKRNRLLRKNYGVDESKGFIDRNLNDTRYICKFFKNYVEEHLQLAAR

ADGDTARRCVVVNGQLTAFLRARWGLTKVRGDSDRHHALDAAVVAACTHGMVK

ALADYSRRKEISFLQEGFPDPETGEILNPAAFDRARQHFPEPWTHFAHELKARLFTDD

LAALREDMQRLGSYTTEDLGRLRTLFVSRAPQRRSGGAVHKETIYAQPESLKQQGG

VIEKILLTSLKLQDFDKLLNPESNDHFVEPHRNERLYAAIRQRLEQFGGRADKAFGPD

NLFHKPDKNNQPTGPVVRSIKLVRGKQTGIPIRGGLAKNDSMLRVDIFTKAGKFHLV

PVYVHH RVTGLPNRAIVAFKDEDEWTLIDESFAFLFSVYPNDYVKVTLKKEQQSGYY

SGADRSTGAMNLWAHDRAASVGKDGLIRGIGVKTALSVEKFNVDVLGRIYLAPPET

RSGLA
```

YP_002342100.1 hypothetical protein NMA0631 [*Neisseria meningitidis* Z2491]

(SEQ ID NO: 86)

MAAFKPNPINYILGLDIGIASVGWAMVEIDEDENPICLIDLGVRVFERAEVPKTGDSL

AMARRLARSVRRLTRRRAHRLLRARRLLKREGVLQAADFDENGLIKSLPNTPWQLR

AAALDRKLTPLEWSAVLLHLIKHRGYLSQRKNEGETADKELGALLKGVADNAHAL

QTGDFRTPAELALNKFEKESGHIRNQRGDYSHTFSRKDLQAELILLFEKQEFGNPHV

SGGLKEGIETLLMTQRPALSGDAVQKMLGHCTFEPAEPKAAKNTYTAERFIWLTKLN

NLRILEQGSERPLTDTERATLMDEPYRKSKLTYAQARKLLGLEDTAFFKGLRYGKDN

AEASTLMEMKAYHAISRALEKEGLKDKKSPLNLSPELQDEIGTAFSLFKTDEDITGRL

KDRIQPEILEALLKHISFDKFVQISLKALRRIVPLMEQGKRYDEACAEIYGDHYGKKN

TEEKIYLPPIPADEIRNPVVLRALSQARKVINGVVRRYGSPARIHIETAREVGKSFKDR

KEIEKRQEENRKDREKAAAKFREYFPNFVGEPKSKDILKLRLYEQQHGKCLYSGKEI

NLGRLNEKGYVEIDHALPFSRTWDDSFNNKVLVLGSENQNKGNQTPYEYFNGKDNS

REWQEFKARVETSRFPRSKKQRILLQKFDEDGFKERNLNDTRYVNRFLCQFVADRM

RLTGKGKKRVFASNGQITNLLRGFWGLRKVRAENDRHHALDAVVVACSTVAMQQ

KITRFVRYKEMNAFDGKTIDKETGEVLHQKTHFPQPWEFFAQEVMIRVFGKPDGKPE

FEEADTPEKLRTLLAEKLSSRPEAVHEYVTPLFVSRAPNRKMSGQGHMETVKSAKRL

DEGVSVLRVPLTQLKLKDLEKMVNREREPKLYEALKARLEAHKDDPAKAFAEPFYK

YDKAGNRTQQVKAVRVEQVQKTGVWVRNHNGIADNATMVRVDVFEKGDKYYLV

PIYSWQVAKGILPDRAVVQGKDEEDWQLIDDSFNFKFSLHPNDLVEVITKKARMFGY

FASCHRGTGNINIRIHDLDHKIGKNGILEGIGVKTALSFQKYQIDELGKEIRPCRLKKR

PPVR

NP_246064.1 hypothetical protein PM1127 [*Pasteurella multocida* subsp. *multocida* str. Pm70]

(SEQ ID NO: 87)

MQTTNLSYILGLDLGIASVGWAVVEINENEDPIGLIDVGVRIFERAEVPKTGESLALSR

RLARSTRRLIRRRAHRLLLAKRFLKREGILSTIDLEKGLPNQAWELRVAGLERRLSATE

WGAVLLHLIKHRGYLSKRKNESQTNNKELGALLSGVAQNHQLLQSDDYRTPAELAL

KKFAKEEGHIRNQRGAYTHTFNRLDLLAELNLLFAQQHQFGNPHCKEHIQQYMTEL

LMWQKPALSGEAILKMLGKCTHEKNEFKAAKHTYSAERFVWLTKLNNLRILEDGAE

RALNEEERQLLINHPYEKSKLTYAQVRKLLGLSEQAIFKHLRYSKENAESATFMELK

AWHAIRKALENQGLKDTWQDLAKKPDLLDEIGTAFSLYKTDEDIQQYLTNKVPNSVI

NALLVSLNFDKFIELSLKSLRKILPLMEQGKRYDQACREIYGHHYGEANQKTSQLLP

AIPAQEIRNPVVLRTLSQARKVINAIIRQYGSPARVHIETGRELGKSFKERREIQKQQE

DNRTKRESAVQKFKELFSDFSSEPKSKDILKFRLYEQQHGKCLYSGKEINIHRLNEKG

YVEIDHALPFSRTWDDSFNNKVLVLASENQNKGNQTPYEWLQGKINSERWKNFVAL

VLGSQCSAAKKQRLLTQVIDDNKFIDRNLNDTRYIARFLSNYIQENLLLVGKNKKNV

FTPNGQITALLRSRWGLIKARENNNRHHALDAIVVACATPSMQQKITRFIRFKEVHPY

KIENRYEMVDQESGEIISPHFPEPWAYFRQEVNIRVFDNHPDTVLKEMLPDRPQANH

QFVQPLFVSRAPTRKMSGQGHMETIKSAKRLAEGISVLRIPLTQLKPNLLENMVNKE

REPALYAGLKARLAEFNQDPAKAFATPFYKQGGQQVKAIRVEQVQKSGVLVRENN

GVADNASIVRTDVFIKNNKFFLVPIYTWQVAKGILPNKAIVAHKNEDEWEEMDEGA

KFKFSLFPNDLVELKTKKEYFFGYYIGLDRATGNISLKEHDGEISKGKDGVYRVGVK

LALSFEKYQVDELGKNRQICRPQQRQPVR

ZP_07738815.1 CRISPR-associated protein, Csn1 family [*Aminomonas paucivorans* DSM 12260]

(SEQ ID NO: 88)

MIGEHVRGGCLFDDHWTPNWGAFRLPNTVRTFTKAENPKDGSSLAEPRRQARGLRR

RLRRKTQRLEDLRRLLAKEGVLSLSDLETLFRETPAKDPYQLRAEGLDRPLSFPEWV

RVLYHITKHRGFQSNRRNPVEDGQERSRQEEEGKLLSGVGENERLLREGGYRTAGE

MLARDPKFQDHRRNRAGDYSHTLSRSLLLEEARRLFQSQRTLGNPHASSNLEEAFLH

LVAFQNPFASGEDIRNKAGHCSLEPDQIRAPRRSASAETFMLLQKTGNLRLIHRRTGE

ERPLTDKEREQIHLLAWKQEKVTHKTLRRHLEIPEEWLFTGLPYHRSGDKAEEKLFV

HLAGIHEIRKALDKGPDPAVWDTLRSRRDLLDSIADTLTFYKNEDEILPRLESLGLSPE

NARALAPLSFSGTAHLSLSALGKLLPHLEEGKSYTQARADAGYAAPPPDRHPKLPPL

EEADWRNPVVFRALTQTRKVVNALVRRYGPPWCIHLETARELSQPAKVRRRIETEQ

QANEKKKQQAEREFLDIVGTAPGPGDLLKMRLWREQGGFCPYCEEYLNPTRLAEPG

YAEMDHILPYSRSLDNGWHNRVLVHGKDNRDKGNRTPFEAFGGDTARWDRLVAW

VQASHLSAPKKRNLLREDFGEEAERELKDRNLTDTRFITKTAATLLRDRLTFHPEAPK

DPVMTLNGRLTAFLRKQWGLHKNRKNGDLHHALDAAVLAVASRSFVYRLSSHNAA

WGELPRGREAENGFSLPYPAFRSEVLARLCPTREEILLRLDQGGVGYDEAFRNGLRP

VFVSRAPSRRLRGKAHMETLRSPKWKDHPEGPRTASRIPLKDLNLEKLERMVGKDR

DRKLYEALRERLAAFGGNGKKAFVAPFRKPCRSGEGPLVRSLRIFDSGYSGVELRDG

GEVYAVADHESMVRVDVYAKKNRFYLVPVYVADVARGIVKNRAIVAHKSEEEWD

LVDGSFDFRFSLFPGDLVEIEKKDGAYLGYYKSCHRGDGRLLLDRHDRMPRESDCG

TFYVSTRKDVLSMSKYQVDPLGEIRLVGSEKPPFVL

ZP_08574780.1 CRISPR-associated protein, Csn1 family [*Lactobacillus coryniformis* subsp. *torquens* KCTC 3535]

(SEQ ID NO: 89)

MGYRIGLDVGITSTGYAVLKTDKNGLPYKILTLDSVIYPRAENPQTGASLAEPRRIKR

GLRRRTRRTKFRKQRTQQLFIHSGLLSKPEIEQILATPQAKYSVYELRVAGLDRRLTN

SELFRVLYFFIGHRGFKSNRKAELNPENEADKKQMGQLLNSIEEIRKAIAEKGYRTVG

ELYLKDPKYNDHKRNKGYIDGYLSTPNRQMLVDEIKQILDKQRELGNEKLTDEFYA

TYLLGDENRAGIFQAQRDFDEGPGAGPYAGDQIKKMVGKDIFEPTEDRAAKATYTF

QYFNLLQKMTSLNYQNTTGDTWHTLNGLDRQAIIDAVFAKAEKPTKTYKPTDFGEL

RKLLKLPDDARFNLVNYGSLQTQKEIETVEKKTRFVDFKAYHDLVKVLPEEMWQSR

QLLDHIGTALTLYSSDKRRRRYFAEELNLPAELIEKLLPLNFSKFGHLSIKSMQNIIPYL

EMGQVYSEATTNTGYDFRKKQISKDTIREEITNPVVRRAVTKTIKIVEQIIRRYGKPDG

INIELARELGRNFKERGDIQKRQDKNRQTNDKIAAELTELGIPVNGQNIIRYKLHKEQ

NGVDPYTGDQIPFERAFSEGYEVDHIIPYSISWDDSYTNKVLTSAKCNREKGNRIPMV

YLANNEQRLNALTNIADNIIRNSRKRQKLLKQKLSDEELKDWKQRNINDTRFITRVL

YNYFRQAIEFNPELEKKQRVLPLNGEVTSKIRSRWGFLKVREDGDLHHAIDATVIAAI

TPKFIQQVTKYSQHQEVKNNQALWHDAEIKDAEYAAEAQRMDADLFNKIFNGFPLP

WPEFLDELLARISDNPVEMMKSRSWNTYTPIEIAKLKPVFVVRLANHKISGPAHLDTI

RSAKLFDEKGIVLSRVSITKLKINKKGQVATGDGIYDPENSNNGDKVVYSAIRQALEA

HNGSGELAFPDGYLEYVDHGTKKLVRKVRVAKKVSLPVRLKNKAAADNGSMVRID

VFNTGKKFVFVPIYIKDTVEQVLPNKAIARGKSLWYQITESDQFCFSLYPGDMVHIES

KTGIKPKYSNKENNTSVVPIKNFYGYFDGADIATASILVRAHDSSYTARSIGIAGLLKF

EKYQVDYFGRYHKVHEKKRQLFVKRDE

ZP_03755025.1 hypothetical protein ROSEINA2194_03455 [*Roseburia inulinivorans* DSM 16841]

(SEQ ID NO: 90)

MNAEHGKEGLLIMEENFQYRIGLDIGITSVGWAVLQNNSQDEPVRITDLGVRIFDVA

ENPKNGDALAAPRRDARTTRRRLRRRRHRLERIKFLLQENGLIEMDSFMERYYKGN

LPDVYQLRYEGLDRKLKDEELAQVLIHIAKHRGFRSTRKAETKEKEGGAVLKATTEN

QKIMQEKGYRTVGEMLYLDEAFHTECLWNEKGYVLTPRNRPDDYKHTILRSMLVEE

VHAIFAAQRAHGNQKATEGLEEAYVEIMTSQRSFDMGPGLQPDGKPSPYAMEGFGD

RVGKCTFEKDEYRAPKATYTAELFVALQKINHTKLIDEFGTGRFFSEEERKTIIGLLLS

SKELKYGTIRKKLNIDPSLKFNSLNYSAKKEGETEEERVLDTEKAKFASMFWTYEYS

KCLKDRTEEMPVGEKADLFDRIGEILTAYKNDDSRSSRLKELGLSGEEIDGLLDLSPA

KYQRVSLKAMRKMQPYLEDGLIYDKACEAAGYDFRALNDGNKKHLLKGEEINAIV

NDITNPVVKRSVSQTIKVINAIIQKYGSPQAVNIELAREMSKNFQDRTNLEKEMKKRQ

QENERAKQQIIELGKQNPTGQDILKYRLWNDQGGYCLYSGKKIPLEELFDGGYDIDHI

LPYSITFDDSYRNKVLVTAQENRQKGNRTPYEYFGADEKRWEDYEASVRLLVRDYK

KQQKLLKKNFTEEERKEFKERNLNDTKYITRVVYNMIRQNLELEPFNHPEKKKQVW

AVNGAVTSYLRKRWGLMQKDRSTDRHHAMDAVVIACCTDGMIHKISRYMQGREL

AYSRNFKFPDEETGEILNRDNFTREQWDEKFGVKVPLPWNSFRDELDIRLLNEDPKN

FLLTHADVQRELDYPGWMYGEEESPIEEGRYINYIRPLFVSRMPNHKVTGSAHDATI

RSARDYETRGVVITKVPLTDLKLNKDNEIEGYYDKDSDRLLYQALVRQLLLHGNDG

KKAFAEDFHKPKADGTEGPVVRKVKIEKKQTSGVMVRGGTGIAANGEMVRIDVFRE

NGKYYFVPVYTADVVRKVLPNRAATHTKPYSEWRVMDDANFVFSLYSRDLIHVKS

KKDIKTNLVNGGLLLQKEIFAYYTGADIATASIAGFANDSNFKFRGLGIQSLEIFEKCQ

VDILGNISVVRHENRQEFH

ZP_10953934.1 HNH endonuclease [*Alicyclobacillus hesperidum* URH17-3-68]

(SEQ ID NO: 91)

MAYRLGLDIGITSVGWAVVALEKDESGLKPVRIQDLGVRIFDKAEDSKTGASLALPR

REARSARRRTRRRRHRLWRVKRLLEQHGILSMEQIEALYAQRTSSPDVYALRVAGL

DRCLIAEEIARVLIHIAHRRGFQSNRKSEIKDSDAGKLLKAVQENENLMQSKGYRTV

AEMLVSEATKTDAEGKLVHGKKHGYVSNVRNKAGEYRHTVSRQAIVDEVRKIFAA

QRALGNDVMSEELEDSYLKILCSQRNFDDGPGGDSPYGHGSVSPDGVRQSIYERMV

GSCTFETGEKRAPRSSYSFERFQLLTKVVNLRIYRQQEDGGRYPCELTQTERARVIDC

AYEQTKITYGKLRKLLDMKDTESFAGLTYGLNRSRNKTEDTVFVEMKFYHEVRKAL

QRAGVFIQDLSIETLDQIGWILSVWKSDDNRRKKLSTLGLSDNVIEELLPLNGSKFGH

LSLKAIRKILPFLEDGYSYDVACELAGYQFQGKTEYVKQRLLPPLGEGEVTNPVVRR

ALSQAIKVVNAVIRKHGSPESIHIELARELSKNLDERRKIEKAQKENQKNNEQIKDEIR

EILGSAHVTGRDIVKYKLFKQQQEFCMYSGEKLDVTRLFEPGYAEVDHIIPYGISFDD

SYDNKVLVKTEQNRQKGNRTPLEYLRDKPEQKAKFIALVESIPLSQKKKNHLLMDK

RAIDLEQEGFRERNLSDTRYITRALMNHIQAWLLFDETASTRSKRVVCVNGAVTAY

MRARWGLTKDRDAGDKHHAADAVVVACIGDSLIQRVTKYDKFKRNALADRNRYV

QQVSKSEGITQYVDKETGEVFTWESFDERKFLPNEPLEPWPFFRDELLARLSDDPSKN

IRAIGLLTYSETEQIDPIFVSRMPTRKVTGAAHKETIRSPRIVKVDDNKGTEIQVVVSK

VALTELKLTKDGEIKDYFRPEDDPRLYNTLRERLVQFGGDAKAAFKEPVYKISKDGS

VRTPVRKVKIQEKLTLGVPVHGGRGIAENGGMVRIDVFAKGGKYYFVPIYVADVLK

RELPNRLATAHKPYSEWRVVDDSYQFKFSLYPNDAVMIKPSREVDITYKDRKEPVG

CRIMYFVSANIASASISLRTHDNSGELEGLGIQGLEVFEKYVVGPLGDTHPVYKERRM

PFRVERKMN

ADI19058.1 uncharacterized protein conserved in bacteria [uncultured delta proteobacterium HF0070_07E19]

(SEQ ID NO: 92)

MSSKAIDSLEQLDLFKPQEYTLGLDLGIKSIGWAILSGERIANAGVYLFETAEELNSTG

NKLISKAAERGRKRRIRRMLDRKARRGRHIRYLLEREGLPTDELEEVVVHQSNRTLW

DVRAEAVERKLTKQELAAVLFHLVRHRGYFPNTKKLPPDDESDSADEEQGKINRATS

RLREELKASDCKTIGQFLAQNRDRQRNREGDYSNLMARKLVFEEALQILAFQRKQG

HELSKDFEKTYLDVLMGQRSGRSPKLGNCSLIPSELRAPSSAPSTEWFKFLQNLGNLQ

ISNAYREEWSIDAPRRAQIIDACSQRSTSSYWQIRRDFQIPDEYRFNLVNYERRDPDV

DLQEYLQQQERKTLANFRNWKQLEKIIGTGHPIQTLDEAARLITLIKDDEKLSDQLAD

LLPEASDKAITQLCELDFTTAAKISLEAMYRILPHMNQGMGFFDACQQESLPEIGVPP

AGDRVPPFDEMYNPVVNRVLSQSRKLINAVIDEYGMPAKIRVELARDLGKGRELRE

RIKLDQLDKSKQNDQRAEDFRAEFQQAPRGDQSLRYRLWKEQNCTCPYSGRMIPVN

SVLSEDTQIDHILPISQSFDNSLSNKVLCFTEENAQKSNRTPFEYLDAADFQRLEAISG

NWPEAKRNKLLHKSFGKVAEEEWKSRALNDTRYLTSALADHLRHHLPDSKIQTVNGR

ITGYLRKQWGLEKDRDKHTHHAVDAIVVACTTPAIVQQVTLYHQDIRRYKKLGEKR

PTPWPETFRQDVLDVEEEIFITRQPKKVSGGIQTKDTLRKHRSKPDRQRVALTKVKLA

DLERLVEKDASNRNLYEHLKQCLEESGDQPTKAFKAPFYMPSGPEAKQRPILSKVTL

LREKPEPPKQLTELSGGRRYDSMAQGRLDIYRYKPGGKRKDEYRVVLQRMIDLMRG

EENVHVFQKGVPYDQGPEIEQNYTFLFSLYFDDLVEFQRSADSEVIRGYYRTFNIANG

QLKISTYLEGRQDFDFFGANRLAHFAKVQVNLLGKVIK

ZP_08157403.1 CRISPR-associated protein, Csn1 family [Ruminococcus albus 8]

(SEQ ID NO: 93)

MGNYYLGLDVGIGSIGWAVINIEKKRIEDFNVRIFKSGEIQEKNRNSRASQQCRRSRG

LRRLYRRKSHRKLRLKNYLSIIGLTTSEKIDYYYETADNNVIQLRNKGLSEKLTPEEIA

ACLIHICNNRGYKDFYEVNVEDIEDPDERNEYKEEHDSIVLISNLMNEGGYCTPAEMI

CNCREFDEPNSVYRKFHNSAASKNHYLITRHMLVKEVDLILENQSKYYGILDDKTIA

KIKDIIFAQRDFEIGPGKNERFRRFTGYLDSIGKCQFFKDQERGSRFTVIADIYAFVNV

LSQYTYTNNRGESVFDTSFANDLINSALKNGSMDKRELKAIAKSYHIDISDKNSDTSL

TKCFKYIKVVKPLFEKYGYDWDKLIENYTDTDNNVLNRIGIVLSQAQTPKRRREKLK

ALNIGLDDGLINELTKLKLSGTANVSYKYMQGSIEAFCEGDLYGKYQAKFNKEIPDID

ENAKPQKLPPFKNEDDCEFFKNPVVFRSINETRKLINAIIDKYGYPAAVNIETADELNK

TFEDRAIDTKRNNDNQKENDRIVKEIIECIKCDEVHARHLIEKYKLWEAQEGKCLYSG

ETITKEDMLRDKDKLFEVDHIVPYSLILDNTINNKALVYAEENQKKGQRTPLMYMNE

AQAADYRVRVNTMFKSKKCSKKKYQYLMLPDLNDQELLGGWRSRNLNDTRYICK

-continued

```
YLVNYLRKNLRFDRSYESSDEDDLKIRDHYRVFPVKSRFTSMFRRWWLNEKTWGR

YDKAELKKLTYLDHAADAIIIANCRPEYVVLAGEKLKLNKMYHQAGKRITPEYEQS

KKACIDNLYKLFRMDRRTAEKLLSGHGRLTPIIPNLSEEVDKRLWDKNIYEQFWKDD

KDKKSCEELYRENVASLYKGDPKFASSLSMPVISLKPDHKYRGTITGEEAIRVKEIDG

KLIKLKRKSISEITAESINSIYTDDKILIDSLKTIFEQADYKDVGDYLKKTNQHFFTTSS

GKRVNKVTVIEKVPSRWLRKEIDDNNFSLLNDSSYYCIELYKDSKGDNNLQGIAMSD

IVHDRKTKKLYLKPDFNYPDDYYTHVMYIFPGDYLRIKSTSKKSGEQLKFEGYFISVK

NVNENSFRFISDNKPCAKDKRVSITKKDIVIKLAVDLMGKVQGENNGKGISCGEPLSL

LKEKN
```

ZP_10010146.1 CRISPR-associated protein Cas9/Csn1, subtype II/NMEMI [*Treponema* sp. JC4]

(SEQ ID NO: 94)

```
MIMKLEKWRLGLDLGTNSIGWSVFSLDKDNSVQDLIDMGVRIFSDGRDPKTKEPLA

VARRTARSQRKLIYRRKLRRKQVFKFLQEQGLFPKTKEECMTLKSLNPYELRIKALD

EKLEPYELGRALFNLAVRRGFKSNRKDGSREEVSEKKSPDEIKTQADMQTHLEKAIK

ENGCRTITEFLYKNQGENGGIRFAPGRMTYYPTRKMYEEEFNLIRSKQEKYYPQVDW

DDIYKAIFYQRPLKPQQRGYCIYENDKERTFKAMPCSQKLRILQDIGNLAYYEGGSK

KRVELNDNQDKVLYELLNSKDKVTFDQMRKALCLADSNSFNLEENRDFLIGNPTAV

KMRSKNRFGKLWDEIPLEEQDLIIETIITADEDDAVYEVIKKYDLTQEQRDFIVKNTIL

QSGTSMLCKEVSEKLVKRLEEIADLKYHEAVESLGYKFADQTVEKYDLLPYYGKVL

PGSTMEIDLSAPETNPEKHYGKISNPTVHVALNQTRVVVNALIKEYGKPSQIAIELSRD

LKNNVEKKAEIARKQNQRAKENIAINDTISALYHTAFPGKSFYPNRNDRMKYRLWSE

LGLGNKCIYCGKGISGAELFTKEIEIEHILPFSRTLLDAESNLTVAHSSCNAFKAERSPF

EAFGTNPSGYSWQEIIQRANQLKNTSKKNKFSPNAMDSFEKDSSFIARQLSDNQYIAK

AALRYLKCLVENPSDVWTTNGSMTKLLRDKWEMDSILCRKFTEKEVALLGLKPEQI

GNYKKNRFDHRHHAIDAVVIGLTDRSMVQKLATKNSHKGNRIEIPEFPILRSDLIEKV

KNIVVSFKPDHGAEGKLSKETLLGKIKLHGKETFVCRENIVSLSEKNLDDIVDEKIKS

KVKDYVAKHKGQKIEAVLSDFSKENGIKKVRCVNRVQTPIEITSGKISRYLSPEDYFA

AVIWEIPGEKKTFKAQYIRRNEVEKNSKGLNVVKPAVLENGKPHPAAKQVCLLHKD

DYLEFSDKGKMYFCRIAGYAATNNKLDIRPVYAVSYCADWINSTNETMLTGYWKPT

PTQNWVSVNVLFDKQKARLVTVSPIGRVFRK
```

ZP_11150502.1 CRISPR-associated protein, Csn1 family [*Alcanivorax pacificus* W11-5]

(SEQ ID NO: 95)

```
MRYRVGLDLGTASVGAAVFSMDEQGNPMELIWHYERLFSEPLVPDMGQLKPKKAA

RRLARQQRRQIDRRASRLRRIAIVSRRLGIAPGRNDSGVHGNDVPTLRAMAVNERIEL

GQLRAVLLRMGKKRGYGGTFKAVRKVGEAGEVASGASRLEEEMVALASVQNKDS

VTVGEYLAARVEHGLPSKLKVAANNEYYAPEYALFRQYLGLPAIKGRPDCLPNMYA

LRHQIEHEFERIWATQSQFHDVMKDHGVKEEIRNAIFFQRPLKSPADKVGRCSLQTN

LPRAPRAQIAAQNFRIEKQMADLRWGMGRRAEMLNDHQKAVIRELLNQQKELSFRK

IYKELERAGCPGPEGKGLNMDRAALGGRDDLSGNTTLAAWRKLGLEDRWQELDEV

TQIQVINFLADLGSPEQLDTDDWSCRFMGKNGRPRNFSDEFVAFMNELRMTDGFDR

LSKMGFEGGRSSYSIKALKALTEWMIAPHWRETPETHRVDEEAAIRECYPESLATPA

QGGRQSKLEPPPLTGNEVVDVALRQVRHTINMMIDDLGSVPAQIVVEMAREMKGGV
```

-continued

TRRNDIEKQNKRFASERKKAAQSIEENGKTPTPARILRYQLWIEQGHQCPYCESNISL

EQALSGAYTNFEHILPRTLTQIGRKRSELVLAHRECNDEKGNRTPYQAFGHDDRRWR

IVEQRANALPKKSSRKTRLLLLKDFEGEALTDESIDEFADRQLHESSWLAKVTTQWL

SSLGSDVYVSRGSLTAELRRRWGLDTVIPQVRFESGMPVVDEEGAEITPEEFEKFRLQ

WEGHRVTREMRTDRRPDKRIDHRHHLVDAIVTALTSRSLYQQYAKAWKVADEKQR

HGRVDVKVELPMPILTIRDIALEAVRSVRISHKPDRYPDGRFFEATAYGIAQRLDERS

GEKVDWLVSRKSLTDLAPEKKSIDVDKVRANISRIVGEAIRLHISNIFEKRVSKGMTP

QQALREPIEFQGNILRKVRCFYSKADDCVRIEHSSRRGHHYKMLLNDGFAYMEVPC

KEGILYGVPNLVRPSEAVGIKRAPESGDFIRFYKGDTVKNIKTGRVYTIKQILGDGGG

KLILTPVTETKPADLLSAKWGRLKVGGRNIHLLRLCAE

ZP_18919511.1 hypothetical protein C882_0672 [*Caenispirillum salinarum* AK4]

(SEQ ID NO: 96)

MPVLSPLSPNAAQGRRRWSLALDIGEGSIGWAVAEVDAEGRVLQLTGTGVTLFPSA

WSNENGTYVAHGAADRAVRGQQQRHDSRRRRLAGLARLCAPVLERSPEDLKDLTR

TPPKADPRAIFFLRADAARRPLDGPELFRVLHHMAAHRGIRLAELQEVDPPPESDAD

DAAPAATEDEDGTRRAAADERAFRRLMAEHMHRHGTQPTCGEIMAGRLRETPAGA

QPVTRARDGLRVGGGVAVPTRALIEQEFDAIRAIQAPRHPDLPWDSLRRLVLDQAPI

AVPPATPCLFLEELRRRGETFQGRTITREAIDRGLTVDPLIQALRIRETVGNLRLHERIT

EPDGRQRYVPRAMPELGLSHGELTAPERDTLVRALMHDPDGLAAKDGRIPYTRLRK

LIGYDNSPVCFAQERDTSGGGITVNPTDPLMARWIDGWVDLPLKARSLYVRDVVAR

GADSAALARLLAEGAHGVPPVAAAAVPAATAAILESDIMQPGRYSVCPWAAEAILD

AWANAPTEGFYDVTRGLFGFAPGEIVLEDLRRARGALLAHLPRTMAAARTPNRAAQ

QRGPLPAYESVIPSQLITSLRRAHKGRAADWSAADPEERNPFLRTWTGNAATDHILN

QVRKTANEVITKYGNRRGWDPLPSRITVELAREAKHGVIRRNEIAKENRENEGRRKK

ESAALDTFCQDNTVSWQAGGLPKERAALRLRLAQRQEFFCPYCAERPKLRATDLFSP

AETEIDHVIERRMGGDGPDNLVLAHKDCNNAKGKKTPHEHAGDLLDSPALAALWQ

GWRKENADRLKGKGHKARTPREDKDFMDRVGWRFEEDARAKAEENQERRGRRML

HDTARATRLARLYLAAAVMPEDPAEIGAPPVETPPSPEDPTGYTAIYRTISRVQPVNG

SVTHMLRQRLLQRDKNRDYQTHHAEDACLLLLAGPAVVQAFNTEAAQHGADAPDD

RPVDLMPTSDAYHQQRRARALGRVPLATVDAALADIVMPESDRQDPETGRVHWRL

TRAGRGLKRRIDDLTRNCVILSRPRRPSETGTPGALHNATHYGRREITVDGRTDTVVT

QRMNARDLVALLDNAKIVPAARLDAAAPGDTILKEICTEIADRHDRVVDPEGTHARR

WISARLAALVPAHAEAVARDIAELADLDALADADRTPEQEARRSALRQSPYLGRAIS

AKKADGRARAREQEILTRALLDPHWGPRGLRHLIMREARAPSLVRIRANKTDAFGRP

VPDAAVWVKTDGNAVSQLWRLTSVVTDDGRRIPLPKPIEKRIEISNLEYARLNGLDE

GAGVTGNNAPPRPLRQDIDRLTPLWRDHGTAPGGYLGTAVGELEDKARSALRGKA

MRQTLTDAGITAEAGWRLDSEGAVCDLEVAKGDTVKKDGKTYKVGVITQGIFGMP

VDAAGSAPRTPEDCEKFEEQYGIKPWKAKGIPLA

YP_425545.1 CRISPR-associated endonuclease Csn1 family protein
[*Rhodospirillum rubrum* ATCC 11170]

(SEQ ID NO: 97)

MRPIEPWILGLDIGTDSLGWAVFSCEEKGPPTAKELLGGGVRLFDSGRDAKDHTSRQ

AERGAFRRARRQTRTWPWRRDRLIALFQAAGLTPPAAETRQIALALRREAVSRPLAP

DALWAALLHLAHHRGFRSNRIDKRERAAAKALAKAKPAKATAKATAPAKEADDEA

GFWEGAEAALRQRMAASGAPTVGALLADDLDRGQPVRMRYNQSDRDGVVAPTRA

LIAEELAEIVARQSSAYPGLDWPAVTRLVLDQRPLRSKGAGPCAFLPGEDRALRALP

TVQDFIIRQTLANLRLPSTSADEPRPLTDEEHAKALALLSTARFVEWPALRRALGLKR

GVKFTAETERNGAKQAARGTAGNLTEAILAPLIPGWSGWDLDRKDRVFSDLWAAR

QDRSALLALIGDPRGPTRVTEDETAEAVADAIQIVLPTGRASLSAKAARAIAQAMAP

GIGYDEAVTLALGUMSHRPRQERLARLPYYAAALPDVGLDGDPVGPPPAEDDGAA

AEAYYGRIGNISVHIALNETRKIVNALLHRHGPILRLVMVETTRELKAGADERKRMIA

EQAERERENAEIDVELRKSDRWMANARERRQRVRLARRQNNLCPYTSTPIGHADLL

GDAYDIDHVIPLARGGRDSLDNMVLCQSDANKTKGDKTPWEAFHDKPGWIAQRDD

FLARLDPQTAKALAWRFADDAGERVARKSAEDEDQGFLPRQLTDTGYIARVALRYL

SLVTNEPNAVVATNGRLTGLLRLAWDITPGPAPRDLLPTPRDALRDDTAARRFLDGL

TPPPLAKAVEGAVQARLAALGRSRVADAGLADALGLTLASLGGGGKNRADHRHHFI

DAAMIAVTTRGLINQINQASGAGRILDLRKWPRTNFEPPYPTFRAEVMKQWDHIHPSI

RPAHRDGGSLHAATVFGVRNRPDARVLVQRKPVEKLFLDANAKPLPADKIAEIIDGF

ASPRMAKRFKALLARYQAAHPEVPPALAALAVARDPAFGPRGMTANTVIAGRSDG

DGEDAGLITPFRANPKAAVRTMGNAVYEVWEIQVKGRPRWTHRVLTRFDRTQPAPP

PPPENARLVMRLRRGDLVYWPLESGDRLFLVKKMAVDGRLALWPARLATGKATAL

YAQLSCPNINLNGDQGYCVQSAEGIRKEKIRTTSCTALGRLRLSKKAT

CCA84553.1 conserved hypothetical protein [*Ralstonia syzygii* R24]

(SEQ ID NO: 98)

MAEKQHRWGLDIGTNSIGWAVIALIEGRPAGLVATGSRIFSDGRNPKDGSSLAVERR

GPRQMRRRRDRYLRRRDRFMQALINVGLMPGDAAARKALVTENPYVLRQRGLDQA

LTLPEFGRALFHLNQRRGFQSNRKTDRATAKESGKVKNAIAAFRAGMGNARTVGEA

LARRLEDGRPVRARMVGQGKDEHYELYIAREWIAQEFDALWASQQRFHAEVLADA

ARDRLRAILLFQRKLLPVPVGKCFLEPNQPRVAAALPSAQRFRLMQELNHLRVMTLA

DKRERPLSFQERNDLLAQLVARPKCGFDMLRKIVFGANKEAYRFTIESERRKELKGC

DTAAKLAKVNALGTRWQALSLDEQDRLVCLLLDGENDAVLADALREHYGLTDAQI

DTLLGLSFEDGHMRLGRSALLRVLDALESGRDEQGLPLSYDKAVVAAGYPAHTADL

ENGERDALPYYGELLWRYTQDAPTAKNDAERKFGKIANPTVHIGLNQLRKLVNALI

QRYGKPAQIVVELARNLKAGLEEKERIKKQQTANLERNERIRQKLQDAGVPDNREN

RLRMRLFEELGQGNGLGTPCIYSGRQISLQRLFSNDVQVDHILPFSKTLDDSFANKVL

AQHDANRYKGNRGPFEAFGANRDGYAWDDIRARAAVLPRNKRNRFAETAMQDWL

HNETDFLARQLTDTAYLSRVARQYLTAICSKDDVYVSPGRLTAMLRAKWGLNRVL

DGVMEEQGRPAVKNRDDHRHHAIDAVVIGATDRAMLQQVATLAARAREQDAERLI

GDMPTPWPNFLEDVRAAVARCVVSHKPDHGPEGGLHNDTAYGIVAGPFEDGRYRV

RHRVSLFDLKPGDLSNVRCDAPLQAELEPIFEQDDARAREVALTALAERYRQRKVW

LEELMSVLPIRPRGEDGKTLPDSAPYKAYKGDSNYCYELFINERGRWDGELISTFRAN

QAAYRRFRNDPARFRRYTAGGRPLLMRLCINDYIAVGTAAERTIFRVVKMSENKITL

AEHFEGGTLKQRDADKDDPFKYLTKSPGALRDLGARRIFVDLIGRVLDPGIKGD

ZP_10898214.1 CRISPR-associated protein, Csn1 family [*Rhodovulum* sp. PH10]

(SEQ ID NO: 99)

MGIRFAFDLGTNSIGWAVWRTGPGVFGEDTAASLDGSGVLIFKDGRNPKDGQSLAT

MRRVPRQSRKRRDRFVLRRRDLLAALRKAGLFPVDVEEGRRLAATDPYHLRAKAL

DESLTPHEMGRVIFHLNQRRGFRSNRKADRQDREKGKIAEGSKRLAETLAATNCRTL

GEFLWSRHRGTPRTRSPTRIRMEGEGAKALYAFYPTREMVRAEFERLWTAQSRFAP

DLLTPERHEEIAGILFRQRDLAPPKIGCCTFEPSERRLPRALPSVEARGIYERLAHLRIT

TGPVSDRGLTRPERDVLASALLAGKSLTFKAVRKTLKILPHALVNFEEAGEKGLDGA

LTAKLLSKPDHYGAAWHGLSFAEKDTFVGKLLDEADEERLIRRLVTENRLSEDAAR

RCASIPLADGYGRLGRTANTEILAALVEETDETGTVVTYAEAVRRAGERTGRNWHH

SDERDGVILDRLPYYGEILQRHVVPGSGEPEEKNEAARWGRLANPTVHIGLNQLRKV

VNRLIAAHGRPDQIVVELARELKLNREQKERLDRENRKNREENERRTAILAEHGQRD

TAENKIRLRLFEEQARANAGIALCPYTGRAIGIAELFTSEVEIDHILPVSLTLDDSLANR

VLCRREANREKRRQTPFQAFGATPAWNDIVARAAKLPPNKRWRFDPAALERFEREG

GFLGRQLNETKYLSRLAKIYLGKICDPDRVYVTPGTLTGLLRARWGLNSILSDSNFKN

RSDHRHHAVDAVVIGVLTRGMIQRIAHDAARAEDQDLDRVFRDVPVPFEDFRDHVR

ERVSTITVAVKPEHGKGGALHEDTSYGLVPDTDPNAALGNLVVRKPIRSLTAGEVDR

VRDRALRARLGALAAPFRDESGRVRDAKGLAQALEAFGAENGIRRVRILKPDASVV

TIADRRTGVPYRAVAPGENHHVDIVQMRDGSWRGFAASVFEVNRPGWRPEWEVKK

LGGKLVMRLHKGDMVELSDKDGQRRVKVVQQIEISANRVRLSPHNDGGKLQDRHA

DADDPFRWDLATIPLLKDRGCVAVRVDPIGVVTLRRSNV

YP_004386148.1 CRISPR-associated protein, Csn1 family [*Alicycliphilus denitrificans* K601]

(SEQ ID NO: 100)

MRSLRYRLALDLGSTSLGWALFRLDACNRPTAVIKAGVRIFSDGRNPKDGSSLAVTR

RAARAMRRRRDRLLKRKTRMQAKLVEHGFFPADAGKRKALEQLNPYALRAKGLQE

ALLPGEFARALFHINQRRGFKSNRKTDKKDNDSGVLKKAIGQLRQQMAEQGSRTVG

EYLWTRLQQGQGVRARYREKPYTTEEGKKRIDKSYDLYIDRAMIEQEFDALWAAQA

AFNPTLFHEAARADLKDTLLHQRPLRPVKPGRCTLLPEEERAPLALPSTQRFRIHQEV

NHLRLLDENLREVALTLAQRDAVVTALETKAKLSFEQIRKLLKLSGSVQFNLEDAKR

TELKGNATSAALARKELFGAAWSGFDEALQDEIVWQLVTEEGEGALIAWLQTHTGV

DEARAQAIVDVSLPEGYGNLSRKALARIVPALRAAVITYDKAVQAAGFDHHSQLGFE

YDASEVEDLVHPETGEIRSVFKQLPYYGKALQRHVAFGSGKPEDPDEKRYGKIANPT

VHIGLNQVRMVVNALIRRYGRPTEVVIELARDLKQSREQKVEAQRRQADNQRRNAR

IRRSIAEVLGIGEERVRGSDIQKWICWEELSFDAADRRCPYSGVQISAAMLLSDEVEV

EHILPFSKTLDDSLNNRTVAMRQANRIKRNRTPWDARAEFEAQGWSYEDILQRAER

MPLRKRYRFAPDGYERWLGDDKDFLARALNDTRYLSRVAAEYLRLVCPGTRVIPGQ

LTALLRGKFGLNDVLGLDGEKNRNDHRHHAVDACVIGVTDQGLMQRFATASAQAR

GDGLTRLVDGMPMPWPTYRDHVERAVRHIWVSHRPDHGFEGAMMEETSYGIRKDG

SIKQRRKADGSAGREISNLIRIHEATQPLRHGVSADGQPLAYKGYVGGSNYCIEITVN

-continued

DKGKWEGEVISTFRAYGVVRAGGMGRLRNPHEGQNGRKLIMRLVIGDSVRLEVDG

AERTMRIVKISGSNGQIFMAPIHEANVDARNTDKQDAFTYTSKYAGSLQKAKTRRVT

ISPIGEVRDPGFKG

YP_003552871.1 CRISPR-associated protein, Csn1 family [Candidatus
Puniceispirillum marinum IMCC1322]

(SEQ ID NO: 101)

MRRLGLDLGTNSIGWCLLDLGDDGEPVSIFRTGARIFSDGRDPKSLGSLKATRREARL

TRRRRDRFIQRQKNLINALVKYGLMPADEIQRQALAYKDPYPIRKKALDEAIDPYEM

GRAIFHINQRRGFKSNRKSADNEAGVVKQSIADLEMKLGEAGARTIGEFLADRQATN

DTVRARRLSGTNALYEFYPDRYMLEQEFDTLWAKQAAFNPSLYIEAARERLKEIVFF

QRKLKPQEVGRCIFLSDEDRISKALPSFQRFRIYQELSNLAWIDHDGVAHRITASLALR

DHLFDELEHKKKLTFKAMRAILRKQGVVDYPVGFNLESDNRDHLIGNLTSCIMRDA

KKMIGSAWDRLDEEEQDSFILMLQDDQKGDDEVRSILTQQYGLSDDVAEDCLDVRL

PDGHGSLSKKAIDRILPVLRDQGLIYYDAVKEAGLGEANLYDPYAALSDKLDYYGK

ALAGHVMGASGKFEDSDEKRYGTISNPTVHIALNQVRAVVNELIRLHGKPDEVVIEI

GRDLPMGADGKRELERFQKEGRAKNERARDELKKLGHIDSRESRQKFQLWEQLAKE

PVDRCCPFTGKMMSISDLFSDKVEIEHLLPFSLTLDDSMANKTVCFRQANRDKGNRA

PFDAFGNSPAGYDWQEILGRSQNLPYAKRWRFLPDAMKRFEADGGFLERQLNDTRY

ISRYTTEYISTIIPKNKIWVVTGRLTSLLRGFWGLNSILRGHNTDDGTPAKKSRDDHRH

HAIDAIVVGMTSRGLLQKVSKAARRSEDLDLTRLFEGRIDPWDGFRDEVKKHIDAIIV

SHRPRKKSQGALHNDTAYGIVEHAENGASTVVHRVPITSLGKQSDIEKVRDPLIKSAL

LNETAGLSGKSFENAVQKWCADNSIKSLRIVETVSIIPITDKEGVAYKGYKGDGNAY

MDIYQDPTSSKWKGEIVSRFDANQKGFIPSWQSQFPTARLIMRLRINDLLKLQDGEIE

EIYRVQRLSGSKILMAPHTEANVDARDRDKNDTFKLTSKSPGKLQSASARKVHISPT

GLIREG

YP_003448082.1 CRISPR-associated protein, Csn1 family [Azospirillum sp.
B510]

(SEQ ID NO: 102)

MARPAFRAPRREHVNGWTPDPHRISKPFFILVSWHLLSRVVIDSSSGCFPGTSRDHTD

KFAEWECAVQPYRLSFDLGTNSIGWGLLNLDRQGKPREIRALGSRIFSDGRDPQDKA

SLAVARRLARQMRRRDRYLTRRTRLMGALVRFGLMPADPAARKRLEVAVDPYLA

RERATRERLEPFEIGRALFHLNQRRGYKPVRTATKPDEEAGKVKEAVERLEAAIAAA

GAPTLGAWFAWRKTRGETLRARLAGKGKEAAYPFYPARRMLEAEFDTLWAEQARH

HPDLLTAEAREILRHRIFHQRPLKPPPVGRCTLYPDDGRAPRALPSAQRLRLFQELAS

LRVIHLDLSERPLTPAERDRIVAFVQGRPPKAGRKPGKVQKSVPFEKLRGLLELPPGT

GFSLESDKRPELLGDETGARIAPAFGPGWTALPLEEQDALVELLLTEAEPERAIAALT

ARWALDEATAAKLAGATLPDFHGRYGRRAVAELLPVLERETRGDPDGRVRPIRLDE

AVKLLRGGKDHSDFSREGALLDALPYYGAVLERHVAFGTGNPADPEEKRVGRVAN

PTVHIALNQLRHLVNAILARHGRPEEIVIELARDLKRSAEDRRREDKRQADNQKRNE

ERKRLILSLGERPTPRNLLKLRLWEEQGPVENRRCPYSGETISMRMLLSEQVDIDHILP

FSVSLDDSAANKVVCLREANRIKRNRSPWEAFGHDSERWAGILARAEALPKNKRWR

FAPDALEKLEGEGGLRARHLNDTRHLSRLAVEYLRCVCPKVRVSPGRLTALLRRRW

GIDAILAEADGPPPEVPAETLDPSPAEKNRADHRHHALDAVVIGCIDRSMVQRVQLA

AASAEREAAAREDNIRRVLEGFKEEPWDGFRAELERRARTIVVSHRPEHGIGGALHK

-continued

ETAYGPVDPPEEGFNLVVRKPIDGLSKDEINSVRDPRLRRALIDRLAIRRRDANDPAT

ALAKAAEDLAAQPASRGIRRVRVLKKESNPIRVEHGGNPSGPRSGGPFHKLLLAGEV

FIHVDVALRADGRRWVGHWVTLFEAHGGRGADGAAAPPRLGDGERFLMRLHKGDC

LKLEHKGRVRVMQVVKLEPSSNSVVVVEPHQVKTDRSKHVKISCDQLRARGARRV

TVDPLGRVRVHAPGARVGIGGDAGRTAMEPAEDIS

YP_571550.1 hypothetical protein Nham_4054 (plasmid)[*Nitrobacter hamburgensis* X14]
(SEQ ID NO: 103)

MHVEIDFPHFSRGDSHLAMNKNEILRGSSVLYRLGLDLGSNSLGWFVTHLEKRGDR

HEPVALGPGGVRIFPDGRDPQSGTSNAVDRRMARGARKRRDRFVERRKELIAALIKY

NLLPDDARERRALEVLDPYALRKTALTDTLPAHHVGRALFHLNQRRGFQSNRKTDS

KQSEDGAIKQAASRLATDKGNETLGVFFADMHLRKSYEDRQTAIRAELVRLGKDHL

TGNARKKIWAKVRKRLFGDEVLPRADAPHGVRARATITGTKASYDYYPTRDMLRD

EFNAIWAGQSAHHATITDEARTEIEHIIFYQRPLKPAIVGKCTLDPATRPFKEDPEGYR

APWSHPLAQRFRILSEARNLEIRDTGKGSRRLTKEQSDLVVAALLANREVKFDKLRT

LLKLPAEARFNLESDRRAALDGDQTAARLSDKKGFNKAWRGFPPERQIAIVARLEET

EDENELIAWLEKECALDGAAAARVANTTLPDGHCRLGLRAIKKIVPIMQDGLDEDG

VAGAGYHIAAKRAGYDHAKLPTGEQLGRLPYYGQWLQDAVVGSGDARDQKEKQY

GQFPNPTVHIGLGQLRRVVNDLIDKYGPPTEISIEFTRALKLSEQQKAERQREQRRNQ

DKNKARAEELAKFGRPANPRNLLKMRLWEELAHDPLDRKCVYTGEQISIERLLSDEV

DIDHILPVAMTLDDSPANKIICMRYANRHKRKQTPSEAFGSSPTLQGHRYNWDDIAA

RATGLPRNKRWRFDANAREEFDKRGGFLARQLNETGWLARLAKQYLGAVTDPNQI

WVVPGRLTSMLRGKWGLNGLLPSDNYAGVQDKAEEFLASTDDMEFSGVKNRADH

RHHAIDGLVTALTDRSLLWKMANAYDEEHEKFVIEPPWPTMRDDLKAALEKMVVS

HKPDHGIEGKLHEDSAYGFVKPLDATGLKEEEAGNLVYRKAIESLNENEVDRIRDIQ

LRTIVRDHVNVEKTKGVALADALRQLQAPSDDYPQFKHGLRHVRILKKEKGDYLVP

IANRASGVAYKAYSAGENFCVEVFETAGGKWDGEAVRRFDANKKNAGPKIAHAPQ

WRDANEGAKLVMRIHKGDLIRLDHEGRARIMVVHRLDAAAGRFKLADHNETGNLD

KRHATNNDIDPFRWLMASYNTLKKLAAVPVRVDELGRVWRVMPN

YP_001239928.1 hypothetical protein BBta_3952 [*Bradyrhizobium* sp. BTAi1]
(SEQ ID NO: 104)

MKRTSLRAYRLGVDLGANSLGWFVVWLDDHGQPEGLGPGGVRIFPDGRNPQSKQS

NAAGRRLARSARRRRDRYLQRRGKLMGLLVKHGLMPADEPARKRLECLDPYGLRA

KALDEVLPLHHVGRALFHLNQRRGLFANRAIEQGDKDASAIKAAAGRLQTSMQACG

ARTLGEFLNRRHQLRATVRARSPVGGDVQARYEFYPTRAMVDAEFEAIWAAQAPH

HPTMTAEAHDTIREAIFSQRAMKRPSIGKCSLDPATSQDDVDGFRCAWSHPLAQRFRI

WQDVRNLAVVETGPTSSRLGKEDQDKVARALLQTDQLSFDEIRGLLGLPSDARFNLE

SDRRDHLKGDATGAILSARRHFGPAWHDRSLDRQIDIVALLESALDEAAIIASLGTTH

SLDEAAAQRALSALLPDGYCRLGLRAIKRVLPLMEAGRTYAEAASAAGYDHALLPG

GKLSPTGYLPYYGQWLQNDVVGSDDERDTNERRWGRLPNPTVHIGIGQLRRVVNEL

IRWHGPPAEITVELTRDLKLSPRRLAELEREQAENQRKNDKRTSLLRKLGLPASTHNL

LKLRLWDEQGDVASECPYTGEAIGLERLVSDDVDIDHLIPFSISWDDSAANKVVCMR

YANREKGNRTPFEAFGHRQGRPYDWADIAERAARLPRGKRWRFGPGARAQFEELG

```
DFQARLLNETSWLARVAKQYLAAVTHPHRIHVLPGRLTALLRATWELNDLLPGSDD

RAAKSRKDHRHHAIDALVAALTDQALLRRMANAHDDTRRKIEVLLPWPTFRIDLET

RLKAMLVSHKPDHGLQARLHEDTAYGTVEHPETEDGANLVYRKTFVDISEKEIDRIR

DRRLRDLVRAHVAGERQQGKTLKAAVLSFAQRRDIAGHPNGIRHVRLTKSIKPDYL

VPIRDKAGRIYKSYNAGENAFVDILQAESGRWIARATTVFQANQANESHDAPAAQPI

MRVFKGDMLRIDHAGAEKFVKIVRLSPSNNLLYLVEHHQAGVFQTRHDDPEDSFRW

LFASFDKLREWNAELVRIDTLGQPWRRKRGLETGSEDATRIGWTRPKKWP
```

YP_001531750.1 CRISPR-associated protein [*Dinoroseobacter shibae* DFL12 = DSM16493]

(SEQ ID NO: 105)

```
MRLGLDIGTSSIGWWLYETDGAGSDARITGVVDGGVRIFSDGRDPKSGASLAVDRR

AARAMRRRRDRYLRRRATLMKVLAETGLMPADPAEAKALEALDPFALRAAGLDEP

LPLPHLGRALFHLNQRRGFKSNRKTDRGDNESGKIKDATARLDMEMMANGARTYG

EFLHKRRQKATDPRHVPSVRTRLSIANRGGPDGKEEAGYDFYPDRRHLEEEFHKLW

AAQGAHHPELTETLRDLLFEKIFFQRPLKEPEVGLCLFSGHHGVPPKDPRLPKAHPLT

QRRVLYETVNQLRVTADGREARPLTREERDQVIHALDNKKPTKSLSSMVLKLPALA

KVLKLRDGERFTLETGVRDAIACDPLRASPAHPDRFGPRWSILDADAQWEVISRIRR

VQSDAEHAALVDWLTEAHGLDRAHAEATAHAPLPDGYGRLGLTATTRILYQLTAD

VVTYADAVKACGWHHSDGRTGECFDRLPYYGEVLERHVIPGSYHPDDDDITRFGRI

TNPTVHIGLNQLRRLVNRIIETHGKPHQIVVELARDLKKSEEQKRADIKRIRDTTEAA

KKRSEKLEELEIEDNGRNRMLLRLWEDLNPDDAMRRFCPYTGTRISAAMIFDGSCDV

DHILPYSRTLDDSFPNRTLCLREANRQKRNQTPWQAWGDTPHWHAIAANLKNLPEN

KRWRFAPDAMTRFEGENGFLDRALKDTQYLARISRSYLDTLFTKGGHVWVVPGRFT

EMLRRHWGLNSLLSDAGRGAVKAKNRTDHRHHAIDAAVIAATDPGLLNRISRAAGQ

GEAAGQSAELIARDTPPPWEGFRDDLRVRLDRIIVSHRADHGRIDHAARKQGRDSTA

GQLHQETAYSIVDDIHVASRTDLLSLKPAQLLDEPGRSGQVRDPQLRKALRVATGGK

TGKDFENALRYFASKPGPYQAIRRVRIIKPLQAQARVPVPAQDPIKAYQGGSNHLFEI

WRLPDGEIEAQVITSFEAHTLEGEKRPHPAAKRLLRVHKGDMVALERDGRRVVGHV

QKMDIANGLFIVPHNEANADTRNNDKSDPFKWIQIGARPAIASGIRRVSVDEIGRLRD

GGTRPI
```

YP_001411379.1 CRISPR-associated endonuclease Csn1 family protein [*Parvibaculum lavamentivorans* DS-1]

(SEQ ID NO: 106)

```
MERIFGFDIGTTSIGFSVIDYSSTQSAGNIQRLGVRIFPEARDPDGTPLNQQRRQKRMM

RRQLRRRRIRRKALNETLHEAGFLPAYGSADWPVVMADEPYELRRRGLEEGLSAYE

FGRAIYHLAQHRHFKGRELEESDTPDPDVDDEKEAANERAATLKALKNEQTTLGAW

LARRPPSDRKRGIHAHRNVVAEEFERLWEVQSKFHPALKSEEMRARISDTIFAQRPVF

WRKNTLGECRFMPGEPLCPKGSWLSQQRRMLEKLNNLAIAGGNARPLDAEERDAIL

SKLQQQASMSWPGVRSALKALYKQRGEPGAEKSLKFNLELGGESKLLGNALEAKLA

DMFGPDWPAHPRKQEIRHAVHERLWAADYGETPDKKRVIILSEKDRKAHREAAANS

FVADFGITGEQAAQLQALKLPTGWEPYSIPALNLFLAELEKGERFGALVNGPDWEG

WRRTNFPHRNQPTGEILDKLPSPASKEERERISQLRNPTVVRTQNELRKVVNNLIGLY

GKPDRIRIEVGRDVGKSKREREEIQSGIRRNEKQRKKATEDLIKNGIANPSRDDVEKW
```

-continued

ILWKEGQERCPYTGDQIGFNALFREGRYEVEHIWPRSRSFDNSPRNKTLCRKDVNIEK

GNRMPFEAFGHDEDRWSAIQIRLQGMVSAKGGTGMSPGKVKRFLAKTMPEDFAAR

QLNDTRYAAKQILAQLKRLWPDMGPEAPVKVEAVTGQVTAQLRKLWTLNNILADD

GEKTRADHRHHAIDALTVACTHPGMTNKLSRYWQLRDDPRAEKPALTPPWDTIRAD

AEKAVSEIVVSHRVRKKVSGPLHKETTYGDTGTDIKTKSGTYRQFVTRKKIESLSKGE

LDEIRDPRIKEIVAAHVAGRGGDPKKAFPPYPCVSPGGPEIRKVRLTSKQQLNLMAQT

GNGYADLGSNHHIAIYRLPDGKADFEIVSLFDASRRLAQRNPIVQRTRADGASFVMS

LAAGEAIMIPEGSKKGIWIVQGVWASGQVVLERDTDADHSTTTRPMPNPILKDDAKK

VSIDPIGRVRPSND

ZP_17295095.1 CRISPR-associated protein cas9/csn1, subtype II/nmemi
[*Bergeyella zoohelcum* ATCC 43767]
(SEQ ID NO: 107)

MKHILGLDLGTNSIGWALIERNIEEKYGKIIGMGSRIVPMGAELSKFEQGQAQTKNAD

RRTNRGARRLNKRYKQRRNKLIYILQKLDMLPSQIKLKEDFSDPNKIDKITILPISKKQ

EQLTAFDLVSLRVKALTEKVGLEDLGKIIYKYNQLRGYAGGSLEPEKEDIFDEEQSKD

KKNKSFIAFSKIVFLGEPQEEIFKNKKLNRRAIIVETEEGNFEGSTFLENIKVGDSLELLI

NISASKSGDTITIKLPNKTNWRKKMENIENQLKEKSKEMGREFYISEFLLELLKENRW

AKIRNNTILRARYESEFEAIWNEQVKHYPFLENLDKKTLIEIVSFIFPGEKESQKKYRE

LGLEKGLKYIIKNQVVFYQRELKDQSHLISDCRYEPNEKAIAKSHPVFQEYKVWEQIN

KLIVNTKIEAGTNRKGEKKYKYIDRPIPTALKEWIFEELQNKKEITFSAIFKKLKAEFD

LREGIDFLNGMSPKDKLKGNETKLQLQKSLGELWDVLGLDSINRQIELWNILYNEKG

NEYDLTSDRTSKVLEFINKYGNNIVDDNAEETAIRISKIKFARAYSSLSLKAVERILPL

VRAGKYFNNDFSQQLQSKILKLLNENVEDPFAKAAQTYLDNNQSVLSEGGVGNSIAT

ILVYDKHTAKEYSHDELYKSYKEINLLKQGDLRNPLVEQIINEALVLIRDIWKNYGIK

PNEIRVELARDLKNSAKERATIHKRNKDNQTINNKIKETLVKNKKELSLANIEKVKL

WEAQRHLSPYTGQPIPLSDLFDKEKYDVDHIIPISRYFDDSFTNKVISEKSVNQEKANR

TAMEYFEVGSLKYSIFTKEQFIAHVNEYFSGVKRKNLLATSIPEDPVQRQIKDTQYIAI

RVKEELNKIVGNENVKTTTGSITDYLRNHWGLTDKFKLLLKERYEALLESEKFLEAE

YDNYKKDFDSRKKEYEEKEVLFEEQELTREEFIKEYKENYIRYKKNKLIIKGWSKRID

HRHHAIDALIVACTEPAHIKRLNDLNKVLQDWLVEHKSEFMPNFEGSNSELLEEILSL

PENERTEIFTQIEKFRAIEMPWKGFPEQVEQKLKEIIISHKPKDKLLLQYNKAGDRQIK

LRGQLHEGTLYGISQGKEAYRIPLTKFGGSKFATEKNIQKIVSPFLSGFIANHLKEYNN

KKEEAFSAEGIMDLNNKLAQYRNEKGELKPHTPISTVKIYYKDPSKNKKKKDEEDLS

LQKLDREKAFNEKLYVKTGDNYLFAVLEGEIKTKKTSQIKRLYDIISFFDATNFLKEE

FRNAPDKKTFDKDLLFRQYFEERNKAKLLFTLKQGDFVYLPNENEEVILDKESPLYN

QYWGDLKERGKNIYVVQKFSKKQIYFIKHTIADIIKKDVEFGSQNCYETVEGRSIKEN

CFKLEIDRLGNIVKVIKR

ZP_07217791.1 conserved hypothetical protein [*Bacteroides* sp. 20_3]
(SEQ ID NO: 108)

MKKIVGLDLGTNSIGWALINAYINKEHLYGIEACGSRIIPMDAAILGNFDKGNSISQTA

DRTSYRGIRRLRERHURRERLHRILDLLGFLPKHYSDSLNRYGKFLNDIECKLPWVK

DETGSYKFIFQESFKEMLANFTEHHPILIANNKKVPYDWTIYYLRKKALTQKISKEEL

AWILLNFNQKRGYYQLRGEEEETPNKLVEYYSLKVEKVEDSGERKGKDTWYNVHL

-continued

ENGMIYRRTSNIPLDWEGKTKEFIVTTDLEADGSPKKDKEGNIKRSFRAPKDDDWTLI

KKKTEADIDKIKMTVGAYIYDTLLQKPDQKIRGKLVRTIERKYYKNELYQILKTQSEF

HEELRDKQLYIACLNELYPNNEPRRNSISTRDFCHLFIEDIIFYQRPLKSKKSLIDNCPY

EENRYIDKESGEIKHASIKCIAKSHPLYQEFRLWQFIVNLRIYRKETDVDVTQELLPTE

ADYVTLFEWLNEKKEIDQKAFFKYPPFGFKKTTSNYRWNYVEDKPYPCNETHAQIIA

RLGKAHIPKAFLSKEKEETLWHILYSIEDKQEIEKALHSFANKNNLSEEFIEQFKNFPPF

KKEYGSYSAKAIKKLLPLMRMGKYWSIENIDNGTRIRINKIIDGEYDENIRERVRQKA

INLTDITHFRALPLWLACYLVYDRHSEVKDIVKWKTPKDIDLYLKSFKQHSLRNPIVE

QVITETLRTVRDIWQQVGHIDEIHIELGREMKNPADKRARMSQQMIKNENTNLRIKA

LLTEFLNPEFGIENVRPYSPSQQDLLRIYEEGVLNSILELPEDIGIILGKFNQTDTLKRPT

RSEILRYKLWLEQKYRSPYTGEMIPLSKLFTPAYEIEHIIPQSRYFDDSLSNKVICESEI

NKLKDRSLGYEFIKNHHGEKVELAFDKPVEVLSVEAYEKLVHESYSHNRSKMKKLL

MEDIPDQFIERQLNDSRYISKVVKSLLSNIVREENEQEAISKNVIPCTGGITDRLKKDW

GINDVWNKIVLPRFIRLNELTESTRFTSINTNNTMIPSMPLELQKGFNKKRIDHRHHA

MDAIIIACANRNIVNYLNNVSASKNTKITRRDLQTLLCHKDKTDNNGNYKWVIDKP

WETFTQDTLTALQKITVSFKQNLRVINKTTNHYQHYENGKKIVSNQSKGDSWAIRKS

MHKETVHGEVNLRMIKTVSFNEALKKPQAIVEMDLKKKILAMLELGYDTKRIKNYF

EENKDTWQDINPSKIKVYYFTKETKDRYFAVRKPIDTSFDKKKIKESITDTGIQQIMLR

HLETKDNDPTLAFSPDGIDEMNRNILILNKGKKHQPIYKVRVYEKAEKFTVGQKGNK

RTKFVEAAKGTNLFFAIYETEEIDKDTKKVIRKRSYSTIPLNVVIERQKQGLSSAPEDE

NGNLPKYILSPNDLVYVPTQEEINKGEVVMPIDRDRIYKMVDSSGITANFIPASTANLI

FALPKATAEIYCNGENCIQNEYGIGSPQSKNQKAITGEMVKEICFPIKVDRLGNIIQVG

SCILTN

YP_005848005.1 hypothetical protein IALB_3034 [*Ignavibacterium album*
JCM 16511]

(SEQ ID NO: 109)

MEFKKVLGLDIGTNSIGCALLSLPKSIQDYGKGGRLEWLTSRVIPLDADYMKAFIDG

KNGLPQVITPAGKRRQKRGSRRLKHRYKLRRSRLIRVFKTLNWLPEDFPLDNPKRIK

ETISTEGKFSFRISDYVPISDESYREFYREFGYPENEIEQVIEEINFRRKTKGKNKNPMI

KLLPEDWVVYYLRKKALIKPTTKEELIRIIYLFNQRRGFKSSRKDLTETAILDYDEFAK

RLAEKEKYSAENYETKFVSITKVKEVVELKTDGRKGKKRFKVILEDSRIEPYEIERKE

KPDWEGKEYTFLVTQKLEKGKFKQNKPDLPKEEDWALCTTALDNRMGSKHPGEFFF

DELLKAFKEKRGYKIRQYPVNRWRYKKELEFIWTKQCQLNPELNNLNINKEILRKLA

TVLYPSQSKFFGPKIKEFENSDVLHIISEDIIYYQRDLKSQKSLISECRYEKRKGIDGEIY

GLKCIPKSSPLYQEFRIWQDIHNIKVIRKESEVNGKKKINIDETQLYINENIKEKLFELF

NSKDSLSEKDILELISLNIINSGIKISKKEEETTHRINLFANRKELKGNETKSRYRKVFK

KLGFDGEYILNHPSKLNRLWHSDYSNDYADKEKTEKSILSSLGWKNRNGKWEKSKN

YDVFNLPLEVAKAIANLPPLKKEYGSYSALAIRKMLVVMRDGKYWQHPDQIAKDQE

NTSLMLFDKNLIQLTNNQRKVLNKYLLTLAEVQKRSTLIKQKLNEIEHNPYKLELVS

DQDLEKQVLKSFLEKKNESDYLKGLKTYQAGYLIYGKHSEKDVPIVNSPDELGEYIR

KKLPNNSLRNPIVEQVIRETIFIVRDVWKSFGIIDEIHIELGRELKNNSEERKKTSESQE

KNFQEKERARKLLKELLNSSNFEHYDENGNKIFSSFTVNPNPDSPLDIEKFRIWKNQS

-continued

```
GLTDEELNKKLKDEKIPTEIEVKKYILWLTQKCRSPYTGKIIPLSKLFDSNVYEIEHIIP

RSKMKNDSTNNLVICELGVNKAKGDRLAANFISESNGKCKFGEVEYTLLKYGDYLQ

YCKDTFKYQKAKYKNLLATEPPEDFIERQINDTRYIGRKLAELLTPVVKDSKNIIFTIG

SITSELKITWGLNGVWKDILRPRFKRLESIINKKLIFQDEDDPNKYHFDLSINPQLDKE

GLKRLDHRHHALDATIIAATTREHVRYLNSLNAADNDEEKREYFLSLCNHKIRDFKL

PWENFTSEVKSKLLSCVVSYKESKPILSDPFNKYLKWEYKNGKWQKVFAIQIKNDR

WKAVRRSMFKEPIGTVWIKKIKEVSLKEAIKIQAIWEEVKNDPVRKKKEKYIYDDYA

QKVIAKIVQELGLSSSMRKQDDEKLNKFINEAKVSAGVNKNLNTTNKTIYNLEGRFY

EKIKVAEYVLYKAKRMPLNKKEYIEKLSLQKMFNDLPNFILEKSILDNYPEILKELES

DNKYIIEPHKKNNPVNRLLLEHILEYHNNPKEAFSTEGLEKLNKKAINKIGKPIKYITR

LDGDINEEEIFRGAVFETDKGSNVYFVMYENNQTKDREFLKPNPSISVLKAIEHKNKI

DFFAPNRLGFSRIILSPGDLVYVPTNDQYVLIKDNSSNETIINWDDNEFISNRIYQVKK

FTGNSCYFLKNDIASLILSYSASNGVGEFGSQNISEYSVDDPPIRIKDVCIKIRVDRLGN

VRPL

YP_213533.1 conserved hypothetical protein [Bacteroides fragilis NCTC 9343]
                                                        (SEQ ID NO: 110)
MKRILGLDLGTNSIGWALVNEAENKDERSSIVKLGVRVNPLTVDELTNFEKGKSITT

NADRTLKRGMRRNLQRYKLRRETLTEVLKEHKLITEDTILSENGNRTTFETYRLRAK

AVTEEISLEEFARVLLMINKKRGYKSSRKAKGVEEGTLIDGMDIARELYNNNLTPGEL

CLQLLDAGKKFLPDFYRSDLQNELDRIWEKQKEYYPEILTDVLKEELRGKKRDAVW

AICAKYFVWKENYTEWNKEKGKTEQQEREHKLEGIYSKRKRDEAKRENLQWRVNG

LKEKLSLEQLVIVFQEMNTQINNSSGYLGAISDRSKELYFNKQTVGQYQMEMLDKNP

NASLRNMVFYRQDYLDEFNMLWEKQAVYHKELTEELKKEIRDIIIFYQRRLKSQKGL

IGFCEFESRQIEVDIDGKKKIKTVGNRVISRSSPLFQEFKIWQILNNIEVTVVGKKRKRR

KLKENYSALFEELNDAEQLELNGSRRLCQEEKELLAQELFIRDKMTKSEVLKLLFDN

PQELDLNFKTIDGNKTGYALFQAYSKMIEMSGHEPVDFKKPVEKVVEYIKAVFDLLN

WNTDILGFNSNEELDNQPYYKLWHLLYSFEGDNTPTGNGRLIQKMTELYGFEKEYA

TILANVSFQDDYGSLSAKAIHKILPHLKEGNRYDVACVYAGYRHSESSLTREEIANKV

LKDRLMLLPKNSLHNPVVEKILNQMVNVINVIIDIYGKPDEIRVELARELKKNAKERE

ELTKSIAQTTKAHEEYKTLLQTEFGLTNVSRTDILRYKLYKELESCGYKTLYSNTYIS

REKLFSKEFDIEHIIPQARLFDDSFSNKTLEARSVNIEKGNKTAYDFVKEKFGESGADN

SLEHYLNNIEDLFKSGKISKTKYNKLKMAEQDIPDGFIERDLRNTQYIAKKALSMLNE

ISHRVVATSGSVTDKLREDWQLIDVMKELNWEKYKALGLVEYFEDRDGRQIGRIKD

WTKRNDHRHHAMDALTVAFTKDVFIQYFNNKNASLDPNANEHAIKNKYFQNGRAI

APMPLREFRAEAKKHLENTLISIKAKNKVITGNINKTRKKGGVNKNMQQTPRGQLHL

ETIYGSGKQYLTKEEKVNASFDMRKIGTVSKSAYRDALLKRLYENDNDPKKAFAGK

NSLDKQPIWLDKEQMRKVPEKVKIVTLEAIYTIRKEISPDLKVDKVIDVGVRKILIDRL

NEYGNDAKKAFSNLDKNPIWLNKEKGISIKRVTISGISNAQSLHVKKDKDGKPILDEN

GRNIPVDFVNTGNNHHVAVYYRPVIDKRGQLVVDEAGNPKYELEEVVVSFFEAVTR

ANLGLPIIDKDYKTTEGWQFLFSMKQNEYFVFPNEKTGFNPKEIDLLDVENYGLISPN

LFRVQKFSLKNYVFRHHLETTIKDTSSILRGITWIDFRSSKGLDTIVKVRVNHIGQIVS

VGEY
```

ZP_10895610.1 CRISPR-associated protein Cas9/Csn1, subtype II/NMEMI
[*Porphyromonas* sp. oral taxon 279 str. F0450]

(SEQ ID NO: 111)

MLMSKHVLGLDLGVGSIGWCLIALDAQGDPAEILGMGSRVVPLNNATKAIEAFNAG

AAFTASQERTARRTMRRGFARYQLRRYRLRRELEKVGMLPDAALIQLPLLELWELR

ERAATAGRRLTLPELGRVLCHINQKRGYRHVKSDAAAIVGDEGEKKKDSNSAYLAG

IRANDEKLQAEHKTVGQYFAEQLRQNQSESPTGGISYRIKDQIFSRQCYIDEYDQIMA

VQRVHYPDILTDEFIRMLRDEVIFMQRPLKSCKHLVSLCEFEKQERVMRVQQDDGK

GGWQLVERRVKFGPKVAPKSSPLFQLCCIYEAVNNIRLTRPNGSPCDITPEERAKIVA

HLQSSASLSFAALKKLLKEKALIADQLTSKSGLKGNSTRVALASALQPYPQYHHLLD

MELETRMMTVQLTDEETGEVTEREVAVVTDSYVRKPLYRLWHILYSIEEREAMRRA

LITQLGMKEEDLDGGLLDQLYRLDFVKPGYGNKSAKFICKLLPQLQQGLGYSEACA

AVGYRHSNSPTSEEITERTLLEKIPLLQRNELRQPLVEKILNQMINLVNALKAEYGIDE

VRVELARELKMSREERERMARNNKDREERNKGVAAKIRECGLYPTKPRIQKYMLW

KEAGRQCLYCGRSIEEEQCLREGGMEVEHIIPKSVLYDDSYGNKTCACRRCNKEKGN

RTALEYIRAKGREAEYMKRINDLLKEKKISYSKHQRLRWLKEDIPSDFLERQLRLTQ

YISRQAMAILQQGIRRVSASEGGVTARLRSLWGYGKILHTLNLDRYDSMGETERVSR

EGEATEELHITNWSKRMDHRHHAIDALVVACTRQSYIQRLNRLSSEFGREDKKKEDQ

EAQEQQATETGRLSNLERWLTQRPHFSVRTVSDKVAEILISYRPGQRVVTRGRNIYR

KKMADGREVSCVQRGVLVPRGELMEASFYGKILSQGRVRIVKRYPLHDLKGEVVDP

HLRELITTYNQELKSREKGAPIPPLCLDKDKKQEVRSVRCYAKTLSLDKAIPMCFDEK

GEPTAFVKSASNHHLALYRTPKGKLVESIVTFWDAVDRARYGIPLVITHPREVMEQV

LQRGDIPEQVLSLLPPSDWVFVDSLQQDEMVVIGLSDEELQRALEAQNYRKISEHLY

RVQKMSSSYYVFRYHLETSVADDKNTSGRIPKFHRVQSLKAYEERNIRKVRVDLLG

RISLL

ZP_11022414.1 CRISPR-associated protein cas9/csn1, subtype II/nmemi
[*Barnesiella intestinihominis* YIT 11860]

(SEQ ID NO: 112)

MKNILGLDLGLSSIGWSVIRENSEEQELVAMGSRVVSLTAAELSSFTQGNGVSINSQR

TQKRTQRKGYDRYQLRRTLLRNKLDTLGMLPDDSLSYLPKLQLWGLRAKAVTQRIE

LNELGRVLLHLNQKRGYKSIKSDFSGDKKITDYVKTVKTRYDELKEMRLTIGELFFR

RLTENAFFRCKEQVYPRQAYVEEFDCIMNCQRKFYPDILTDETIRCIRDEIIYYQRPLK

SCKYLVSRCEFEKRFYLNAAGKKTEAGPKVSPRTSPLFQVCRLWESINNIVVKDRRN

EIVFISAEQRAALFDFLNTHEKLKGSDLLKLLGLSKTYGYRLGEQFKTGIQGNKTRVE

IERALGNYPDKKRLLQFNLQEESSSMVNTETGEIIPMISLSFEQEPLYRLWHVLYSIDD

REQLQSVLRQKFGIDDDEVLERLSAIDLVKAGFGNKSSKAIRRILPFLQLGMNYAEAC

EAAGYNHSNNYTKAENEARALLDRLPAIKKNELRQPVVEKILNQMVNVVNALMEK

YGRFDEIRVELARELKQSKEERSNTYKSINKNQRENEQIAKRIVEYGVPTRSRIQKYK

MWEESKHCCIYCGQPVDVGDFLRGFDVEVEHIIPKSLYFDDSFANKVCSCRSCNKEK

NNRTAYDYMKSKGEKALSDYVERVNTMYTNNQISKTKWQNLLTPVDKISIDFIDRQ

LRESQYIARKAKEILTSICYNVTATSGSVTSFLRHVWGWDTVLHDLNFDRYKKVGLT

EVIEVNHRGSVIRREQIKDWSKRFDHRHHAIDALTIACTKQAYIQRLNNLRAEEGPDF

NKMSLERYIQSQPHFSVAQVREAVDRILVSFRAGKRAVTPGKRYIRKNRKRISVQSV

-continued

LIPRGALSEESVYGVIHVWEKDEQGHVIQKQRAVMKYPITSINREMLDKEKVVDKRI

HRILSGRLAQYNDNPKEAFAKPVYIDKECRIPIRTVRCFAKPAINTLVPLKKDDKGNP

VAWVNPGNNHHVAIYRDEDGKYKERTVTFWEAVDRCRVGIPAIVTQPDTIWDNILQ

RNDISENVLESLPDVKWQFVLSLQQNEMFILGMNEEDYRYAMDQQDYALLNKYLY

RVQKLSKSDYSFRYHTETSVEDKYDGKPNLKLSMQMGKLKRVSIKSLLGLNPHKVH

ISVLGEIKEIS

ZP_09642280.1 CRISPR-associated protein cas9/csn1, subtype II/nmemi
[*Odoribacter laneus* YIT12061]
(SEQ ID NO: 113)
METTLGIDLGTNSIGLALVDQEEHQILYSGVRIFPEGINKDTIGLGEKEESRNATRRAK

RQMRRQYFRKKLRKAKLLELLIAYDMCPLKPEDVRRWKNWDKQQKSTVRQFPDTP

AFREWLKQNPYELRKQAVTEDVTRPELGRILYQMIQRRGFLSSRKGKEEGKIFTGKD

RMVGIDETRKNLQKQTLGAYLYDIAPKNGEKYRFRTERVRARYTLRDMYIREFEIIW

QRQAGHLGLAHEQATRKKNIFLEGSATNVRNSKLITHLQAKYGRGHVLIEDTRITVT

FQLPLKEVLGGKIEIEEEQLKFKSNESVLFWQRPLRSQKSLLSKCVFEGRNFYDPVHQ

KWIIAGPTPAPLSHPEFEEFRAYQFINNIIYGKNEHLTAIQREAVFELMCTESKDFNFE

KIPKHLKLFEKFNFDDTTKVPACTTISQLRKLFPHPVWEEKREEIWHCFYFYDDNTLL

FEKLQKDYALQTNDLEKIKKIRLSESYGNVSLKAIRRINPYLKKGYAYSTAVLLGGIR

NSFGKRFEYFKEYEPEIEKAVCRILKEKNAEGEVIRKIKDYLVHNRFGFAKNDRAFQK

LYHHSQAITTQAQKERLPETGNLRNPIVQQGLNELRRTVNKLLATCREKYGPSFKFD

HIHVEMGRELRSSKTEREKQSRQIRENEKKNEAAKVKLAEYGLKAYRDNIQKYLLY

KEIEEKGGTVCCPYTGKTLNISHTLGSDNSVQIEHIIPYSISLDDSLANKTLCDATFNRE

KGELTPYDFYQKDPSPEKWGASSWEEIEDRAFRLLPYAKAQRFIRRKPQESNEFISRQ

LNDTRYISKKAVEYLSAICSDVKAFPGQLTAELRHLWGLNNILQSAPDITFPLPVSATE

NHREYYVITNEQNEVIRLFPKQGETPRTEKGELLLTGEVERKVFRCKGMQEFQTDVS

DGKYWRRIKLSSSVTWSPLFAPKPISADGQIVLKGRIEKGVFVCNQLKQKLKTGLPD

GSYWISLPVISQTFKEGESVNNSKLTSQQVQLFGRVREGIFRCHNYQCPASGADGNF

WCTLDTDTAQPAFTPIKNAPPGVGGGQIILTGDVDDKGIFHADDDLHYELPASLPKG

KYYGIFTVESCDPTLIPIELSAPKTSKGENLIEGNIWVDEHTGEVRFDPKKNREDQRHH

AIDAIVIALSSQSLFQRLSTYNARRENKKRGLDSTEHFPSPWPGFAQDVRQSVVPLLV

SYKQNPKTLCKISKTLYKDGKKIHSCGNAVRGQLHKETVYGQRTAPGATEKSYHIRK

DIRELKTSKHIGKVVDITIRQMLLKHLQENYHIDITQEFNIPSNAFFKEGVYRIFLPNKH

GEPVPIKKIRMKEELGNAERLKDNINQYVNPRNNHHVMIYQDADGNLKEEIVSFWSV

IERQNQGQPIYQLPREGRNIVSILQINDTFLIGLKEEEPEVYRNDLSTLSKHLYRVQKLS

GMYYTFRHHLASTLNNEREEFRIQSLEAWKRANPVKVQIDEIGRITFLNGPLC

YP_004843922.1 putative CRISPR-associated (Cas) protein [*Flavobacterium branchiophilum* FL-15]
(SEQ ID NO: 114)
MAKILGLDLGTNSIGWAVVERENIDFSLIDKGVRIFSEGVKSEKGIESSRAAERTGYRS

ARKIKYRRKLRKYETLKVLSLNRMCPLSIEEVEEWKKSGFKDYPLNPEFLKWLSTDE

ESNVNPYFFRDRASKHKVSLFELGRAFYHIAQRRGFLSNRLDQSAEGILEEHCPKIEAI

VEDLISIDEISTNITDYFFETGILDSNEKNGYAKDLDEGDKKLVSLYKSLLAILKKNES

DFENCKSEIIERLNKKDVLGKVKGKIKDISQAMLDGNYKTLGQYFYSLYSKEKIRNQ

YTSREEHYLSEFITICKVQGIDQINEEEKINEKKFDGLAKDLYKAIFFQRPLKSQKGLIG

-continued

```
KCSFEKSKSRCAISHPDFEEYRMWTYLNTIKIGTQSDKKLRFLTQDEKLKLVPKFYRK

NDFNFDVLAKELIEKGSSFGFYKSSKKNDFFYWFNYKPTDTVAACQVAASLKNAIGE

DWKTKSFKYQTINSNKEQVSRTVDYKDLWHLLTVATSDVYLYEFAIDKLGLDEKNA

KAFSKTKLKKDFASLSLSAINKILPYLKEGLLYSHAVFVANIENIVDENIWKDEKQRD

YIKTQISEIIENYTLEKSRFEIINGLLKEYKSENEDGKRVYYSKEAEQSFENDLKKKLV

LFYKSNEIENKEQQETIFNELLPIFIQQLKDYEFIKIQRLDQKVLIFLKGKNETGQIFCTE

EKGTAEEKEKKIKNRLKKLYHPSDIEKFKKKIIKDEFGNEKIVLGSPLTPSIKNPMAMR

ALHQLRKVLNALILEGQIDEKTIIHIEMARELNDANKRKGIQDYQNDNKKFREDAIKE

IKKLYFEDCKKEVEPTEDDILRYQLWMEQNRSEIYEEGKNISICDIIGSNPAYDIEHTIP

RSRSQDNSQMNKTLCSQRFNREVKKQSMPIELNNHLEILPRIAHWKEEADNLTREIEII

SRSIKAAATKEIKDKKIRRRHYLTLKRDYLQGKYDRFIWEEPKVGFKNSQIPDTGIITK

YAQAYLKSYFKKVESVKGGMVAEFRKIWGIQESFIDENGMKHYKVKDRSKHTHHTI

DAITIACMTKEKYDVLAHAWTLEDQQNKKEARSIIEASKPWKTFKEDLLKIEEEILVS

HYTPDNVKKQAKKIVRVRGKKQFVAEVERDVNGKAVPKKAASGKTIYKLDGEGKK

LPRLQQGDTIRGSLHQDSIYGAIKNPLNTDEIKYVIRKDLESIKGSDVESIVDEVVKEKI

KEAIANKVLLLSSNAQQKNKLVGTVWMNEEKRIAINKVRIYANSVKNPLHIKEHSLL

SKSKHVHKQKVYGQNDENYAMAIYELDGKRDFELINIFNLAKLIKQGQGFYPLHKK

KEIKGKIVFVPIEKRNKRDVVLKRGQQVVFYDKEVENPKDISEIVDFKGRIYIIEGLSIQ

RIVRPSGKVDEYGVIMLRYFKEARKADDIKQDNFKPDGVFKLGENKPTRKMNHNQF

TAFVEGIDFKVLPSGKFEKI

ZP_08837074.1 hypothetical protein HMPREF0666_03250 [Prevotella sp.
C561]
                                                                (SEQ ID NO: 115)
MTQKVLGLDLGTNSIGSAVRNLDLSDDLQWQLEFFSSDIFRSSVNKESNGREYSLAA

QRSAHRRSRGLNEVRRRRLWATLNLLIKHGFCPMSSESLMRWCTYDKRKGLFREYP

IDDKDFNAWILLDFNGDGRPDYSSPYQLRRELVTRQFDFEQPIERYKLGRALYHIAQH

RGFKSSKGETLSQQETNSKPSSTDEIPDVAGAMKASEEKLSKGLSTYMKEHNLLTVG

AAFAQLEDEGVRVRNNNDYRAIRSQFQHEIETIFKFQQGLSVESELYERLISEKKNVG

TIFYKRPLRSQRGNVGKCTLERSKPRCAIGHPLFEKFRAWTLINNIKVRMSVDTLDEQ

LPMKLRLDLYNECFLAFVRTEFKFEDIRKYLEKRLGIHFSYNDKTINYKDSTSVAGCP

ITARFRKMLGEEWESFRVEGQKERQAHSKNNISFHRVSYSIEDIWHFCYDAEEPEAVL

AFAQETLRLERKKAEELVRIWSAMPQGYAMLSQKAIRNINKILMLGLKYSDAVILAK

VPELVDVSDEELLSIAKDYYLVEAQVNYDKRINSIVNGLIAKYKSVSEEYRFADHNY

EYLLDESDEKDIIRQIENSLGARRWSLMDANEQTDILQKVRDRYQDFFRSHERKFVES

PKLGESFENYLTKKFPMVEREQWKKLYHPSQITIYRPVSVGKDRSVLRLGNPDIGAIK

NPTVLRVLNTLRRRVNQLLDDGVISPDETRVVVETARELNDANRKWALDTYNRIRH

DENEKIKKILEEFYPKRDGISTDDIDKARYVIDQREVDYFTGSKTYNKDIKKYKFWLE

QGGQCMYTGRTINLSNLFDPNAFDIEHTIPESLSFDSSDMNLTLCDAHYNRFIKKNHIP

TDMPNYDKAITIDGKEYPAITSQLQRWVERVERLNRNVEYWKGQARRAQNKDRKD

QCMREMHLWKMELEYWKKKLERFTVTEVTDGFKNSQLVDTRVITRHAVLYLKSIFP

HVDVQRGDVTAKFRKILGIQSVDEKKDRSLHSHHAIDATTLTIIPVSAKRDRMLELFA

KIEEINKMLSFSGSEDRTGLIQELEGLKNKLQMEVKVCRIGHNVSEIGTFINDNIIVNH
```

HIKNQALTPVRRRLRKKGYIVGGVDNPRWQTGDALRGEIHKASYYGAITQFAKDDE

GKVLMKEGRPQVNPTIKFVIRRELKYKKSAADSGFASWDDLGKAIVDKELFALMKG

QFPAETSFKDACEQGIYMIKKGKNGMPDIKLHHIRHVRCEAPQSGLKIKEQTYKSEKE

YKRYFYAAVGDLYAMCCYTNGKIREFRIYSLYDVSCHRKSDIEDIPEFITDKKGNRL

MLDYKLRTGDMILLYKDNPAELYDLDNVNLSRRLYKINRFESQSNLVLMTHHLSTS

KERGRSLGKTVDYQNLPESIRSSVKSLNFLIMGENRDFVIKNGKIIFNHR

ZP_06288774.1 CRISPR-associated protein, Csn1 family [*Prevotella timonensis*
CRIS5C-B1]

(SEQ ID NO: 116)

MNKRILGLDTGTNSLGWAVVDWDEHAQSYELIKYGDVIFQEGVKIEKGIESSKAAER

SGYKAIRKQYFRRRLRKIQVLKVLVKYHLCPYLSDDDLRQWHLQKQYPKSDELML

WQRTSDEEGKNPYYDRHRCLHEKLDLTVEADRYTLGRALYHLTQRRGFLSNRLDTS

ADNKEDGVVKSGISQLSTEMEEAGCEYLGDYFYKLYDAQGNKVRIRQRYTDRNKH

YQHEFDAICEKQELSSELIEDLQRAIFFQLPLKSQRHGVGRCTFERGKPRCADSHPDY

EEFRMLCFVNNIQVKGPHDLELRPLTYEEREKIEPLFFRKSKPNFDFEDIAKALAGKK

NYAWIHDKEERAYKFNYRMTQGVPGCPTIAQLKSIFGDDWKTGIAETYTLIQKKNGS

KSLQEMVDDVWNVLYSFSSVEKLKEFAHHKLQLDEESAEKFAKIKLSHSFAALSLKA

IRKFLPFLRKGMYYTHASFFANIPTIVGKEIWNKEQNRKYIMENVGELVFNYQPKHR

EVQGTIEMLIKDFLANNFELPAGATDKLYHPSMIETYPNAQRNEFGILQLGSPRTNAI

RNPMAMRSLHILRRVVNQLLKESIIDENTEVHVEYARELNDANKRRAIADRQKEQD

KQHKKYGDEIRKLYKEETGKDIEPTQTDVLKFQLWEEQNHHCLYTGEQIGITDFIGSN

PKFDIEHTIPQSVGGDSTQMNLTLCDNRFNREVKKAKLPTELANHEEILTRIEPWKNK

YEQLVKERDKQRTFAGMDKAVKDIRIQKRHKLQMEIDYWRGKYERFTMTEVPEGFS

RRQGTGIGLISRYAGLYLKSLFHQADSRNKSNVYVVKGVATAEFRKMWGLQSEYEK

KCRDNHSHHCMDAITIACIGKREYDLMAEYYRMEETFKQGRGSKPKFSKPWATFTE

DVLNIYKNLLVVHDTPNNMPKHTKKYVQTSIGKVLAQGDTARGSLHLDTYYGAIER

DGEIRYVVRRPLSSFTKPEELENIVDETVKRTIKEAIADKNFKQAIAEPIYMNEEKGILI

KKVRCFAKSVKQPINIRQHRDLSKKEYKQQYHVMNENNYLLAIYEGLVKNKVVREF

EIVSYIEAAKYYKRSQDRNIFSSIVPTHSTKYGLPLKTKLLMGQLVLMFEENPDEIQV

DNTKDLVKRLYKVVGIEKDGRIKFKYHQEARKEGLPIFSTPYKNNDDYAPIFRQSINN

INILVDGIDFTIDILGKVTLKE

YP_001875142.1 CRISPR-associated endonuclease Csn1 family protein
[*Elusimicrobium minutum* Pei191]

(SEQ ID NO: 117)

MQKNINTKQNHIYIKQAQKIKEKLGDKPYRIGLDLGVGSIGFAIVSMEENDGNVLLPK

EIIMVGSRIFKASAGAADRKLSRGQRNNHRHTRERMRYLWKVLAEQKLALPVPADL

DRKENSSEGETSAKRFLGDVLQKDIYELRVKSLDERLSLQELGYVLYHIAGHRGSSAI

RTFENDSEEAQKENTENKKIAGNIKRLMAKKNYRTYGEYLYKEFFENKEKHKREKIS

NAANNHKFSPTRDLVIKEAEAILKKQAGKDGFHKELTEEYIEKLTKAIGYESEKLIPES

GFCPYLKDEKRLPASHKLNEERRLWETLNNARYSDPIVDIVTGEITGYYEKQFTKEQ

KQKLFDYLLTGSELTPAQTKKLLGLKNTNFEDIILQGRDKKAQKIKGYKLIKLESMPF

WARLSEAQQDSFLYDWNSCPDEKLLTEKLSNEYHLTEEEIDNAFNEIVLSSSYAPLGK

SAMLIILEKIKNDLSYTEAVEEALKEGKLTKEKQAIKDRLPYYGAVLQESTQKIIAKG

-continued

FSPQFKDKGYKTPHTNKYELEYGRIANPVVHQTLNELRKLVNEIIDILGKKPCEIGLET

ARELKKSAEDRSKLSREQNDNESNRNRIYEIYIRPQQQVIITRRENPRNYILKFELLEE

QKSQCPFCGGQISPNDIINNQADIEHLFPIAESEDNGRNNLVISHSACNADKAKRSPW

AAFASAAKDSKYDYNRILSNVKENIPHKAWRFNQGAFEKFIENKPMAARFKTDNSYI

SKVAHKYLACLFEKPNIICVKGSLTAQLRMAWGLQGLMIPFAKQLITEKESESFNKD

VNSNKKIRLDNRHHALDAIVIAYASRGYGNLLNKMAGKDYKINYSERNWLSKILLPP

NNIVWENIDADLESFESSVKTALKNAFISVKHDHSDNGELVKGTMYKIFYSERGYTL

TTYKKLSALKLTDPQKKKTPKDFLETALLKFKGRESEMKNEKIKSAIENNKRLFDVIQ

DNLEKAKKLLEEENEKSKAEGKKEKNINDASIYQKAISLSGDKYVQLSKKEPGKFFAI

SKPTPTTTGYGYDTGDSLCVDLYYDNKGKLCGEIIRKIDAQQKNPLKYKEQGFTLFE

RIYGGDILEVDFDIHSDKNSFRNNTGSAPENRVFIKVGTFTEITNNNIQIWFGNIIKSTG

GQDDSFTINSMQQYNPRKLILS SCGFIKYRSPILKNKEG

YP_004248194.1 CRISPR-associated protein, Csn1 family [*Sphaerochaeta globosa* str. Buddy]

(SEQ ID NO: 118)

MSKKVSRRYEEQAQEICQRLGSRPYSIGLDLGVGSIGVAVAAYDPIKKQPSDLVFVSS

RIFIPSTGAAERRQKRGQRNSLRHRANRLKFLWKLLAERNLMLSYSEQDVPDPARLR

FEDAVVRANPYELRLKGLNEQLTLSELGYALYHIANHRGSSSVRTFLDEEKSSDDKK

LEEQQAMTEQLAKEKGISTFIEVLTAFNTNGLIGYRNSESVKSKGVPVPTRDIISNEID

VLLQTQKQFYQEILSDEYCDRIVSAILFENEKIVPEAGCCPYFPDEKKLPRCHFLNEER

RLWEAINNARIKMPMQEGAAKRYQSASFSDEQRHILFHIARSGTDITPKLVQKEFPAL

KTSIIVLQGKEKAIQKIAGFRFRRLEEKSFWKRLSEEQKDDFFSAWTNTPDDKRLSKY

LMKHLLLTENEVVDALKTVSLIGDYGPIGKTATQLLMKHLEDGLTYTEALERGMET

GEFQELSVWEQQSLLPYYGQILTGSTQALMGKYWHSAFKEKRDSEGFFKPNTNSDE

EKYGRIANPVVHQTLNELRKLMNELITILGAKPQEITVELARELKVGAEKREDIIKQQ

TKQEKEAVLAYSKYCEPNNLDKRYIERFRLLEDQAFVCPYCLEHISVADIAAGRADV

DHIFPRDDTADNSYGNKVVAHRQCNDIKGKRTPYAAFSNTSAWGPIMHYLDETPGM

WRKRRKFETNEEEYAKYLQSKGFVSRFESDNSYIAKAAKEYLRCLFNPNNVTAVGS

LKGMETSILRKAWNLQGIDDLLGSRHWSKDADTSPTMRKNRDDNRHHGLDAIVAL

YCSRSLVQMINTMSEQGKRAVEIEAMIPIPGYASEPNLSFEAQRELFRKKILEFMDLH

AFVSMKTDNDANGALLKDTVYSILGADTQGEDLVFVVKKKIKDIGVKIGDYEEVAS

AIRGRITDKQPKWYPMEMKDKIEQLQSKNEAALQKYKESLVQAAAVLEESNRKLIES

GKKPIQLSEKTISKKALELVGGYYYLISNNKRTKTFVVKEPSNEVKGFAFDTGSNLCL

DFYHDAQGKLCGEIIRKIQAMNPSYKPAYMKQGYSLYVRLYQGDVCELRASDLTEA

ESNLAKTTHVRLPNAKPGRTFVIIITFTEMGSGYQIYFSNLAKSKKGQDTSFTLTTIKN

YDVRKVQLSSAGLVRYVSPLLVDKIEKDEVALCGE

YP_873709.1 HNH endonuclease [*Acidothermus cellulolyticus* 11B]

(SEQ ID NO: 119)

MGGSEVGTVPVTWRLGVDVGERSIGLAAVSYEEDKPKEILAAVSWIHDGGVGDERS

GASRLALRGMARRARRLRRFRRARLRDLDMLLSELGWTPLPDKNVSPVDAWLARK

RLAEEYVVDETERRRLLGYAVSHMARHRGWRNPWTTIKDLKNLPQPSDSWERTRES

LEARYSVSLEPGTVGQWAGYLLQRAPGIRLNPTQQSAGRRAELSNATAFETRLRQED

VLWELRCIADVQGLPEDVVSNVIDAVFCQKRPSVPAERIGRDPLDPSQLRASRACLEF

-continued

QEYRIVAAVANLRIRDGSGSRPLSLEERNAVIEALLAQTERSLTWSDIALEILKLPNES

DLTSVPEEDGPSSLAYSQFAPFDETSARIAEFIAKNRRKIPTFAQWWQEQDRTSRSDL

VAALADNSIAGEEEQELLVHLPDAELEALEGLALPSGRVAYSRLTLSGLTRVMRDDG

VDVHNARKTCFGVDDNWRPPLPALHEATGHPVVDRNLAILRKFLSSATMRWGPPQS

IVVELARGASESRERQAEEEAARRAHRKANDRIRAELRASGLSDPSPADLVRARLLE

LYDCHCMYCGAPISWENSELDHIVPRTDGGSNRHENLAITCGACNKEKGRRPFASW

AETSNRVQLRDVIDRVQKLKYSGNMYWTRDEFSRYKKSVVARLKRRTSDPEVIQSIE

STGYAAVALRDRLLSYGEKNGVAQVAVFRGGVTAEARRWLDISIERLFSRVAIFAQS

TSTKRLDRRHHAVDAVVLTTLTPGVAKTLADARSRRVSAEFWRRPSDVNRHSTEEP

QSPAYRQWKESCSGLGDLLISTAARDSIAVAAPLRLRPTGALHEETLRAFSEHTVGA

AWKGAELRRIVEPEVYAAFLALTDPGGRFLKVSPSEDVLPADENRHIVLSDRVLGPR

DRVKLFPDDRGSIRVRGGAAYIASFHHARVFRWGSSHSPSFALLRVSLADLAVAGLL

RDGVDVFTAELPPWTPAWRYASIALVKAVESGDAKQVGWLVPGDELDFGPEGVTT

AAGDLSMFLKYFPERHWVVTGFEDDKRINLKPAFLSAEQAEVLRTERSDRPDTLTEA

GEILAQFFPRCWRATVAKVLCHPGLTVIRRTALGQPRWRRGHLPYSWRPWSADPWS

GGTP

ZP_07880770.1 conserved hypothetical protein [*Actinomyces* sp. oral taxon 180 str. F0310]
(SEQ ID NO: 120)

MLHCIAVIRVPPSEEPGFFETHADSCALCHHGCMTYAANDKAIRYRVGIDVGLRSIGF

CAVEVDDEDHPIRILNSVVHVHDAGTGGPGETESLRKRSGVAARARRRGRAEKQRL

KKLDVLLEELGWGVSSNELLDSHAPWHIRKRLVSEYIEDETERRQCLSVAMAHIARH

RGWRNSFSKVDTLLLEQAPSDRMQGLKERVEDRTGLQFSEEVTQGELVATLLEHDG

DVTIRGFVRKGGKATKVHGVLEGKYMQSDLVAELRQICRTQRVSETTFEKLVLSIFH

SKEPAPSAARQRERVGLDELQLALDPAAKQPRAERAHPAFQKFKVVATLANMRIRE

QSAGERSLTSEELNRVARYLLNHTESESPTWDDVARKLEVPRHRLRGSSRASLETGG

GLTYPPVDDTTVRVMSAEVDWLADWWDCANDESRGHMIDAISNGCGSEPDDVEDE

EVNELISSATAEDMLKLELLAKKLPSGRVAYSLKTLREVTAAILETGDDLSQAITRLY

GVDPGWVPTPAPIEAPVGNPSVDRVLKQVARWLKFASKRWGVPQTVNIEHTREGLK

SASLLEEERERWERFEARREIRQKEMYKRLGISGPFRRSDQVRYEILDLQDCACLYCG

NEINFQTFEVDHIIPRVDASSDSRRTNLAAVCHSCNSAKGGLAFGQWVKRGDCPSGV

SLENAIKRVRSWSKDRLGLTEKAMGKRKSEVISRLKTEMPYEEFDGRSMESVAWMA

IELKKRIEGYFNSDRPEGCAAVQVNAYSGRLTACARRAAHVDKRVRLIRLKGDDGH

HKNRFDRRNHAMDALVIALMTPAIARTIAVREDRREAQQLTRAFESWKNFLGSEER

MQDRWESWIGDVEYACDRLNELIDADKIPVTENLRLRNSGKLHADQPESLKKARRG

SKRPRPQRYVLGDALPADVINRVTDPGLWTALVRAPGFDSQLGLPADLNRGLKLRG

KRISADFPIDYFPTDSPALAVQGGYVGLEFHHARLYRIIGPKEKVKYALLRVCAIDLC

GIDCDDLFEVELKPSSISMRTADAKLKEAMGNGSAKQIGWLVLGDEIQIDPTKFPKQS

IGKFLKECGPVSSWRVSALDTPSKITLKPRLLSNEPLLKTSRVGGHESDLVVAECVEK

IMKKTGWVVEINALCQSGLIRVIRRNALGEVRTSPKSGLPISLNLR

ZP_03925169.1 conserved hypothetical protein [*Actinomyces coleocanis* DSM 15436]
(SEQ ID NO: 121)

MDKNYRIGIDVGLNSIGFCAVEVDQHDTPLGFLNLSVYRHDAGIDPNGKKTNTTRL

AMSGVARRTRRLFRKRKRRLAALDRFIEAQGWTLPDHADYKDPYTPWLVRAELAQ

TPIRDENDLHEKLAIAVRHIARHRGWRSPWVPVRSLHVEQPPSDQYLALKERVEAKT

LLQMPEGATPAEMVVALDLSVDVNLRPKNREKTDTRPENKKPGFLGGKLMQSDNA

NELRKIAKIQGLDDALLRELIELVFAADSPKGASGELVGYDVLPGQHGKRRAEKAHP

AFQRYRIASIVSNLRIRHLGSGADERLDVETQKRVFEYLLNAKPTADITWSDVAEEIG

VERNLLMGTATQTADGERASAKPPVDVTNVAFATCKIKPLKEWWLNADYEARCVM

VSALSHAEKLTEGTAAEVEVAEFLQNLSDEDNEKLDSFSLPIGRAAYSVDSLERLTKR

MIENGEDLFEARVNEFGVSEDWRPPAEPIGARVGNPAVDRVLKAVNRYLMAAEAE

WGAPLSVNIEHVREGFISKRQAVEIDRENQKRYQRNQAVRSQIADHINATSGVRGSD

VTRYLAIQRQNGECLYCGTAITFVNSEMDHIVPRAGLGSTNTRDNLVATCERCNKSK

SNKPFAVWAAECGIPGVSVAEALKRVDFWIADGFASSKEHRELQKGVKDRLKRKVS

DPEIDNRSMESVAWMARELAHRVQYYFDEKHTGTKVRVFRGSLTSAARKASGFESR

VNFIGGNGKTRLDRRHHAMDAATVAMLRNSVAKTLVLRGNIRASERAIGAAETWK

SFRGENVADRQIFESWSENMRVLVEKFNLALYNDEVSIFSSLRLQLGNGKAHDDTIT

KLQMHKVGDAWSLTEIDRASTPALWCALTRQPDFTWKDGLPANEDRTIIVNGTHYG

PLDKVGIFGKAAASLLVRGGSVDIGSAIHHARIYRIAGKKPTYGMVRVFAPDLLRYR

NEDLFNVELPPQSVSMRYAEPKVREAIREGKAEYLGWLVVGDELLLDLSSETSGQIA

ELQQDFPGTTHWTVAGFFSPSRLRLRPVYLAQEGL

GEDVSEGSKSIIAGQGWRPAVNKVFGSAMPEVIRRDGLGRKRRFSYSGLPVSWQG

YP_001955845.1 restriction endonuclease [*Bifidobacterium longum* DJO10A]
(SEQ ID NO: 122)

MLSRQLLGASHLARPVSYSYNVQDNDVHCSYGERCFMRGKRYRIGIDVGLNSVGLA

AVEVSDENSPVRLLNAQSVIHDGGVDPQKNKEAITRKNMSGVARRTRRMRRRKRER

LHKLDMLLGKFGYPVIEPESLDKPFEEWHVRAELATRYIEDDELRRESISIALRHMAR

HRGWRNPYRQVDSLISDNPYSKQYGELKEKAKAYNDDATAAEEESTPAQLVVAML

DAGYAEAPRLRWRTGSKKPDAEGYLPVRLMQEDNANELKQIFRVQRVPADEWKPL

FRSVFYAVSPKGSAEQRVGQDPLAPEQARALKASLAFQEYRIANVITNLRIKDASAEL

RKLTVDEKQSIYDQLVSPSSEDITWSDLCDFLGFKRSQLKGVGSLTEDGEERISSRPPR

LTSVQRIYESDNKIRKPLVAWWKSASDNEHEAMIRLLSNTVDIDKVREDVAYASAIE

FIDGLDDDALTKLDSVDLPSGRAAYSVETLQKLTRQMLTTDDDLHEARKTLFNVTDS

WRPPADPIGEPLGNPSVDRVLKNVNRYLMNCQQRWGNPVSVNIEHVRSSFSSVAFA

RKDKREYEKNNEKRSIFRSSLSEQLRADEQMEKVRESDLRRLEAIQRQNGQCLYCGR

TITFRTCEMDHIVPRKGVGSTNTRTNFAAVCAECNRMKSNTPFAIWARSEDAQTRGV

SLAEAKKRVTMFTFNPKSYAPREVKAFKQAVIARLQQTEDDAAIDNRSIESVAWMA

DELHRRIDWYFNAKQYVNSASIDDAEAETMKTTVSVFQGRVTASARRAAGIEGKIHF

IGQQSKTRLDRRHHAVDASVIAMMNTAAAQTLMERESLRESQRLIGLMPGERSWKE

YPYEGTSRYESFHLWLDNMDVLLELLNDALDNDRIAVMQSQRYVLGNSIAHDATIH

PLEKVPLGSAMSADLIRRASTPALWCALTRLPDYDEKEGLPEDSHREIRVHDTRYSA

DDEMGFFASQAAQIAVQEGSADIGSAIHHARVYRCWKTNAKGVRKYFYGMIRVFQT

-continued

DLLRACHDDLFTVPLPPQSISMRYGEPRVVQALQSGNAQYLGSLVVGDEIEMDFSSL

DVDGQIGEYLQFFSQFSGGNLAWKHWVVDGFFNQTQLRIRPRYLAAEGLAKAFSDD

VVPDGVQKIVTKQGWLPPVNTASKTAVRIVRRNAFGEPRLSSAHHMPCSWQWRHE

YP_001878601.1 hypothetical protein Amuc_2010 [*Akkermansia muciniphila* ATCC BAA-835]
(SEQ ID NO: 123)

MSRSLTFSFDIGYASIGWAVIASASHDDADPSVCGCGTVLFPKDDCQAFKRREYRRL

RRNIRSRRVRIERIGRLLVQAQIITPEMKETSGHPAPFYLASEALKGHRTLAPIELWHV

LRWYAHNRGYDNNASWSNSLSEDGGNGEDTERVKHAQDLMDKHGTATMAETICR

ELKLEEGKADAPMEVSTPAYKNLNTAFPRLIVEKEVRRILELSAPLIPGLTAEIIELIAQ

FIHPLTTEQRGVLLQHGIKLARRYRGSLLFGQLIPRFDNRIISRCPVTWAQVYEAELKK

GNSEQSARERAEKLSKVPTANCPEFYEYRMARILCNIRADGEPLSAEIRRELMNQAR

QEGKLTKASLEKAISSRLGKETETNVSNYFTLHPDSEEALYLNPAVEVLQRSGIGQILS

PSVYRIAANRLRRGKSVTPNYLLNLLKSRGESGEALEKKIEKESKKKEADYADTPLK

PKYATGRAPYARTVLKKVVEEILDGEDPTRPARGEAHPDGELKAHDGCLYCLLDTD

SSVNQHQKERRLDTMTNNHLVRHRMLILDRLLKDLIQDFADGQKDRISRVCVEVGK

ELTTFSAMDSKKIQRELTLRQKSHTDAVNRLKRKLPGKALSANLIRKCRIAMDMNVV

TCPFTGATYGDHELENLELEHIVPHSFRQSNALSSLVLTWPGVNRMKGQRTGYDFVE

QEQENPVPDKPNLHICSLNNYRELVEKLDDKKGHEDDRRRKKKRKALLMVRGLSH

KHQSQNHEAMKEIGMTEGMMTQSSHLMKLACKSIKTSLPDAHIDMIPGAVTAEVRK

AWDVFGVFKELCPEAADPDSGKILKENLRSLTHLHHALDACVLGLIPYIIPAHHNGLL

RRVLAMRRIPEKLIPQVRPVANQRHYVLNDDGRMMLRDLSASLKENIREQLMEQRV

IQHVPADMGGALLKETMQRVLSVDGSGEDAMVSLSKKKDGKKEKNQVKASKLVG

VFPEGPSKLKALKAAIEIDGNYGVALDPKPVVIRHIKVFKRIMALKEQNGGKPVRILK

KGMLIHLTSSKDPKHAGVWRIESIQDSKGGVKLDLQRAHCAVPKNKTHECNWREVD

LISLLKKYQMKRYPTSYTGTPR

YP_004168469.1 CRISPR-associated protein, csn1 family [*Nitratifractor salsuginis* DSM 16511]
(SEQ ID NO: 124)

MKKILGVDLGITSFGYAILQETGKDLYRCLDNSVVMRNNPYDEKSGESSQSIRSTQKS

MRRLIEKRKKRIRCVAQTMERYGILDYSETMKINDPKNNPIKNRWQLRAVDAWKRP

LSPQELFAIFAHMAKHRGYKSIATEDLIYELELELGLNDPEKESEKKADERRQVYNAL

RHLEELRKKYGGETIAQTIHRAVEAGDLRSYRNHDDYEKMIRREDIEEEIEKVLLRQA

ELGALGLPEEQVSELIDELKACITDQEMPTIDESLFGKCTFYKDELAAPAYSYLYDLY

RLYKKLADLNIDGYEVTQEDREKVIEWVEKKIAQGKNLKKITHKDLRKILGLAPEQK

IFGVEDERIVKGKKEPRTFVPFFFLADIAKFKELFASIQKHPDALQIFRELAEILQRSKT

PQEALDRLRALMAGKGIDTDDRELLELFKNKRSGTRELSHRYILEALPLFLEGYDEKE

VQRILGFDDREDYSRYPKSLRHLHLREGNLFEKEENPINNHAVKSLASWALGLIADLS

WRYGPFDEIILETTRDALPEKIRKEIDKAMREREKALDKIIGKYKKEFPSIDKRLARKI

QLWERQKGLDLYSGKVINLSQLLDGSADIEHIVPQSLGGLSTDYNTIVTLKSVNAAK

GNRLPGDWLAGNPDYRERIGMLSEKGLIDWKKRKNLLAQSLDEIYTENTHSKGIRAT

SYLEALVAQVLKRYYPFPDPELRKNGIGVRMIPGKVTSKTRSLLGIKSKSRETNFHHA

EDALILSTLTRGWQNRLHRMLRDNYGKSEAELKELWKKYMPHIEGLTLADYIDEAF

-continued

RRFMSKGEESLFYRDMFDTIRSISYWVDKKPLSASSHKETVYSSRHEVPTLRKNILEA

FDSLNVIKDRHKLTTEEFMKRYDKEIRQKLWLHRIGNTNDESYRAVEERATQIAQILT

RYQLMDAQNDKEIDEKFQQALKELITSPIEVTGKLLRKMRFVYDKLNAMQIDRGLV

ETDKNMLGIHISKGPNEKLIFRRMDVNNAHELQKERSGILCYLNEMLFIFNKKGLIHY

GCLRSYLEKGQGSKYIALFNPRFPANPKAQPSKFTSDSKIKQVGIGSATGIIKAHLDLD

GHVRSYEVFGTLPEGSIEWFKEESGYGRVEDDPHH

ZP_08015909.1 hypothetical protein HMPREF9464_01128 [*Sutterella wadsworthensis* 3_1_45B]
(SEQ ID NO: 125)

MTQSERRFSCSIGIDMGAKYTGVFYALFDREELPTNLNSKAMTLVMPETGPRYVQA

QRTAVRHRLRGQKRYTLARKLAFLVVDDMIKKQEKRLTDEEWKRGREALSGLLKR

RGYSRPNADGEDLTPLENVRADVFAAHPAFSTYFSEVRSLAEQWEEFTANISNVEKF

LGDPNIPADKEFIEFAVAEGLIDKTEKKAYQSALSTLRANANVLTGLRQMGHKPRSE

YFKAIEADLKKDSRLAKINEAFGGAERLARLLGNLSNLQLRAERWYFNAPDIMKDR

GWEPDRFKKTLVRAFKFFHPAKDQNKQHLELIKQIENSEDIIETLCTLDPNRTIPPYED

QNNRRPPLDQTLLLSPEKLTRQYGEIWKTWSARLTSAEPTLAPAAEILERSTDRKSRV

AVNGHEPLPTLAYQLSYALQRAFDRSKALDPYALRALAAGSKSNKLTSARTALENCI

GGQNVKTFLDCARRYYREADDAKVGLWFDNADGLLERSDLHPPMKKKILPLLVANI

LQTDETTGQKFLDEIWRKQIKGRETVASRCARIETVRKSFGGGFNIAYNTAQYREVN

KLPRNAQDKELLTIRDRVAETADFIAANLGLSDEQKRKFANPFSLAQFYTLIETEVSG

FSATTLAVHLENAWRMTIKDAVINGETVRAAQCSRLPAETARPFDGLVRRLVDRQA

WEIAKRVSTDIQSKVDFSNGIVDVSIFVEENKFEFSASVADLKKNKRVKDKMLSEAE

KLETRWLIKNERIKKASRGTCPYTGDRLAEGGEIDHILPRSLIKDARGIVFNAEPNLIY

ASSRGNQLKKNQRYSLSDLKANYRNEIFKTSNIAAITAEIEDVVTKLQQTHRLKFFDL

LNEHEQDCVRHALFLDDGSEARDAVLELLATQRRTRVNGTQIWMIKNLANKIREEL

QNWCKTTNNRLHFQAAATNVSDAKNLRLKLAQNQPDFEKPDIQPIASHSIDALCSFA

VGSADAERDQNGFDYLDGKTVLGLYPQSCEVIHLQAKPQEEKSHFDSVAIFKEGIYA

EQFLPIFTLNEKIWIGYETLNAKGERCGAIEVSGKQPKELLEMLAPFFNKPVGDLSAH

ATYRILKKPAYEFLAKAALQPLSAEEKRLAALLDALRYCTSRKSLMSLFMAANGKSL

KKREDVLKPKLFQLKVELKGEKSFKLNGSLTLPVKQDWLRICDSPELADAFGKPCSA

DELTSKLARIWKRPVMRDLAHAPVRREFSLPAIDNPSGGFRIRRTNLFGNELYQVHAI

NAKKYRGFASAGSNVDWSKGILFNELQHENLTECGGRFITSADVTPMSEWRKVVAE

DNLSIWIAPGTEGRRYVRVETTFIQASHWFEQSVENWAITSPLSLPASFKVDKPAEFQ

KAVGTELSELLGQPRSEIFIENVGNAKHIRFWYIVVSSNKKMNESYNNVSKS

J7RUA5.1 CRISPR-associated endonuclease Cas9 [*Staphylococcus aureus*]
(SEQ ID NO: 126)

MKRNYILGLDIGITSVGYGIIDYETRDVIDAGVRLFKEANVENNEGRRSKRGARRLKR

RRRHRIQRVKKLLFDYNLLTDHSELSGINPYEARVKGLSQKLSEEEFSAALLHLAKRR

GVHNVNEVEEDTGNELSTKEQISRNSKALEEKYVAELQLERLKKDGEVRGSINRFKT

SDYVKEAKQLLKVQKAYHQLDQSFIDTYIDLLETRRTYYEGPGEGSPFGWKDIKEW

YEMLMGHCTYFPEELRSVKYAYNADLYNALNDLNNLVITRDENEKLEYYEKFQIIEN

VFKQKKKPTLKQIAKEILVNEEDIKGYRVTSTGKPEFTNLKVYHDIKDITARKEIIENA

ELLDQIAKILTIYQSSEDIQEELTNLNSELTQEEIEQISNLKGYTGTHNLSLKAINLILDE

-continued

LWHTNDNQIAIFNRLKLVPKKVDLSQQKEIPTTLVDDFILSPVVKRSFIQSIKVINAIIK

KYGLPNDIIIELAREKNSKDAQKMINEMQKRNRQTNERIEEIIRTTGKENAKYLIEKIK

LHDMQEGKCLYSLEAIPLEDLLNNPFNYEVDHIIPRSVSFDNSFNNKVLVKQEENSKK

GNRTPFQYLSSSDSKISYETFKKHILNLAKGKGRISKTKKEYLLEERDINRFSVQKDFI

NRNLVDTRYATRGLMNLLRSYFRVNNLDVKVKSINGGFTSFLRRKWKFKKERNKG

YKHHAEDALIIANADFIFKEWKKLDKAKKVMENQMFEEKQAESMPEIETEQEYKEIF

ITPHQIKHIKDFKDYKYSHRVDKKPNRELINDTLYSTRKDDKGNTLIVNNLNGLYDK

DNDKLKKLINKSPEKLLMYHHDPQTYQKLKLIMEQYGDEKNPLYKYYEETGNYLTK

YSKKDNGPVIKKIKYYGNKLNAHLDITDDYPNSRNKVVKLSLKPYRFDVYLDNGVY

KFVTVKNLDVIKKENYYEVNSKCYEEAKKLKKISNQAEFIASFYNNDLIKINGELYRV

IGVNNDLLNRIEVNMIDITYREYLENMNDKRPPRIIKTIASKTQSIKKYSTDILGNLYE

VKSKKHPQIIKKG

AEX66236.1 CRISPR-associated endonuclease [*Corynebacterium diphtheriae*
C7 (beta)]
(SEQ ID NO: 127)

MKYHVGIDVGTFSVGLAAIEVDDAGMPIKTLSLVSHIHDSGLDPDKIKSAVTRLASSG

IARRTRRLYRRKRRRLQQLDKFIQRQGWPVIELEDYSDPLYPWKVRAELAASYIADE

KERGEKLSVALRHIARHRGWRNPYAKVSSLYLPDEPSDAFKAIREEIKRASGQPVPET

ATVGQMVTLCELGTLKLRGEGGVLSARLQQSDHAREIQEICRMQEIGQELYRKIIDV

VFAAESPKGSASSRVGKDPLQPGKNRALKASDAFQRYRIAALIGNLRVRVDGEKRIL

SVEEKNLVFDHLVNLAPKKEPEWVTIAEILGIDRGQLIGTATMTDDGERAGARPPTH

DTNRSIVNSRIAPLVDWWKTASALEQHAMVKALSNAEVDDFDSPEGAKVQAFFADL

DDDVHAKLDSLHLPVGRAAYSEDTLVRLTRRMLADGVDLYTARLQEFGIEPSWTPP

APRIGEPVGNPAVDRVLKTVSRWLESATKTWGAPERVIIEHVREGFVTEKRAREMDG

DMRRRAARNAKLFQEMQEKLNVQGKPSRADLWRYQSVQRQNCQCAYCGSPITFSN

SEMDHIVPRAGQGSTNTRENLVAVCHRCNQSKGNTPFAIWAKNTSIEGVSVKEAVER

TRHWVTDTGMRSTDFKKFTKAVVERFQRATMDEEIDARSMESVAWMANELRSRVA

QHFASHGTTVRVYRGSLTAEARRASGISGKLEFLDGVGKSRLDRRHHAIDAAVIAFT

SDYVAETLAVRSNLKQSQAHRQEAPQWREFTGKDAEHRAAWRVWCQKMEKLSAL

LTEDLRDDRVVVMSNVRLRLGNGSAHEETIGKLSKVKLGSQLSVSDIDKASSEALWC

ALTREPDFDPKDGLPANPERHIRVNGTHVYAGDNIGLFPVSAGSIALRGGYAELGSSF

HHARVYKITSGKKPAFAMLRVYTIDLLPYRNQDLFSVELKPQTMSRQAEKKLRDA

LATGNAEYLGWLVVDDELVVDTSKIATDQVKAVEAELGTIRRWRVDGFFGDTRLRL

RPLQMSKEGIKKESAPELSKIIDRPGWLPAVNKLFSEGNVTVVRRDSLGRVRLESTAH

LPVTWKVQ

WP_013852048.1 type II CRISPR RNA-guided endonuclease Cas9
[*Streptococcus pasteurianus*]
(SEQ ID NO: 128)

MTNGKILGLDIGIASVGVGIIEAKTGKVVHANSRLFSAANAENNAERRGFRGSRRLN

RRKKHRVKRVRDLFEKYGIVTDFRNLNLNPYELRVKGLTEQLKNEELFAALRTISKR

RGISYLDDAEDDSTGSTDYAKSIDENRRLLKNKTPGQIQLERLEKYGQLRGNFTVYD

ENGEAHRLINVFSTSDYEKEARKILETQADYNKKITAEFIDDYVEILTQKRKYYHGPG

NEKSRTDYGRFRTDGTTLENIFGILIGKCNFYPDEYRASKASYTAQEYNFLNDLNNLK

VSTETGKLSTEQKESLVEFAKNTATLGPAKLLKEIAKILDCKVDEIKGYREDDKGKPD

-continued

LHTFEPYRKLKFNLESINIDDLSREVIDKLADILTLNTEREGIEDAIKRNLPNQFTEEQIS

EIIKVRKSQSTAFNKGWHSFSAKLMNELIPELYATSDEQMTILTRLEKFKVNKKSSKN

TKTIDEKEVTDEIYNPVVAKSVRQTIKIINAAVKKYGDFDKIVIEMPRDKNADDEKKF

IDKRNKENKKEKDDALKRAAYLYNSSDKLPDEVFHGNKQLETKIRLWYQQGERCLY

SGKPISIQELVHNSNNFEIDHILPLSLSFDDSLANKVLVYAWTNQEKGQKTPYQVIDS

MDAAWSFREMKDYVLKQKGLGKKKRDYLLTTENIDKIEVKKKFIERNLVDTRYASR

VVLNSLQSALRELGKDTKVSVVRGQFTSQLRRKWKIDKSRETYHHHAVDALIIAASS

QLKLWEKQDNPMFVDYGKNQVVDKQTGEILSVSDDEYKELVFQPPYQGFVNTISSK

GFEDEILFSYQVDSKYNRKVSDATIYSTRKAKIGKDKKEETYVLGKIKDIYSQNGFDT

FIKKYNKDKTQFLMYQKDSLTWENVIEVILRDYPTTKKSEDGKNDVKCNPFEEYRRE

NGLICKYSKKGKGTPIKSLKYYDKKLGNCIDITPEESRNKVILQSINPWRADVYFNPE

TLKYELMGLKYSDLSFEKGTGNYHISQEKYDAIKEKEGIGKKSEFKFTLYRNDLILIK

DIASGEQEIYRFLSRTMPNVNHYVELKPYDKEKFDNVQELVEALGEADKVGRCIKGL

NKPNISIYKVRTDVLGNKYFVKKKGDKPKLDFKNNKK

EEZ71796.1 CRISPR-associated protein, Csn1 family [*Neisseria cinerea* ATCC 14685]
(SEQ ID NO: 129)

MAAFKPNPMNYILGLDIGIASVGWAIVEIDEEENPIRLIDLGVRVFERAEVPKTGDSLA

AARRLARSVRRLTRRRAHRLLRARRLLKREGVLQAADFDENGLIKSLPNTPWQLRA

AALDRKLTPLEWSAVLLHLIKHRGYLSQRKNEGETADKELGALLKGVADNTHALQT

GDFRTPAELALNKFEKESGHIRNQRGDYSHTFNRKDLQAELNLLFEKQKEFGNPHVS

DGLKEGIETLLMTQRPALSGDAVQKMLGHCTFEPTEPKAAKNTYTAERFVWLTKLN

NLRILEQGSERPLTDTERATLMDEPYRKSKLTYAQARKLLDLDDTAFFKGLRYGKDN

AEASTLMEMKAYHAISRALEKEGLKDKKSPLNLSPELQDEIGTAFSLFKTDEDITGRL

KDRVQPEILEALLKHISFDKFVQISLKALRRIVPLMEQGNRYDEACTEIYGDHYGKKN

TEEKIYLPPIPADEIRNPVVLRALSQARKVINGVVRRYGSPARIHIETAREVGKSFKDR

KEIEKRQEENRKDREKSAAKFREYFPNFVGEPKSKDILKLRLYEQQHGKCLYSGKEIN

LGRLNEKGYVEIDHALPFSRTWDDSFNNKVLALGSENQNKGNQTPYEYFNGKDNSR

EWQEFKARVETSRFPRSKKQRILLQKFDEDGFKERNLNDTRYINRFLCQFVADHMLL

TGKGKRRVFASNGQITNLLRGFWGLRKVRAENDRHHALDAVVVACSTIAMQQKITR

FVRYKEMNAFDGKTIDKETGEVLHQKAHFPQPWEFFAQEVMIRVFGKPDGKPEFEE

ADTPEKLRTLLAEKLSSRPEAVHKYVTPLFISRAPNRKMSGQGHMETVKSAKRLDEG

ISVLRVPLTQLKLKDLEKMVNEREREPKLYEALKARLEAHKDDPAKAFAEPFYKYDK

AGNRTQQVKAVRVEQVQKTGVWVHNHNGIADNATIVRVDVFEKGGKYYLVPIYS

WQVAKGILPDRAVVQGKDEEDWTVMDDSFEFKFVLYANDLIKLTAKKNEFLGYFV

SLNRATGAIDIRTHDTDSTKGKNGIFQSVGVKTALSFQKYQIDELGKEIRPCRLKKRPP

VR

BAK69486.1 putative CRISPR associated protein [*Campylobacter lari*]
(SEQ ID NO: 130)

MRILGFDIGINSIGWAFVENDELKDCGVRIFTKAENPKNKESLALPRRNARSSRRRLK

RRKARLIAIKRILAKELKLNYKDYVAADGELPKAYEGSLASVYELRYKALTQNLETK

DLARVILHIAKHRGYMNKNEKKSNDAKKGKILSALKNNALKLENYQSVGEYFYKEF

FQKYKKNTKNFIKIRNTKDNYNNCVLSSDLEKELKLILEKQKEFGYNYSEDFINEILK

-continued

VAFFQRPLKDFSHLVGACTFFEEEKRACKNSYSAWEFVALTKIINEIKSLEKISGEIVP

TQTINEVLNLILDKGSITYKKFRSCINLHESISFKSLKYDKENAENAKLIDFRKLVEFK

KALGVHSLSRQELDQISTHITLIKDNVKLKTVLEKYNLSNEQINNLLEIEFNDYINLSF

KALGMILPLMREGKRYDEACEIANLKPKTVDEKKDFLPAFCDSIFAHELSNPVVNRAI

SEYRKVLNALLKKYGKVHKIHLELARDVGLSKKAREKIEKEQKENQAVNAWALKE

CENIGLKASAKNILKLKLWKEQKEICIYSGNKISIEHLKDEKALEVDHIYPYSRSFDDS

FINKVLVFTKENQEKLNKTPFEAFGKNIEKWSKIQTLAQNLPYKKKNKILDENFKDK

QQEDFISRNLNDTRYIATLIAKYTKEYLNFLLLSENENANLKSGEKGSKIHVQTISGM

LTSVLRHTWGFDKKDRNNHLHHALDAIIVAYSTNSIIKAFSDFRKNQELLKARFYAK

ELTSDNYKHQVKFFEPFKSFREKILSKIDEIFVSKPPRKRARRALHKDTFHSENKIIDK

CSYNSKEGLQIALSCGRVRKIGTKYVENDTIVRVDIFKKQNKFYAIPIYAMDFALGILP

NKIVITGKDKNNNPKQWQTIDESYEFCFSLYKNDLILLQKKNMQEPEFAYYNDFSIST

SSICVEKHDNKFENLTSNQKLLFSNAKEGSVKVESLGIQNLKVFEKYIITPLGDKIKAD

FQPRENISLKTSKKYGLR

OJ107263.1 hypothetical protein BK997_03320 [*Candidatus Micrarchaeum acidiphilum* ARMAN-1]
(SEQ ID NO: 131)

MRDSITAPRYSSALAARIKEFNSAFKLGIDLGTKTGGVALVKDNKVLLAKTFLDYHK

QTLEERRIHRRNRRSRLARRKRIARLRSWILRQKIYGKQLPDPYKIKKMQLPNGVRK

GENWIDLVVSGRDLSPEAFVRAITLIFQKRGQRYEEVAKEIEEMSYKEFSTHIKALTS

VTEEEFTALAAEIERRQDVVDTDKEAERYTQLSELLSKVSESKSESKDRAQRKEDLG

KVVNAFCSAHRIEDKDKWCKELMKLLDRPVRHARFLNKVLIRCNICDRATPKKSRP

DVRELLYFDTVRNFLKAGRVEQNPDVISYYKKIYMDAEVIRVKILNKEKLTDEDKKQ

KRKLASELNRYKNKEYVTDAQKKMQEQLKTLLFMKLTGRSRYCMAHLKERAAGK

DVEEGLHGVVQKRHDRNIAQRNHDLRVINLIESLLFDQNKSLSDAIRKNGLMYVTIE

APEPKTKHAKKGAAVVRDPRKLKEKLFDDQNGVCIYTGLQLDKLEISKYEKDHIFPD

SRDGPSIRDNLVLTTKEINSDKGDRTPWEWMHDNPEKWKAFERRVAEFYKKGRINE

RKRELLLNKGTEYPGDNPTELARGGARVNNFITEFNDRLKTHGVQELQTIFERNKPIV

QVVRGEETQRLRRQWNALNQNFIPLKDRAMSFNHAEDAAIAASMPPKFWREQIYRT

AWHFGPSGNERPDFALAELAPQWNDFFMTKGGPIIAVLGKTKYSWKHSIIDDTIYKP

FSKSAYYVGIYKKPNAITSNAIKVLRPKLLNGEHTMSKNAKYYHQKIGNERFLMKSQ

KGGSIITVKPHDGPEKVLQISPTYECAVLTKHDGKIIVKFKPIKPLRDMYARGVIKAM

DKELETSLSSMSKHAKYKELHTHDITYLPATKKHVDGYFIITKLSAKHGIKALPESMV

KVKYTQIGSENNSEVKLTKPKPEITLDSEDITNIYNFTR

APG80630.1 CRISPR-associated endonuclease Cas9 [*Candidatus Parvarchaeum acidiphilum* ARMAN-4]
(SEQ ID NO: 132)

MLGSSRYLRYNLTSFEGKEPFLIMGYYKEYNKELSSKAQKEFNDQISEFNSYYKLGID

LGDKTGIAIVKGNKIILAKTLIDLHSQKLDKRREARRNRRTRLSRKKRLARLRSWVM

RQKVGNQRLPDPYKIMHDNKYWSIYNKSNSANKKNWIDLLIHSNSLSADDFVRGLTI

IFRKRGYLAFKYLSRLSDKEFEKYIDNLKPPISKYEYDEDLEELSSRVENGEIEEKKFE

GLKNKLDKIDKESKDFQVKQREEVKKELEDLVDLFAKSVDNKIDKARWKRELNNLL

DKKVRKIRFDNRFILKCKIKGCNKNTPKKEKVRDFELKMVLNNARSDYQISDEDLNS

-continued

FRNEVINIFQKKENLKKGELKGVTIEDLRKQLNKTFNKAKIKKGIREQIRSIVFEKISGR

SKFCKEHLKEFSEKPAPSDRINYGVNSAREQHDFRVLNFIDKKIFKDKLIDPSKLRYITI

ESPEPETEKLEKGQISEKSFETLKEKLAKETGGIDIYTGEKLKKDFEIEHIFPRARMGPS

IRENEVASNLETNKEKADRTPWEWFGQDEKRWSEFEKRVNSLYSKKKISERKREILL

NKSNEYPGLNPTELSRIPSTLSDFVESIRKMFVKYGYEEPQTLVQKGKPIIQVVRGRDT

QALRWRWHALDSNIIPEKDRKSSFNHAEDAVIAACMPPYYLRQKIFREEAKIKRKVS

NKEKEVTRPDMPTKKIAPNWSEFMKTRNEPVIEVIGKVKPSWKNSIMDQTFYKYLLK

PFKDNLIKIPNVKNTYKWIGVNGQTDSLSLPSKVLSISNKKVDSSTVLLVHDKKGGK

RNWVPKSIGGLLVYITPKDGPKRIVQVKPATQGLLIYRNEDGRVDAVREFINPVIEMY

NNGKLAFVEKENEEELLKYFNLLEKGQKFERIRRYDMITYNSKFYYVTKINKNHRVT

IQEESKIKAESDKVKSSSGKEYTRKETEELSLQKLAELISI tr|I0AP30|I0AP30_IGNAJ CRISPR-associated endonuclease Cas9
OS = Ignavibacterium album (strain DSM 19864 / JCM16511 / NBRC101810 / Mat9-16)
OX = 945713 GN = cas9 PE = 3 SV = 1
(SEQ ID NO: 133)

MEFKKVLGLDIGTNSIGCALLSLPKSIQDYGKGGRLEWLTSRVIPLDADYMKAFIDG

KNGLPQVITPAGKRRQKRGSRRLKHRYKLRRSRLIRVFKTLNWLPEDFPLDNPKRIK

ETISTEGKFSFRISDYVPISDESYREFYREFGYPENEIEQVIEEINFRRKTKGKNKNPMI

KLLPEDWVVYYLRKKALIKPTTKEELIRIIYLFNQRRGFKSSRKDLTETAILDYDEFAK

RLAEKEKYSAENYETKFVSITKVKEVVELKTDGRKGKKRFKVILEDSRIEPYEIERKE

KPDWEGKEYTFLVTQKLEKGKFKQNKPDLPKEEDWALCTTALDNRMGSKHPGEFFF

DELLKAFKEKRGYKIRQYPVNRWRYKKELEFIWTKQCQLNPELNNLNINKEILRKLA

TVLYPSQSKFFGPKIKEFENSDVLHIISEDIIYYQRDLKSQKSLISECRYEKRKGIDGEIY

GLKCIPKSSPLYQEFRIWQDIHNIKVIRKESEVNGKKKINIDETQLYINENIKEKLFELF

NSKDSLSEKDILELISLNIINSGIKISKKEEETTHRINLFANRKELKGNETKSRYRKVFK

KLGFDGEYILNHPSKLNRLWHSDYSNDYADKEKTEKSILSSLGWKNRNGKWEKSKN

YDVFNLPLEVAKAIANLPPLKKEYGSYSALAIRKMLVVMRDGKYWQHPDQIAKDQE

NTSLMLFDKNLIQLTNNQRKVLNKYLLTLAEVQKRSTLIKQKLNEIEHNPYKLELVS

DQDLEKQVLKSFLEKKNESDYLKGLKTYQAGYLIYGKHSEKDVPIVNSPDELGEYIR

KKLPNNSLRNPIVEQVIRETIFIVRDVWKSFGIIDEIHIELGRELKNNSEERKKTSESQE

KNFQEKERARKLLKELLNSSNFEHYDENGNKIFSSFTVNPNPDSPLDIEKFRIWKNQS

GLTDEELNKKLKDEKIPTEIEVKKYILWLTQKCRSPYTGKIIPLSKLFDSNVYEIEHIIP

RSKMKNDSTNNLVICELGVNKAKGDRLAANFISESNGKCKFGEVEYTLLKYGDYLQ

YCKDTFKYQKAKYKNLLATEPPEDFIERQINDTRYIGRKLAELLTPVVKDSKNIIFTIG

SITSELKITWGLNGVWKDILRPRFKRLESIINKKLIFQDEDDPNKYHFDLSINPQLDKE

GLKRLDHRHHALDATIIAATTREHVRYLNSLNAADNDEEKREYFLSLCNHKIRDFKL

PWENFTSEVKSKLLSCVVSYKESKPILSDPFNKYLKWEYKNGKWQKVFAIQIKNDR

WKAVRRSMFKEPIGTVWIKKIKEVSLKEAIKIQAIWEEVKNDPVRKKKEKYIYDDYA

QKVIAKIVQELGLSSSMRKQDDEKLNKFINEAKVSAGVNKNLNTTNKTIYNLEGRFY

EKIKVAEYVLYKAKRMPLNKKEYIEKLSLQKMFNDLPNFILEKSILDNYPEILKELES

DNKYIIEPHKKNNPVNRLLLEHILEYHNNPKEAFSTEGLEKLNKKAINKIGKPIKYITR

LDGDINEEEIFRGAVFETDKGSNVYFVMYENNQTKDREFLKPNPSISVLKAIEHKNKI

DFFAPNRLGFSRIILSPGDLVYVPTNDQYVLIKDNSSNETIINWDDNEFISNRIYQVKK

```
FTGNSCYFLKNDIASLILSYSASNGVGEFGSQNISEYSVDDPPIRIKDVCIKIRVDRLGN

VRPL

Ga0054994_10813 Geobacillus stearothermophilus Cas9
                                                                (SEQ ID NO: 134)
MRYKIGLDIGITSVGWAVMNLDIPRIEDLGVRIFDRAENPQTGESLALPRRLARSARR

RLRRRKHRLERIRRLVIREGILTKEELDKLFEEKHEIDVWQLRVEALDRKLNNDELAR

VLLHLAKRRGFKSNRKSERSNKENSTMLKHIEENRAILSSYRTVGEMIVKDPKFALH

KRNKGENYTNTIARDDLEREIRLIFSKQREFGNMSCTEEFENEYITIWASQRPVASKD

DIEKKVGFCTFEPKEKRAPKATYTFQSFIAWEHINKLRLISPSGARGLTDEERRLLYEQ

AFQKNKITYHDIRTLLHLPDDTYFKGIVYDRGESRKQNENIRFLELDAYHQIRKAVDK

VYGKGKSSSFLPIDFDTFGYALTLFKDDADIHSYLRNEYEQNGKRMPNLANKVYDN

ELIEELLNLSFTKFGHLSLKALRSILPYMEQGEVYSSACERAGYTFTGPKKKQKTMLL

PNIPPIANPVVMRALTQARKVVNAIIKKYGSPVSIHIELARDLSQTFDERRKTKKEQDE

NRKKNETAIRQLMEYGLTLNPTGHDIVKFKLWSEQNGRCAYSLQPIEIERLLEPGYVE

VDHVIPYSRSLDDSYTNKVLVLTRENREKGNRIPAEYLGVGTERWQQFETFVLTNKQ

FSKKKRDRLLRLHYDENEETEFKNRNLNDTRYISRFFANFIREHLKFAESDDKQKVY

TVNGRVTAHLRSRWEFNKNREESDLHHAVDAVIVACTTPSDIAKVTAFYQRREQNK

ELAKKTEPHFPQPWPHFADELRARLSKHPKESIKALNLGNYDDQKLESLQPVFVSRM

PKRSVTGAAHQETLRRYVGIDERSGKIQTVVKTKLSEIKLDASGHFPMYGKESDPRT

YEAIRQRLLEHNNDPKKAFQEPLYKPKKNGEPGPVIRTVKIIDTKNQVIPLNDGKTVA

YNSNIVRVDVFEKDGKYYCVPVYTMDIMKGILPNKAIEPNKPYSEWKEMTEDYTFR

FSLYPNDLIRIELPREKTVKTAAGEEINVKDVFVYYKTIDSANGGLELISHDHRFSLRG

VGSRTLKRFEKYQVDVLGNIYKVRGEKRVGLASSAHSKPGKTIRPLQSTRD

WP_036475267.1 type II CRISPR RNA-guided endonuclease Cas9 [Neisseria
lactamica]
                                                                (SEQ ID NO: 135)
MAAFKPNPMNYILGLDIGIASVGWAMVEVDEEENPIRLIDLGVRVFERAEVPKTGDS

LAMARRLARSVRRLTRRRAHRLLRARRLLKREGVLQDADFDENGLVKSLPNTPWQ

LRAAALDRKLTCLEWSAVLLHLVKHRGYLSQRKNEGETADKELGALLKGVADNAH

ALQTGDFRTPAELALNKFEKESGHIRNQRGDYSHTFSRKDLQAELNLLFEKQKEFGN

PHVSDGLKEDIETLLMAQRPALSGDAVQKMLGHCTFEPAEPKAAKNTYTAERFIWL

TKLNNLRILEQGSERPLTDTERATLMDEPYRKSKLTYAQARKLLGLEDTAFFKGLRY

GKDNAEASTLMEMKAYHAISRALEKEGLKDKKSPLNLSTELQDEIGTAFSLFKTDKD

ITGRLKDRVQPEILEALLKHISFDKFVQISLKALRRIVPLMEQGKRYDEACAEIYGDH

YCKKNAEEKIYLPPIPADEIRNPVVLRALSQARKVINCVVRRYGSPARIHIETAREVGK

SFKDRKEIEKRQEENRKDREKAAAKFREYFPNFVGEPKSKDILKLRLYEQQHGKCLY

SGKEINLVRLNEKGYVEIDHALPFSRTWDDSFNNKVLVLGSENQNKGNQTPYEYFN

GKDNSREWQEFKARVETSRFPRSKKQRILLQKFDEEGFKERNLNDTRYVNRFLCQFV

ADHILLTGKGKRRVFASNGQITNLLRGFWGLRKVRTENDRHHALDAVVVACSTVA

MQQKITRFVRYKEMNAFDGKTIDKETGEVLHQKAHFPQPWEFFAQEVMIRVFGKPD

GKPEFEEADTPEKLRTLLAEKLSSRPEAVHEYVTPLFVSRAPNRKMSGQGHMETVKS

AKRLDEGISVLRVPLTQLKLKGLEKMVNREREPKLYDALKAQLETHKDDPAKAFAE

PFYKYDKAGSRTQQVKAVRIEQVQKTGVWVRNHNGIADNATMVRVDVFEKGGKY
```

-continued

```
YLVPIYSWQVAKGILPDRAVVAFKDEEDWTVMDDSFEFRFVLYANDLIKLTAKKNE

FLGYFVSLNRATGAIDIRTHDTDSTKGKNGIFQSVGVKTALSFQKNQIDELGKEIRPC

RLKKRPPVR
```

The term "cell" as used herein may refer to either a prokaryotic or eukaryotic cell, optionally obtained from a subject or a commercially available source.

As used herein, the term "CRISPR" refers to Clustered Regularly Interspaced Short Palindromic Repeats (CRISPR). CRISPR may also refer to a technique or system of sequence-specific genetic manipulation relying on the CRISPR pathway. A CRISPR recombinant expression system can be programmed to cleave a target polynucleotide using a CRISPR endonuclease and a guideRNA. A CRISPR system can be used to cause double stranded or single stranded breaks in a target polynucleotide. A CRISPR system can also be used to recruit proteins or label a target polynucleotide. In some aspects, CRISPR-mediated gene editing utilizes the pathways of nonhomologous end-joining (NHEJ) or homologous recombination to perform the edits. These applications of CRISPR technology are known and widely practiced in the art. See, e.g., U.S. Pat. No. 8,697,359 and Hsu et al. (2014) Cell 156(6): 1262-1278.

As used herein, the term "comprising" is intended to mean that the compositions and methods include the recited elements, but do not exclude others. As used herein, the transitional phrase "consisting essentially of" (and grammatical variants) is to be interpreted as encompassing the recited materials or steps "and those that do not materially affect the basic and novel characteristic(s)" of the recited embodiment. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising." "Consisting of" shall mean excluding more than trace elements of other ingredients and substantial method steps for administering the compositions disclosed herein. Aspects defined by each of these transition terms are within the scope of the present disclosure.

The term "encode" as it is applied to nucleic acid sequences refers to a polynucleotide which is said to "encode" a polypeptide if, in its native state or when manipulated by methods well known to those skilled in the art, can be transcribed and/or translated to produce the mRNA for the polypeptide and/or a fragment thereof. The antisense strand is the complement of such a nucleic acid, and the encoding sequence can be deduced therefrom.

The terms "equivalent" or "biological equivalent" are used interchangeably when referring to a particular molecule, biological, or cellular material and intend those having minimal homology while still maintaining desired structure or functionality.

As used herein, the term "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell. The expression level of a gene may be determined by measuring the amount of mRNA or protein in a cell or tissue sample; further, the expression level of multiple genes can be determined to establish an expression profile for a particular sample.

As used herein, the term "functional" may be used to modify any molecule, biological, or cellular material to intend that it accomplishes a particular, specified effect.

The term "gRNA" or "guide RNA" as used herein refers to the guide RNA sequences used to target specific genes for correction employing the CRISPR technique. Techniques of designing gRNAs and donor therapeutic polynucleotides for target specificity are well known in the art. For example, Doench, J., et al. Nature biotechnology 2014; 32(12):1262-7, Mohr, S. et al. (2016) FEBS Journal 283: 3232-38, and Graham, D., et al. Genome Biol. 2015; 16: 260. gRNA comprises or alternatively consists essentially of, or yet further consists of a fusion polynucleotide comprising CRISPR RNA (crRNA) and trans-activating CRIPSPR RNA (tracrRNA); or a polynucleotide comprising CRISPR RNA (crRNA) and trans-activating CRIPSPR RNA (tracrRNA). In some aspects, a gRNA is synthetic (Kelley, M. et al. (2016) J of Biotechnology 233 (2016) 74-83).

As used herein, the term "immune orthogonal" refers to a lack of immune cross-reactivity between two or more antigens. In some embodiments, the antigens are proteins (e.g., Cas9). In some embodiments, the antigens are viruses (e.g., AAV). In some embodiments, antigens that are immune orthogonal do not share an amino acid sequence of greater than 5, greater than 6, greater than 7, greater than 8, greater than 9, greater than 10, greater than 11, greater than 12, greater than 13, greater than 14, greater than 15, or greater than 16 consecutive amino acids. In some embodiments, antigens that are immune orthogonal do not share any highly immunogenic peptides. In some embodiments, antigens that are immune orthogonal do not share affinity for a major histocompatibility complex (e.g., MHC class I or class II). Antigens that are immune orthogonal are amenable for sequential dosing to evade a host immune system.

The term "immunosilent" refers to an antigen that does not elicit an immune response from a host upon administration. In some embodiments, the antigen does not elicit an adaptive immune response. In some embodiments, the antigen does not elicit an innate immune response. In some embodiments, the antigen does not elicit either an adaptive or an innate immune response. In some embodiments, an immunosilent antigen has reduced immunogenicity.

The term "intein" refers to a class of protein that is able to excise itself and join the remaining portion(s) of the protein via protein splicing. A "split intein" comes from two genes. A non-limiting example of a "split-intein" are the C-intein and N-intein sequences originally derived from *N. punctiforme*.

The term "isolated" as used herein refers to molecules or biologicals or cellular materials being substantially free from other materials.

As used herein, the terms "nucleic acid sequence" and "polynucleotide" are used interchangeably to refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The term "Major Histocompatibility Complex" (MHC) refers to a family of proteins responsible for the presentation of peptides, including self and non-self (antigenic) to T-cells. T-cells recognize antigenic peptides and trigger a cascade of events which leads to the destruction of pathogens and infected cells. The MHC family is divided into three subgroups: class I, class II, and class III. Class I MHC molecules have β2 subunits that are only recognized by CD8 co-receptors. Class II MHC molecules have β1 and β2 subunits that are only recognized by CD4 co-receptors. In this way MHC molecules chaperone which type of lymphocytes may bind to the given antigen with high affinity, since different lymphocytes express different T-Cell Receptor (TCR) co-receptors. In general, MHC class I molecules bind short peptides, whose N- and C-terminal ends are anchored into pockets located at the ends of a peptide binding groove. While the majority of the peptides are nine amino acid residues in length, longer peptides can be accommodated by the bulging of their central portion, resulting in binding peptides of length 8 to 15. Peptides binding to class II proteins are not constrained in size and can vary from 11 to 30 amino acids long. The peptide binding groove in the MHC class II molecules is open at both ends, which enables binding of peptides with relatively longer length. The "core" refers to the amino acid residues that contribute the most to the recognition of the peptide. In some embodiments, the core is nine amino acids in length. In addition to the core, the flanking regions are also important for the specificity of the peptide to the MHC molecule.

As used herein, the term "organ" a structure which is a specific portion of an individual organism, where a certain function or functions of the individual organism is locally performed and which is morphologically separate. Non-limiting examples of organs include the skin, blood vessels, cornea, thymus, kidney, heart, liver, umbilical cord, intestine, nerve, lung, placenta, pancreas, thyroid and brain.

The term "ortholog" is used in reference of another gene or protein and intends a homolog of said gene or protein that evolved from the same ancestral source. Orthologs may or may not retain the same function as the gene or protein to which they are orthologous. Non-limiting examples of Cas9 orthologs include *S. aureus* Cas9 ("spCas9"), *S. thermophiles* Cas9, *L. pneumophilia* Cas9, *N. lactamica* Cas9, *N. meningitides* Cas9, *B. longum* Cas9, *A. muciniphila* Cas9, and *O. laneus* Cas9.

The term "promoter" as used herein refers to any sequence that regulates the expression of a coding sequence, such as a gene. Promoters may be constitutive, inducible, repressible, or tissue-specific, for example. A "promoter" is a control sequence that is a region of a polynucleotide sequence at which initiation and rate of transcription are controlled. It may contain genetic elements at which regulatory proteins and molecules may bind such as RNA polymerase and other transcription factors. Non-limiting exemplary promoters include CMV promoter and U6 promoter.

The term "protein", "peptide" and "polypeptide" are used interchangeably and in their broadest sense to refer to a compound of two or more subunits of amino acids, amino acid analogs or peptidomimetics. The subunits may be linked by peptide bonds. In another aspect, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

As used herein, the term "recombinant expression system" refers to a genetic construct for the expression of certain genetic material formed by recombination.

As used herein, the term "subject" is intended to mean any animal. In some embodiments, the subject may be a mammal; in further embodiments, the subject may be a bovine, equine, feline, murine, porcine, canine, human, or rat.

The term "tissue" is used herein to refer to tissue of a living or deceased organism or any tissue derived from or designed to mimic a living or deceased organism. The tissue may be healthy, diseased, and/or have genetic mutations. The biological tissue may include any single tissue (e.g., a collection of cells that may be interconnected) or a group of tissues making up an organ or part or region of the body of an organism. The tissue may comprise a homogeneous cellular material or it may be a composite structure such as that found in regions of the body including the thorax which for instance can include lung tissue, skeletal tissue, and/or muscle tissue. Exemplary tissues include, but are not limited to those derived from liver, lung, thyroid, skin, pancreas, blood vessels, bladder, kidneys, brain, biliary tree, duodenum, abdominal aorta, iliac vein, heart and intestines, including any combination thereof.

As used herein, "treating" or "treatment" of a disease in a subject refers to (1) preventing the symptoms or disease from occurring in a subject that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable.

As used herein, the term "vector" intends a recombinant vector that retains the ability to infect and transduce non-dividing and/or slowly-dividing cells and integrate into the target cell's genome. The vector may be derived from or based on a wild-type virus. Aspects of this disclosure relate to an adeno-associated virus vector.

It is to be inferred without explicit recitation and unless otherwise intended, that when the present disclosure relates to a polypeptide, protein, polynucleotide or antibody, an equivalent or a biologically equivalent of such is intended within the scope of this disclosure. As used herein, the term "biological equivalent thereof" is intended to be synonymous with "equivalent thereof" when referring to a reference protein, antibody, polypeptide or nucleic acid, intends those having minimal homology while still maintaining desired structure or functionality. Unless specifically recited herein, it is contemplated that any polynucleotide, polypeptide or protein mentioned herein also includes equivalents thereof. For example, an equivalent intends at least about 70% homology or identity, or at least 80% homology or identity and alternatively, or at least about 85%, or alternatively at least about 90%, or alternatively at least about 95%, or alternatively 98% percent homology or identity and exhibits substantially equivalent biological activity to the reference protein, polypeptide or nucleic acid. Alternatively, when referring to polynucleotides, an equivalent thereof is a polynucleotide that hybridizes under stringent conditions to the reference polynucleotide or its complement.

Applicants have provided herein the polypeptide and/or polynucleotide sequences for use in gene and protein transfer and expression techniques described below. It should be understood, although not always explicitly stated that the sequences provided herein can be used to provide the expression product as well as substantially identical sequences that produce a protein that has the same biological properties. These "biologically equivalent" or "biologically active" polypeptides are encoded by equivalent polynucleotides as described herein. They may possess at least 60%, or alternatively, at least 65%, or alternatively, at least 70%, or alternatively, at least 75%, or alternatively, at least 80%, or alternatively at least 85%, or alternatively at least 90%, or alternatively at least 95% or alternatively at least 98%, identical primary amino acid sequence to the reference polypeptide when compared using sequence identity methods run under default conditions. Specific polypeptide sequences are provided as examples of particular embodiments. Modifications to the sequences to amino acids with alternate amino acids that have similar charge. Additionally, an equivalent polynucleotide is one that hybridizes under stringent conditions to the reference polynucleotide or its complement or in reference to a polypeptide, a polypeptide encoded by a polynucleotide that hybridizes to the reference encoding polynucleotide under stringent conditions or its complementary strand. Alternatively, an equivalent polypeptide or protein is one that is expressed from an equivalent polynucleotide.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PC reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention.

MODES OF CARRYING OUT THE DISCLOSURE

Methods of Generating Immunosilent Proteins and Identifying Immune Orthogonal Proteins Disclosed herein are methods of identifying or modifying a protein sequence to reduce immunogenicity, and optionally be immunosilent. In some aspects, the method comprises, consists of, or consists essentially of identifying affinity for a major histocompatibility complex (MHC) for one or more regions of a protein. Those protein regions which have no affinity to an MHC may be immunosilent without further modification. In contrast, those protein regions which have affinity, optionally high affinity, to an MHC may be modified through one or more amino acid substitutions, such that the modified region has no affinity for the MHC. In some embodiments the MHC is MHC class I. In some embodiments, the MHC is MHC class II.

Figure 5A:
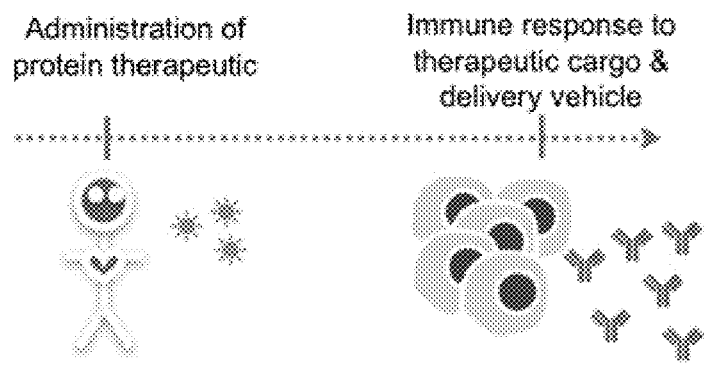
FIGS. 5A-5H: shows that protein Protein based therapeutics elicit an adaptive immune response: experimental and in silico analyses.
Figure 5B:
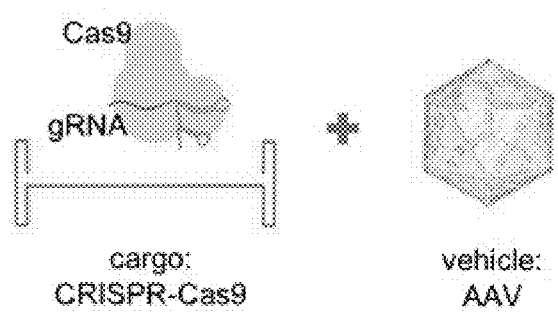
Figure 5C:
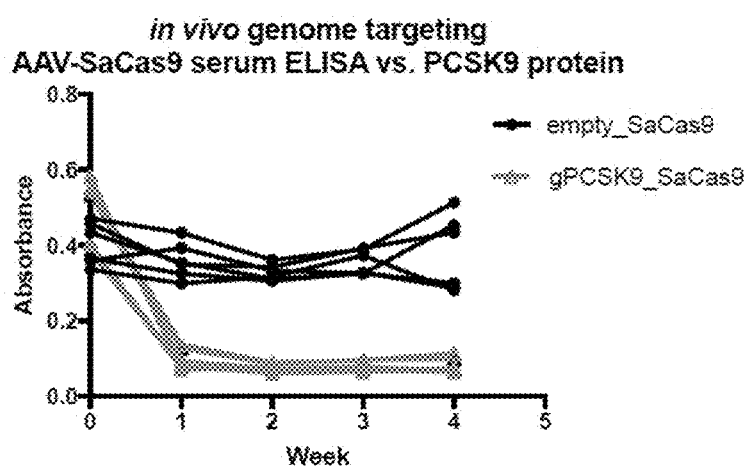
Figure 5D:
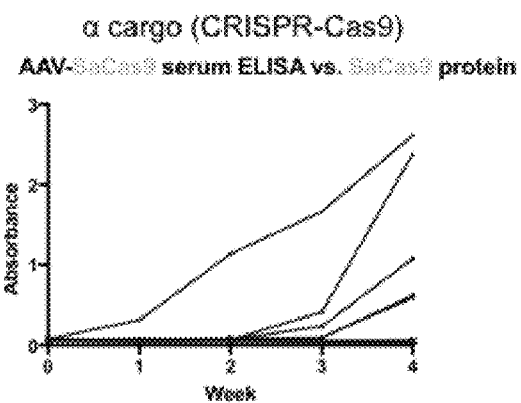

Simultaneously or sequentially, orthologs of the protein may be identified, optionally through alignment or alignment free methods (e.g. k-mer analysis. Regions of the orthologous may, thus, be targeted for similar modifications or may be considered immunosilent without further modification based on the results above. Alternatively, orthologs may be selected for sequential administration based on the fact that they are immune orthogonal, for example having affinity for different MHCs from those for the initially screened protein. Sequential administration of such immune orthogonal proteins an alternative FIG. 5F provides an exemplary schematic of the workflow to identify and/or modify these proteins.

Techniques to identify orthologous proteins are known in the art and include but are not limited to both traditional alignment based methods and alignment free methods. Further, databases of orthologous proteins are well known and include but are not limited to COGs, eggNOG, InParanoid, OrthoDB, Ortholuge, CDD, Ensmbl Compara, and KEGG. Thus, it is appreciated that one of ordinary skill may readily identify orthologs. For example, k-mer analysis is a computational method that identifies all possible substrings of a length k that are contained in a string, e.g. a sequence. The frequency of k-mers creates a "signature" of an underlying sequence, which in turn may be utilized as an alignment free means of comparing sequences and determining comprehensive peptide overlap. Other computations methods include those based on alignments, for example BLOSM (block substitution matrix) or PAM (point accepted mutation) matricies.

Methods of determining MHC affinity are likewise known in the art and may include computational methods available through software or publicly accessible databases or "wet lab" assays. Examples of computational methods of predicting MHC affinity include but are not limited to the MHC binding prediction model available through the IEDB Analysis Resource (tools.immuneepitope.org/mhci/ (MHC I) and tools.immuneepitope.org/mhcii/ (MHC II)) or NetMHC (.cbs.dtu.dk/services/NetMHC/). Alternatively or in addition, MHC affinity can be determined or computational predictions thereof can be validated using assays, such as but not limited to immunoassays, such as ELISA, microarray, tetramer assay, and peptide-induced MHC stabilization assay. Using such assays and computational methods can further be adapted to account for the MHC profile of a specific subject or patient being treated. Thus, modifications in the proteins can be optimized to be immunosilent in a particular subject or patient. Similarly the comparisons can be host-restricted, such that the protein is identified or modified to be specific to a particular host, e.g., a mouse or a human.

Applicants contemplate use of this method for a variety of proteins that present a risk of eliciting an immune response. Non-limiting exemplary proteins of interest include cytidine deaminases, which can be used for gene editing via catalysis of DNA base change from C to T (e.g. APOBEC—Conserved across many species e.g. Rat APOBEC3, Rat APOBEC1, Resus Macaque APOBEC3G, human APOBEC1 (A1), AID, APOBEC2 (A2), APOBEC3A (A3A), APOBEC3B (A3B), APOBEC3C (A3C), APOBEC3DE (A3DE), APOBEC3F (A3F), APOBEC3G (A3G), APOBEC3H (A3H) and APOBEC4 (A4)); adenosine deaminases, which can be used for gene editing via catalysis of DNA base change from A to G (e.g. ADA (DNA editor)—Widely conserved across virtually all species and ADAR (RNA editor)—Conserved across most metazoan species); Zing Finger nucleases (ZFNs), which can be used for genome engineering in a similar manner to CRISPR/Cas9 and are engineered site-specific nucleases consisting of: 3-6 repeated zinc finger domains, which is a widely conserved DNA-binding motif and a nuclease domain; transcriptional activator-like effector nucleases (TALENs), which be used for genome engineering in a similar manner to CRISPR/Cas9 and are similar to ZFNs in that they are engineered site-specific nucleases consisting of: a TAL effector DNA binding domain (generally derived from a species of *Xanthomonas proteobacteria*) and a nuclease domain. The domains of the site specific enzymes mentioned above (ZFNs and TALENs) are well characterized and subject of extensive engineering to generate the desired specificity. Thus, many variants exist of such proteins. Additional proteins for which MHC affinity analysis is relevant include Cas9 proteins and AAV capsids, both of which are used in CRISPR based gene editing.

Aspects of the disclosure relate to a method of generating a protein comprising: identifying one or more regions of a protein with affinity for a major histocompatibility complex (MHC), and modifying the one or more regions of the protein with affinity for the MHC through one or more amino acid substitutions, such that the modified region has no affinity for the MHC, wherein the resulting modified protein is immunosilent upon administration of the modified protein or a polynucleotide encoding the modified protein to a subject. In some embodiments, the affinity for the MHC is high affinity. In some embodiments, at least one substituted amino acid is an amino acid which does not serve as an MHC protein core residue. In some embodiments, the protein is selected from the group of a cytidine deaminase, an adenosine deaminase, a zinc finger nuclease, a transcriptional activator-like effector nuclease, a Cas9, or an AAV capsid protein. In some embodiments, the protein is Cas9, optionally SpCas9.

For example, in order to optimize and broaden the application of CRIPSR based therapeutics the inventors correspondingly developed a couple of technologies: 1) "humanize" the Cas9 protein by swapping high immunogenic domains or peptides with less immunogenic counterparts. This is particularly useful to enable the application of Cas9 arsenal for repeat treatments. Upon mapping highly immunogenic peptides in SpCas9, Applicants computed single amino acid swaps at each position in these immunogenic peptides that are predicted to lower overall immunogenicity without potentially modifying the activity. The disclosure teaches which region to mutate and what to mutate to. In addition, applicants identified natural Cas9 ortholog proteins that are orthogonal in the immune space i.e. that do not share any highly immunogenic peptides, and are thus amenable for sequential dosing to evade host immune system and improve therapeutic regimen.

Thus, aspects of the disclosure relate to a modified Cas9 for immune stealth and use of a Cas9 ortholog to enhance immune evasion. The modified Cas9 can replace the existing wildtype Cas9 for any application requiring in vivo delivery, which would potentially have no loss of efficacy after repetitive use. The Cas9 proteins that are orthologous in the immune space can also be utilized for in vivo applications, where Cas9 proteins that are orthologous in the immune space can be utilized sequentially, if repetitive treatments are required. Such non-limiting aspects relating to Cas9 are described herein below.

Figure 4:
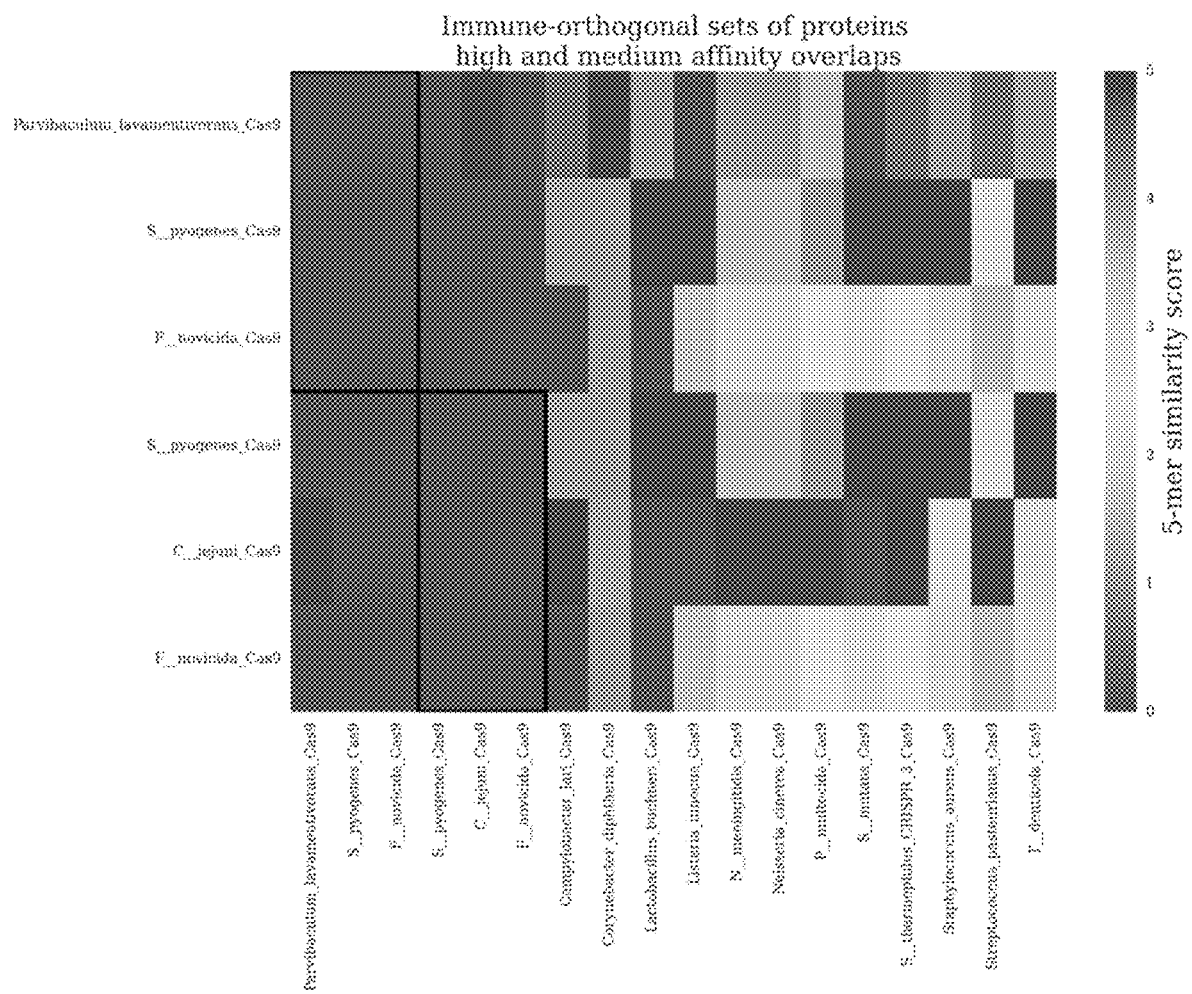
FIG. 4: shows a clique consists of strains of Cas9 with no high affinity peptides overlapping, accordingly providing five sets of five Cas9 proteins with no high affinity peptides overlapping.

Some embodiments disclosed herein relate to a method of generating a modified Cas9 comprising: identifying one or more regions of a Cas9 with high affinity for a major histocompatibility complex (MHC), and modifying the one or more regions of the Cas9 with high affinity for the MHC through one or more amino acid substitutions, such that the modified region has no affinity for the MHC, wherein the resulting modified Cas9 is immunosilent upon administration to a subject. In some embodiments, the Cas9 is SpCas9. Further embodiments relate to a modified Cas9 generated according to this method. Some embodiments disclosed herein relate to a modified SpCas9 comprising one or more of the amino acid modifications provided in Table 1 (SEQ ID NOs: 295-336). Some embodiments disclosed herein relate to a method of avoiding an immune response in a subject being administering a regimen requiring Cas9 comprising: administering, in sequence, each of a group of orthologous Cas9 proteins with no shared affinity for a major histocompatibility complex (MHC). In some embodiments, the group of Cas9 proteins is selected from the groups of Cas9 proteins provided in FIG. 4.

In some aspects, provided herein are methods of generating a modified Cas9 comprising, consisting of, or consisting essentially of: identifying one or more regions of a Cas9 with affinity for a major histocompatibility complex (MHC), and modifying the one or more regions of the Cas9 with affinity for the MHC through one or more amino acid substitutions, such that the modified region has no affinity for the MHC, wherein the resulting modified Cas9 has reduced immunogenicity upon administration to a subject. In some embodiments, the affinity for an MHC is high affinity. In some embodiments, the Cas9 is SpCas9. In some embodiments, at least one substituted amino acid is an amino acid which does not serve as an MHC protein core residue. In some aspects, provided herein is a modified Cas9 generated by identifying one or more regions of a Cas9 with affinity for a major histocompatibility complex (MHC), and modifying the one or more regions of the Cas9 with affinity for the MHC through one or more amino acid substitutions, such that the modified region has no affinity for the MHC, wherein the resulting modified Cas9 has reduced immunogenicity upon administration to a subject.

In some aspects, provided herein is a modified Cas9 comprising, consisting of, or consisting essentially of one or more, two or more, three or more, four or more, five or more, six or more, seven or more, eight or more, nine or more, ten or more, fifteen or more, or twenty or more of the amino acid modifications provided in Table 1.

In some aspects, provided herein are isolated polynucleotides encoding a modified Cas9 protein, wherein the modified Cas9 is generated by identifying one or more regions of a Cas9 with affinity for a major histocompatibility complex (MHC), and modifying the one or more regions of the Cas9 with affinity for the MHC through one or more amino acid substitutions, such that the modified region has no affinity for the MHC, wherein the resulting modified Cas9 has reduced immunogenicity upon administration to a subject. In some aspects, provided herein are isolated polynucleotides encoding a modified Cas9 protein, wherein the modified Cas9 comprises, consists of, or consists essentially of one or more, two or more, three or more, four or more, five or more, six or more, seven or more, eight or more, nine or more, ten or more, fifteen or more, or twenty or more of the amino acid modifications provided in Table 1. In some aspects, provided herein are vectors comprising the isolated polynucleotide. In some embodiments, the vector is an AAV vector, optionally wherein the AAV vector is AAV5.

It is further appreciated that the AAV capsid may be modified to be immunosilent according to the same method, i.e. identifying one or more regions of one or more AAV capsid proteins with affinity for a major histocompatibility complex (MHC), and modifying the one or more regions of the one or more AAV capsid proteins with affinity for the MHC through one or more amino acid substitutions, such that the modified region has no affinity for the MHC, wherein the resulting capsid comprising the one or more AAV capsid proteins has reduced immunogenicity upon administration to a subject. A modified AAV generated according to this method may be employed in any one or the embodiments disclosed herein to evade the immune system.

Further, immune orthogonal AAV may be identified according to the method disclosed herein. Thus, contemplated herein are embodiments in which the immune orthogonal Cas9 is comprised in an immune orthogonal AAV.

Additional aspects to a method of identifying immune orthogonal orthologs comprising: determining a set of affinities of a protein or regions thereof to a plurality of major histocompatibility complexes (MHCs), comparing the set of affinities of the protein or regions thereof to sets of affinities of orthologs of the protein to the plurality of MHCs, and determining a set of immune orthogonal orthologs based on non-overlapping sets of affinites. In some embodiments, the affinity for the MHC is high affinity. In some embodiments, the protein is selected from the group of a cytidine deaminase, an adenosine deaminase, a zinc finger nuclease, a transcriptional activator-like effector nuclease, a Cas9, or an AAV capsid protein. In some embodiments, the protein is Cas9, optionally SpCas9 or SaCas9. In some embodiments, the Cas9 proteins the orthologs are selected from *S. pyogenes* Cas9 (spCas9), *S. aureus* Cas9 (saCas9), *B. longum* Cas9, *A. muiciniphilia* Cas9, or *O. laneus* Cas9.

Not to be bound by theory, Applicants contemplate that even after MHC screening, a subject may still have a repitoire of pre-existing immunity that could result in cross-reactivity against proteins or their orthologs. Thus, there exists some risk of confounding in sequential administration of proteins that are immune orthogonal. Non-limiting exemplary proteins which may present this concern are those derived from organisms that are pathogenic in a subject (e.g. *S. aureus* or *S. pyogenes* in humans). Accordingly, Applicants propose identifying immune orthogonal orthologs of such proteins that are extremophiles (and, thus, unlikely to come into contact with humans or other subjects under normal circumstances) and/or highly abundant commensal species for which the subject's immune system has developed tolerance. Species abundant in a normal microbiome or in the particular subject's microbiome can be determined based on the literature and/or based on sampling over a population of subjects or the particular subjects. In some embodiments, the commensal species is one present at early stages of development, when tolerance is established.

Proteins and Vectors

Further aspects relate to a modified Cas9 protein produced according to the method disclosed above. Still further aspects relate to a modified Cas9 protein comprising one or more, two or more, three or more, four or more, five or more, six or more, seven or more, eight or more, nine or more, ten or more, fifteen or more, or twenty or more of the amino acid modifications provided in Table 1. Some embodiments relate to an isolated polynucleotide encoding the modified Cas9. Further embodiments, relate to a vector comprising the isolated polynucleotide, optionally an AAV vector, and still further optionally an AAV5 vector. Additional embodiments relate to an AAV capsid comprising the vector. In some embodiments, one or more of the AAV capsid proteins has been modified to be immunosilent.

In general methods of packaging genetic material such as RNA into one or more vectors is well known in the art. For example, the genetic material may be packaged using a packaging vector and cell lines and introduced via traditional recombinant methods.

In some embodiments, the packaging vector may include, but is not limited to retroviral vector, lentiviral vector, adenoviral vector, and adeno-associated viral vector (optionally AAV8). The packaging vector contains elements and sequences that facilitate the delivery of genetic materials into cells. For example, the retroviral constructs are packaging plasmids comprising at least one retroviral helper DNA sequence derived from a replication-incompetent retroviral genome encoding in trans all virion proteins required to package a replication incompetent retroviral vector, and for producing virion proteins capable of packaging the replication-incompetent retroviral vector at high titer, without the production of replication-competent helper virus. The retroviral DNA sequence lacks the region encoding the native enhancer and/or promoter of the viral 5' LTR of the virus, and lacks both the psi function sequence responsible for packaging helper genome and the 3' LTR, but encodes a foreign polyadenylation site, for example the SV40 polyadenylation site, and a foreign enhancer and/or promoter which directs efficient transcription in a cell type where virus production is desired. The retrovirus is a leukemia virus such as a Moloney Murine Leukemia Virus (MMLV), the Human Immunodeficiency Virus (HIV), or the Gibbon Ape Leukemia virus (GALV). The foreign enhancer and promoter may be the human cytomegalovirus (HCMV) immediate early (IE) enhancer and promoter, the enhancer and promoter (U3 region) of the Moloney Murine Sarcoma Virus (MMSV), the U3 region of Rous Sarcoma Virus (RSV), the U3 region of Spleen Focus Forming Virus (SFFV), or the HCMV IE enhancer joined to the native Moloney Murine Leukemia Virus (MMLV) promoter.

The retroviral packaging plasmid may consist of two retroviral helper DNA sequences encoded by plasmid based expression vectors, for example where a first helper sequence contains a cDNA encoding the gag and pol proteins of ecotropic MMLV or GALV and a second helper sequence contains a cDNA encoding the env protein. The Env gene, which determines the host range, may be derived from the genes encoding xenotropic, amphotropic, ecotropic, polytropic (mink focus forming) or 10A1 murine leukemia virus env proteins, or the Gibbon Ape Leukemia Virus (GALV env protein, the Human Immunodeficiency Virus env (gp160) protein, the Vesicular Stomatitis Virus (VSV) G protein, the Human T cell leukemia (HTLV) type I and II env gene products, chimeric envelope gene derived from combinations of one or more of the aforementioned env genes or chimeric envelope genes encoding the cytoplasmic and transmembrane of the aforementioned env gene products and a monoclonal antibody directed against a specific surface molecule on a desired target cell. Similar vector based systems may employ other vectors such as sleeping beauty vectors or transposon elements.

The resulting packaged expression systems may then be introduced via an appropriate route of administration, discussed in detail with respect to the method aspects disclosed herein.

Methods of Treatment

Some aspects relate to a method of avoiding immune response in a subject being administered a regimen requiring a protein, the method comprising: administering to the subject, in sequence, two or more proteins that are immune orthogonal. In some embodiments, the proteins that are immune orthogonal do not share an amino acid sequence of greater than 5 consecutive amino acids. In some embodiments, the proteins that are immune orthogonal do not share affinity for a major histocompatibility complex (MHC). In some embodiments, three or more, four or more, five or more, six or more, seven or more, eight or more, nine or more, or ten or more proteins that are immune orthogonal are administered in sequence.

Non-limiting exemplary aspects relate to Cas9. In some embodiments, the Cas9 proteins that are immune orthogonal do not share an amino acid sequence of greater than 5 consecutive amino acids. In some embodiments, the Cas9 proteins that are immune orthogonal do not share affinity for a major histocompatibility complex (MHC). In some embodiments, at least one of the two or more Cas9 proteins is modified according the method disclosed above. In some embodiments, at least one of the two or more Cas9 proteins or polynucleotides encoding said Cas9 proteins is comprised in an AAV vector. In some embodiments, the AAV vector is an AAV5 vector. In some embodiments, the AAV vector is comprised in an AAV capsid. In some embodiments, two or more Cas9 proteins or polynucleotides encoding said Cas9 proteins are comprised in AAV vectors. In some embodiments, each AAV vector is comprised in an AAV capsid, optionally wherein the AAV capsids are immune orthogonal to one another.

Disclosed herein is a method of gene editing comprising contacting a cell sequentially with two or more immune orthogonal Cas9s or polynucleotides encoding said Cas9s, optionally comprised in an AAV capsid. In some embodiments, the AAV capsids comprising each of the Cas9 or the polynucleotides encoding them may be immune orthogonal. In some aspects, the contact is in vitro. In other aspects, the contact is in vivo. In some aspects, the contact is in vivo or in vitro. In some aspects, at least one of the polynucleotides comprises or consists essentially of, or yet further consists of a polynucleotide encoding a guide RNA (gRNA). In some aspects, at least one of the polynucleotides comprises or alternatively consists essentially of, or yet further consists of a therapeutic polypeptide.

Further disclosed herein is a method of gene editing in a subject in need thereof, comprising administering sequentially to the subject an effective amount of two or more immune orthogonal Cas9 or polynucleotides encoding said Cas9s, optionally comprised in an AAV. In some embodiments, the AAV capsids comprising each of the Cas9 or the polynucleotides encoding them may be immune orthogonal. In some aspects, at least one of the polynucleotides comprises or consists essentially of, or yet further consists of a polynucleotide encoding a guide RNA (gRNA). In some aspects, at least one of the polynucleotides comprises or alternatively consists essentially of, or yet further consists of a therapeutic polypeptide.

In some aspects, the polynucleotide encoding the gRNA comprises or alternatively consists essentially of, or yet further consists of a fusion polypeptide comprising CRISPR RNA (crRNA) and trans-activating CRIPSPR RNA (tracrRNA); or a polypeptide comprising CRISPR RNA (crRNA) and trans-activating CRIPSPR RNA (tracrRNA). In one aspect, the polynucleotide encoding the gRNA comprises or consists of one or more sequence from Table 2 or Table 3 or an equivalent each thereof. In some aspects, the gRNA is specific for a region of DNA that is in need of gene editing in the subject or cell in need thereof.

In some aspects, provided herein are methods of treating a subject in need of gene editing or gene regulation, the method comprising: administering to the subject, in sequence, two or more Cas9 proteins that are immune orthogonal. In some embodiments, the Cas9 proteins that are immune orthogonal do not share an amino acid sequence of greater than 5 consecutive amino acids. In some embodiments, the Cas9 proteins that are immune orthogonal do not share affinity for a major histocompatibility complex (MHC). In some embodiments, three or more, four or more, five or more, six or more, seven or more, eight or more, nine or more, or ten or more Cas9 proteins that are immune orthogonal are administered in sequence. In some embodiments, each Cas9 protein that is immune orthogonal is a Cas9 derived from a distinct species of bacteria. In some embodiments, the Cas9 proteins that are immune orthogonal are selected from *S. pyogenes* Cas9 (spCas9), *S. aureus* Cas9 (saCas9), *B. longum* Cas9, *A. muiciniphilia* Cas9, or *O. laneus* Cas9. In particular embodiments, the Cas9 proteins that are immune orthogonal comprise spCas9 and saCas9. In some embodiments, at least one Cas9 is modified to reduce immunogenicity upon administration to the subject. In some embodiments, the methods further comprise administering at least one of the two or more Cas9 proteins in an AAV5 vector. In some embodiments, the methods further comprise administering one or more guide RNAs to the subject.

In some embodiments, the guide RNA is selected to treat a disease, disorder, or condition selected from the group of achromatopsia, adenosine deaminase (ADA) deficiency, alpha-1-antitrypsin deficiency, Alzheimer's disease, amyotrophic lateral sclerosis, aromatic amino acid decarboxylase deficiency, Batten disease, choroideremia, Crigler Najjar syndrome, cystic fibrosis, fragile X syndrome, hemophilia, hepatitis B, hepatitis C, homozygous familial hypercholesteremia, Huntington's Disease, Leber congenital amaurosis, macular degeneration, maple syrup urine disease (MSUD), mucopolysarccharidosis (I-IX), multiple sclerosis, muscular dystrophy, myotonic dystrophy, neurofibramotosis type 1, omithine transcarbamylase deficiency, pachyonychia congenita, Parkinson's disease, phenylketonuria, polycystic kidney disease, Pompe disease, retinal degeneration, Rett's syndrome, rickets, spinal muscular atrophy, severe combined immunodeficiency, sickle cell disease, Smith-Lemli-Opitz syndrome, Y-linked nonobstructive spermatogenic failure, thalassemia, and X-linked retinoschisis.

In some aspects, the guide RNA is designed and/or selected to target or repair a gene selected from the group of: Nav 1.7 (SCN9A), Nav 1.8 (SCN10A gene), 1.9 (SCN11A gene) and 1.3 (SCN3A gene); transient receptor potential cation channel subfamily V member 1 (TrpV1), also known as the capsaicin receptor and the vanilloid receptor 1; PRDM12; or HCN2.

It is appreciated by those skilled in the art that gRNAs can be generated for target specificity to target a specific gene, optionally a gene associated with a disease, disorder, or condition. Thus, in combination with Cas9, the guide RNAs facilitate the target specificity of the CRISPR/Cas9 system. Further aspects such as promoter choice, as discussed above, may provide additional mechanisms of achieving target specificity—e.g., selecting a promoter for the guide RNA encoding polynucleotide that facilitates expression in a particular organ or tissue. Accordingly, the selection of suitable gRNAs for the particular disease, disorder, or condition is contemplated herein. Non-limiting examples of suitable gRNA for genes in humans are provided in Table 2 and in mice in Table 3.

Administration of the modified AAV or compositions can be effected in one dose, continuously or intermittently throughout the course of treatment. Administration may be through any suitable mode of administration, including but not limited to: intravenous, intra-arterial, intramuscular, intracardiac, intrathecal, subventricular, epidural, intracerebral, intracerebroventricular, sub-retinal, intravitreal, intraarticular, intraocular, intraperitoneal, intrauterine, intradermal, subcutaneous, transdermal, transmuccosal, and inhalation.

Methods of determining the most effective means and dosage of administration are known to those of skill in the art and will vary with the composition used for therapy, the purpose of the therapy and the subject being treated. Single or multiple administrations can be carried out with the dose level and pattern being selected by the treating physician. It is noted that dosage may be impacted by the route of administration. Suitable dosage formulations and methods of administering the agents are known in the art. Non-limiting examples of such suitable dosages may be as low as 1E+9 vector genomes to as much as 1E+17 vector genomes per administration.

In a further aspect, the modified viral particle and compositions of the invention can be administered in combination with other treatments, e.g. those approved treatments suitable for the particular disease, disorder, or condition. A non-limiting example includes the treatment of muscular dystrophy with a combination of the modified viral particle and one or more steroids.

This administration of the modified viral particle or compositions of the invention can be done to generate an animal model of the desired disease, disorder, or condition for experimental and screening assays.

Doses suitable for uses herein may be delivered via any suitable route, e.g. intravenous, transdermal, intranasal, oral, mucosal, or other delivery methods, and/or via single or multiple doses. It is appreciated that actual dosage can vary depending on the recombinant expression system used (e.g. AAV or lentivirus), the target cell, organ, or tissue, the subject, as well as the degree of effect sought. Size and weight of the tissue, organ, and/or patient can also affect dosing. Doses may further include additional agents, including but not limited to a carrier. Non-limiting examples of suitable carriers are known in the art: for example, water, saline, ethanol, glycerol, lactose, sucrose, dextran, agar, pectin, plant-derived oils, phosphate-buffered saline, and/or diluents. Additional materials, for instance those disclosed in paragraph [00533] of WO 2017/070605 may be appropriate for use with the compositions disclosed herein. Paragraphs [00534] through [00537] of WO 2017/070605 also provide non-limiting examples of dosing conventions for CRISPR-Cas systems which can be used herein. In general, dosing considerations are well understood by those in the art.

Compositions and Kits

Also provided by this invention is a composition or kit comprising any one or more of the immunosilent and/or immune orthogonal proteins. In one aspect, the carrier is a pharmaceutically acceptable carrier. These compositions can be used therapeutically as described herein and can be used in combination with other known therapies and/or according to the method aspects described herein.

Briefly, pharmaceutical compositions of the present invention may comprise an immunosilent and/or immune orthogonal Cas9 or a polynucleotide encoding said Cas9, optionally comprised in an AAV, which is optionally also immune orthogonal, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure may be formulated for oral, intravenous, topical, enteral, and/or parenteral administration. In certain embodiments, the compositions of the present disclosure are formulated for intravenous administration.

EXAMPLES

The following examples are non-limiting and illustrative of procedures which can be used in various instances in carrying the disclosure into effect. Additionally, all reference disclosed herein are incorporated by reference in their entirety.

Example 1—Immunogenicity of Cas9 Proteins

Several in silico epitope binding prediction methods have been developed that employ machine learning methods to predict peptide-MHC class I binding affinity. Applicants have utilized the NetMHC 4.0 Server 4, a neural network and weight matrix based predictive algorithm, to determine the immunogenic level of peptides in previously identified Cas9 protein sequences from 88 strains 6, over all HLA allele supertypes.

NetMHC was run with default parameters, predicting immunogenic scores for each allele over peptide sequences of 8 to 11 amino acids. Highly immunogenic peptides were defined as having an affinity score <50 nM and intermediate as 50 nM 500 nM.

After identifying the most immunogenic peptides, Applicants utilized two in silico methods to determine which modifications were necessary to reduce SpCas9 immunogenicity 1) determined the effect that single amino acid swaps in each highly immunogenic peptide would have on reducing immunogenicity 2) found which Cas9 orthologs are the closest in their 'immunogenic space' to determine which Cas9 proteins could be utilized sequentially for repetitive treatments.

An overall workflow is described in FIG. 1.

Example 2—Effect of Single Amino Acid Swaps in Immunogenic Peptides in SpCas9

After mapping the highly immunogenic peptides in SpCas9, Applicants did single amino acid swaps at each position in these immunogenic peptides to determine whether these swaps would lower the peptides' overall immunogenicity. This new list of peptides was first submitted to the NetMHC server to predict their immunogenicity scores. The goal was to find if changing the single AA in such peptides would significantly modify the affinity.

Affinity scores were calculated for every single amino acid swap in an immunogenic peptide. For example, the peptide 'HHQDLTLL' (SEQ ID NO:307), located at amino acid position 327-334 in the original protein, has 32 no-affinity scoring peptides with a single amino acid swap (e.g. the last position of SEQ ID NO:307 "L" is swapped to K, N or D). Top scoring peptides were defined as those that displayed the lowest affinity value out of all possible peptide swaps. Subsequently, the 'no' affinity peptides were submitted to the PROVEAN Server, which predicts the effect that single amino acid changes at certain positions can have on a protein's functionality. 7 The single amino acid swaps leading to 'no' or 'low' immunogenicity and that are non-deleterious will subsequently be utilized for experimental mutagenesis of SpCas9. These mutations are listed in Table 1, with the matching colors corresponding to peptides whose immunogenicity can change with the same AA swap.

One can then use this mutated SpCas9 sequentially for in vivo genome therapy. Not to bound by theory it is believed this may be accomplished without lowering its efficacy after repetitive treatments without eliciting an immunogenic response.

Example 3—Orthogonality of Cas9 Proteins for Sequential Dosing to Evade Host Immune System The goal was to determine Cas9 orthologs that are orthogonal in the 'immunogenicity space'. This will allow Applicants to prescribe a sequential regimen of Cas9s for therapeutic interventions. The analysis reveals that for the most conservative data, there are always at the very least groups of 35 proteins that are mutually orthogonal and that include SpCas9. The methodology implemented goes as follows: high affinity peptides from one protein were selected and the number of times those exact peptide sequences occurred in the entire other sequence was determined. If no peptides were found, the proteins are determined to be orthogonal. The peptides selected, usually composed of 8 to 11 amino acids, were further split up into subpeptides of lengths 5 to 11. This allowed for the identification of more subtle similarities between protein sequences. This analysis was carried over every possible protein pair. The groups of mutually orthogonal proteins here presented had no matches of even length 5. The algorithm used to determined mutual orthogonality, 'find_cliques', is provided in the Python package Networkx.

Applicants created a network where two proteins (nodes) were connected by an edge if they were orthogonal. Applicants then applied the clique-finding algorithm to locate all maximal cliques in the graph, where a maximal clique is a complete subgraph such that no other node may be added while maintaining completeness. See, e.g. FIG. 4.

Example 4—Mouse Experiments

Two month old mice are injected with AAV virus at 6E+11 GC/mouse. Applicants will be testing two different AAV capsids, AAV8 and AAVDJ, as well as two orthogonal Cas9 proteins, SpCas9 and SaCas9, to test whether sequential rounds of AAV virus injections with differing capsid or differing SpCas9 proteins has any effect on reducing efficacy of genome editing, due to an immunogenic response.

| Week 0 | Week 3 | Week 6 |
|---|---|---|
| A1 | B2 | Assay (baseline and role of AAVs) |
| A2 | A1 | Assay (baseline and role of AAVs) |
| B1 | B2 | Assay (baseline and role of AAVs) |
| B2 | B1 | Assay (baseline and role of AAVs) |
| A1 | B2 | Assay (Cas9 orthogonality) |
| B2 | A1 | Assay (Cas9 orthogonality) |
| A2 | B1 | Assay (Cas9 orthogonality) |
| B1 | A2 | Assay (Cas9 orthogonality) |

Legend:
A1: AAV8 SpCas9 CD81;
A2: AAVDJ SpCas9 Scarb1;
B1: AAV8 SaCas9 CD81;
B2: AAVDJ SaCas9 Scarb1

Example 5—Determining Presence of Memory T-Cell Populations to Predicted Peptides Memory T-cell populations present in the human populations are assessed for the presence of T-cells directed to any of the predicted Cas9 orthologs. In particular, *S. aureus* peptides are studied, as approximately 30% of the human population is colonized with this pathogen.

Example 6—Screening for "Immune Orthogonal" Orthologs

A major hurdle in protein-based therapeutics is the interaction with the adaptive immune system, which can lead to neutralization by circulating antibodies and clearance of treated cells by cytotoxic T-lymphocytes. One method of circumventing these issues is to use human or humanized proteins which avoid the immune response by self-recognition. However, this approach limits potential protein therapeutics to those of human origin, excluding many exciting effectors and delivery vehicles such as CRISPR-Cas9 and adeno-associated viruses (AAVs). To address this issue, Applicants propose here the sequential use of orthologous proteins whose function is constrained by natural selection, but whose structure is subject to diversification by genetic drift. This would, in principle, allow for repeated treatments by 'immune orthogonal' orthologs without reduced efficacy due to lack of immune cross-reactivity among the proteins. To explore and validate this concept, Applicants chose 91 Type II CRISPR-Cas9 orthologs and 167 AAV capsid protein orthologs, and developed a pipeline to compare total sequence similarity as well as predicted binding to class I and class II Major Histocompatibility Complex (MHC) proteins. Interestingly, MHC binding predictions revealed wide diversity among the set of Cas9 orthologs, with 83% of pairs predicted to have non cross-reacting immune responses, while no global immune orthogonality among AAV serotypes was observed. To confirm these findings Applicants selected two Cas9 orthologs, from *S. pyogenes* and *S. aureus*, predicted to be orthogonal in immune space, and delivered them into mice via multiple AAV serotypes. Applicants observed cross-reacting antibodies against AAV but not Cas9 orthologs in sera from immunized mice, validating the computationally predicted immune orthogonality among these proteins. Moving forward, Applicants anticipate this framework can be applied to rationally engineer immune orthogonality among protein orthologs.

Protein therapeutics, including protein-based gene therapy, have several advantages over small-molecule drugs. They generally serve complex, specific functions, and have minimal off-target interference with normal biological processes. However, one of the fundamental challenges to any protein-based therapeutic is the interaction with the adaptive immune system. Neutralization by circulating antibodies through B-cell activation and clearance of treated cells by CD8+ cytotoxic T-lymphocytes (CTLs) create a substantial barrier to effective protein therapies[10]. Although the delay in the adaptive immune response to novel proteins may allow sufficient time for the initial dose to work, subsequent doses face faster and stronger secondary immune responses due to the presence of memory T- and B-cells. In addition, gene transfer studies have shown that host immune responses against the delivery vector and/or therapeutic transgene can eliminate treated cells, thus limiting the efficacy of the treatment[11-16].

A common approach to circumventing these issues has been to utilize human proteins, or to humanize proteins by substitution of non-human components[17,18]. However, this approach is limited to a small set of therapeutic proteins naturally occurring in humans or closely related species. In addition, although the humanization of proteins can result in a significantly less immunogenic product, they still carry immunological risk[18]. Another way to circumvent an immune response to protein therapeutics is the removal of immunogenic T cell epitopes.[19,20] Once immunogenic T cell epitopes are identified, substitution of key amino acids may reduce the protein's immunogenicity since modification of amino acids at critical anchor residues can abrogate binding to MHC molecules and prevent antigen presentation. However, this can prove difficult due to the massive diversity at HLA loci. As epitope engineering must account for the substrate specificity of each different HLA allele, therapeutics would likely have to be uniquely modified for each patient. All the same, epitope deletion has been successfully applied to several proteins,[21] but can only preserve protein function when limited to small numbers of HLA alleles unrepresentative of the full diversity. Structural modifications such as PEGylation have also been known to reduce immunogenicity by interfering with antigen-processing mechanisms. However, there is evidence that PEG-specific antibodies are elicited in patients treated with PEGylated therapeutic enzymes[22-25].

Furthermore, protein therapies have required repeated treatments due to degradation of the protein or turnover of treated cells, or, in the case of gene therapy, reduced expression of the transgene[26,27]. This provides an even greater challenge as repeated exposure to the same antigen can elicit a more robust secondary immune response[28], which may completely inhibit subsequent dosage or even sensitize the immune system to antigens remaining from the initial exposure. In order to facilitate efficacious repeat protein therapies, Applicants propose the use of orthologous proteins whose function is constrained by natural selection, but whose structure is subject to diversification by genetic drift. An ortholog, given sufficient sequence divergence, will not cross-react with the immune response generated by exposure to the others, allowing repeat doses to avoid neutralization by existing antibodies and treated cells to avoid clearance by activated CTLs.

As a case study for exploring this approach, Applicants focused on the CRISPR-Cas9 system, perhaps the most anticipated therapeutic for gene editing[29-36]. Comparative genomics has demonstrated that Cas9 proteins are widely distributed across bacterial species and have diversified over an extensive evolutionary history[37-39]. Applicants hypothesized this diversity could provide a mechanism to circumvent inducing immunological memory by utilizing orthologous Cas9 proteins for each treatment. Additionally, the immunogenicity due to the delivery vehicle or administration route for the Cas9 and the associated guide RNA (gRNA) must also be considered. In this regard, adeno-associated viruses (AAVs) have emerged as a highly preferred vehicle for gene delivery, as these are associated with low immunogenicity and toxicity[14,15], which promotes long-term transgene expression[40,41] and treatment efficacy. Despite the relatively low immunogenicity of AAV vectors, antibodies against both the capsid and transgene may still be elicited[42-46]. Additionally, the prevalence of neutralizing antibodies (NAB) against AAVs in the human population[47] and cross-reactivity between serotypes[48] remains a hurdle for efficacious AAV therapy. Although AAVs were initially considered non-immunogenic due to their poor transduction of antigen-presenting cells (APCs)[49], it is now known that they can transduce dendritic cells (DCs)[50] and trigger innate immune responses through Toll-like receptor (TLR) signaling pathways[51]. The ability to transduce DCs is dependent on AAV serotype and genome, and may be predictive of overall immunogenicity[52].

To evaluate the immune orthogonality of AAV-delivered CRISPR-Cas systems, Applicants analyzed 91 Cas9 orthologs, and 167 AAV VP1 orthologs. By comparing total sequence similarity as well as predicted binding strengths to class I and class II MHC molecules, Applicants constructed graphs of immune cross-reactivity and computed cliques of proteins that are orthogonal in immunogenicity profiles. Although MHC epitopes do not predict antibody epitopes, the induction of the more powerful memory response is primarily dependent on reactivation of memory B-cells with help from memory T-cells through the presentation of antigens on class II MHC molecules.[53,54] Finally, Applicants experimentally confirmed these immunological predictions by assaying treated mice for induction of protein-targeting antibodies.

Humoral Immune Response to AAV and Cas9

One of the major obstacles for sequential gene therapy treatments is the presence of neutralizing antibodies against the delivery vehicle and transgene cargo induced by the first administration of the therapy. To determine the humoral immune response kinetics to the AAV-8 capsid and the Cas9 transgene, Applicants first injected C57BL/6J mice retro-orbitally with $10^{12}$ vg of AAV-8-SaCas9 targeting proprotein convertase subtilisin/kexin type 9 (PCSK9), a promising gene target that when disrupted can reduce Low Density Lipoprotein (LDL) levels and protect against cardiovascular disease. Consistent with a previous stud[55], mice had reduced PCSK9 serum levels as early as one week post-injection due to successful SaCas9 mediated gene-editing, which was sustained for the entire duration of the experiment (4 weeks) (FIG. 5C). Notably, mice developed humoral immunity to the AAV8 capsid within one week post-injection (FIG. 5D).

Figure 5E:
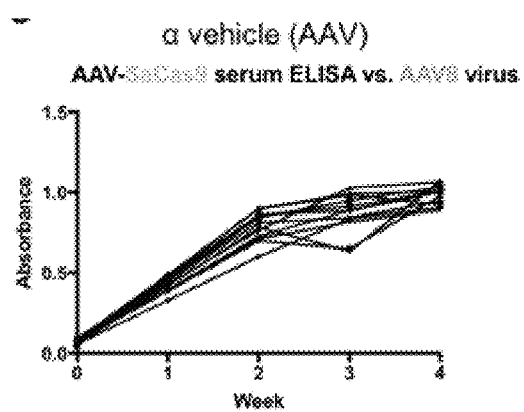
Figure 5F:
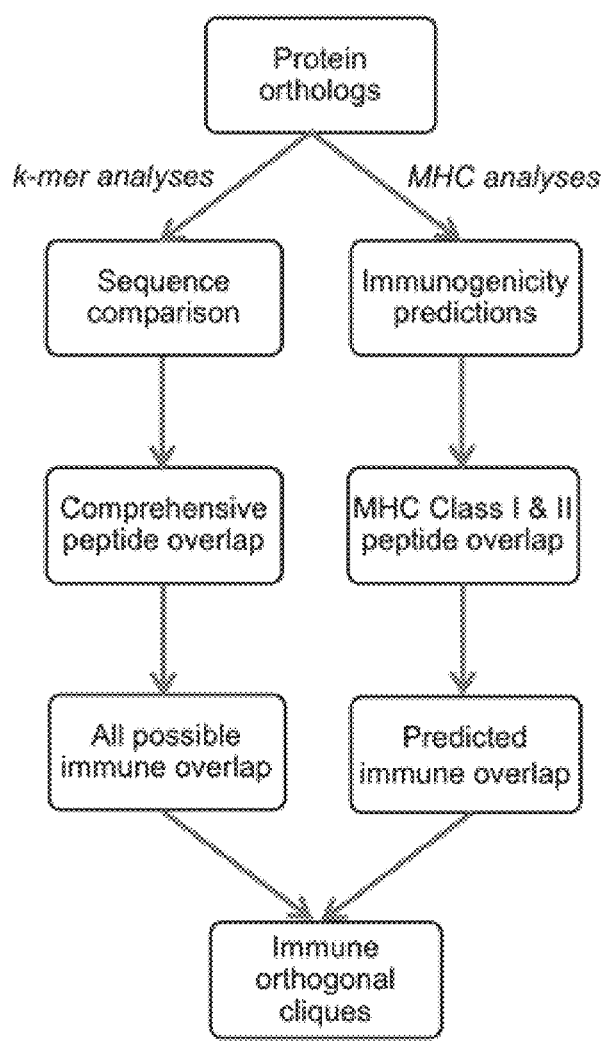

Additionally, Applicants noted that a subset of the mice developed IgG1 antibodies against the SaCas9 protein (FIG. 5E). To evaluate the feasibility of multiple dosing with AAV-Cas9, Applicants next investigated whether immune orthogonal sets of AAV and Cas9 orthologs exist.

Identifying Immune-Orthogonal Proteins

Figure 5G:
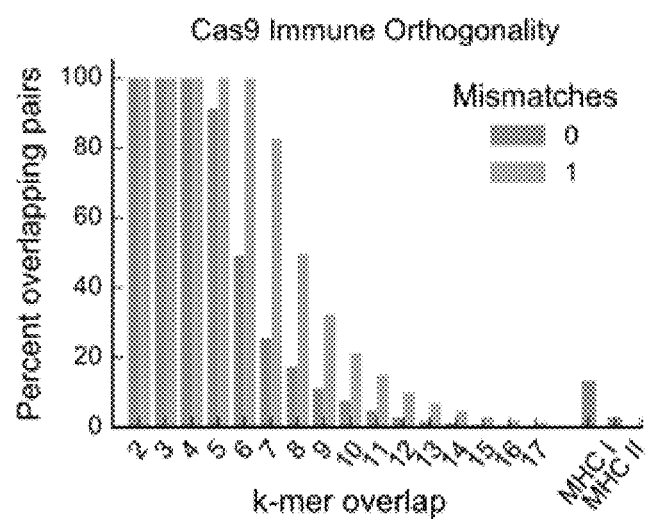
Figure 5H:
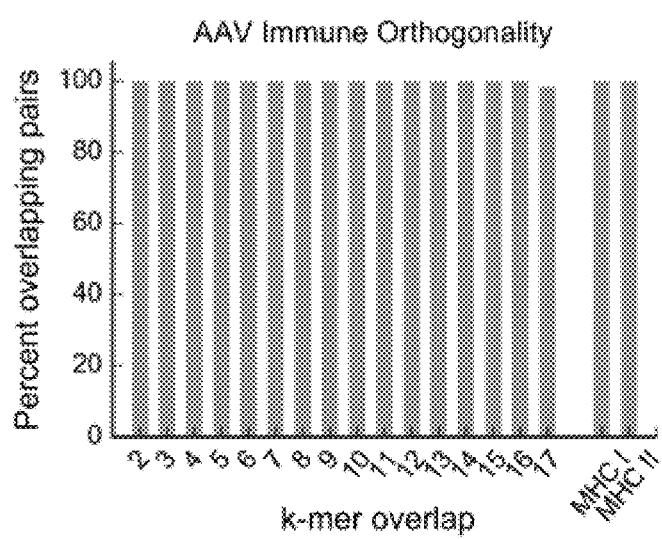
Figure 7:
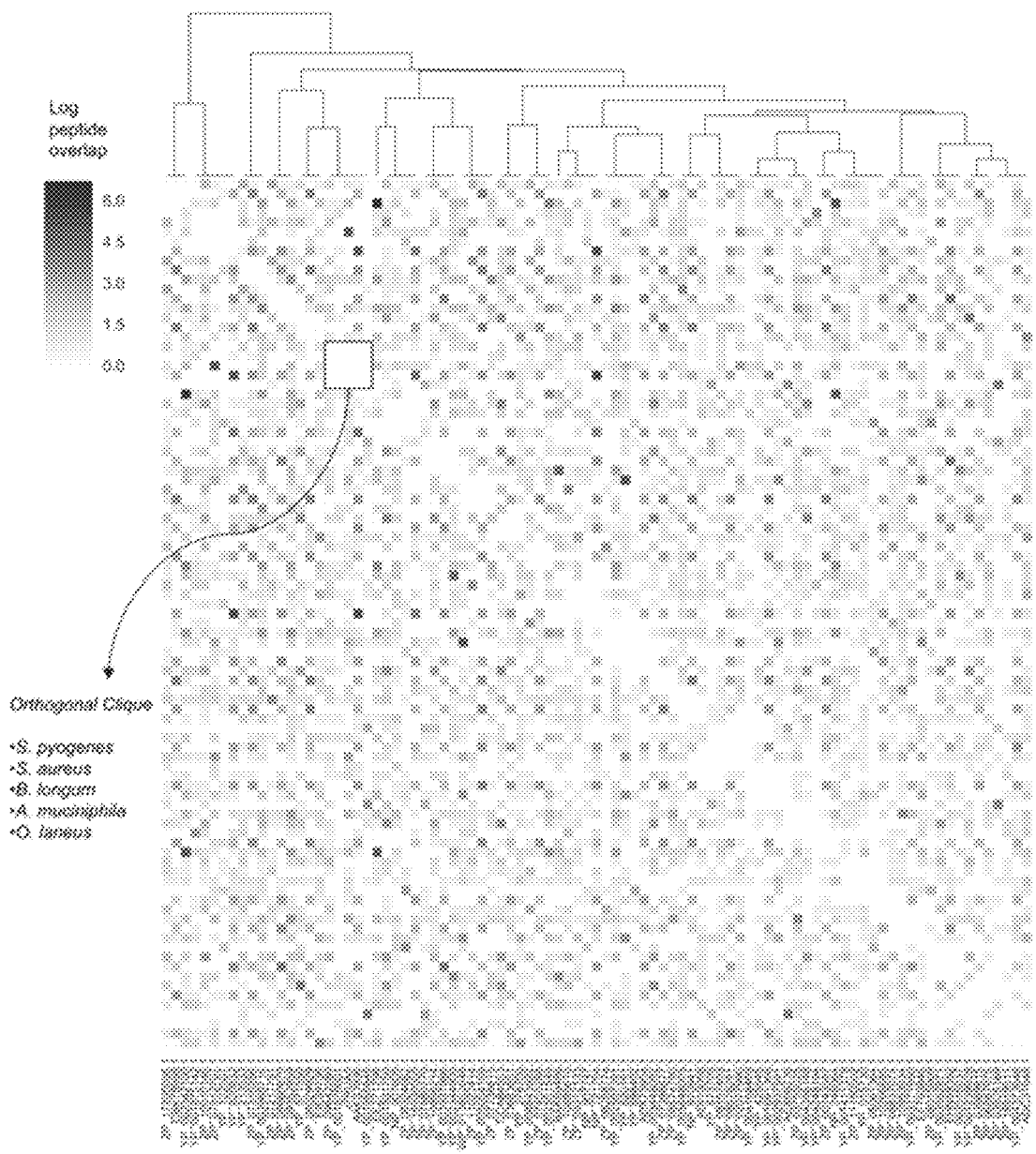
FIG. 7: depicts Cas9 immune orthogonal cliques. Cliques corresponding to 6-mer overlaps are depicted. An example of an orthogonal clique is highlighted, which includes Cas9s from: *S. pyogenes, S. aureus, B. longum, A. muciniphila*, and *O. laneus*.
Figure 8A:
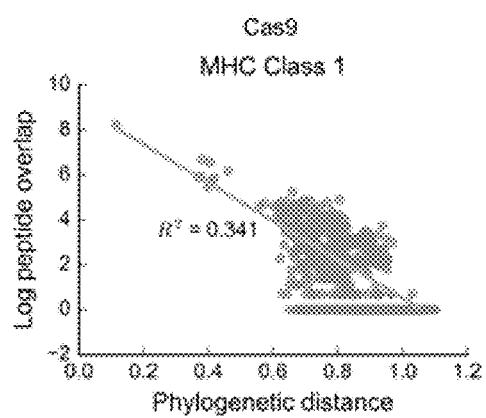
FIGS. 8A-8D: show the results of in silico analyses and comparisons of immunogenicity of Cas9 and AAV orthologs. Linear regressions exclude pairs with no overlap.
Figure 8B:
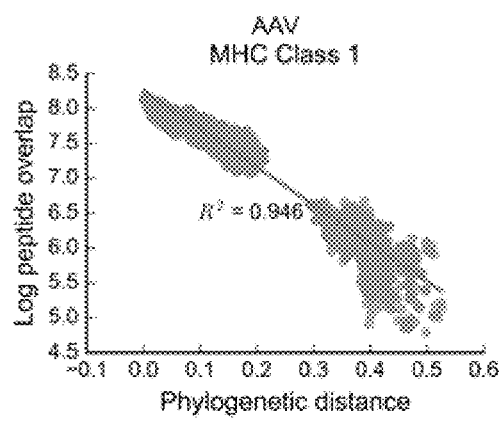
Figure 8C:
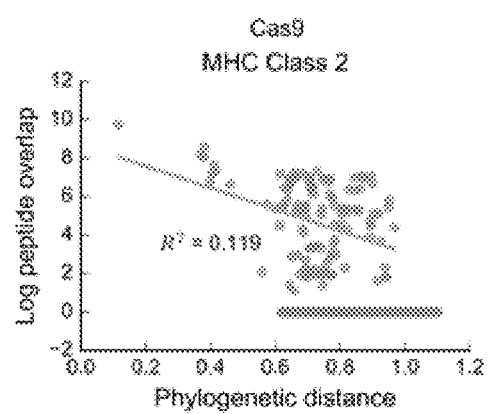
Figure 8D:
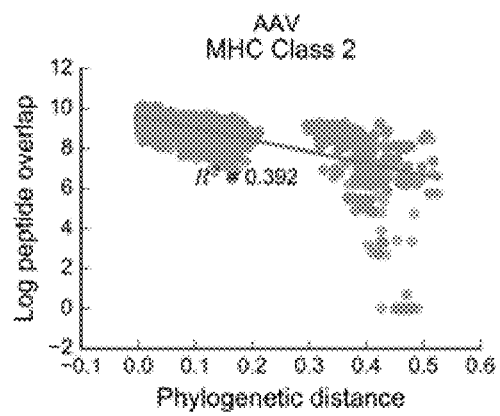

Natural selection produces diverse structural variants with conserved function in the form of orthologous genes. Applicants assayed the relevance of this diversity for immunological cross-reactivity of 91 Type II Cas9 orthologs and 167 AAV orthologs by first comparing their overall amino acid sequence similarities, and second, using a more specific constraint of how their respective amino acid sequences are predicted to bind MHC Type I and II molecules (FIG. 5F). From these analyses Applicants obtained first an estimate of the comprehensive immune overlap among Cas9 and AAV orthologs based purely at the sequence level, and second a more stringent estimate of predicted immune overlap based on predicted MHC binding. By sequence-level clustering and clique finding methods, Applicants defined many sets of Cas9 orthologs containing up to 9 members with no 6-mer overlap (FIG. 7). Notably, based on MHC-binding predictions, Applicants find among the set of Cas9 orthologs that 83% of pairs are predicted to have non cross-reacting immune responses, i.e. they are predicted to be orthogonal in immune space (FIG. 5G). On the contrary, among AAV capsid (VP1 protein) orthologs, Applicants did not find full orthogonality up to the 16-mer level, even when restricting predictions with MHC-binding strengths (FIG. 5H), likely reflecting the strong sequence conservation and shorter evolutionary history of AAVs[56]. This analysis suggests, consistent with previous observations[57,58], that exposure to one AAV serotype can induce broad immunity to all AAVs, which presents a significant challenge to AAV delivery platforms, as some serotypes are prevalent in human populations. Despite the most divergent AAV serotype (AAV-5) showing the fewest shared immunogenic peptides, there remain tracts of sequences fully conserved within the VP1 orthologs. As expected, predicted immune cross-reaction negatively correlates with phylogenetic distance (FIG. 8), though there is significant variation not captured by that regression, suggesting that MHC-binding predictions can refine the choice of sequential orthologs beyond phylogenetic distance alone.

Confirming Humoral Immune-Orthogonality Among Cas9 Proteins

Figure 6A:
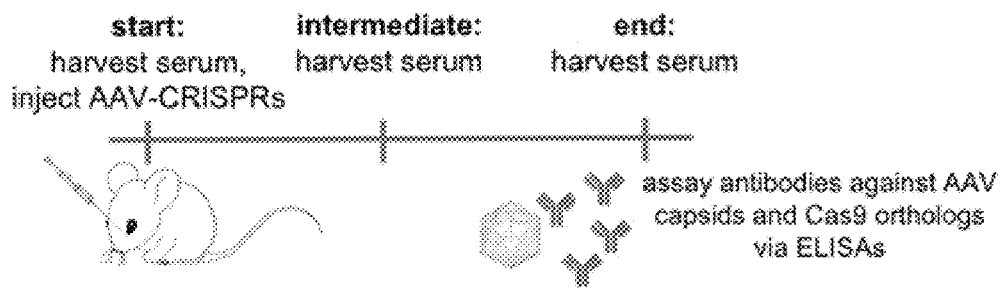
FIGS. 6A-6E: shows experimental validation of Cas9 and AAV immunogenicity predictions.
Figure 6B:
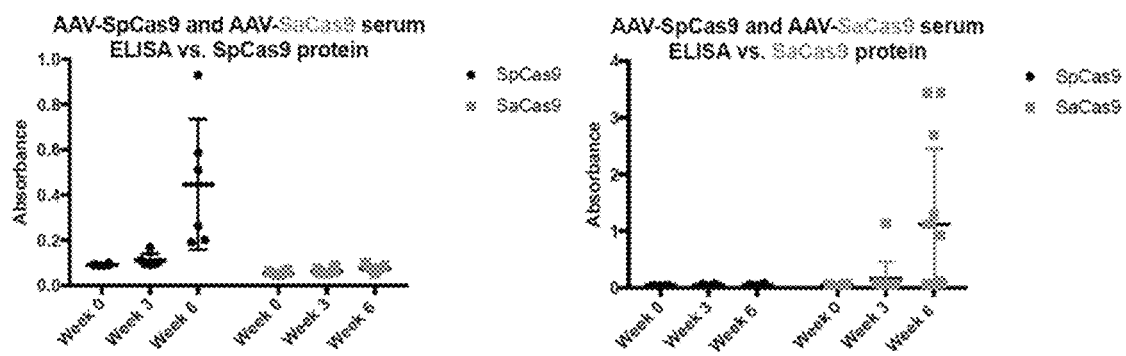
Figure 6C:
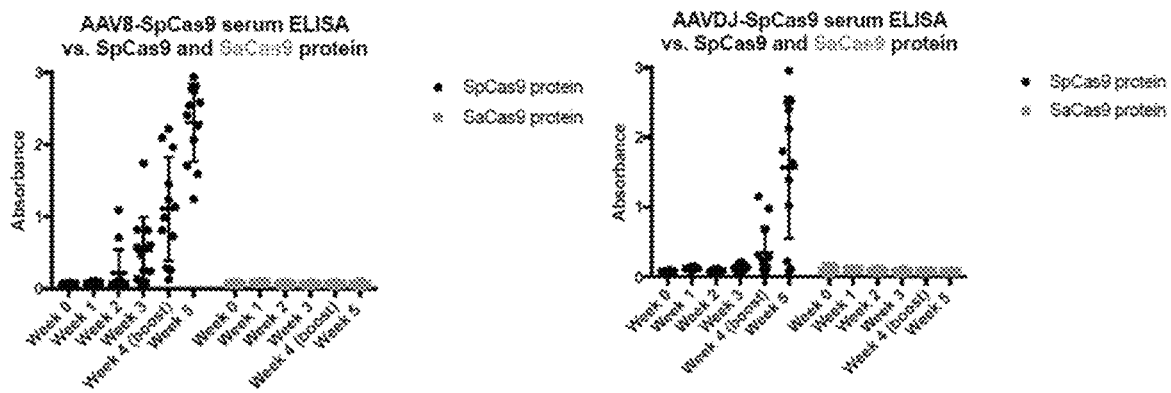

To test these immunological predictions and to establish the utility of this approach, Applicants narrowed in on a 5-member clique containing the ubiquitously used *S. pyogenes* Cas9 in addition to the well-characterized *S. aureus* Cas9 (FIG. 7). To determine whether either of these proteins have cross-reacting antibody responses, Applicants injected mice with $10^{12}$ vg of either AAV8-SaCas9 or AAV8-SpCas9 via retro-orbital injections and harvested serum at days 0 (pre-injection), and periodically over 4-6 weeks (FIG. 6A). SpCas9-specific antibodies were detected in the plasma of all mice injected with SpCas9 (n=6), and notably none of the mice injected with SaCas9 (n=12) (FIG. 6B). Although SaCas9 appeared to induce a weaker response, as only half of the mice injected with SaCas9 AAVs (n=12) developed detectable antibodies against SaCas9, none of the mice injected with SpCas9 AAVs (n=6) developed an antibody response against SaCas9. These results were confirmed in an independent study in which SpCas9-specific antibodies, but not SaCas9-specific antibodies, were detected in the plasma of mice injected with AAV-SpCas9 (n=12). These mice were injected retro-orbitally with $10^{12}$ vg of AAV8-SpCas9 or AAVDJ-SpCas9, and also received an additional intramuscular injection with $10^{11}$ vg at week 4. (FIG. 6C). Taken together, this data confirms that SpCas9 and SaCas9 have humoral immune-orthogonality.

Broad Cross-Reactivity Among AAV Serotypes

Figure 6D:
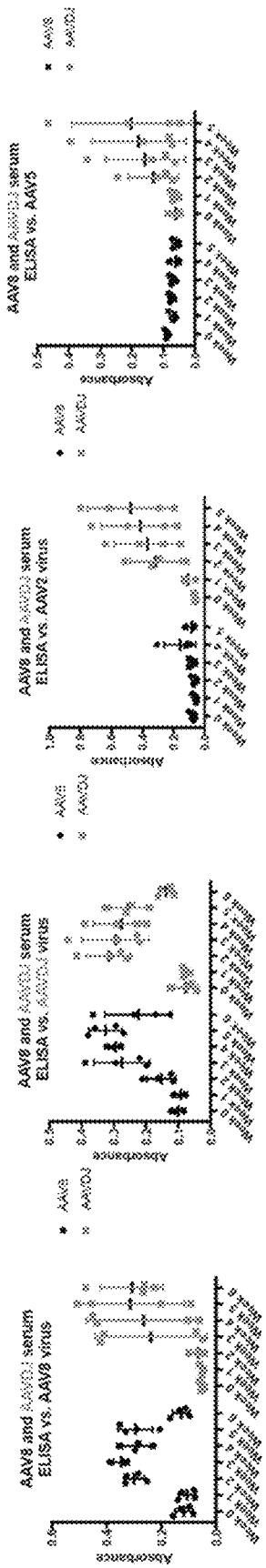
Figure 6E:
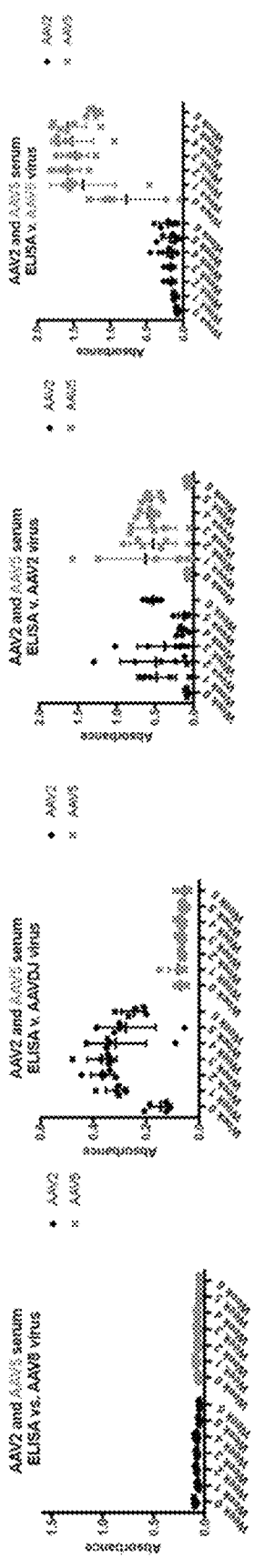
Figure 9A:
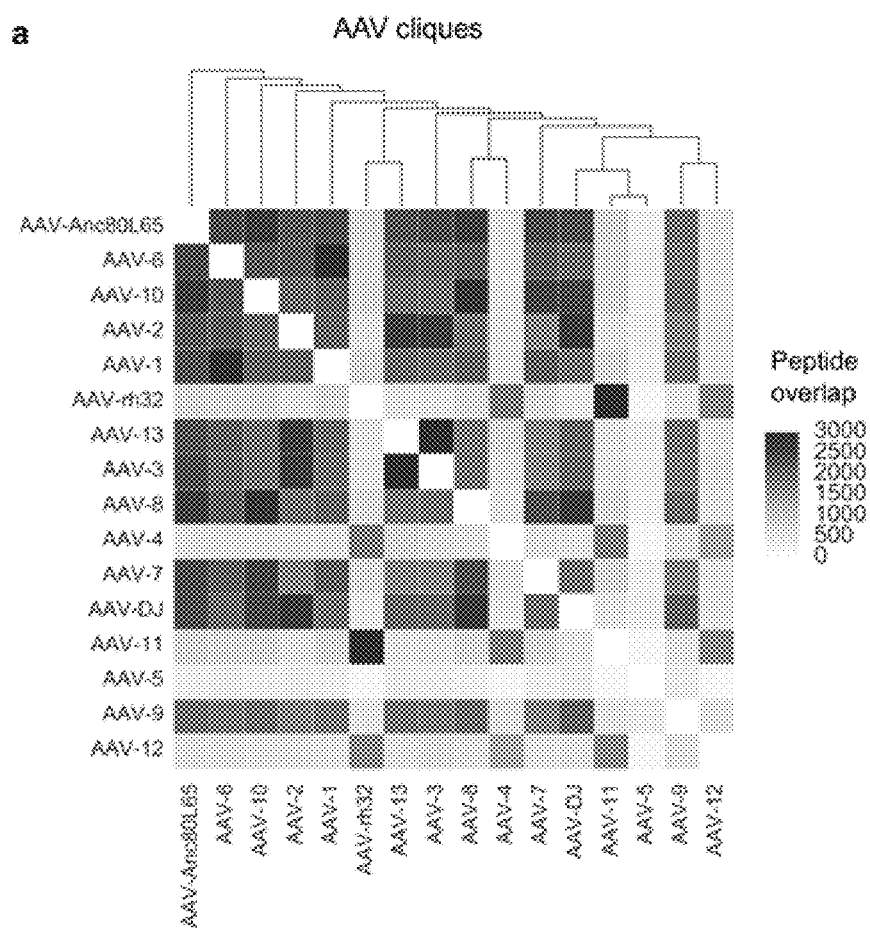
FIGS. 9A-9B: shows the major AAV serotype groups.
Figure 9B:
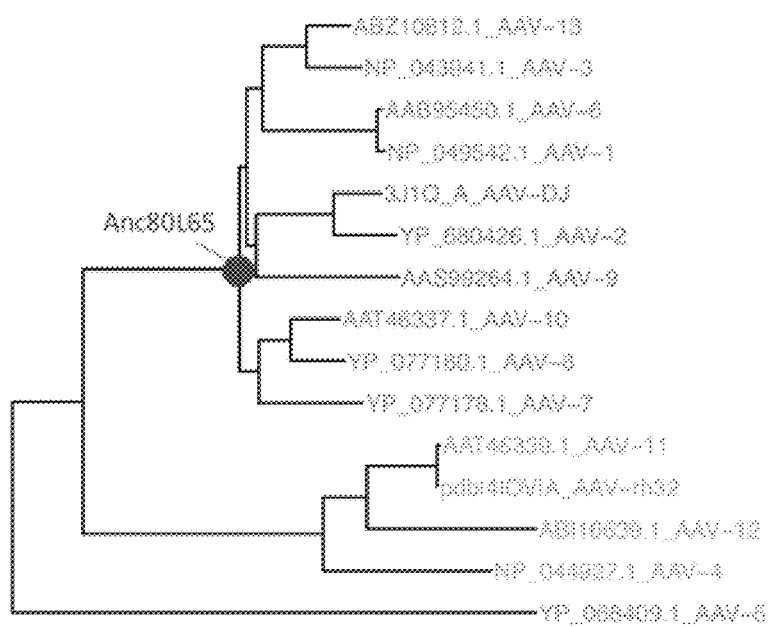

AAVs are becoming a preferred delivery vehicle due to their ability to avoid induction of a strong CD8+ T-cell response, however, the presence of neutralizing antibodies remains a significant barrier to successful application of AAV therapies. Consistent with previous results,[57] Applicants found shared immunogenic peptides among all the various human AAV serotypes, (FIG. 9). Applicants confirmed the lack of orthogonality for two serotypes, AAV8 and AAVDJ, in which Applicants found that antibodies produced in mice injected with AAV8 and AAVDJ react to both AAV8 and AAVDJ antigens (FIG. 6D). This analysis suggests that there are no two known AAVs for which exposure to one would guarantee immune naïveté to another across all HLA genotypes. However, immune cross-reaction could be minimized through the use of AAV5[58,59], the most phylogenetically divergent serotype. These predictions identify only a single shared highly immunogenic peptide between AAV5 and the commonly used AAV2 and AAV8 in the mouse model (though several other shared peptides of mild MHC affinity exist). Applicants confirmed this via ELISAs, where mice injected with AAV2 did not elicit antibodies against AAV5 and AAV8, and mice injected with AAV5 did not elicit antibodies against AAVDJ and AAV8 (FIG. 6E).

The use of protein therapeutics requires ways to evade the host's immune response. Cas9, as an example, has prokaryotic origins and can evoke a T-cell response, which may lead to clearance of transduced cells. In addition, circulating antibodies can neutralize the AAV vector and prevent efficient transduction upon repeated doses. Immunosuppressive drugs could mitigate some of these aspects, but not without significant side-effects, as well as not being applicable to patients in poor health[60-63]. Similar to what has been done in cancer antibody therapeutics[64], the SpCas9 protein could also be de-immunized by swapping high-immunogenicity domains. This is a promising approach, however, it will be complex and laborious as Applicants anticipate tens of mutations to achieve stealth, and could result in a reduction in activity and an overall less effective therapy.

To circumvent this issue, Applicants developed here a framework to compare protein orthologs and their predicted binding to MHC I and MHC II by checking a sliding window of all k-mers in a protein for their presence in another, focusing on peptides predicted to bind to at least one MHC allele. Through this analysis, Applicants identified cliques of Cas9 proteins that are immune orthogonal. Based on these predictions, specific T-cell responses from one ortholog would not cross-react with another ortholog of the same clique, preventing the re-activation of CD8+ cytotoxic T-cells, as well as the CD4+ T-cell help necessary to re-activate memory B-cells. Applicants confirmed these results through ELISAs, and verified two well-characterized Cas9 proteins to be immune orthogonal, SpCas9 and SaCas9. Therefore, Applicants expect that proteins belonging to the same clique can be used sequentially without eliciting memory T- and B-cell responses.

Due to the importance of AAVs as a delivery agent in gene therapy, Applicants also analyzed AAV serotypes through this MHC I and II comparison framework, and have demonstrated that no two AAVs are mutually immune orthogonal. However, with a known HLA genotype, it may be possible to define a personalized regimen of immune orthogonal AAVs using currently defined serotypes. For instance, use of AAV5 minimizes immune cross-reactivity in mice and primates, as demonstrated by a recent study in which chimeric-AAV5 immunized mice and primates successfully received a second dose of treatment with AAV1[59]. However, in the human setting Applicants predict that there will be substantially more immune overlap between AAV5 and other AAVs. This analysis suggests that creating a pair of globally orthogonal AAV capsids for human application would require [0053] 10 mutations in one of the two proteins. This hypothetical orthogonal AAV capsid presents a substantial engineering challenge, as it requires mutating many of the most conserved regions to achieve immune orthogonality.

Previous work has identified that MHC affinity is highly dependent on anchor residues at either end of the binding pocket[56]. Residue diversity is more tolerated in the center of the binding pocket, though it may be these residues that most impact antigen specificity, as it is thought that they are central to interaction with the T-cell receptor (TCR). Comparing the number of orthologous pairs in 9-mer space with the number of predicted orthologous pairs based on class II binding predictions suggests that only approximately 65% of 9-mer peptides serve as appropriate MHC class II binding cores, even across the thousands of HLA-2 combinations Applicants explore here. This under-sampling of peptide space by MHC molecules likely reflects the requirement for hydrophobic anchor residues and leaves some space for protein de-immunization by mutation of immunogenic peptides to ones which never serve as MHC binding cores. Achieving this while preserving protein function however, has proven difficult even for few HLA alleles, and remains a significant protein engineering challenge.

Figure 10:
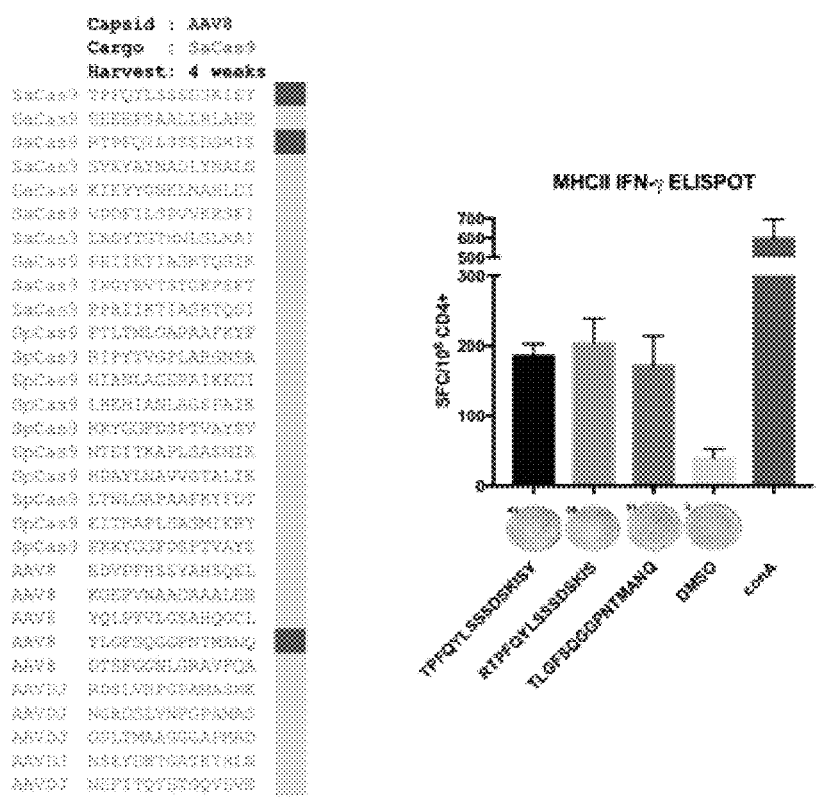
FIG. 10: shows experimental validation of a MHCII peptide predictions via the ELISPOT assay; SaCA9 see SEQ ID NO:18; spCAS9 see SEQ ID NO:17; AAV8 see SEQ ID NO:5; AAVDJ see SEQ ID NO:11, 11, 15, 15 and 6, respectively).

Applicant also notes some limitations to this work. Mainly, Applicants have used inbred C57BL/6J as the mice model, which have very limited MHC diversity,[66] and might not recapitulate other human immunological features, such as differences in antigen processing and presentation. In this regard, Applicants attempted to measure the T-cell response with the ELISPOT assay for a subset of predicted MHC II peptides and indeed confirmed immunogenicity against some, although Applicants also noted the C57BL/6J mice did not show robust responses in general to the AAV-CRISPRs (FIG. 10). Moving forward, this work can be potentially repeated using other mouse models, such as mice expressing human HLA allotypes, however, these models come with their own technical challenges, such as restricted HLA alleles (representing only main MHC II subgroups) as well as a restricted TCR repertoire[66]. In addition, B-cell epitopes can also be predicted and incorporated into immune orthogonality analysis. However, since B-cell epitopes may be both linear and conformational, these are more difficult to predict. Advances and further validation of these in silico models will allow for better predictions in the future[67-71]. Finally, recent work has indicated that MHC class I peptides may have significant contribution from spliced host and pathogen-derived peptides created by proteasomal processing[72]. It is unclear how this may affect cross-recognition of proteins Applicants predict to be immune orthogonal. On the one hand, it provides a mechanism whereby very short antigenic sequences spliced to the same host protein may result in cross-recognition of substantially different foreign antigens, however, Applicants expect this to be unlikely due to the massive number of possible spliced peptides between the antigen and entire host proteome.

Overall, Applicants believe this framework provides a potential solution for efficacious gene therapy, not solely for Cas9-mediated genome engineering, but also for other protein therapeutics that might necessitate repetitive treatments. Although using this approach still requires mitigating the primary immune response, particularly CTL clearance, Applicants expect that epitope deletion and low-immunogenicity delivery vectors such as AAVs will mitigate this problem, and the potential for repeated dosage will reduce the need for very high first-dose efficiency.

Computational Methods

For Cas9, Applicants chose 91 orthologs cited in exploratory studies cataloguing the diversity of the Cas9 protein,[73] including several that are experimentally well-characterized. For AAVs, Applicants analyzed 167 sequences, focusing in on all 13 characterized human serotypes, as well as one isolate from rhesus macaque (rh32), one engineered variant (DJ), and one reconstructed ancestral protein (Anc80L65). Applicants then compared total sequence similarity (immunologically uninformed) as well as predicted binding to class I and class II MHC molecules (immunologically informed) between these proteins. Immunologically uninformed sequence comparison was carried out by checking a sliding window of all contiguous k-mers in a protein for their presence in another protein sequence with either zero or one mismatch. Immunologically informed comparison was done in a similar fashion, but using only those k-mers predicted to bind to at least one of 81 HLA-1 alleles using netMHC 4.0[74] for class I (alleles can be found at .cbs.dtu.dk/services/NetMHC/MHC_allele_names.txt), and at least one of 5,620 possible MHC II molecules based on 936 HLA-2 alleles using netMHCIIpan 3.1[75] for class II (alleles can be found at .cbs.dtu.dk/services/NetMHCIIpan-3.1/alleles_name.list). Applicants compared the use of netMHC to alternative immune epitope prediction platforms such as the Immune Epitope Database (iedb.org)[76] and found very strong agreement across software. Ultimately, Applicants chose netMHC because of the larger number of HLA alleles it supports. Sequences were defined as binding if the predicted affinity ranked in the top 2% of a test library of 400,000 random peptides as suggested in the software guidelines. Generation of immune orthogonal cliques was carried out using the Bron-Kerbosch algorithm. Briefly, a graph was constructed with each ortholog as a vertex, where the edges are defined by the number of shared immunogenic peptides between the connecting vertices. Sets of proteins for which every pair in the set is immune orthogonal constitutes a clique. Phylogenetic distance between protein sequences was measured using the BLOSUM 62 matrix excluding indels. All software, input and output files are available at GitHub.

Experimental Methods

AAV Production

AAV2/8, AAV2/2, AAV2/DJ virus particles were produced using HEK293T cells via the triple transfection method and purified via an iodixanol gradient (Grieger et al., 2006). Confluency at transfection was between 80% and 90%. Media was replaced with pre-warmed media 2 hours before transfection. Each virus was produced in 5×15 cm plates, where each plate was transfected with 7.5 μg of pXR-capsid (pXR-8, pXR-2, pXR-DJ), 7.5 of μg recombinant transfer vector, and 22.5 μg of pAdS helper vector using PEI (1 ug/uL linear PEI in 1×DPBS pH 4.5, using HCl) at a PEI:DNA mass ratio of 4:1. The mixture was incubated for 10 minutes at RT and then applied dropwise onto the media. The virus was harvested after 72 hours and purified using an iodixanol density gradient ultracentrifugation method. The virus was then dialyzed with 1×PBS (pH 7.2) supplemented with 50 mM NaCl and 0.0001% of Pluronic F68 (Thermo Fisher) using 100 kDA filters (Millipore), to a final volume of ~1 mL and quantified by qPCR using primers specific to the ITR region, against a standard (ATCC VR-1616).

AAV-ITR-F: 5'-CGGCCTCAGTGAGCGA-3' (SEQ ID NO:136) and

AA V-ITR-R: 5'-GGAACCCCTAGTGATGGAGTT-3' (SEQ ID NO: 137).

Animal Studies

All animal procedures were performed in accordance with protocols approved by the Institutional Animal Care and Use Committee (IACUC) of the University of California, San Diego. All mice were acquired from Jackson labs. AAV injections were done in adult C57BL/6J mice (10 weeks) through retro-orbital injections using $1\times10^{12}$ vg/mouse.

ELISA

PCSK9:

Levels of serum PCSK9 were measured using the Mouse Proprotein Convertase 9/PCSK9 Quantikine ELISA kit (R&D Systems) according to manufacturer's guidelines. Briefly, serum samples were diluted 1:200 in Calibrator diluent and allowed to bind for 2 h onto microplate wells that were precoated with the capture antibody. Samples were then sequentially incubated with PCSK9 conjugate followed by the PCSK9 substrate solution with extensive intermittent washes between each step. The amount of PCSK9 in serum was estimated colorimetrically using a standard microplate reader (BioRad iMark).

Cas9 and AAV:

Recombinant SpCas9 protein (PNA Bio, cat. no. CP01), or SaCas9 protein (ABM good, cat no. K144), was diluted in 1× coating buffer (Bethyl), and 0.5 µg was used to coat each well of 96-well Nunc MaxiSorp Plates (ab210903) overnight at 4° C. For AAV experiments, $10^9$ vg of AAV-2, -5,-8 or -DJ in 1× coating buffer was used to coat each well of 96-well Nuc MaxiSorp Plates. Plates were washed three times for 5 min with 350 µl of 1× Wash Buffer (Bethyl) and blocked with 300 µl of 1×BSA Blocking Solution (Bethyl) for 2 h at RT. The wash procedure was repeated. Serum samples were added at 1:40 dilution, and plates were incubated for 5 h at 4° C. with shaking. Wells were washed three times for 5 min, and 100 µl of HRP-labeled goat anti-mouse IgG1 (Bethyl; diluted 1:100,000 in 1% BSA Blocking Solution) was added to each well. After incubating for 1 hr at RT, wells were washed four times for 5 min, and 100 µl of TMB Substrate (Behtyl) was added to each well. Optical density (OD) at 450 nm was measured using a plate reader (BioRad iMark).

Example 7—Extremophile Cas9

Applicants explored the strategy of selecting additional orthologs from extremophile species which would not be expected to come into contact with humans under normal circumstances and/or orthologs from commensal species which are highly abundant in the normal microbiome, perhaps especially at early stages of development, to which the immune system has developed tolerance.

Figure 11:
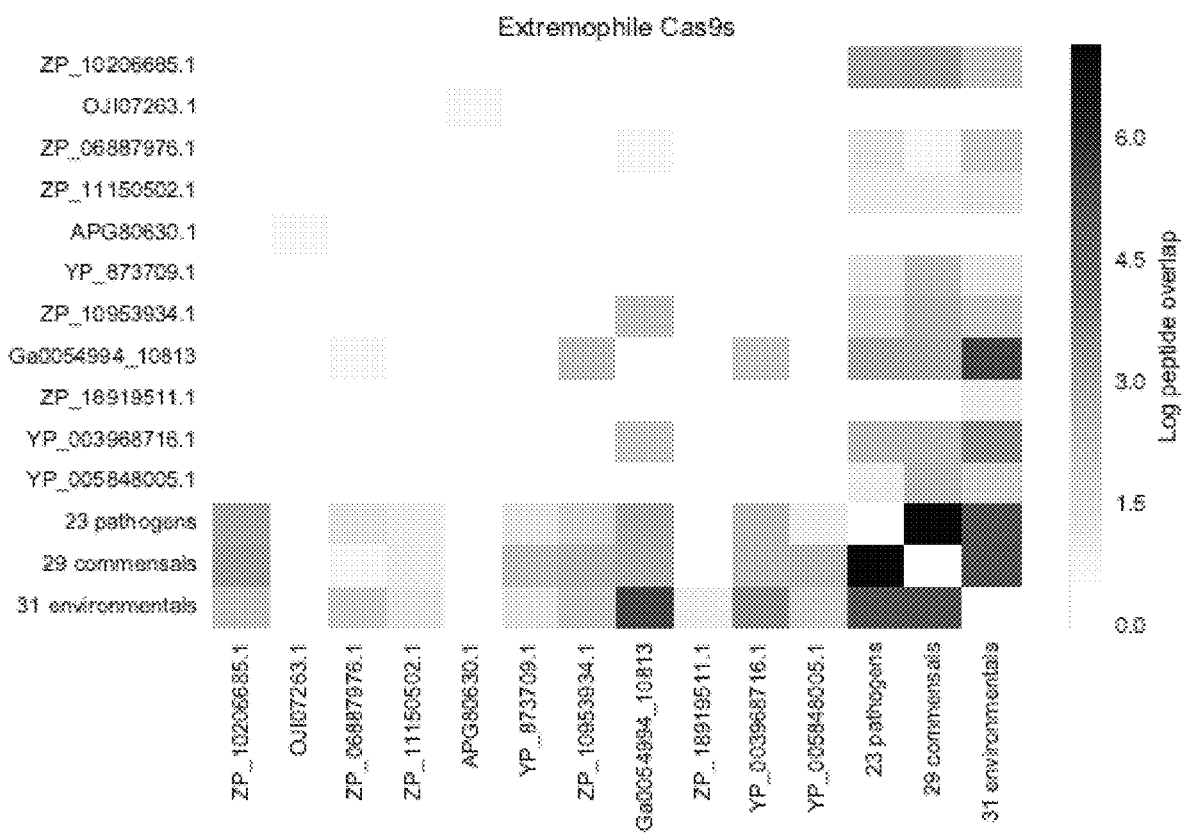
FIG. 11: shows immune orthogonal cliques of extremophile Cas9s and peptide overlap with pools of Cas9s from commensal, pathogenic, and environmental species.

Applicants mined Cas9 sequences from species fitting into these categories of extremophiles, commensals, pathogens, and non-extreme environmental species. Using these sequences, Applicants explored the orthogonality of Cas9s across these categories to identify orthologs which are good candidates to not cross-react with pre-existing immunity (FIG. 11). Although there is broad orthogonality among the extremophile Cas9s, some overlapping peptides are observed when comparing to the larger groups of commensals, pathogens, and environmental species. A few Cas9 orthologs do not show substantial overlap, and these may be useful candidates for characterization, testing, and future use. Furthermore, exploring the diversity of Cas9 orthologs in extreme environments may well provide additional promising targets for immune orthogonality.

EQUIVALENTS

Unless otherwise defined, all technical and scientific terms used herein have the same meaning as commonly understood by one of ordinary skill in the art to which this technology belongs.

The present technology illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the present technology claimed.

Thus, it should be understood that the materials, methods, and examples provided here are representative of preferred aspects, are exemplary, and are not intended as limitations on the scope of the present technology.

The present technology has been described broadly and generically herein. Each of the narrower species and subgeneric groupings falling within the generic disclosure also form part of the present technology. This includes the generic description of the present technology with a proviso or negative limitation removing any subject matter from the genus, regardless of whether or not the excised material is specifically recited herein.

In addition, where features or aspects of the present technology are described in terms of Markush groups, those skilled in the art will recognize that the present technology is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control. Other aspects are set forth within the following claims.

REFERENCES

1. Chew W, et al. (2016) A multifunctional AAV-CRISPR-Cas9 and its host response. Nature Methods, 13(10):868-874.
2. Wang D, Mou H, Li S, Li Y, Hough S, Tran K, et al. Adenovirus Mediated Somatic Genome Editing of Pten by CRISPR/Cas9 in Mouse Liver in Spite of Cas9-Specific Immune Responses. Hum Gene Ther. 2015; 26
3. Riechmann L, et al. (1988) Reshaping human antibodies for therapy. Nature 332:323-327.
4. Lundegaard C, et al. (2010) "Major Histocompatibility Complex Class I Binding Predictions as a Tool in Epitope Discovery." Immunology 130.3 (2010): 309-318. PMC. Web. 7 Nov. 2016.
5. Massimo A, et al. (2016) Gapped sequence alignment using artificial neural networks: application to the MHC class I system. Bioinformatics, 32(4):5117.

6. Fonfara I, et al. (2014) Phylogeny of Cas9 Determines Functional Exchangeability of Dual-RNA and Cas9 among Orthologous Type II CRISPR-Cas Systems. Nucleic Acids Research 42.4: 2577-2590.
7. Choi Y and Chan A P (2015) PROVEAN web server: a tool to predict the functional effect of amino acid substitutions and indels. Bioinformatics 31(16): 27452747.
8. Massimo Andreatta and Morten Nielsen. Gapped sequence alignment using artificial neural networks: application to the MHC class I system. Bioinformatics, February 15; 32(4):5117 2016.
9. Tong, S Y C et al. (2015) *Staphylococcus aureus* Infections: Epidemiology, Pathophysiology, Clinical Manifestations, and Management. Clinical Microbiology Reviews. 28: 603661.
10. Mingozzi, F. & High, K. A. Immune responses to AAV vectors: overcoming barriers to successful gene therapy. *Blood* 122, 23-36 (2013).
11. Mays, L. E. & Wilson, J. M. The Complex and Evolving Story of T cell Activation to AAV Vector-encoded Transgene Products. *Mol. Ther.* 19, 16-27 (2011).
12. Basner-Tschakarjan, E., Bijjiga, E. & Martino, A. T. Pre-clinical assessment of immune responses to adeno-associated virus (AAV) vectors. *Front. Immunol.* 5, (2014).
13. Ertl, H. C. J. & High, K. A. Impact of AAV Capsid-Specific T-Cell Responses on Design and Outcome of Clinical Gene Transfer Trials with Recombinant Adeno-Associated Viral Vectors: An Evolving Controversy. *Hum. Gene Ther.* 28, 328-337 (2017).
14. Kotterman, M. A., Chalberg, T. W. & Schaffer, D. V. Viral Vectors for Gene Therapy: Translational and Clinical Outlook. *Annu. Rev. Biomed. Eng.* 17, 63-89 (2015).
15. Mingozzi, F. & High, K. A. Therapeutic in vivo gene transfer for genetic disease using AAV: progress and challenges. *Nat. Rev. Genet.* 12, 341-355 (2011).
16. Manno, C. S. et al. Successful transduction of liver in hemophilia by AAV-Factor IX and limitations imposed by the host immune response. *Nat. Med.* 12, 342-347 (2006).
17. Sathish, J. G. et al. Challenges and approaches for the development of safer immunomodulatory biologics. *Nat Rev Drug Discov* 12, 306-324 (2013).
18. Harding, F. A., Stickler, M. M., Razo, J. & DuBridge, R. B. The immunogenicity of humanized and fully human antibodies: Residual immunogenicity resides in the CDR regions. *MAbs* 2, 256-265 (2010).
19. De Groot, a S., Knopp, P. M. & Martin, W. De-immunization of therapeutic proteins by T-cell epitope modification. *Dev. Biol. (Basel).* 122, 171-194 (2005).
20. Tangri, S. et al. Rationally Engineered Therapeutic Proteins with Reduced Immunogenicity. *J. Immunol.* 174, 3187 LP-3196 (2005).
21. Salvat, R. S., Choi, Y., Bishop, A., Bailey-Kellogg, C. & Griswold, K. E. Protein deimmunization via structure-based design enables efficient epitope deletion at high mutational loads. *Biotechnol. Bioeng.* 112, 1306-1318 (2015).
22. Armstrong, J. K. et al. Antibody against poly(ethylene glycol) adversely affects PEG-asparaginase therapy in acute lymphoblastic leukemia patients. *Cancer* 110, 103-111 (2007).
23. Ganson, N. J., Kelly, S. J., Scarlett, E., Sundy, J. S. & Hershfield, M. S. Control of hyperuricemia in subjects with refractory gout, and induction of antibody against poly(ethylene glycol) (PEG), in a phase I trial of subcutaneous PEGylated urate oxidase. *Arthritis Res. Ther.* 8, R12-R12 (2006).
24. Veronese, F. M. & Mero, A. The impact of PEGylation on biological therapies. *BioDrugs* 22, 315-329 (2008).
25. Jevsevar, S., Kunstelj, M. & Porekar, V. G. PEGylation of therapeutic proteins. *Biotechnol. J.* 5, 113-128 (2010).
26. Jacobs, F., Gordts, S. C., Muthuramu, I. & De Geest, B. The liver as a target organ for gene therapy: state of the art, challenges, and future perspectives. *Pharmaceuticals (Basel).* 5, 1372-92 (2012).
27. Kok, C. Y. et al. Adeno-associated Virus-mediated Rescue of Neonatal Lethality in Argininosuccinate Synthetase-deficient Mice. *Mol. Ther.* 21, 1823-1831 (2013).
28. Courtenay-Luck, N. S., Epenetos, A. A. & Moore, R. Development of primary and secondary immune responses to mouse monoclonal antibodies used in the diagnosis and therapy of malignant neoplasms. *Cancer Res.* 46, 6489-6493 (1986).
29. Jinek, M. et al. A Programmable Dual-RNA—Guided DNA Endonuclease in Adaptice Bacterial Immunity. *Science* 337, 816-822 (2012).
30. Mali, P. et al. RNA-guided human genome engineering via Cas9. *Science* 339, 823-6 (2013).
31. Gasiunas, G., Barrangou, R., Horvath, P. & Siksnys, V. Cas9-crRNA ribonucleoprotein complex mediates specific DNA cleavage for adaptive immunity in bacteria. *Proc. Natl. Acad. Sci.* 109, E2579-E2586 (2012).
32. Cong, L. et al. Multiplex genome engineering using CRISPR/Cas systems. *Science* 339, 819-23 (2013).
33. Ran, F. A. et al. In vivo genome editing using *Staphylococcus aureus* Cas9. *Nature* 520, 186-190 (2015).
34. Jinek, M. et al. RNA-programmed genome editing in human cells. *Elife* 2013, (2013).
35. *Mali*, P., Esvelt, K. M. & Church, G. M. Cas9 as a versatile tool for engineering biology. *Nat. Methods* 10, 957-963 (2013).
36. Hsu, P. D., Lander, E. S. & Zhang, F. Development and applications of CRISPR-Cas9 for genome engineering. *Cell* 157, 1262-1278 (2014).
37. Makarova, K. S. et al. An updated evolutionary classification of CRISPR-Cas systems. *Nat. Rev. Microbiol.* 13, 722-736 (2015).
38. Chylinski, K., Makarova, K. S., Charpentier, E. & Koonin, E. V. Classification and evolution of type II CRISPR-Cas systems. *Nucleic Acids Research* 42, 6091-6105 (2014).
39. Shmakov, S. et al. Diversity and evolution of class 2 CRISPR-Cas systems. *Nat. Rev. Microbiol.* 15, 169-182 (2017).
40. Wagner, J. a et al. Safety and biological efficacy of an adeno-associated virus vector-cystic fibrosis transmembrane regulator (AAV-CFTR) in the cystic fibrosis maxillary sinus. *Laryngoscope* 109, 266-74 (1999).
41. Song, S. et al. Sustained secretion of human alpha-1-antitrypsin from murine muscle transduced with adeno-associated virus vectors. *Proc. Natl. Acad. Sci. U.S.A.* 95, 14384-8 (1998).
42. Chirmule, N. et al. Humoral Immunity to Adeno-Associated Virus Type 2 Vectors following Administration to Murine and Nonhuman Primate Muscle. *J. Virol.* 74, 2420-2425 (2000).
43. Fields, P. a et al. Risk and prevention of anti-factor IX formation in AAV-mediated gene transfer in the context of a large deletion of F9. *Mol. Ther.* 4, 201-210 (2001).
44. Herzog, R. W. et al. Influence of vector dose on factor IX-specific T and B cell responses in muscle-directed gene therapy. *Hum. Gene Ther.* 13, 1281-91 (2002).

45. Lozier, J. N., Tayebi, N. & Zhang, P. Mapping of genes that control the antibody response to human factor IX in mice. Blood 105, 1029-1035 (2005).
46. Zhang, H. G. et al. Genetic analysis of the antibody response to AAV2 and factor IX. Mol. Ther. 11, 866-874 (2005).
47. Benveniste, O. et al. Prevalence of Serum IgG and Neutralizing Factors Against Adeno-Associated Virus (AAV) Types 1, 2, 5, 6, 8, and 9 in the Healthy Population: Implications for Gene Therapy Using AAV Vectors. Hum. Gene Ther. 21, 704-712 (2010).
48. Gao, G.-P. et al. Novel adeno-associated viruses from rhesus monkeys as vectors for human gene therapy. Proc. Natl. Acad. Sci. 99, 11854-11859 (2002).
49. Jooss, K., Yang, Y., Fisher, K. J. & Wilson, J. M. Transduction of Dendritic Cells by DNA Viral Vectors Directs the Immune Response to Transgene Products in Muscle Fibers. J. Virol. 72, 4212-4223 (1998).
50. Gemoux, G. et al. Early Interaction of Adeno-Associated Virus Serotype 8 Vector with the Host Immune System Following Intramuscular Delivery Results in Weak but Detectable Lymphocyte and Dendritic Cell Transduction. Hum. Gene Ther. 26, 1-13 (2015).
51. Zhu, J., Huang, X. & Yang, Y. The TLR9-MyD88 pathway is critical for adaptive immune responses to adeno-associated virus gene therapy vectors in mice. J. Clin. Invest. 119, 2388-2398 (2009).
52. Gemoux, G., Wilson, J. M. & Mueller, C. Regulatory and Exhausted T Cell Responses to AAV Capsid. Hum. Gene Ther. 28, 338-349 (2017).
53. Kurosaki, T., Kometani, K. & Ise, W. Memory B cells. Nat. Rev. Immunol. 15, 149-159 (2015).
54. Zabel, F. et al. Distinct T helper cell dependence of memory B-cell proliferation versus plasma cell differentiation. Immunology 150, 329-342 (2017).
55. Ding, Q. et al. Permanent Alteration of PCSK9 With In Vivo CRISPR-Cas9 Genome Editing. Circ. Res. 115, 488-492 (2014).
56. Zinn, E. et al. In Silico Reconstruction of the Viral Evolutionary Lineage Yields a Potent Gene Therapy Vector. Cell Rep. 12, 1056-1068 (2017).
57. Calcedo, R. & Wilson, J. M. AAV Natural Infection Induces Broad Cross-Neutralizing Antibody Responses to Multiple AAV Serotypes in Chimpanzees. Hum. Gene Ther. Clin. Dev. 27, 79-82 (2016).
58. Harbison, C. E. et al. Examining the cross-reactivity and neutralization mechanisms of a panel of mabs against adeno-associated virus serotypes 1 and 5. J. Gen. Virol. 93, (2012).
59. Majowicz, A. et al. Successful Repeated Hepatic Gene Delivery in Mice and Non-human Primates Achieved by Sequential Administration of AAV5$^{ch}$ and AAV1. Mol. Ther. 25, 1831-1842 (2017).
60. McIntosh, J. H. et al. Successful attenuation of humoral immunity to viral capsid and transgenic protein following AAV-mediated gene transfer with a non-depleting CD4 antibody and cyclosporine. Gene Ther 19, 78-85 (2012).
61. Mingozzi, F. et al. Prevalence and pharmacological modulation of humoral immunity to AAV vectors in gene transfer to synovial tissue. Gene Ther 20, 417-424 (2013).
62. Mingozzi, F. et al. Pharmacological Modulation of Humoral Immunity in a Nonhuman Primate Model of AAV Gene Transfer for Hemophilia B. Mol. Ther. 20, 1410-1416 (2017).
63. Unzu, C. et al. Transient and intensive pharmacological immunosuppression fails to improve AAV-based liver gene transfer in non-human primates. J. Transl. Med. 10, 122 (2012).
64. Riechmann, L., Clark, M., Waldmann, H. & Winter, G. Reshaping human antibodies for therapy. Nature 332, 323-7 (1988).
65. Ruppert, J. et al. Prominent role of secondary anchor residues in peptide binding to HLA-A2.1 molecules. Cell 74, 929-937 (2017).
66. Baker, M. P., Reynolds, H. M., Lumicisi, B. & Bryson, C. J. Immunogenicity of protein therapeutics: The key causes, consequences and challenges. Self Nonself 1, 314-322 (2010).
67. EL-Manzalawy, Y., Dobbs, D. & Honavar, V. Predicting linear B-cell epitopes using string kernels. J. Mol. Recognit. 21, 243-255 (2008).
68. Larsen, J. E. P., Lund, O. & Nielsen, M. Improved method for predicting linear B-cell epitopes. Immunome Res. 2, 2 (2006).
69. Sollner, J. et al. Analysis and prediction of protective continuous B-cell epitopes on pathogen proteins. Immunome Res. 4, 1 (2008).
70. Dalkas, G. A. & Rooman, M. SEPIa, a knowledge-driven algorithm for predicting conformational B-cell epitopes from the amino acid sequence. BMC Bioinformatics 18, 95 (2017).
71. Sun, P. et al. Bioinformatics resources and tools for conformational B-cell epitope prediction. Computational and Mathematical Methods in Medicine 2013, (2013).
72. Liepe, J. et al. A large fraction of HLA class I ligands are proteasome-generated spliced peptides. Science (80-). 354, (2016).
73. Fonfara, I. et al. Phylogeny of Cas9 determines functional exchangeability of dual-RNA and Cas9 among orthologous type II CRISPR-Cas systems. Nucleic Acids Res. 42, 2577-2590 (2014).
74. Andreatta, M. & Nielsen, M. Gapped sequence alignment using artificial neural networks: application to the MHC class I system. Bioinformatics 32, 511-517 (2015).
75. Andreatta, M. et al. Accurate pan-specific prediction of peptide-MHC class II binding affinity with improved binding core identification. Immunogenetics 67, 641-650 (2015).
76. Vita, R. et al. The immune epitope database (IEDB) 3.0. Nucleic Acids Res. 43, D405-12 (2015).
77. Güiell, M., Yang, L. & Church, G. M. Genome editing assessment using CRISPR Genome Analyzer (CRISPR-GA). Bioinformatics 30, 2968-2970 (2014).

TABLE 1

| No. | Pos | Peptide | ID | Allele | Affinity Level | n-mer | Score | Actual position | Surf | Mutation | Pos | Peptide | nM | Rank | ID | Allele | Affinity Level | n-mer |
|---|---|---|---|---|---|---|---|---|---|---|---|---|---|---|---|---|---|---|
| 1 | 197 | IVDEVA-Y | StreptococcusP | HLA-A01:01 | High | 8 | 0 | 121-128 | Yes | Y128N | 142 | 0 | IVDEVA-N | 38015 | 80 | Streptococcus_I | HLA-A0101 | No | 8 |
| 2 | 1196 | LFGNLIAL | StreptococcusP | HLA-A02:01 | High | 9 | 0 | 236-244 | No | L236H | 28 | 0 | HFGNLIAL | 6395.2 | 11 | Streptococcus_- | HLA-A0201 | No | 9 |
| 3 | 2523 | ILEDIVLTL | StreptococcusP | HLA-A02:01 | High | 9 | 0 | 614-612 | No | L615D/E616V | 23 | 0 | IDEDIVLTL | 14725.8 | 21 | Streptococcus_I | HLA-A0201 | No | 9 |
| 4 | 2454 | GTYHDL-L-K | StreptococcusP | HLA-A03:01 | High | 10 | 0 | 591-599 | No | K599D | 183 | 0 | GTYHDL-L-D | 12613.3 | 11 | Streptococcus_G | HLA-A0301 | No | 10 |
| 5 | 2189 | ETITPWNF | StreptococcusP | HLA-A26:01 | High | 8 | 0 | 470-478 | Yes | T471C | 24 | 0 | ECITPWNF | 34785.2 | 60 | Streptococcus_E | HLA-A2601 | No | 8 |
| 6 | 196 | NIVDEVA-Y | StreptococcusP | HLA-A26:01 | High | 9 | 0 | 120-128 | Yes | Y128N | 162 | 0 | NIVDEVA-N | 16237.6 | 6.5 | Streptococcus_N | HLA-A2601 | No | 9 |
| 7 | 3215 | EVVKKMKNY | StreptococcusP | HLA-A26:01 | High | 9 | 0 | 873-882 | Yes | Y882N | 162 | 0 | EVVKKMKNN | 11513.6 | 4 | Streptococcus_E | HLA-A2601 | No | 9 |
| 8 | 2141 | IPYYVGPL | StreptococcusP | HLA-B07:02 | High | 8 | 0.063905 | 447-455 | No | P448C | 24 | 0 | ICYYVGPL | 34157.5 | 48 | Streptococcus_I | HLA-B0702 | No | 8 |
| 9 | 40 | PSKKFKVL | StreptococcusP | HLA-B07:02 | High | 9 | 0 | 27-35 | Yes | P27D | 23 | 0 | DSKKFKVL | 26712.9 | 25 | Streptococcus_- | HLA-B0702 | No | 9 |
| 10 | 40 | PSKKFKVL | StreptococcusP | HLA-B08:01 | High | 9 | 0 | 27-35 | Yes | P27D | 23 | 0 | DSKKFKVL | 26712.9 | 25 | Streptococcus_- | HLA-B0801 | No | 9 |
| 11 | 2613 | LKRRRYTG | StreptococcusP | HLA-B08:01 | High | 9 | 0 | 650-658 | No | R653P | 94 | 0 | LKRPRYTG | 3079.4 | 3.5 | Streptococcus_- | HLA-B0801 | Low | 9 |
| 12 | 2617 | RRYTGWG- | StreptococcusP | HLA-B27:05 | High | 8 | 0 | 653-660 | No | R653P | 14 | 0 | PRYTGWG | 7382.2 | 7.5 | Streptococcus_P | HLA-B2705 | No | 8 |
| 13 | 2165 | SRFAWMTRK | StreptococcusP | HLA-B27:05 | High | 9 | 0 | 459-468 | Yes | R460D | 23 | 0 | SDFAWMTRK | 13809.5 | 12 | Streptococcus_S | HLA-B2705 | No | 9 |

TABLE 1-continued

| | POS | Peptide | Allele | Affinity Level | | | ID | | Mutation | Rank | nM | | n-mer | | | | | |
|---|---|---|---|---|---|---|---|---|---|---|---|---|---|---|---|---|---|---|
| 14 | 1688 | HHQDLTLL | HLA-B39:01 | High | 8 | 0 | 327-335 | Yes | H328D | 23 | 0 | HDQDLTLL | 14138.9 | 6 | Streptococcus_H | HLA-B3901 | No | 8 |
| 15 | 1689 | HQDLTLLKAL | HLA-B39:01 | High | 10 | 0 | 328-338 | Yes | H328D | 23 | 0 | HDQDLTLLKAL | 22112.3 | 12 | Streptococcus_H | HLA-B3901 | No | 11 |
| 16 | 1688 | HHQDLTLLKAL | HLA-B39:01 | High | 11 | 0 | 327-338 | Yes | H328D | 3 | 0 | DQDLTLLKAL | 17106.3 | 8 | Streptococcus_D | HLA-B3901 | No | 10 |
| 17 | 2524 | LEDIVLTL | HLA-B40:01 | High | 8 | 0 | 615-623 | No | L615D/E616V | 39 | 0 | LVDIVLTL | 29463.8 | 34 | Streptococcus_L | HLA-B4001 | No | 8 |
| 18 | 2556 | REMIEERL | HLA-B40:01 | High | 8 | 0.020848 | 628-638 | No | E629P | 34 | 0 | RPMIEERL | 35930.5 | 65 | Streptococcus_R | HLA-B4001 | No | 8 |
| 19 | 2445 | EDRFNASL | HLA-B40:01 | High | 9 | 0 | 583-591 | No | E583G | 27 | 0 | GDRFNASL | 20438.3 | 13 | Streptococcus_- | HLA-B4001 | No | 9 |
| 20 | 3045 | KELGS-QIL | HLA-B40:01 | High | 9 | 0 | 788-796 | Yes | E789G | 27 | 0 | KGLGS-QIL | 17094.3 | 10 | Streptococcus_K | HLA-B4001 | No | 9 |
| 21 | 2524 | LEDIVLTLTL | HLA-B40:01 | High | 10 | 0 | 615-625 | No | L615D/E616V | 39 | 0 | LVDIVLTLTL | 19888.8 | 13 | Streptococcus_L | HLA-B4001 | No | 10 |
| 22 | 2323 | KAIV-DLLF | HLA-B58:01 | High | 9 | 0 | 545-553 | Yes | F553R | 161 | 0 | KAIVDLLR | 4677.9 | 4.5 | Streptococcus_K | HLA-B5801 | Low | 9 |

Peptides Nos. 1-22 = SEQ ID NOS: 295-315; mutant peptides = SEQ ID NOS: 316-336
Contd. Of rows 4, 18, 22; same rows (SEQ ID NOS: 337-339):

| | POS | Peptide | Allele | Affinity Level | nM | Rank | ID | n-mer |
|---|---|---|---|---|---|---|---|---|
| | 59 | ILVDIVLTL | HLA:A0201 | High | 13.4 | 0.175 | Streptococcus_I | 9 |
| | 3 | DEDIVLTL | HLA:B4001 | No | 9479 | 5 | Streptococcus_D | 8 |
| | 3 | DEDIVLTLTL | HLA:B4001 | Low | 2017 | 1.7 | Streptococcus_D | 10 |

TABLE 2

| sgID | gene | transcript | protospacer sequence |
|---|---|---|---|
| [gene_strandtargeted_PAMcoordinate.sgRNA length-transcript] | [gene targeted by the sgRNA, or "negative_control"] | [TSS targeted by the sgRNA] | [protospacer sequence; 5'G is included whether or not it is present in the genome |
| SCN3A_+_166060543.23-P1P2 | SCN3A | P1P2 | GATCTCAGAACAGGAAGCGG (SEQ ID NO: 138) |
| SCN3A_+_166060199.23-P1P2 | SCN3A | P1P2 | GTGTAAATTACAGGAACCAA (SEQ ID NO: 139) |
| SCN3A_+_166060301.23-P1P2 | SCN3A | P1P2 | GACCTGGTAGCTAGGTTCTA (SEQ ID NO: 140) |
| SCN3A_+_166060552.23-P1P2 | SCN3A | P1P2 | GATAGAGTGAATCTCAGAAC (SEQ ID NO: 141) |
| SCN3A_+_166060129.23-P1P2 | SCN3A | P1P2 | GAATAGAGCCTGTCTGGAAA (SEQ ID NO: 142) |
| SCN3A_+_166060346.23-P1P2 | SCN3A | P1P2 | GTGTTATGCTGTAATTCATA (SEQ ID NO: 143) |
| SCN3A_+_166060119.23-P1P2 | SCN3A | P1P2 | GGTCTGGAAATGGTGATTTA (SEQ ID NO: 144) |
| SCN3A_+_166060135.23-P1P2 | SCN3A | P1P2 | GAAAGAAAATAGAGCCTGTC (SEQ ID NO: 145) |
| SCN3A_+_166060371.23-P1P2 | SCN3A | P1P2 | GCCTAACCATCTTGGATGCT (SEQ ID NO: 146) |
| SCN3A_+_166060281.23-P1P2 | SCN3A | P1P2 | GACCATAGAACCTAGCTACC (SEQ ID NO: 147) |
| SCN9A_+_167232419.23-P1P2 | SCN9A | P1P2 | GGCGGTCGCCAGCGCTCCAG (SEQ ID NO: 148) |
| SCN9A_+_167232052.23-P1P2 | SCN9A | P1P2 | GCCACCTGGAAAGAAGAGAG (SEQ ID NO: 149) |
| SCN9A_+_167232416.23-P1P2 | SCN9A | P1P2 | GGTCGCCAGCGCTCCAGCGG (SEQ ID NO: 150) |
| SCN9A_+_167232010.23-P1P2 | SCN9A | P1P2 | GCCAGCAATGGGAGGAAGAA (SEQ ID NO: 151) |
| SCN9A_-_167232085.23-P1P2 | SCN9A | P1P2 | GTTCCAGGTGGCGTAATACA (SEQ ID NO: 152) |
| SCN9A_+_167232476.23-P1P2 | SCN9A | P1P2 | GGCGGGGCTGCTACCTCCAC (SEQ ID NO: 153) |
| SCN9A_+_167232437.23-P1P2 | SCN9A | P1P2 | GGGCGCAGTCTGCTTGCAGG (SEQ ID NO: 154) |
| SCN9A_+_167232409.23-P1P2 | SCN9A | P1P2 | GGCGCTCCAGCGGCGGCTGT (SEQ ID NO: 155) |
| SCN9A_+_167232021.23-P1P2 | SCN9A | P1P2 | GACCGGGTGGTTCCAGCAAT (SEQ ID NO: 156) |
| SCN9A_+_167232018.23-P1P2 | SCN9A | P1P2 | GGGGTGGTTCCAGCAATGGG (SEQ ID NO: 157) |
| SCN10A_-_38835462.23-ENST00000449082.2 | SCN10A | ENST00000449082.2 | GTGACTCCGGAGTAAAGCGA (SEQ ID NO: 158) |
| SCN10A_-_38835311.23-ENST00000449082.2 | SCN10A | ENST00000449082.2 | GGGAGCTCACCATAGAACTT (SEQ ID NO: 159) |
| SCN10A_-_38835269.23-ENST00000449082.2 | SCN10A | ENST00000449082.2 | GACGGATCTAGATCCTCCAG (SEQ ID NO: 160) |
| SCN10A_+_38835213.23-ENST00000449082.2 | SCN10A | ENST00000449082.2 | GCCGGGTAAGAGCTACTAGT (SEQ ID NO: 161) |

TABLE 2-continued

| | | | |
|---|---|---|---|
| SCN10A_-_38835251.23-ENST00000449082.2 | SCN10A | ENST00000449082.2 | GCCCGGTGTGTGCTGTAGAA(SEQ ID NO: 162) |
| SCN10A_+_38835434.23-ENST00000449082.2 | SCN10A | ENST00000449082.2 | GTTTACTCCGGAGTCACTGG(SEQ ID NO: 163) |
| SCN10A_-_38835449.23-ENST00000449082.2 | SCN10A | ENST00000449082.2 | GCTATCTCCACCAGTGACTC(SEQ ID NO: 164) |
| SCN10A_-_38835156.23-ENST00000449082.2 | SCN10A | ENST00000449082.2 | GACATCACCCAGGGCCAAGG(SEQ ID NO: 165) |
| SCN10A_-_38835491.23-ENST00000449082.2 | SCN10A | ENST0000044902.28 | GTAGTTTCGAGGGATCCAAT(SEQ ID NO: 166) |
| SCN10A_+_38835272.23-ENST00000449082.2 | SCN10A | ENST00000449082.2 | GCTCCCAGCAGAACTGATCG(SEQ ID NO: 167) |
| SCN11A_-_38991624.23-ENST00000302328.3,ENST00000450244.1 | SCN11A | ENST00000302328.3,ENST00000450244.1 | GATGGGTCCAAGTCTTCCAG(SEQ ID NO: 168) |
| SCN11A_+_38992032.23-ENST00000302328.3,ENST00000450244.1 | SCN11A | ENST00000302328.3,ENST00000450244.1 | GGTTCCTGCTATACCCACAG(SEQ ID NO: 169) |
| SCN11A_-_38991801.23-ENST00000302328.3,ENST00000450244.1 | SCN11A | ENST00000302328.3,ENST00000450244.1 | GCCAGAGAGTCGGAAGTGAA(SEQ ID NO: 170) |
| SCN11A_+_38992029.23-ENST00000302328.3,ENST00000450244.1 | SCN11A | ENST00000302328.3,ENST00000450244.1 | GCCTGCTATACCCACAGTGG(SEQ ID NO: 171) |
| SCN11A_+_38991609.23-ENST00000302328.3,ENST00000450244.1 | SCN11A | ENST00000302328.3,ENST00000450244.1 | GGGAAAGCCTCTGGAAGACT(SEQ ID NO: 172) |
| SCN11A_-_38992040.23-ENST00000302328.3,ENST00000450244.1 | SCN11A | ENST00000302328.3,ENST00000450244.1 | GGAAGAGATGACCACCACTG(SEQ ID NO: 173) |
| SCN11A_-_38991666.23-ENST00000302328.3,ENST00000450244.1 | SCN11A | ENST00000302328.3,ENST00000450244.1 | GGAATGTCGCCATAGAGCTT(SEQ ID NO: 174) |
| SCN11A_+_38991618.23-ENST00000302328.3,ENST00000450244.1 | SCN11A | ENST00000302328.3,ENST00000450244.1 | GGAGCTCATAGGAAAGCCTC(SEQ ID NO: 175) |
| SCN11A_+_38991924.23-ENST00000302328.3,ENST00000450244.1 | SCN11A | ENST00000302328.3,ENST00000450244.1 | GCTTTAAGACTGGAATCCTA(SEQ ID NO: 176) |
| SCN11A_+_38991653.23-ENST00000302328.3,ENST00000450244.1 | SCN11A | ENST00000302328.3,ENST00000450244.1 | GGGAAGTTGCCCAAGCTCTA(SEQ ID NO: 177) |
| SHANK3_+_51135959.23-P1P2 | SHANK3 | P1P2 | GGAATTCGAATACAGCTCCT(SEQ ID NO: 178) |
| SHANK3_+_51136404.23-P1P2 | SHANK3 | P1P2 | GCTTCAGGCAGAGACCCCCG(SEQ ID NO: 179) |
| SHANK3_+_51136356.23-P1P2 | SHANK3 | P1P2 | GGAGCCTCCGTGGTGACACA(SEQ ID NO: 180) |
| SHANK3_+_51136302.23-P1P2 | SHANK3 | P1P2 | GCACGGCAGGAACCTTCCCC(SEQ ID NO: 181) |
| SHANK3_+_51136319.23-P1P2 | SHANK3 | P1P2 | GAGCACCGGAGGGACCCGCA(SEQ ID NO: 182) |
| SHANK3_+_51136333.23-P1P2 | SHANK3 | P1P2 | GGCCCGGAACGACAGAGCAC(SEQ ID NO: 183) |
| SHANK3_+_51136329.23-P1P2 | SHANK3 | P1P2 | GGGAACGACAGAGCACCGGA(SEQ ID NO: 184) |

TABLE 2-continued

| | | | |
|---|---|---|---|
| SHANK3_-_51136143.23-P1P2 | SHANK3 | P1P2 | GACcgcggcgaggccgtgaa (SEQ ID NO: 185) |
| SHANK3_-_51136336.23-P1P2 | SHANK3 | P1P2 | GCCTGCCGTGCGGGTCCCTC (SEQ ID NO: 186) |
| SHANK3_+_51135950.23-P1P2 | SHANK3 | P1P2 | GTACAGCTCCTGGGCGCGCC (SEQ ID NO: 187) |
| TRPV1_+_3500355.23-P1P2 | TRPV1 | P1P2 | GAGCGACTCCTGCTAGTGCA (SEQ ID NO: 188) |
| TRPV1_+_3500317.23-P1P2 | TRPV1 | P1P2 | GCGGGCCCGGGACCCCACGG (SEQ ID NO: 189) |
| TRPV1_+_3499964.23-P1P2 | TRPV1 | P1P2 | GCTCCTTGGAAGCACCTGGG (SEQ ID NO: 190) |
| TRPV1_-_3500391.23-P1P2 | TRPV1 | P1P2 | GAGTCGCTGTGGACGCCCTT (SEQ ID NO: 191) |
| TRPV1_-_3500224.23-P1P2 | TRPV1 | P1P2 | GGGACTCACCAGCTAGACGC (SEQ ID NO: 192) |
| TRPV1_-_3500327.23-P1P2 | TRPV1 | P1P2 | GTGGTCTCCCCGCCTCCGTG (SEQ ID NO: 193) |
| TRPV1_-_3500298.23-P1P2 | TRPV1 | P1P2 | GGGGAGAGCTGGGCTCGTGT (SEQ ID NO: 194) |
| TRPV1_+_3500017.23-P1P2 | TRPV1 | P1P2 | Gtgcctcaaaggtggtcgtg (SEQ ID NO: 195) |
| TRPV1_+_3499899.23-P1P2 | TRPV1 | P1P2 | GCTGCATCAGCCGTCCTCGG (SEQ ID NO: 196) |
| TRPV1_-_3500400.23-P1P2 | TRPV1 | P1P2 | GGGACGCCCTTCGGCACTCA (SEQ ID NO: 197) |
| GRIN2B_-_14133341.23-P1P2 | GRIN2B | P1P2 | GGATTCGCGTGTCCCCCGGA (SEQ ID NO: 198) |
| GRIN2B_+_14132929.23-P1P2 | GRIN2B | P1P2 | GGATATGCAAGCGAGAAGAA (SEQ ID NO: 199) |
| GRIN2B_-_14132903.23-P1P2 | GRIN2B | P1P2 | GCTCTAGACGGACAGATTAA (SEQ ID NO: 200) |
| GRIN2B_-_14133316.23-P1P2 | GRIN2B | P1P2 | GGGGGAAAAAGAGGCGGTCA (SEQ ID NO: 201) |
| GRIN2B_+_14132924.23-P1P2 | GRIN2B | P1P2 | GGCAAGCGAGAAGAAGGGAC (SEQ ID NO: 202) |
| GRIN2B_-_14133295.23-P1P2 | GRIN2B | P1P2 | GCCAAAGCGTCCCCTTCCTA (SEQ ID NO: 203) |
| GRIN2B_-_14133298.23-P1P2 | GRIN2B | P1P2 | GAAGCGTCCCCTTCCTAAGG (SEQ ID NO: 204) |
| GRIN2B_+_14132855.23-P1P2 | GRIN2B | P1P2 | GGCTTCTACAAACCAAGGTA (SEQ ID NO: 205) |
| GRIn2B_+_14133247.23-P1P2 | GRIN2B | P1P2 | GACCATGCTCCACCGAGGGA (SEQ ID NO: 206) |
| GRIN2B_+_14133252.23-P1P2 | GRIN2B | P1P2 | GGAATGACCATGCTCCACCG (SEQ ID NO: 207) |
| PRDM12_-_133540047.23-P1P2 | PRDM12 | P1P2 | GgctccgggccgcccATGAT (SEQ ID NO: 208) |
| PRDM12_+_133540034.23-P1P2 | PRDM12 | P1P2 | GGCACGGAGCCCATCATggg (SEQ ID NO: 209) |
| PRDM12_+_133540230.23-P1P2 | PRDM12 | P1P2 | GGACTGCGCCAGCACCTCGG (SEQ ID NO: 210) |
| PRDM12_+_133539846.23-P1P2 | PRDM12 | P1P2 | Gctgggaggaaagcgaacga (SEQ ID NO: 211) |

TABLE 2-continued

| | | | |
|---|---|---|---|
| PRDM12_-_133540263.23-P1P2 | PRDM12 | P1P2 | GTGGCGCAGTCCTTCTCCG G(SEQ ID NO: 212) |
| PRDM12_-_133540260.23-P1P2 | PRDM12 | P1P2 | GTGCTGGCGCAGTCCTTCTC (SEQ ID NO: 213) |
| PRDM12_+_133540257.23-P1P2 | PRDM12 | P1P2 | GCGACGGCTGGACTCACCG C(SEQ ID NO: 214) |
| PRDM12_+_133540233.23-P1P2 | PRDM12 | P1P2 | GAAGGACTGCGCCAGCACC T(SEQ ID NO: 215) |
| PRDM12_-_133540304.23-P1P2 | PRDM12 | P1P2 | GCCGGCGCAATCCCTCCTCC (SEQ ID NO: 216) |
| PRDM12_+_133539961.23-P1P2 | PRDM12 | P1P2 | Ggggcgagaggggagcccaa (SEQ ID NO: 217) |
| HCN2_+_589972.23-P1P2 | HCN2 | P1P2 | Gtcgcgcccgggctctcccc (SEQ ID NO: 218) |
| HCN2_+_590106.23-P1P2 | HCN2 | P1P2 | GCAACGCCTcggcccggggc (SEQ ID NO: 219) |
| HCN2_+_589880.23-P1P2 | HCN2 | P1P2 | GgccgccggccggAGCCCGA (SEQ ID NO: 220) |
| HCN2_+_590306.23-P1P2 | HCN2 | P1P2 | GcggcACGAGAACGACACCT (SEQ ID NO: 221) |
| HCN2_-_590253.23-P1P2 | HCN2 | P1P2 | GCAGCCCGAACGGCGAGTG C(SEQ ID NO: 222) |
| HCN2_+_590235.23-P1P2 | HCN2 | P1P2 | GGCGCCCGCACTCGCCGTT C(SEQ ID NO: 223) |
| HCN2_-_590335.23-P1P2 | HCN2 | P1P2 | GTCGTTCTCGTgccgcgggg (SEQ ID NO: 224) |
| HCN2_+_590407.23-P1P2 | HCN2 | P1P2 | GAGCTGGCCTGGCTgccgcg (SEQ ID NO: 225) |
| HCN2_+_590332.23-P1P2 | HCN2 | P1P2 | GGTGTCGTTCTCGTgccgcg (SEQ ID NO: 226) |
| HCN2_+_590204.23-P1P2 | HCN2 | P1P2 | GGCCGTGCTcgccgcgcccg (SEQ ID NO: 227) |

TABLE 3

| sgID | gene | transcript | protospacer sequence |
|---|---|---|---|
| [gene_strandtargeted_PAMcoordinate.sgRNA length-transcript] | [gene targeted by the sgRNA, or "negative_control"] | TSS targeted by the sgRNA | [protospacer sequence; 5'G is included whether or not it is present in the genome |
| Scn3a_+_65567459.23-P1P2 | Scn3a | P1P2 | GTGAATCTCAGAACAGGAA G(SEQ ID NO: 228) |
| Scn3a_+_65567442.23-P1P2 | Scn3a | P1P2 | GAGCGGAGGCATAAGCAG AA(SEQ ID NO: 229) |
| Scn3a_-_65567234.23-P1P2 | Scn3a | P1P2 | GATCTGGTGGCTAGATTCT A(SEQ ID NO: 230) |
| Scn3a_-_65567301.23-P1P2 | Scn3a | P1P2 | GAGGAATCACAGCTCAACA A(SEQ ID NO: 231) |
| Scn3a_-_65567522.23-P1P2 | Scn3a | P1P2 | GATCAGAAAACGGCCCTGG A(SEQ ID NO: 232) |
| Scn3a_-_65567271.23-P1P2 | Scn3a | P1P2 | GGTTTTGTCAGCTTACCTGA (SEQ ID NO: 233) |

TABLE 3-continued

| | | | |
|---|---|---|---|
| Scn3a_-_65567326.23-P1P2 | Scn3a | P1P2 | GGCATCCAAGATGGTTAGAA(SEQ ID NO: 234) |
| Scn3a_+_65567264.23-P1P2 | Scn3a | P1P2 | GATTCCTAAGGCTCTCCATC(SEQ ID NO: 235) |
| Scn3a_+_65567031.23-P1P2 | Scn3a | P1P2 | GCAATACAGACTAGGAATTA(SEQ ID NO: 236) |
| Scn9a_+_66634758.23-P1P2 | Scn9a | P1P2 | GAGCTCAGGGAGCATCGAGG(SEQ ID NO: 237) |
| 5cn9a_-_66634675.23-P1P2 | Scn9a | P1P2 | GAGAGTCGCAATTGGAGCGC(SEQ ID NO: 238) |
| 5cn9a_-_66634637.23-P1P2 | Scn9a | P1P2 | GCCAGACCAGCCTGCACAGT(SEQ ID NO: 239) |
| 5cn9a_-_66634689.23-P1P2 | Scn9a | P1P2 | GAGCGCAGGCTAGGCCTGCA(SEQ ID NO: 240) |
| 5cn9a_-_66634610.23-P1P2 | Scn9a | P1P2 | GCTAGGAGTCCGGGATACCC(SEQ ID NO: 241) |
| 5cn9a_+_66634478.23-P1P2 | Scn9a | P1P2 | GAATCCGCAGGTGCACTCAC(SEQ ID NO: 242) |
| 5cn9a_-_66634641.23-P1P2 | Scn9a | P1P2 | GACCAGCCTGCACAGTGGGC(SEQ ID NO: 243) |
| 5cn9a_+30_66634731.23-P1P2 | Scn9a | P1P2 | GCGACGCGGTTGGCAGCCGA(SEQ ID NO: 244) |
| Scn10a_+_119719110.23-P1P2 | Scn10a | P1P2 | GGCAGGGTGGAACTCGTGAC(SEQ ID NO: 245) |
| Scn10a_+_119719123.23-P1P2 | Scn10a | P1P2 | GCACCATCCAGCAAGCAGGG(SEQ ID NO: 246) |
| Scn10a_-_119719078.23-P1P2 | Scn10a | P1P2 | GCGTCACTCAAGGATCTACA(SEQ ID NO: 247) |
| Scn10a_+_119719086.23-P1P2 | Scn10a | P1P2 | GATGGGAATGGCACCCACGA(SEQ ID NO: 248) |
| Scn10a_+_119718921.23-P1P2 | Scn10a | P1P2 | GCCTTTAGACGGAGAACAGA(SEQ ID NO: 249) |
| Scn10a_+_119719051.23-P1P2 | Scn10a | P1P2 | GAGATCCTTGAGTGACGGAC(SEQ ID NO: 250) |
| Scn10a_-_119719025.23-P1P2 | Scn10a | P1P2 | GCGGGGCTCCTCCACGAAGG(SEQ ID NO: 251) |
| Scn10a_-_119719095.23-P1P2 | Scn10a | P1P2 | GCAAGGAATCACGCCTTCGT(SEQ ID NO: 252) |
| Scn10a_+_119718881.23-P1P2 | Scn10a | P1P2 | GGCCATGCGCGAATGCTGAG(SEQ ID NO: 253) |
| Scn10a_+_119719014.23-P1P2 | Scn10a | P1P2 | GGCAAGCCCAGCCACCTTCG(SEQ ID NO: 254) |
| Scn11a_+_119825404.23-P1P2 | Scn11a | P1P2 | GAGGTAAGCCATCCAGGCTG(SEQ ID NO: 255) |
| Scn11a_-_119825450.23-P1P2 | Scn11a | P1P2 | GTTCCTGCTAGGGAGGCTCA(SEQ ID NO: 256) |
| Scn11a_-_119825400.23-P1P2 | Scn11a | P1P2 | GCCTGAAACGACAGAGGATG(SEQ ID NO: 257) |
| Scnna_+_119825277.23-P1P2 | Scn11a | P1P2 | GTCAGAGGTGGAGACCAGGT(SEQ ID NO: 258) |
| Scn11a_-_119825394.23-P1P2 | Scn11a | P1P2 | GCCCCAGCCTGAAACGACAG(SEQ ID NO: 259) |

TABLE 3-continued

| | | | |
|---|---|---|---|
| Scnna_+_119825463.23-P1P2 | Scn11a | P1P2 | GGCCAAGAGCGAGAATCTCC(SEQ ID NO: 260) |
| Scnna_+_119825246.23-P1P2 | Scn11a | P1P2 | GGTCAGGTGTCAGAGCCCAT(SEQ ID NO: 261) |
| Scnna_+_119825242.23-P1P2 | Scn11a | P1P2 | GGGTGTCAGAGCCCATCGGT(SEQ ID NO: 262) |
| Scn11a_+_119825431.23-P1P2 | Scn11a | P1P2 | GTGCCCTGAGCCTCCCTAGC(SEQ ID NO: 263) |
| Scn11a_-_119825253.23-P1P2 | Scn11a | P1P2 | GTCTGTGAGAACCGACCGAT(SEQ ID NO: 264) |
| Shank3_+_89499659.23-P1P2 | Shank3 | P1P2 | GGGCTCCGCAGGCGCAGCGG(SEQ ID NO: 265) |
| Shank3_+_89499688.23-P1P2 | Shank3 | P1P2 | GgggccagcgcggggACAG(SEQ ID NO: 266) |
| Shank3_+_89499943.23-P1P2 | Shank3 | P1P2 | GCCGCTAGCGGGCCACACAG(SEQ ID NO: 267) |
| Shank3_+_89499679.23-P1P2 | Shank3 | P1P2 | GcggggACAGCGGCTCCGG(SEQ ID NO: 268) |
| Shank3_+_89499612.23-P1P2 | Shank3 | P1P2 | GCATCGGCCCCGGCTTCGAG(SEQ ID NO: 269) |
| Shank3_+_89499924.23-P1P2 | Shank3 | P1P2 | GGGGTACGGCGAGATCGCAA(SEQ ID NO: 270) |
| Shank3_+_89499878.23-P1P2 | Shank3 | P1P2 | GATGCCGACGCGCACGACCA(SEQ ID NO: 271) |
| Shank3_-_89499676.23-P1P2 | Shank3 | P1P2 | GGCCGCCGCCGCTGCGCCTG(SEQ ID NO: 272) |
| Shank3_+_89499818.23-P1P2 | Shank3 | P1P2 | GGGGCCCGGACTGTTCCCGG(SEQ ID NO: 273) |
| Shank3_+_89499938.23-P1P2 | Shank3 | P1P2 | GAGCGGGCCACACAGGGGTA(SEQ ID NO: 274) |
| Trpv1_+_73234353.23-P1P2 | Trpv1 | P1P2 | GGGACTTACCAGCTAGGTGC(SEQ ID NO: 275) |
| Trpv1_-_73234330.23-P1P2 | Trpv1 | P1P2 | GCCCACAAAGAACAGCTCCA(SEQ ID NO: 276) |
| Trpv1_-_73234384.23-P1P2 | Trpv1 | P1P2 | GGCTGGTAAGTCCTTCTCAT(SEQ ID NO: 277) |
| Trpv1_+_73234339.23-P1P2 | Trpv1 | P1P2 | GGGTGCAGGCACACTCCAA(SEQ ID NO: 278) |
| Trpv1_-_73234537.23-P1P2 | Trpv1 | P1P2 | GACTTAACTTGGCTGACTGT(SEQ ID NO: 279) |
| Trpv1_+_73234478.23-P1P2 | Trpv1 | P1P2 | GTCAGCCTCCCAGAAGTCCA(SEQ ID NO: 280) |
| Trpv1_-_73234495.23-P1P2 | Trpv1 | P1P2 | GGCTGCCTTGGACTTCTGGG(SEQ ID NO: 281) |
| Trpv1_+_73234635.23-P1P2 | Trpv1 | P1P2 | GCCACGGAAGGCCTCCAGAT(SEQ ID NO: 282) |
| Trpv1_-_73234346.23-P1P2 | Trpv1 | P1P2 | GCCAAGGCACTTGCTCCATT(SEQ ID NO: 283) |
| Trpv1_+_73234280.23-P1P2 | Trpv1 | P1P2 | GGGCTGCTGTGTGGTAAGAG(SEQ ID NO: 284) |
| Grin2b_-_136172154.23-P1P2 | Grin2b | P1P2 | GCCAACCTGAATGGAAGAGA(SEQ ID NO: 285) |

TABLE 3-continued

| Name | Gene | Type | Sequence |
|---|---|---|---|
| Grin2b_-_136172179.23-P1P2 | Grin2b | P1P2 | GAGGGAAGTGGAAAGCAAGG(SEQ ID NO: 286) |
| Grin2b_-_136172123.23-P1P2 | Grin2b | P1P2 | GTGGGACAGGCATGGATGAA(SEQ ID NO: 287) |
| Grin2b_+_136172089.23-P1P2 | Grin2b | P1P2 | GCCTGTCCCAGGAACGGCAT(SEQ ID NO: 288) |
| Grin2b_-_136172145.23-P1P2 | Grin2b | P1P2 | GTGAGAAAAGCCAACCTGAA(SEQ ID NO: 289) |
| Grin2b_-_136171934.23-P1P2 | Grin2b | P1P2 | GGATTCGAGTGTCTCCCGGA(SEQ ID NO: 290) |
| Grin2b_-_136171999.23-P1P2 | Grin2b | P1P2 | GACCAAGTCGTTATAAGGAA(SEQ ID NO: 291) |
| Grin2b_-_136172002.23-P1P2 | Grin2b | P1P2 | GAAGTCGTTATAAGGAAAGG(SEQ ID NO: 292) |
| Grin2b_+_136171844.23-P1P2 | Grin2b | P1P2 | GGAATGACCACGCTCCACGG(SEQ ID NO: 293) |
| Grin2b_+_136172019.23-P1P2 | Grin2b | P1P2 | GCCTCTGGTGTGTACTCTGT(SEQ ID NO: 294) |

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11332727B2). An electronic copy of the "Sequence Listing" will also be available from the USPTO upon request and payment of the fee set forth in 37 CFR 1.19(b)(3).

What is claimed:

1. A method for reducing an immune response in a subject administered a therapeutic regime that comprises a first viral vector, wherein the first vector is an adeno-associated virus 5 (AAV5) vector, the method comprising administering an immune-evading composition to the subject, wherein
the immune-evading composition comprises: a second viral vector, wherein the second vector is an AAV8 vector or an AAVDJ vector, wherein the second vector is immune-orthogonal to the first vector, as determined by:
a) administering the first viral vector to an animal model;
b) administering the second viral vector to the animal model,
c) measuring a total antibody response using an enzyme-linked immunosorbent assay (ELISA) of serum obtained from the animal model, and
d) detecting a reduced total antibody response of at least about 1-fold against the second viral vector, as compared to a comparable animal model administered the first viral vector at least twice.

2. The method of claim 1, wherein the subject has a disease, and wherein the disease comprises achromatopsia, adenosine deaminase (ADA) deficiency, alpha-1-antitrypsin deficiency, Alzheimer's disease, amyotrophic lateral sclerosis, aromatic amino acid decarboxylase deficiency, Batten disease, choroideremia, Crigler Najjar syndrome, cystic fibrosis, fragile X syndrome, hemophilia, hepatitis B, hepatitis C, homozygous familial hypercholesteremia, Huntington's Disease, Leber congenital amaurosis, macular degeneration, maple syrup urine disease (MSUD), mucopolysarccharidosis (1-LX), multiple sclerosis, muscular dystrophy, myotonic dystrophy, neurofibramotosis type1, ornithine transcarbamylase deficiency, pachyonychia congenita, Parkinson's disease, phenylketonuria, polycystic kidney disease, Pompe disease, retinal degeneration, Rett syndrome, rickets, spinal muscular atrophy, severe combined immunodeficiency, sickle cell disease, Smith-Lemli-Opitz syndrome, Y-linked nonobstructive spermatogenic failure, thalassemia, Tay-Sachs disease, Wilson's disease, and X-linked retinoschisis.

3. The method of claim 1, wherein the immune-evading composition is administered at least about 3 weeks, at least about 6 weeks, or at least about 3 weeks and at least about 6 weeks after the therapeutic regimen.

4. The method of claim 1, wherein the ELISA is performed on serum collected at 3 weeks, 6 weeks, or 3 weeks and 6 weeks after the administering of the second viral vector to the animal model.

5. The method of claim 1, further comprising administering to the subject (i) a vector that encodes for one or more guide RNAs (gRNAs), (ii) one or more gRNAs, (iii) a transgene, or any combination thereof.

6. The method of claim 1, wherein at least one of the first viral vector or the second viral vector comprise an organ- or tissue-specific promoter.

7. The method of claim 1, further comprising administering an immunosuppressive to the subject.

8. The method of claim 1, further comprising administering to the subject a third viral vector that encodes for one or more guide RNAs (gRNAs), wherein the one or more gRNA independently bind to a protospacer sequence having at least 95% homology to a sequence selected from Table 2 or Table 3, wherein the subject has disease, wherein the disease is muscular dystrophy, Rett syndrome, or ornithine transcarbamylase deficiency, wherein the second viral vector is the AAV8 vector, wherein the first viral vector encodes a first protein or the fragment thereof and the second viral vector encodes a second protein or the fragment thereof that are each independently selected from the group consisting of *S. pyogenes* Cas9 (spCas9), *S. aureus* Cas9 (saCas9), *B. longum* Cas9, *A. muiciniphilia* Cas9, and *O. laneus* Cas9, and wherein the subject is human.

9. The method of claim 1, further comprising administering to the subject a third viral vector that encodes for one or more guide RNAs (gRNAs), wherein the one or more gRNA independently bind to a protospacer sequence having at least 95% homology to a sequence selected from Table 2 or Table 3, wherein the subject has disease, wherein the disease is muscular dystrophy, Rett syndrome, or ornithine transcarbamylase deficiency, wherein the second viral vector is the AAVDJ vector, wherein the first viral vector encodes a first protein or fragment thereof and the second viral vector encodes a second protein or fragment thereof that are each independently selected from the group consisting of *S. pyogenes* Cas9 (spCas9), *S. aureus* Cas9 (saCas9), *B. longum* Cas9, *A. muiciniphilia* Cas9, and *O. laneus* Cas9, and wherein the subject is a human.

* * * * *